(12) United States Patent
Chen et al.

(10) Patent No.: US 12,247,234 B2
(45) Date of Patent: *Mar. 11, 2025

(54) BIOCATALYSTS AND METHODS FOR HYDROXYLATION OF CHEMICAL COMPOUNDS

(71) Applicant: Codexis, Inc., Redwood City, CA (US)

(72) Inventors: Haibin Chen, Beijing (CN); Yong Koy Bong, Singapore (SG); Fabien L. Cabirol, Dusseldorf (DE); Anupam Gohel Prafulchandra, Bekasi (ID); Tao Li, Cincinnati, OH (US); Jeffrey C. Moore, Westfield, NJ (US); Martina Quintanar-Audelo, Edinburgh (GB); Yang Hong, Singapore (SG); Steven J. Collier, Concord, MA (US); Derek Smith, Singapore (SG)

(73) Assignee: Codexis, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/059,949

(22) Filed: Nov. 29, 2022

(65) Prior Publication Data
US 2023/0227875 A1 Jul. 20, 2023

Related U.S. Application Data

(60) Continuation of application No. 17/221,613, filed on Apr. 2, 2021, now Pat. No. 11,549,132, which is a continuation of application No. 16/913,761, filed on Jun. 26, 2020, now Pat. No. 10,995,349, which is a continuation of application No. 16/446,866, filed on Jun. 20, 2019, now Pat. No. 10,731,189, which is a continuation of application No. 15/357,668, filed on Nov. 21, 2016, now Pat. No. 10,370,688, which is a division of application No. 14/399,034, filed as application No. PCT/US2013/039874 on May 7, 2013, now Pat. No. 9,790,527.

(60) Provisional application No. 61/644,135, filed on May 8, 2012.

(51) Int. Cl.
| C12P 17/12 | (2006.01) |
| C12N 9/02 | (2006.01) |
| C12P 13/04 | (2006.01) |
| C12P 13/24 | (2006.01) |
| C12P 17/18 | (2006.01) |

(52) U.S. Cl.
CPC ............ *C12P 17/12* (2013.01); *C12N 9/0071* (2013.01); *C12P 13/04* (2013.01); *C12P 13/24* (2013.01); *C12P 17/188* (2013.01); *C12Y 114/11002* (2013.01); *Y02P 20/52* (2015.11)

(58) Field of Classification Search
None
See application file for complete search history.

(56) References Cited

U.S. PATENT DOCUMENTS

| 5,364,775 A | 11/1994 | Katsumata et al. |
| 5,854,040 A | 12/1998 | Ozaki et al. |
| 5,962,292 A | 10/1999 | Ozaki et al. |
| 5,963,254 A | 10/1999 | Kim et al. |
| 6,117,679 A | 9/2000 | Stemmer |
| 6,376,246 B1 | 4/2002 | Crameri et al. |
| 6,537,746 B2 | 3/2003 | Arnold et al. |
| 6,586,182 B1 | 7/2003 | Patten et al. |
| 8,541,209 B2 | 9/2013 | Kino et al. |
| 8,883,459 B2 | 11/2014 | Kino et al. |
| 9,790,527 B2 | 10/2017 | Chen et al. |
| 10,370,688 B2 | 8/2019 | Chen et al. |
| 10,731,189 B2 | 8/2020 | Chen et al. |
| 10,995,349 B2 | 5/2021 | Chen et al. |
| 11,549,132 B2 * | 1/2023 | Chen ............... C12Y 114/11002 |
| 2006/0195947 A1 | 8/2006 | Davis et al. |
| 2008/0220990 A1 | 9/2008 | Fox |
| 2009/0312196 A1 | 12/2009 | Colbeck et al. |
| 2011/0046102 A1 | 2/2011 | Ledoussal et al. |
| 2011/0091942 A1 | 4/2011 | Kino et al. |
| 2021/0230654 A1 | 7/2021 | Chen et al. |
| 2023/0227875 A1 * | 7/2023 | Chen ...................... C12P 13/24 435/178 |

FOREIGN PATENT DOCUMENTS

| EP | 0641862 B1 | 12/2001 |
| EP | 2290065 B1 | 8/2014 |
| WO | 95/22625 A1 | 8/1995 |
| WO | 95/33836 A1 | 12/1995 |
| WO | 96/00787 A1 | 1/1996 |
| WO | 97/0078 A1 | 1/1997 |

(Continued)

OTHER PUBLICATIONS

Adams, D.R., et al., "An efficient route to the alpha-methyl ester of L-glutamic acid, and its conversion into cis-5-hydroxy-L-pipecolic acid," Chem. Commun., 3:349-350 [1996].

Altamura, M., et al., "2-Substituted penems with amino acid-related side chains: synthesis and antibacterial activity of a new series of beta-lactam antibiotics," J Med Chem., 38(21):4244-56 [1995].

Altschul, S., et al., "Basic local alignment search tool," J. Mol. Biol., 215: 403-410 (1990).

Altschul, S.F., et al., "Gapped BLAST and PSI-BLAST: a new generation of protein database search programs," Nucleic Acids Res., 25(17):3389-3402 (1997).

(Continued)

*Primary Examiner* — Hope A Robinson
(74) *Attorney, Agent, or Firm* — Codexis, Inc.

(57) ABSTRACT

The present disclosure provides engineered proline hydroxylase polypeptides for the production of hydroxylated compounds, polynucleotides encoding the engineered proline hydroxylases, host cells capable of expressing the engineered proline hydroxylases, and methods of using the engineered proline hydroxylases to prepare compounds useful in the production of active pharmaceutical agents.

12 Claims, No Drawings

Specification includes a Sequence Listing.

(56) References Cited

FOREIGN PATENT DOCUMENTS

| WO | 97/35966 A1 | 10/1997 |
|---|---|---|
| WO | 98/27230 A1 | 6/1998 |
| WO | 2000/42651 A1 | 7/2000 |
| WO | 2001/75767 A2 | 10/2001 |
| WO | 2009/008908 A2 | 1/2009 |
| WO | 2009/091856 A2 | 7/2009 |
| WO | 2009/139365 A1 | 11/2009 |
| WO | 2010/126820 A2 | 11/2010 |

OTHER PUBLICATIONS

Batzer, M.A., "Erratum: Structure and variability of recently inserted Alu family members", Nucleic Acids Res 19:698-699 [1991].

Beaucage, S.L., et al., "Deoxynucleoside phosphoamidites—A new class of key intermediates for deoxypolynucleotide synthesis," Tetrahedron Letters, 22(20):1859-62 (1981).

Beyerman, H.C., et al., "Stereospecific synthesis and optical resolution of 5-hydroxypipecolic acid," Recueil des Travaux Chimiques des Pays-Bas, 78(9):648-658 [1959].

Black, M.E., et al., "Creation of drug-specific herpes simplex virus type 1 thymidine kinase mutants for gene therapy," Proc Natl Acad Sci USA, 93:3525-3529 (1996).

Bolton, E.T., et al., "A General Method for the Iisolation of RNA Complementary to DNA," Proc. Natl. Acad. Sci. USA 48:1390 ( 1962).

Botman, P.N., et al., "Diastereoselective synthesis of (2S,5R)-5-hydroxypipecolic acid and 6-substituted derivatives," Organic Letters, 6(26):4941-4944 [2004].

Botstein, D., et al., "Strategies and applications of in vitro mutagenesis," Science, 229(4719):1193-1201, 1985.

Breslauer, K.J., et al., "Predicting DNA duplex stability from the base sequence," Proc. Natl. Acad. Sci. USA, 83:3746-3750 (1986).

Caldwell, R.C., et al., "Mutagenic PCR," PCR Methods Appl., 3:S136-S140 (1994).

Callens, R.E.A., et al., "Preparation of Trans-5-Hydroxy-L-Pipecolic Acid and Cis-4-Hydroxy-L-Pipecolic Acid From L-Baikiain (1,2,5,6-L-Tetrahydropyridine-2-Carboxylic Acid)," Bulletin des Sociétés Chimiques Belges, 91(8):713-723 [1982].

Carter, P., "Site-directed mutagenesis," Biochem. J., 237:1-7 (1986).

Chen, K.X., et al., "Novel potent hepatitis C virus NS3 serine protease inhibitors derived from proline-based macrocycles," J Med Chem., 49(3):995-1005 [2006].

Chen, K.X., et al., "Syntheses of novel 4-tert-alkyl ether proline-based 16- and 17-membered macrocyclic compounds," J Org Chem., 67(8):2730-3 [2002].

Chiou, W.H., et al., "Facile syntheses of enantiopure 3-hydroxypiperidine derivatives and 3-hydroxypipecolic acids," J Org Chem., 75(5):1748-51 [2010].

Christians, F.C., et al., "Directed evolution of thymidine kinase for AZT phosphorylation using DNA family shuffling," Nat. Biotechnol., 17:259-264 (1999).

Clark-Lewis, J.W., et al., "Occurrence of 4-hydroxypipecolic acid in Acacia species," Nature, 184(Suppl 16):1234-5 [1959].

Cohen, L.A., et al., "Synthesis of 5-Hydroxypipecolic Acid and Separation of Its Diastereoisomers," Science, 123(3202):842-843 [1956].

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling," Nat. Biotechnol., 14(3):315-319 (1996).

Crameri, A., et al., "Molecular evolution of an arsenate detoxification pathway by DNA shuffling," Nat. Biotechnol., 15(5):436-438 (1997).

Dale, S.J., et al., "Oligonucleotide-directed random mutagenesis using the phosphorothioate method," Methods Mol. Biol., 57:369-74 (1996).

De Boer, H.A., et al., "The tac promoter: A functional hybrid derived from the trp and lac promoters," Proc. Natl Acad. Sci. USA, 80: 21-25 (1983).

Efimov, V.A., et al., "Hydroxyproline-based DNA mimics provide an efficient gene silencing in vitro and in vivo," Nucleic Acids Res., 34(8):2247-2257 [2006].

Eguchi, C., et al., "The novel synthesis of L-Hydroxyproline from D-Glutamic Acid," Bull. Chem. Soc. Japan, 47(7):1704-08 [1974].

Ermolaeva, M.D., et al., "Prediction of transcription terminators in bacterial genomes," J. Mol. Biol., 301:27-33 [2000].

Fasman, G.D.,CRC Practical Handbook of Biochemistry and Molecular Biology, CRC Press, Boca Raton, FL, pp. 3-70 [1989].

Fowden, L., "Some observations on a hydroxypipecolic acid from thrift (Armeria maritima)," Biochem J., 70(4):629-33 [1958].

Freier, S.M., et al., "Improved free-energy parameters for predictions of RNA duplex stability," Proc. Natl. Acad. Sci USA, 83:9373-9377 (1986).

Guo, Z., et al., "3'-End-Forming Signals of Yeast mRNA," Mol. Cell. Biol., 15(11):5983-5990 [1995].

Hara, R., "Characterization of novel 2-oxoglutarate dependent dioxygenases converting L-proline to cis-4-hydroxy-l-proline," Biochem Biophys Res Commun., 379(4):882-6 [2009].

Henaut and Danchin in Neidhardt et al. [eds.], Escherichia coli and Salmonella, "Analysis and predictions from Escherichia coli Sequences, or E. coli in silico," ASM Press, Washington D.C., [1987], pp. 2047-2066.

Henikoff, S.,et al., "Amino acid substitution matrices from protein blocks," Proc. Natl. Acad. Sci., 89:10915-10919 (1992).

Jourdant, A., et al., "An efficient stereoselective and stereodivergent synthesis of (2R,3R)- and (2R,3S)-3-hydroxypipecolic acids," Tetrahedron Lett., 41(36):7033-7036 [2000].

Kalamkar, N.B., et al., "Chiron approach to the synthesis of (2S,3R)-3-hydroxypipecolic acid and (2R,3R)-3-hydroxy-2-hydroxymethylpiperidine from D-glucose," J Org Chem., 73(9):3619-22 [2008].

Kierzek, R., et al., "Polymer-Supported RNA Synthesis and Its Application To Test the Nearest-Neighbor Model for Duplex Stability," Biochemistry, 25:7840-7846 (1986).

Klein, C., et al., "A Simple Procedure for Selective Hydroxylation of I-Proline and I-Pipecolic Acid with Recombinantly Expressed ProlineHydroxylases," Adv Synth. Catal., 353:1375-1383 [2011].

Koszelewski, D., et al., "Immobilization of omega-transaminases by encapsulation in a sol-gel/celite matrix," Journal of Molecular Catalysis B: Enzymatic, 63: 39-44 (2010).

Kramer, B., et al., "Different base/base mismatches are corrected with different efficiencies by the methyl-directed DNA mismatch-repair system of E. coli," Cell, 38(3):879-887 [1984].

Kumar, P., et al., "Asymmetric synthesis of both the enantiomers of trans-3-hydroxypipecolic acid," J Org Chem., 70(1):360-3 [2005].

Lawrence, C.C., et al., "Purification and initial characterization of proline 4-hydroxylase from Streptomyces griseoviridus P8648: a 2-oxoacid, ferrous-dependent dioxygenase involved in etamycin biosynthesis," Biochem. J., 313:185-191 [1996].

Lee, Y.K., et al., "The novel synthesis of two diastereomers of gamma-hydroxyproline," Bull. Chem. Soc. Japan, 46:2924-26 [1973].

Lemire, A., et al., "Stereoselective syntheses of L-pipecolic acid and (28,3S)-3-hydroxypipecolic acid from a chiral N-imino-2-phenyl-1,2-dihydropyridine intermediate," J Org Chem., 75(6):2077-80 [2010].

Letavic, M.A., et al., "Synthesis and biological activity of selective pipecolic acid-based TNF-α converting enzyme (TACE) inhibitors," Bioorg Medicinal Chem Lett., 12(10):1387-1390 [2002].

Liang, N., et al., "Stereoselective total synthesis of cis- and trans-3-hydroxypipecolic acid," J Org Chem., 70(24):10182-5 [2005].

Ling, M., et al., "Approaches to DNA Mutagenesis:An Overview," Anal. Biochem., 254:157-78 (1997).

Ma, J., et al., "Correlations between Shine-Dalgarno Sequences and Gene Features Such as Predicted Expression Levels and Operon Structures," J Bacteriol., 184(20): 5733-5745 [2002].

Majamaa, K., et al., "Differences between collagen hydroxylases and 2-oxoglutarate dehydrogenase in their inhibition by structural analogues of 2-oxoglutarate," Biochem. J., 229:127-133 [1985].

(56) References Cited

OTHER PUBLICATIONS

Marin, J., et al., "Synthesis of enantiopure 4-hydroxypipecolate and 4-hydroxylysine derivatives from a common 4,6-dioxopiperidinecarboxylate precursor," J Org Chem., 69(1):130-41 [2004].
Martin, A.R., et al., "Characterization of free and immobilized (S)-aminotransferase for acetophenone production," Applied Microbiology and Biotechnology, 76(4): 843-851 (2007).
Mateo, C., et al., "Epoxy sepabeads: a novel epoxy support for stabilization of industrial enzymes via very intense multipoint covalent attachment," Biotechnology Progress 18(3):629-34 (2002).
Matthes, H.W.D., et al., "Simultaneous rapid chemical synthesis of over one hundred oligonucleotides on a microscale," EMBO J., 3(4):801-05 (1984).
McInerney, J.O., "GCUA: general codon usage analysis," Bioinformatics, 14(4):372-73, 1998.
Minshull, J., et al., "Protein evolution by molecular breeding," Curr. Op. Chem. Biol., 3(3):284-290 (1999).
Mori, H., et al., "Detection of Novel Proline 3-Hydroxylase Activities in *Streptomyces* and *Bacillus* spp. by Regio- and Stereospecific Hydroxylation of I-Proline," Appl. Environ. Microbiol., 62:1903-1907 [1996].
Nakamura, Y., et al., "Codon usage tabulated from international DNA sequence databases: status for the year 2000," Nucl. Acids Res., 28:292 [2000].
Needleman, S., et al., "A general method applicable to the search for similarities in the amino acid sequence of two proteins," J. Mol. Biol. 48:443-453 (1970).
O'Connell, C.E., et al., "Synthesis and evaluation of some hydroxyproline-derived peptidomimetics as soprenyltransferase inhibitors" Chem Pharm Bull., 48(5):740-742 [2000].
Pearson, W.R., "Improved tools for biological sequence comparison," Proc. Nat'l. Acad. Sci. USA, 85:2444-2448 (1988).
Petersen, L. et al., "Novel proline hydroxylase activities in the pneumocandin-producing fungus *Glarea lozoyensis* responsible for the formation of trans 3- and trans 4-hydroxyproline," Appl Microbiol Biotechnol., 62(2-3):263-7 [2003].
Ramaswarmy, S.G., et al., "One-vessel synthesis of 4-hydroxyproline from glyoxal and oxaloacetic acid," J. Org. Chem., 42(21):3440-3443 [1977].
Remuzon, P., "Trans-4-hydroxy-L-proline, a useful and versatile chiral starting block," Tetrahedron, 52(44):13803-13835 [1996].
Romanos, M.A., et al., "Foreign gene expression in yeast: a review," Yeast 8:423-488 [1992].
Romeo, J.T., et al., "CIs-4-Hydroxypipecolic Acid and 2,4-Cis-4,5-Trans-4,5-Dihydroxypipecolic Acid From Calliandra," Phytochemistry 22(7):1615-1617 [1983].
Rychlik, W., et al., "Optimization of the annealing temperature for DNA amplification in vitro," Nucleic Acids Res, 18(21):6409-6412 (1990).
Sakai, H., et al., "Correlation between Shine-Dalgarno sequence conservation and codon usage of bacterial genes," J. Mol. Evol. 52(2):164-170 [2001].
Shibasaki, T., et al., "Microbial Proline 4-Hydroxylase Screening and Gene Cloning," Appl. Environ. Microbiol, 65(9):4028-31 [1999].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Stellwagen, E., "Dye Affinity Chromatography," Current Protocols in Protein Science, Chapter 9, Unit 9.2-9.2.16 [2001].
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Stenico, M., et al., "Codon usage in Caenorhabditis elegans: delineation of translational selection and mutational biases," Nucl. Acids Res. 22(13):2437-46 [1994].
Suggs, S.V., et al., "Use of synthetic oligodeoxyribonucleotides for the isolation of specific cloned DNA sequenes," In Developmental Biology Using Purified Genes (Brown et al., eds.), pp. 683-693, Academic Press (1981).
Tiwari, S., et al., "Prediction of probable genes by Fourier analysis of genomic sequences," Comput. Appl. Biosci. 13(3):263-270 [1997].
Truppo, M.D., et al., "Development of an Improved Immobilized CAL-B for the Enzymatic Resolution of a Key Intermediate to Odanacatib," Organic Process Research & Development, 15:1033-1035 (2011).
Vergnon, A.L., et al., "Solid-phase synthesis of a library of hydroxyproline derivatives," J Comb Chem., 6(1):91-8 [2004].
Mlla-Komaroff, L., et al., "A bacterial clone synthesizing proinsulin," Proc. Natl Acad. Sci. USA, 75:3727-3731 (1978).
Vimberg, V., et al., "Translation initiation region sequence preferences in *Escherichia coli*," BMC Molecular Biology, 8:100, pp. 1-13 [2007].
Wada, K., et al., "Codon usage tabulated from the GenBank genetic sequence data," Nucl. Acids Res., 20:2111-2118 [1992].
Wells, J.A., et al., "Cassette mutagenesis: an efficient method for generation of multiple mutations at defined sites," Gene, 34:315-323 (1985).
Wetmur, J. G., "DNA Probes: Applications of the Principles of Nucleic Acid Hybridization," Crit Rev Biochem Mol Biol, 26(3/4):227-259 (1991).
Wright, F., "The 'effective number of codons' used in a gene," Gene 87:23-29 [1990].
Yaegaki, K.,et al., "Improved high-performance liquid chromatography method for quantitation of proline and hydroxyproline in biological materials," J Chromatogr., 356(1):163-70 [1986].
Yi, S., et al., "Covalent immobilization of omega-transaminase from Vibrio fluvialis JS17 on chitosan beads," Process Biochemistry 42(5): 895-898 (2007).
Zhang, J-H., et al., "Directed evolution of a fucosidase from a galactosidase by DNA shuffling and screening ," Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
Gorres, K.L., et al., "Prolyl 4-hydroxylase," Crit Rev Biochem Mol Biol., 45(2):106-124 [2010].

\* cited by examiner

BIOCATALYSTS AND METHODS FOR HYDROXYLATION OF CHEMICAL COMPOUNDS

The present application is a Continuation of co-pending U.S. patent application Ser. No. 17/221,613, filed Apr. 2, 2021, now U.S. Pat. No. 11,549,132, which is a Continuation of U.S. patent application Ser. No. 16/913,761, filed Jun. 26, 2020, now U.S. Pat. No. 10,995,349, which is a Continuation of U.S. patent application Ser. No. 16/446,866, filed Jun. 20, 2019, now U.S. Pat. No. 10,731,189, which is a Continuation of U.S. patent application Ser. No. 15/357,668, filed Nov. 21, 2016, now U.S. Pat. No. 10,370,688, which is a Divisional of U.S. patent application Ser. No. 14/399,034, filed Nov. 5, 2014, now U.S. Pat. No. 9,790,527, which is a national stage application filed under 35 USC § 371 and claims priority to PCT International Application No. PCT/US2013/039874, filed May 7, 2013, and U.S. Prov. Appln. Ser. No. 61/644,135, filed on May 8, 2012. The present application hereby incorporates each of these applications by reference, in their entireties and for all purposes.

1. TECHNICAL FIELD

The disclosure relates to biocatalysts for the hydroxylation of chemical compounds.

2. REFERENCE TO SEQUENCE LISTING, TABLE OR COMPUTER PROGRAM

The official copy of the Sequence Listing is submitted concurrently with the specification as an XML file, with a file name of "CX2-095WO2UD1C4_ST26.xml", a creation date of Nov. 28, 2022, and a size of 422,257 bytes. The Sequence Listing is part of the specification and is incorporated in its entirety by reference herein.

3. BACKGROUND

Proline derivatives with functional groups on the ring carbons are useful building blocks for synthesis of pharmaceutical compounds because of the constrained conformation of proline. One such derivative, hydroxylated proline, is a starting material for the synthesis of various therapeutic compounds, including carbapenem antibiotics (see, e.g., Altamura et al., 1995, J Med Chem. 38(21):4244-56), angiotensin-converting enzyme inhibitors, protease inhibitors (see, e.g., Chen et al., 2002, J Org Chem. 67(8):2730-3; Chen et al., 2006, J Med Chem. 49(3):995-1005), nucleic acid analogs (Efimov et al., 2006, Nucleic Acids Res. 34(8):2247-2257), isoprenyltransferase inhibitors (O'Connell et al., 2000, Chem Pharm Bull. 48(5):740-742), and drug library construction (Vergnon et al., 2004, J Comb Chem. 6(1):91-8; Remuzon P., 1996, Tetrahedron 52:13803-13835). Similarly, hydroxylated derivatives of a proline homolog, L-pipecolic acid, also known as homoproline, also serve as building blocks for pharmaceutical compounds. For example, hydroxypipecolic acid is an intermediate in the synthesis of β-lactamase inhibitors (see, e.g., WO2009091856, WO2010126820 and US20110046102) and TNF-alpha converting enzyme (TACE) inhibitors (Levatic et al., 2002, Bioorg Medicinal Chem Lett. 12(10):1387-1390).

Hydroxyproline can be obtained from natural sources, such as plant materials and hydrolyzates of collagen. Hydroxyproline can also be chemically synthesized, such as from starting materials allyl bromide and diethylacetamidomalonic acid (Kyun Lee et al., 1973, Bull. Chem. Soc. Japan, 46:2924), D-glutamic acid (Eguchi et al., 1974, Bull. Chem. Soc. Japan, 47:1704-08), glyoxal and oxaloacetic acid (Ramaswamy et al., 1977, J. Org. Chem. 42(21):3440-3443), and β-alanine (Sinha et al., 2000, Proc. ECSOC-4, The Fourth International Electronic Conference on Synthetic Organic Chemistry, ISBN 3-906980-05-7).

Hydroxypipecolic acid can also be obtained from plants and other natural sources (see, e.g., Romeo et al., 1983, Phytochemistry 22(7):1615-1617; Fowden, L., 1958, Biochem J. 70(4):629-33; Clark-Lewis and Mortimer, 1959, Nature 184(Suppl 16):1234-5). Chemical synthesis of hydroxypipecolic acid is described in Callens et al., 2010, Bulletin des Socidtds Bulletin des Socidtds Chimiques Belges 91(8):713-723; Adams et al., 1996, Chem. Commun. 3:349-350; Botman et al., 2004, Organic Letters 6(26):4941-4944; Cohen et al., 1956, Science 123(3202):842-843; Beyerman et al., 1959, Recueil des Travaux Chimiques des Pays-Bas, 78(9):648-658; Marin et al., 2004, J Org Chem. 69(1):130-41; Kumar et al., 2005, J Org Chem. 70(1):360-3; Liang et al., 2005, J Org Chem. 70(24):10182-5; Kalamkar et al., 2008, J Org Chem. 73(9):3619-22; Chiou et al., 2010, J Org Chem. 75(5):1748-51; Lemire et al., 2010, J Org Chem. 75(6):2077-80; and Angelique et al., 2000, Tetrahedron Lett. 41(36):7033-7036.

Isolation from natural sources is limited by the availability of raw materials, requires purification from a significant amount of background contaminants, and lacks certain desired diastereomers. Chemical synthetic methods can require complex steps, be difficult to scale up to industrial scale levels, and require additional purification steps due to formation of multiple hydroxylated products.

Another approach for preparing hydroxylated proline uses proline hydroxylases, which are 2-oxoglutarate-dependent dioxygenases, utilizing 2-oxoglutarate (α-ketoglutarate) and $O_2$ as co-substrates and ferrous ion as a cofactor (see, e.g., Klein et al., 2011, Adv Synth. Catal. 353:1375-1383; U.S. Pat. No. 5,364,775; and Shibasaki et al., 1999, Appl Environ Microbiol. 65(9):4028-4031). Unlike prolyl hydroxylases that specifically recognize peptidyl proline in procollagen and related peptides, proline hydroxylases are capable of converting free proline to hydroxyproline. Several microbial enzymes that produce cis-3-, cis-4- or trans-4-hydroxyproline are known (see, e.g., U.S. Pat. Nos. 5,962,292; 5,963,254; 5,854,040; WO2009139365; and EP2290065) and an enzyme that produces trans-3-hydroxyproline have been identified in extracts of the fungus *Glarea lozoyensis*. Many of the proline hydroxylases are found in bacteria, where they are associated with the biosynthesis of peptide antibiotics. The cis-4-proline hydroxylase enzyme also shows activity in converting L-pipecolic acid (i.e., (2S)-piperidine-2-carboxylic acid) to cis-5-hydroxypipecolic acid (i.e., (2S,5S)-5-hydroxypiperidine-2-carboxylic acid; Klein et al. supra). In vitro conversions for preparing 5-hydroxypipecolic acid using these enzymes have been demonstrated, but isolated proline hydroxylases are found to denature under reaction conditions and have relatively low specific activity, rendering in vitro uses impracticable for commercial applications (Klein et al., supra). While recombinant whole cells expressing cloned proline hydroxylases are better suited for large scale industrial processes, the use of whole cells limits variations in reaction conditions, such as high substrate concentrations; restricts the types of substrates that can be used with whole cells to those that are permeable to the cells; and results in undesirable by-products that must be separated from the final product. In addition, in vivo systems may require defined growth media not optimal or cost effective because the use of rich growth media prepared from protein hydrolyzates contain free proline, which can be a competitive inhibitor when substrates other than proline are being targeted. Desirable are alternative methods for synthesizing hydroxylated forms of proline and proline analogs, as well as other chemical compounds, that can be readily scaled up and result in substantially pure stereometric product.

4. SUMMARY

The present disclosure provides engineered proline hydroxylase biocatalysts, polynucleotides encoding the biocatalysts, methods of their preparation, and processes for preparing hydroxylated compounds using these engineered biocatalysts. The proline hydroxylases of the present disclosure have been engineered to have improved properties relative to the naturally occurring cis-4-proline hydroxylase (SEQ ID NO:2) of Sinorhizobium meliloti, a nitrogen fixing Gram negative bacterium. The improved biocatalyst properties of the engineered proline hydroxylases include, among others, activity, regioselectivity, substrate tolerance, and stability. The engineered proline hydroxylases are also found to hydroxylate a variety of substrate compounds, including the selective conversion of (2S)-piperidine-2-carboyxlic acid (i.e., L-pipecolic acid) to (2S,5S)-5-hydroxylpiperidine-2-carboxylic acid (i.e., cis-5-hydroxypipecolic acid). The engineered enzymes with improved properties have one or more residue differences as compared to the naturally occurring proline hydroxylase, where the residue differences occur at residue positions affecting the foregoing enzyme properties.

Accordingly, in one aspect, the present disclosure provides engineered polypeptides having proline hydroxylase activity, where the polypeptides comprises an amino acid sequence having at least 80% identity to SEQ ID NO:2 and one or more residue differences as compared to SEQ ID NO:2 at residue positions selected from: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271.

In some embodiments, the residue differences at residue positions X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271 can be selected from X2K; X2T; X3S; X4Q; X4L; X4E; X4S; X51; X5L; X5M; X9I; X13T; X17V; X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R. The following detailed description provides guidance on the choices of the residue differences that can be used to prepare engineered proline hydroxylases with the desired improved biocatalytic properties.

In some embodiments, the engineered proline hydroxylase polypeptide has an amino acid sequence comprising at least a combination of features selected from: (a) X103L and X166Q; (b) X52P and X255Y; (c) X4E/L/S and X115A; (d) X25R and X58A; (e) X29A and X166T/Q/L; (f) X115H/D/G and X121F; (g) X3S, X103L, and X166Q; (h) X103L, X131Y/F, and X166T/Q/L; (i) X26T, X103L and X166T/Q/L; (j) X25R, X66Q, X92V and X115E; (k) X25R, X66Q, X92V, X103L, X115E, and X166Q; and (1) X3S, X25R, X66Q, X92V, X103L, X115E, and X166Q.

As noted above, the engineered polypeptides having proline hydroxylase activity, are also capable of converting substrate compound (2), (2S)-piperidine-2-carboxylic acid to product compound (1), (2S,5S)-5-hydroxylpiperidine, as shown in Scheme 1,

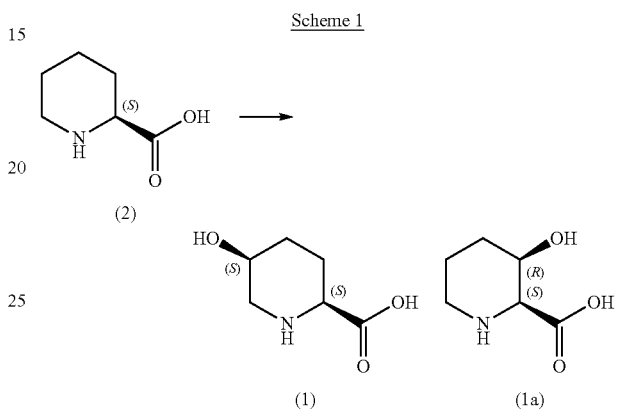

with improved properties as compared to the naturally occurring enzyme. In some embodiments, the engineered polypeptides are capable of converting substrate compound (2) to product compound (1) with at least 1.2 fold, 1.5 fold, 2 fold, 3 fold, 4 fold, 5 fold, or 10 fold or more the activity of the naturally occurring enzyme, and with greater than 90%, 91%, 92%, 93%, 94%, 95%, 96%, 97%, 98%, 99% or more diastereomeric excess of (2S,5R)-5-hydroxypiperidine-2-carboxylic acid.

In some embodiments, the engineered polypeptides having proline hydroxylase activity also display increased regioselectivity for forming (2S,5S)-5-hydroxypiperidine-2-carboxylic acid in excess of other regioisomers, for example (2S,3R)-3-hydroxypiperidine-2-carboxylic acid, shown in Scheme 1 as compound (1a). Thus, in some embodiments, the engineered proline hydroxylases are capable of converting substrate compound (2) to product compound (1) in excess of product compound (1a), where the ratio of product compound (1) formed over product compound (1a) is at least 1.5, 2, 3, 4, 5 or 6 or more. In some embodiments, the engineered proline hydroxylases with increased selectivity for forming product compound (1) in excess of product compound (1a) comprises an amino acid sequence having one or more of the following features: X103L; X115E; X131Y and X166Q, particularly the combination of features X103L and X166Q.

In some embodiments, the engineered polypeptides having improved properties has an amino acid sequence comprising a sequence selected from the group consisting of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In another aspect, the present disclosure provides polynucleotides encoding the engineered proline hydroxylase polypeptides with improved properties. Exemplary polynucleotide sequences are provided in the Sequence Listing incorporated by reference herein and include SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, and 227.

In a further aspect, the present disclosure also provides codon optimized polynucleotides encoding a polypeptide that comprises an amino acid sequence of the wild-type proline hydroxylase (SEQ ID NO:2). In some embodiments, the codon optimized polynucleotides have increased expression in a bacterial host cell as compared to the naturally occurring polynucleotide encoding the proline hydroxylase enzyme. In some embodiments, the codon optimized polynucleotides can have at least 80%, 85%, 90%, 91%, 92%, 93%, 94%, 95%, 96%, 97%, 98%, 99% or more identity to the codon optimized nucleic acid sequence of SEQ ID NO: 1, 3, or 5, which encodes the identical polypeptide sequences of SEQ ID NO:2, 4, or 6, respectively. The codon optimized sequence of SEQ ID NO:1, 3, or 5 can enhance expression of the encoded, wild-type proline hydroxylase by at least 1.2 fold, 1.5 fold or 2 fold or greater as compared to the naturally occurring polynucleotide sequence.

In another aspect, the polynucleotides of the disclosure can be incorporated into expression vectors and host cells for expression of the polynucleotides and the corresponding encoded proline hydroxylase polypeptides. As such, in some embodiments, the present disclosure provides methods of preparing the proline hydroxylase polypeptides by culturing a host cell comprising the polynucleotide or expression vector capable of expressing a proline hydroxylase of the disclosure under conditions suitable for expression of the engineered polypeptide. In some embodiments, the method of preparing the proline hydroxylase can comprise the additional step of isolating the expressed polypeptide.

In some embodiments, the present disclosure also provides methods of manufacturing an engineered proline hydroxylase polypeptide, where the method can comprise: (a) synthesizing a polynucleotide encoding a polypeptide comprising an amino acid sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, and having one or more residue differences as compared to SEQ ID NO:2 at residue positions selected from: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271, and (b) expressing the proline hydroxylase polypeptide encoded by the polynucleotide. As noted above, the residue differences at positions X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271 are selected from X2K; X2T; X3S; X4Q; X4L; X4E; X4S; X51; X5L; X5M; X9I; X13T; X17V; X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R. As further provided in the detailed description, additional variations can be incorporated during the synthesis of the polynucleotide to prepare engineered proline hydroxylases with corresponding differences in the expressed amino acid sequences.

In another aspect, the engineered proline hydroxylase polypeptides can be used in a process for preparing various hydroxylated compounds, such as hydroxylated proline or hydroxylated piperidine-2-carboxylic acids. Accordingly, in some embodiments, the engineered proline hydroxylase polypeptides can be used in a process for the conversion of a substrate compound of formula (II) to product compound of formula (I), as shown below:

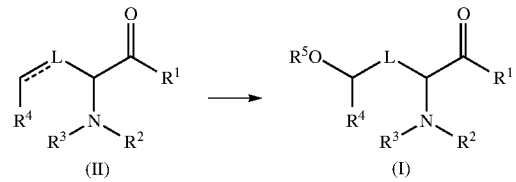

Wherein
  L is selected from the group consisting of a bond, $(C_1\text{-}C_4)$alkylene and $(C_2\text{-}C_4)$alkenylene; $R^1$ is selected from the group consisting of hydroxy, amino, $(C_1\text{-}C_6)$alkyloxy, aryloxy, $(C_1\text{-}C_6)$alkylthio and arylthio;
  $R^2$ and $R^3$ are each independently selected from the group consisting of hydrogen and optionally substituted $(C_1\text{-}C_6)$alkyl, $(C_2\text{-}C_6)$alkenyl, and $(C_2\text{-}C_6)$alkynyl;
  $R^4$ is selected from the group consisting of optionally substituted $(C_1\text{-}C_6)$alkyl, $(C_2\text{-}C_6)$alkenyl, $(C_2\text{-}C_6)$alkynyl, aryl, heteroaryl, cycloalkyl, heterocycloalkyl; or $R^4$ together with one of $R^1$ or $R^2$ is a $(C_1\text{-}C_5)$alkylene or $(C_2\text{-}C_5)$alkenylene and forms a 5- to 8-membered heterocyclic ring containing the nitrogen atom, wherein the ring is optionally substituted with 1 to 4 independently selected $R^6$ groups;
  $R^5$ is hydrogen or a bond that forms an epoxide with a carbon atom of L;
  each occurrence of $R^6$ is independently selected from the group consisting of halo, $(C_1\text{-}C_6)$alkyl, and $(C_1\text{-}C_6)$alkyloxy; and
  --- represents an optional bond to a carbon atom of L to form a double bond;
  with the provisos that
  (i) when $R^4$ does not form a ring with one $R^2$ or $R^3$, or when $R^4$ forms a 5-membered heterocyclic ring containing the nitrogen atom with one of $R^2$ or $R^3$, then L is a methylene;

(ii) when $R^4$ forms a 6-membered heterocyclic ring containing the nitrogen atom with one of $R^2$ or $R^3$, then L is a bond or ethylene; and (iii) when $R^5$ is a bond to a carbon atom of L to form an epoxide, then $R^4$ forms the heterocyclic ring containing the nitrogen atom with one of $R^2$ or $R^3$ and L is a $(C_1-C_4)$alkylene or $(C_2-C_4)$alkenylene.

In some embodiments, the engineered proline hydroxylase can be used for the conversion of a ring compound of structural formula (IIa) to the hydroxylated product compound of structural formula (Ia);

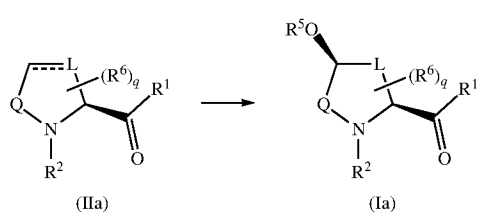

(IIa) (Ia)

wherein

Q is selected from the group consisting of a $(C_1-C_5)$ alkylene and $(C_2-C_5)$alkenylene;

L is selected from the group consisting of a bond, $(C_1-C_4)$alkylene and $(C_2-C_4)$alkenylene;

$R^1$ is selected from the group consisting of hydroxy, amino, $(C_1-C_6)$alkyloxy, aryloxy, $(C_1-C_6)$alkylthio and arylthio;

$R^2$ is selected from the group consisting of hydrogen and optionally substituted $(C_1-C_6)$alkyl, $(C_2-C_6)$alkenyl, and $(C_2-C_6)$alkynyl;

$R^5$ is hydrogen, or a direct bond to a carbon atom of L to form an epoxide;

each occurrence of $R^6$ is selected from the group consisting of halo, $(C_1-C_6)$alkyl, and $(C_1-C_6)$alkyloxy;

q is an integer from 0 to 4; and

--- represents an optional bond to a carbon atom of L to form a double bond;

wherein the sum of ring carbon atoms for Q+L is an integer from 2 to 5;

with the provisos that (i) when the sum of ring carbon atoms for Q+L is 2, then L is a methylene; and (ii) (ii) when the sum of ring carbon atoms for Q+L is 3, then L is either a bond or ethylene.

In some embodiments, the engineered proline hydroxylase can be used for the conversion of a substrate compound of structural formula (IV) to the hydroxylated product compound of structural formula (III);

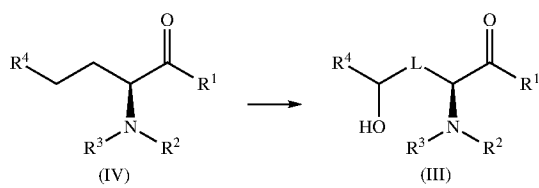

(IV) (III)

wherein, $R^1$ is selected from the group consisting of hydroxy, amino, $(C_1-C_6)$alkyloxy, aryloxy, $(C_1-C_6)$alkylthio and arylthio;

$R^2$ and $R^3$ are each independently selected from the group consisting of hydrogen and optionally substituted $(C_1-C_6)$ alkyl, $(C_2-C_6)$alkenyl, and $(C_2-C_6)$alkynyl; and $R^4$ is selected from the group consisting of optionally substituted alkyl, alkenyl, alkynyl, aryl, heteroaryl, cycloalkyl, and heterocycloalkyl.

In some embodiments, the engineered proline hydroxylase can be used for the conversion of a substrate compound of structural formula (VI) to the hydroxylated product compound of structural formula (V);

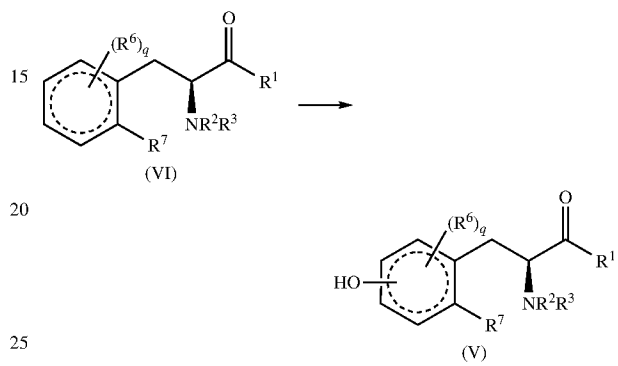

wherein, $R^1$ is selected from the group consisting of hydroxy, amino, $(C_1-C_6)$alkyloxy, aryloxy, $(C_1-C_6)$alkylthio and arylthio;

$R^2$ and $R^3$ are independently selected from the group consisting of hydrogen and optionally substituted $(C_1-C_6)$ alkyl, $(C_2-C_6)$alkenyl, and $(C_2-C_6)$alkynyl;

each occurrence of $R^6$ is independently selected from the group consisting of halo, $(C_1-C_6)$alkyl, and $(C_1-C_6)$alkyloxy;

$R^7$ is selected from the group consisting of hydrogen, halo, and optionally substituted $(C_1-C_6)$alkyl and $(C_1-C_6)$ alkyloxy; or $R^7$ together with one of $R^2$ or $R^3$ forms a 5- to 7-membered heterocyclic ring containing the nitrogen atom;

q is an integer from 0 to 4; and

--- represent optional double bonds that form an aryl ring.

The hydroxylation reactions above using the engineered proline hydroxylases are carried out under suitable reaction conditions in presence of a co-substrate (e.g., α-ketoglutarate), a divalent transition metal (e.g., $Fe^{+2}$), and molecular oxygen (i.e., $O_2$). The suitable reaction conditions can comprise ranges of co-substrate, divalent transition metal, molecular oxygen as well as ranges of other parameters, such as reductant (e.g., ascorbic acid) concentration, detergent concentration, pH, temperature, buffer, solvent system, substrate loading, polypeptide loading, pressure, and reaction time. In some embodiments, the hydroxylation reaction can be carried out, wherein the engineered proline hydroxylase is immobilized on a solid support.

In some embodiments, the suitable reaction conditions can comprise the following: (a) substrate loading at about 5 g/L to 30 g/L; (b) about 0.1 g/L to 10 g/L of the engineered polypeptide; (c) about 19 g/L (0.13 M) to 57 g/L (0.39 M) of α-ketoglutarate; (d) about 14 g/L (0.08 M) to 63 g/L (0.36 M) ascorbic acid; (e) about 1.5 g/L (3.8 mM) to 4.5 g/L (11.5 mM) of $FeSO_4$; (f) a pH of about 6 to 7; (g) temperature of about 20° to 40° C.; and (h) reaction time of 2-24 h. In some embodiments, the suitable reaction conditions comprise forced aeration of the reaction solution with $O_2$ at a rate of about 3 L/h.

In some embodiments, the suitable reaction conditions can comprise the following: (a) substrate loading at about 10 g/L to 100 g/L; (b) about 1 g/L to about 50 g/L of engineered polypeptide; (c) α-ketoglutarate at about 1 to 2 molar equivalents of substrate compound; (d) ascorbic acid at about 0.25 to 0.75 molar equivalents of substrate compound; (e) about 0.5 mM to about 12 mM of $FeSO_4$; (f) pH of about 6 to 8; (g) temperature of about 20° to 40° C.; and (h) reaction time of 6 to 120 h. In some embodiments, the suitable reaction conditions comprise forced aeration of the reaction solution with $O_2$ at a rate of about 2 L/h to about 5 L/h.

Guidance on the choice of engineered proline hydroxylases, preparation of the biocatalysts, the choice of enzyme substrates, and parameters for carrying out the processes are further described in the detailed description that follow.

5. DETAILED DESCRIPTION

As used in this specification and the appended claims, the singular forms "a", "an" and "the" include plural referents unless the context clearly indicates otherwise. Thus, for example, reference to "a polypeptide" includes more than one polypeptide.

Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description and the following detailed description are exemplary and explanatory only and are not restrictive of this disclosure.

The section headings used herein are for organizational purposes only and not to be construed as limiting the subject matter described.

5.1 Abbreviations

The abbreviations used for the genetically encoded amino acids are conventional and are as follows:

| Amino Acid | Three-Letter Abbreviation | One-Letter Abbreviation |
|---|---|---|
| Alanine | Ala | A |
| Arginine | Arg | R |
| Asparagine | Asn | N |
| Aspartate | Asp | D |
| Cysteine | Cys | C |
| Glutamate | Glu | E |
| Glutamine | Gln | Q |
| Glycine | Gly | G |
| Histidine | HIS | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

When the three-letter abbreviations are used, unless specifically preceded by an "L" or a "D" or clear from the context in which the abbreviation is used, the amino acid may be in either the L- or D-configuration about α-carbon ($C_\alpha$). For example, whereas "Ala" designates alanine without specifying the configuration about the α-carbon, "D-Ala" and "L-Ala" designate D-alanine and L-alanine, respectively. When the one-letter abbreviations are used, upper case letters designate amino acids in the L-configuration about the α-carbon and lower case letters designate amino acids in the D-configuration about the α-carbon. For example, "A" designates L-alanine and "a" designates D-alanine. When polypeptide sequences are presented as a string of one-letter or three-letter abbreviations (or mixtures thereof), the sequences are presented in the amino (N) to carboxy (C) direction in accordance with common convention.

The abbreviations used for the genetically encoding nucleosides are conventional and are as follows: adenosine (A); guanosine (G); cytidine (C); thymidine (T); and uridine (U). Unless specifically delineated, the abbreviated nucleosides may be either ribonucleosides or 2'-deoxyribonucleosides. The nucleosides may be specified as being either ribonucleosides or 2'-deoxyribonucleosides on an individual basis or on an aggregate basis. When nucleic acid sequences are presented as a string of one-letter abbreviations, the sequences are presented in the 5' to 3' direction in accordance with common convention, and the phosphates are not indicated.

5.2 Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings:

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Polynucleotide" or "nucleic acid" refers to two or more nucleosides that are covalently linked together. The polynucleotide may be wholly comprised ribonucleotides (i.e., an RNA), wholly comprised of 2' deoxyribonucleotides (i.e., a DNA) or mixtures of ribo- and 2' deoxyribonucleotides. While the nucleosides will typically be linked together via standard phosphodiester linkages, the polynucleotides may include one or more non-standard linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. Preferably, such modified or synthetic nucleobases will be encoding nucleobases.

"Proline hydroxylase" refers to a polypeptide having an enzymatic capability of converting free proline to hydroxyproline in presence of co-substrate α-ketoglutarate and dioxygen, as illustrated below:

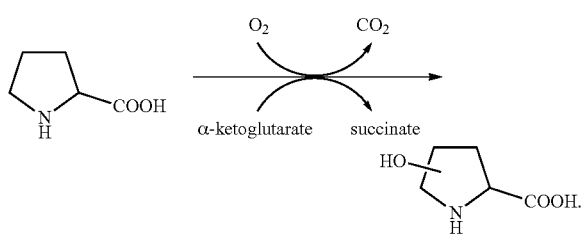

It is to be understood that proline hydroxylases are not limited to the foregoing reaction with proline, but may hydroxylate other substrates, for example pipecolic acid. Proline hydroxylases as used herein include naturally occurring (wild-type) proline hydroxylase as well as non-naturally occurring engineered polypeptides generated by human manipulation.

"Co-substrate" of a proline hydroxylase refers to α-ketoglutarate and co-substrate analogs that can replace α-ketoglutarate in hydroxylation of proline and proline substrate analogs. Co-substrate analogs include, by way of example and not limitation, 2-oxoadipate (see, e.g., Majamaa et al., 1985, Biochem. J. 229:127-133).

"Coding sequence" refers to that portion of a nucleic acid (e.g., a gene) that encodes an amino acid sequence of a protein.

"Naturally occurring" or "wild-type" refers to the form found in nature. For example, a naturally occurring or wild-type polypeptide or polynucleotide sequence is a sequence present in an organism that can be isolated from a source in nature and which has not been intentionally modified by human manipulation.

"Recombinant" or "engineered" or "non-naturally occurring" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, Greene Publishing Associates, Inc. and John Wiley & Sons, Inc., (1995 Supplement) (Ausubel)). Examples of algorithms that are suitable for determining percent sequence identity and sequence similarity are the BLAST and BLAST 2.0 algorithms, which are described in Altschul et al., 1990, J. Mol. Biol. 215: 403-410 and Altschul et al., 1977, Nucleic Acids Res. 3389-3402, respectively. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as, the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915). Exemplary determination of sequence alignment and % sequence identity can employ the BESTFIT or GAP programs in the GCG Wisconsin Software package (Accelrys, Madison WI), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, or the full length of the nucleic acid or polypeptide. Since two polynucleotides or polypeptides may each (1) comprise a sequence (i.e., a portion of the complete sequence) that is similar between the two sequences, and (2)

may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Substantial identity" refers to a polynucleotide or polypeptide sequence that has at least 80 percent sequence identity, at least 85 percent identity and 89 to 95 percent sequence identity, more usually at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, at least 95 percent sequence identity or more (e.g., 99 percent sequence identity). Preferably, residue positions which are not identical differ by conservative amino acid substitutions.

"Corresponding to", "reference to" or "relative to" when used in the context of the numbering of a given amino acid or polynucleotide sequence refers to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered proline hydroxylase, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" or "residue difference" refers to a change in the amino acid residue at a position of a polypeptide sequence relative to the amino acid residue at a corresponding position in a reference sequence. In some instances, residue differences are also referred to as "features" of the polypeptide sequence. The positions of amino acid differences generally are referred to herein as "Xn," where n refers to the corresponding position in the reference sequence upon which the residue difference is based. For example, a "residue difference at position X103 as compared to SEQ ID NO: 2" refers to a change of the amino acid residue at the polypeptide position corresponding to position 103 of SEQ ID NO:2. Thus, if the reference polypeptide of SEQ ID NO: 2 has a isoleucine at position 103, then a "residue difference at position X103 as compared to SEQ ID NO:2" refers to an amino acid substitution of any residue other than isoleucine at the position of the polypeptide corresponding to position 103 of SEQ ID NO: 2. In most instances herein, the specific amino acid residue difference at a position is indicated as "XnY" where "Xn" specifies the corresponding position as described above, and "Y" is the single letter identifier of the amino acid found in the engineered polypeptide (i.e., the different residue than in the reference polypeptide). In some embodiments, where more than one amino acid can appear in a specified residue position, the alternative amino acids can be listed in the form XnY/Z, where Y and Z represent alternate amino acid residues, or be presented as "Xn" followed by a list of the specified residues. In some instances (e.g., in Table 2A, 2B, 2C, 2D and 2E), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. The present disclosure includes engineered polypeptide sequences comprising one or more amino acid differences that include either/or both conservative and non-conservative amino acid substitutions.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Exemplary conservative substitutions are provided in Table 1 below.

TABLE 1

| Residue | Possible Conservative Substitutions |
| --- | --- |
| A, L, V, I | Other aliphatic (A, L, V, I) |
|  | Other non-polar (A, L, V, I, G, M) |
| G, M | Other non-polar (A, L, V, I, G, M) |
| D, E | Other acidic (D, E) |
| K, R | Other basic (K, R) |
| N, Q, S, T | Other polar |
| H, Y, W, F | Other aromatic (H, Y, W, F) |
| C, P | None |

"Non-conservative substitution" refers to substitution of an amino acid in the polypeptide with an amino acid with significantly differing side chain properties. Non-conservative substitutions may use amino acids between, rather than within, the defined groups and affects (a) the structure of the peptide backbone in the area of the substitution (e.g., proline for glycine), (b) the charge or hydrophobicity, or (c) the bulk of the side chain. By way of example and not limitation, an exemplary non-conservative substitution can be an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered proline hydroxylase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. In some embodiments, the improved engineered proline hydroxylase enzymes comprise insertions of one or more amino acids to the naturally occurring proline hydroxylase polypeptide as well as insertions of one or more amino acids to other improved proline hydroxylase polypeptides. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the reference sequence.

"Fragment" as used herein refers to a polypeptide that has an amino-terminal and/or carboxy-terminal deletion, but where the remaining amino acid sequence is identical to the corresponding positions in the sequence. Fragments can be at least 14 amino acids long, at least 20 amino acids long, at least 50 amino acids long or longer, and up to 70%, 80%, 90%, 95%, 98%, and 99% of the full-length proline hydroxylase polypeptide, for example the polypeptide of SEQ ID NO:2 or engineered polypeptide of SEQ ID NO:34.

"Isolated polypeptide" refers to a polypeptide which is substantially separated from other contaminants that naturally accompany it, e.g., protein, lipids, and polynucleotides. The term embraces polypeptides which have been removed or purified from their naturally occurring environment or expression system (e.g., host cell or in vitro synthesis). The improved proline hydroxylase enzymes may be present within a cell, present in the cellular medium, or prepared in various forms, such as lysates or isolated preparations. As such, in some embodiments, the improved proline hydroxylase enzyme can be an isolated polypeptide.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure proline hydroxylase composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated improved proline hydroxylases polypeptide is a substantially pure polypeptide composition.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereometric excess.

"Highly stereoselective" refers to a chemical or enzymatic reaction that is capable of converting a substrate, e.g., compound (2), to its corresponding hydroxylated product, e.g., compound (1), with at least about 85% stereometric excess.

"Regioselectivity" or "regioselective reaction" refers to a reaction in which one direction of bond making or breaking occurs preferentially over all other possible directions. Reactions can completely (100%) regioselective if the discrimination is complete, substantially regioselective (at least 75%), or partially regioselective (x %), if the product of reaction at one site predominates over the product of reaction at other sites, for example, preferential formation of product compound (1) over product compound (1a)).

"Improved enzyme property" refers to a proline hydroxylase polypeptide that exhibits an improvement in any enzyme property as compared to a reference proline hydroxylase. For the engineered proline hydroxylase polypeptides described herein, the comparison is generally made to the wild-type proline hydroxylase enzyme, although in some embodiments, the reference proline hydroxylase can be another engineered proline hydroxylase. Enzyme properties for which improvement is desirable include, but are not limited to, enzymatic activity (which can be expressed in terms of percent conversion of the substrate), thermo stability, solvent stability, pH activity profile, cofactor requirements, refractoriness to inhibitors (e.g., substrate or product inhibition), and stereoselectivity.

"Increased enzymatic activity" refers to an improved property of the engineered proline hydroxylase polypeptides, which can be represented by an increase in specific activity (e.g., product produced/time/weight protein) or an increase in percent conversion of the substrate to the product (e.g., percent conversion of starting amount of substrate to product in a specified time period using a specified amount of proline hydroxylase) as compared to the reference proline hydroxylase enzyme. Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.2 times the enzymatic activity of the corresponding wild-type proline hydroxylase enzyme, to as much as 2 times, 5 times, 10 times, 20 times, 25 times, 50 times or more enzymatic activity than the naturally occurring proline hydroxylase or another engineered proline hydroxylase from which the proline hydroxylase polypeptides were derived. Proline hydroxylase activity can be measured by any one of standard assays, such as by monitoring changes in spectrophotometric properties of reactants or products. In some embodiments, the amount of products produced can be measured by High-Performance Liquid Chromatography (HPLC) separation combined with UV absorbance or fluorescent detection following derivatization, such as with o-phthalaldehyde (OPA) or dansyl chloride. Comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells to minimize variations in amount of enzyme produced by the host cells and present in the lysates.

"Conversion" refers to the enzymatic conversion of the substrate(s) to the corresponding product(s). "Percent conversion" refers to the percent of the substrate that is converted to the product within a period of time under specified conditions. Thus, the "enzymatic activity" or "activity" of a proline hydroxylase polypeptide can be expressed as "percent conversion" of the substrate to the product.

"Thermostable" refers to a proline hydroxylase polypeptide that maintains similar activity (more than 60% to 80% for example) after exposure to elevated temperatures (e.g., 40-80° C.) for a period of time (e.g., 0.5-24 h) compared to the wild-type enzyme.

"Solvent stable" refers to a proline hydroxylase polypeptide that maintains similar activity (more than e.g., 60% to 80%) after exposure to varying concentrations (e.g., 5-99%) of solvent (ethanol, isopropyl alcohol, dimethylsulfoxide (DMSO), tetrahydrofuran, 2-methyltetrahydrofuran, acetone, toluene, butyl acetate, methyl tert-butyl ether, etc.) for a period of time (e.g., 0.5-24 h) compared to the wild-type enzyme.

"Thermo- and solvent stable" refers to a proline hydroxylase polypeptide that is both thermostable and solvent stable.

"Stringent hybridization" is used herein to refer to conditions under which nucleic acid hybrids are stable. As known to those of skill in the art, the stability of hybrids is reflected in the melting temperature ($T_m$) of the hybrids. In general, the stability of a hybrid is a function of ion strength, temperature, G/C content, and the presence of chaotropic agents. The $T_m$ values for polynucleotides can be calculated using known methods for predicting melting temperatures (see, e.g., Baldino et al., Methods Enzymology 168:761-777; Bolton et al., 1962, Proc. Natl. Acad. Sci. USA 48:1390; Bresslauer et al., 1986, Proc. Natl. Acad. Sci USA 83:8893-8897; Freier et al., 1986, Proc. Natl. Acad. Sci USA 83:9373-9377; Kierzek et al., Biochemistry 25:7840-7846; Rychlik et al., 1990, Nucleic Acids Res 18:6409-6412 (erratum, 1991, Nucleic Acids Res 19:698); Sambrook et al., supra); Suggs et al., 1981, In Developmental Biology Using Purified Genes (Brown et al., eds.), pp. 683-693, Academic Press; and Wetmur, 1991, Crit Rev Biochem Mol Biol 26:227-259. All publications incorporate herein by reference). In some embodiments, the polynucleotide encodes the polypeptide disclosed herein and hybridizes under defined conditions, such as moderately stringent or highly stringent conditions, to the complement of a sequence encoding an engineered proline hydroxylase enzyme of the present disclosure.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Heterologous" polynucleotide refers to any polynucleotide that is introduced into a host cell by laboratory techniques, and includes polynucleotides that are removed from a host cell, subjected to laboratory manipulation, and then reintroduced into a host cell.

"Codon optimized" refers to changes in the codons of the polynucleotide encoding a protein to those preferentially used in a particular organism such that the encoded protein is efficiently expressed in the organism of interest. Although the genetic code is degenerate in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the proline hydroxylase enzymes may be codon optimized for optimal production in the host organism selected for expression.

"Preferred, optimal, high codon usage bias codons" refers interchangeably to codons that are used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O, 1998, Bioinformatics 14:372-73; Stenico et al., 1994, Nucleic Acids Res. 222437-46; Wright, F., 1990, Gene 87:23-29). Codon usage tables are available for many different organisms (see, e.g., Wada et al., 1992, Nucleic Acids Res. 20:2111-2118; Nakamura et al., 2000, Nucl. Acids Res. 28:292; Duret, et al., supra; Henaut and Danchin, "*Escherichia coli* and *Salmonella*," 1996, Neidhardt, et al. Eds., ASM Press, Washington D.C., p. 2047-2066). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D., Bioinformatics: Sequence and Genome Analysis, Chapter 8, Cold Spring Harbor Laboratory Press, Cold Spring Harbor, N.Y., 2001; Uberbacher, E. C., 1996, Methods Enzymol. 266:259-281; Tiwari et al., 1997, Comput. Appl. Biosci. 13:263-270).

"Control sequence" is defined herein to include all components, which are necessary or advantageous for the expression of a polynucleotide and/or polypeptide of the present disclosure. Each control sequence may be native or foreign to the nucleic acid sequence encoding the polypeptide. Such control sequences include, but are not limited to, promoter, transcription terminator a leader (i.e., translation initiation) sequence, polyadenylation sequence, propeptide sequence, and a signal peptide sequence. The control sequences may be provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide and/or polypeptide of interest.

"Promoter sequence" refers to a nucleic acid sequence that is recognized by a host cell for expression of a polynucleotide of interest, such as a coding sequence. The promoter sequence contains transcriptional control sequences, which mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refer to those conditions in the biocatalytic reaction solution (e.g., ranges of enzyme loading, substrate loading, co-substrate loading, cofactor loading, temperature, pH, buffers, co-solvents, etc.) under which a proline hydroxylase polypeptide of the present disclosure is capable of converting a substrate compound to a product compound (e.g., conversion of compound (2) to compound (1)). Exemplary "suitable reaction conditions" are provided in the present disclosure and illustrated by the Examples.

"Loading", such as in "compound loading" or "enzyme loading" or "cofactor loading" refers to the concentration or amount of a component in a reaction mixture at the start of the reaction.

"Substrate" in the context of a biocatalyst mediated process refers to the compound or molecule acted on by the biocatalyst. For example, an exemplary substrate for the proline hydroxylase biocatalyst in the process disclosed herein is compound (2).

"Product" in the context of a biocatalyst mediated process refers to the compound or molecule resulting from the action of the biocatalyst. For example, an exemplary product for the proline hydroxylase biocatalyst in the process disclosed herein is compound (1).

"Reductant" refers to a compound or agent capable of converting $Fe^{+3}$ to $Fe^{+2}$. An exemplary reductant is ascorbic acid, which is generally in the form of L-ascorbic acid.

"Alkyl" refers to saturated hydrocarbon groups of from 1 to 18 carbon atoms inclusively, either straight chained or branched, more preferably from 1 to 8 carbon atoms inclusively, and most preferably 1 to 6 carbon atoms inclusively. An alkyl with a specified number of carbon atoms is denoted in parenthesis, e.g., $(C_1-C_6)$alkyl refers to an alkyl of 1 to 6 carbon atoms.

"Alkenyl" refers to hydrocarbon groups of from 2 to 12 carbon atoms inclusively, either straight or branched containing at least one double bond but optionally containing more than one double bond.

"Alkynyl" refers to hydrocarbon groups of from 2 to 12 carbon atoms inclusively, either straight or branched containing at least one triple bond but optionally containing more than one triple bond, and additionally optionally containing one or more double bonded moieties.

"Alkylene" refers to a straight or branched chain divalent hydrocarbon radical having from 1 to 18 carbon atoms inclusively, more preferably from 1 to 8 carbon atoms inclusively, and most preferably 1 to 6 carbon atoms inclusively, optionally substituted with one or more suitable substituents. Exemplary "alkylenes" include, but are not limited to, methylene, ethylene, propylene, butylene, and the like.

"Alkenylene" refers to a straight or branched chain divalent hydrocarbon radical having 2 to 12 carbon atoms inclusively and one or more carbon-carbon double bonds, more preferably from 2 to 8 carbon atoms inclusively, and most preferably 2 to 6 carbon atoms inclusively, optionally substituted with one or more suitable substituents.

"Heteroalkyl, "heteroalkenyl," and heteroalkynyl," refer to alkyl, alkenyl and alkynyl as defined herein in which one or more of the carbon atoms are each independently replaced with the same or different heteroatoms or heteroatomic groups. Heteroatoms and/or heteroatomic groups which can replace the carbon atoms include, but are not limited to, —O—, —S—, —S—O—, —$NR^Y$—, —PH—, —S(O)—, —$S(O)_2$—, —S(O) $NR^Y$—, —$S(O)_2NR^Y$—, and the like, including combinations thereof, where each $R^Y$ is independently selected from hydrogen, alkyl, heteroalkyl, cycloalkyl, heterocycloalkyl, aryl, and heteroaryl.

"Aryl" refers to an unsaturated aromatic carbocyclic group of from 6 to 12 carbon atoms inclusively having a single ring (e.g., phenyl) or multiple condensed rings (e.g., naphthyl or anthryl). Exemplary aryls include phenyl, pyridyl, naphthyl and the like.

"Arylalkyl" refers to an alkyl substituted with an aryl, i.e., aryl-alkyl-groups, preferably having from 1 to 6 carbon atoms inclusively in the alkyl moiety and from 6 to 12 carbon atoms inclusively in the aryl moiety. Such arylalkyl groups are exemplified by benzyl, phenethyl and the like.

"Aryloxy" refers to —OR groups, where R is an aryl group, which can be optionally substituted.

"Cycloalkyl" refers to cyclic alkyl groups of from 3 to 12 carbon atoms inclusively having a single cyclic ring or multiple condensed rings which can be optionally substituted with from 1 to 3 alkyl groups. Exemplary cycloalkyl groups include, but are not limited to, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures, including bridged ring systems, such as adamantyl, and the like.

"Cycloalkylalkyl" refers to an alkyl substituted with a cycloalkyl, i.e., cycloalkyl-alkyl- groups, preferably having from 1 to 6 carbon atoms inclusively in the alkyl moiety and from 3 to 12 carbon atoms inclusively in the cycloalkyl moiety. Such cycloalkylalkyl groups are exemplified by cyclopropylmethyl, cyclohexylethyl and the like.

"Amino" refers to the group —NH$_2$. Substituted amino refers to the group —NHR$^\eta$—, NR$^\eta$R$^\eta$, and NR$^\eta$R$^\eta$R$^\eta$, where each R$^\eta$ is independently selected from substituted or unsubstituted alkyl, cycloalkyl, cycloheteroalkyl, alkoxy, aryl, heteroaryl, heteroarylalkyl, acyl, alkoxycarbonyl, sulfanyl, sulfinyl, sulfonyl, and the like. Typical amino groups include, but are limited to, dimethylamino, diethylamino, trimethylammonium, triethylammonium, methylsulfonylamino, furanyl-oxy-sulfamino, and the like.

"Aminoalkyl" refers to an alkyl group in which one or more of the hydrogen atoms are replaced with one or more amino groups, including substituted amino groups.

"Aminocarbonyl" refers to —C(O)NH$_2$. Substituted aminocarbonyl refers to —C(O)NR$^\eta$R$^\eta$, where the amino group NR$^\eta$R$^\eta$ is as defined herein.

"Oxy" refers to a divalent group —O—, which may have various substituents to form different oxy groups, including ethers and esters.

"Alkoxy" or "alkyloxy" are used interchangeably herein to refer to the group —OR$^\xi$, wherein R$^\xi$ is an alkyl group, including optionally substituted alkyl groups.

"Carboxy" refers to —COOH.

"Carbonyl" refers to —C(O)—, which may have a variety of substituents to form different carbonyl groups including acids, acid halides, aldehydes, amides, esters, and ketones.

"Carboxyalkyl" refers to an alkyl in which one or more of the hydrogen atoms are replaced with one or more carboxy groups.

"Aminocarbonylalkyl" refers to an alkyl substituted with an aminocarbonyl group, as defined herein.

"Halogen" or "halo" refers to fluoro, chloro, bromo and iodo.

"Haloalkyl" refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C$_1$ C$_2$) haloalkyl" includes 1-fluoromethyl, difluoromethyl, trifluoromethyl, 1-fluoroethyl, 1,1-difluoroethyl, 1,2-difluoroethyl, 1,1,1 trifluoroethyl, perfluoroethyl, etc.

"Hydroxy" refers to —OH.

"Hydroxyalkyl" refers to an alkyl group in which in which one or more of the hydrogen atoms are replaced with one or more hydroxy groups.

"Thiol" or "sulfanyl" refers to —SH. Substituted thiol or sulfanyl refers to —S—R$^\eta$, where R$^\eta$ is an alkyl, aryl or other suitable substituent.

"Alkylthio" refers to —SR$^\xi$, where R$^\xi$ is an alkyl, which can be optionally substituted. Exemplary alkylthio group include, but are not limited to, methylthio, ethylthio, n-propylthio, and the like.

"Arylthio" refers to —SR$^\lambda$, where R$^\lambda$ is an aryl, which can be optionally substituted. Exemplary arylthio groups include, but are not limited to, phenylthio, (4-methylphenyl) thio, pyridinylthio, and the like.

"Alkylthioalkyl" refers to an alkyl substituted with an alkylthio group, —SR$^\xi$, where R$^\xi$ is an alkyl, which can be optionally substituted.

"Thiolalkyl" refers to an alkyl group in which one or more of the hydrogen atoms are replaced with one or more -SH groups.

"Sulfonyl" refers to —SO$_2$—. Substituted sulfonyl refers to —SO$_2$—R$^\eta$, where R$^\eta$ is an alkyl, aryl or other suitable substituent.

"Alkylsulfonyl" refers to —SO$_2$—R$^\xi$, where R$^\xi$ is an alkyl, which can be optionally substituted. Typical alkylsulfonyl groups include, but are not limited to, methylsulfonyl, ethylsulfonyl, n-propylsulfonyl, and the like.

"Alkylsulfonylalkyl" refers to an alkyl substituted with an alkylsulfonyl group, —SO$_2$—R$^\xi$, where R$^\xi$ is an alkyl, which can be optionally substituted.

"Heteroaryl" refers to an aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heteroarylalkyl" refers to an alkyl substituted with a heteroaryl, i.e., heteroaryl-alkyl- groups, preferably having from 1 to 6 carbon atoms inclusively in the alkyl moiety and from 5 to 12 ring atoms inclusively in the heteroaryl moiety. Such heteroarylalkyl groups are exemplified by pyridylmethyl and the like.

"Heterocycle", "heterocyclic" and interchangeably "heterocycloalkyl" refer to a saturated or unsaturated group having a single ring or multiple condensed rings, from 2 to 10 carbon ring atoms inclusively and from 1 to 4 hetero ring atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Examples of heterocycles include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

"Heterocycloalkylalkyl" refers to an alkyl substituted with a heterocycloalkyl, i.e., heterocycloalkyl-alkyl- groups, preferably having from 1 to 6 carbon atoms inclusively in the alkyl moiety and from 3 to 12 ring atoms inclusively in the heterocycloalkyl moiety.

"Membered ring" is meant to embrace any cyclic structure. The number preceding the term "membered" denotes the number of skeletal atoms that constitute the ring. Thus, for example, cyclohexyl, pyridine, pyran and thiopyran are 6-membered rings and cyclopentyl, pyrrole, furan, and thiophene are 5-membered rings.

"Fused bicyclic ring" as used herein refers to both unsubstituted and substituted carbocyclic and/or heterocyclic ring moieties having 5 to 8 atoms in each ring, the rings having 2 common atoms.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoxime, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present disclosure, and is otherwise chemically reasonable.

"Optional" or "optionally" means that the subsequently described event or circumstance may or may not occur, and that the description includes instances where the event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term or series of chemical groups. For example, in the term "optionally substituted arylalkyl, the "alkyl" portion and the "aryl" portion of the molecule may or may not be substituted, and for the series "optionally substituted alkyl, cycloalkyl, aryl and heteroaryl," the alkyl, cycloalkyl, aryl, and heteroaryl groups, independently of the others, may or may not be substituted.

5.3 Engineered Proline Hydroxylase Polypeptides

The present disclosure provides polypeptides having proline hydroxylase activity, polynucleotides encoding the polypeptides, methods of preparing the polypeptides, and methods for using the polypeptides. Where the description relates to polypeptides, it is to be understood that it also describes the polynucleotides encoding the polypeptides.

Proline hydroxylases belong to a class of diooxygenase enzymes that catalyze hydroxylation of proline in presence of α-ketoglutarate and oxygen ($O_2$). The α-ketoglutarate is stoichiometrically decarboxylated during hydroxylation, with one atom of the $O_2$ molecule being incorporated into the succinate and the other into the hydroxyl group formed on the proline residue. As noted above, proline hydroxylases are distinguished from prolyl hydroxylase by their ability to hydroxylate free proline.

Several types of proline hydroxylases have been identified based on the major diastereomeric products formed in the enzymatic reaction: cis-3-proline hydroxylase (cis-P3H), cis-4-proline hydroxylase (cis-P4H), trans-3-proline hydroxylase (trans-P3H), and trans-4-proline hydroxylase (trans-P4H). cis-P3H enzymes have been identified in *Streptomyces* sp. TH1, *Streptomyces canus* and *Bacillus* sp. TH2 and TH3 (Mori H. et al., 1996, Appl. Environ. Microbiol. 62 (6):1903-1907). trans-P3H has been identified in *Glarea lozoyensis* (Petersen, L. et al., 2003, Appl Microbiol Biotechnol. 62(2-3):263-7). cis-P4H have been identified in *Lotus corniculatus rhizobia, Mesorhibozium loti, Sinorhizobium meliloti*, and *Medicago sativa rhizobia*, (Hara and Kino, 2009, Biochem Biophys Res Commun. 379(4):882-6; US Patent publication no. 20110091942). trans-P4H have been identified in *Dactylosporangium* sp., *Amycolatopsis* sp., *Streptomyces griseoviridis, Streptomyces* sp. and *Glarea lozoyensis* (Shibasaki T. et al., 1999, Appl. Environ. Microbiol 65(9):4028-31; 2003, Petersen, L. et al., 2003, Appl Microbiol Biotechnol. 62(2-3):263-7; Mori, H. et al., 1996, Appl. Environ. Microbiol. 62:1903-1907; Lawrence, C. C., et al., 1996, Biochem. J. 313:185-191; and EP0641862).

The cis-4-proline hydroxylase from *Sinorhizobium meliloti* converts free proline to the primary product cis-4-hydroxyproline. According to Klein et al., supra, the enzyme also recognizes L-pipecolic acid, converting it to a mixture of cis-5- and cis-3-hydroxypipecolic acid. However, the activity on pipecolic acid is lower than on proline, and the enzyme is reported to have low specific activity and denature under reaction conditions (Klein et al., supra). Consequently, in vitro conversion reactions for preparing hydroxyproline and hydroxypipecolic acid with a recombinant wild-type enzyme expressed in *E. coli* was unsuitable as a synthetic strategy for commercial scale preparations. Whole cells expressing the enzyme was found to be more effective, but necessitated the use of defined growth medium lacking proline to minimize competition by free proline and also simplify purification of the hydroxypipecolic acid product (Klein et al., supra).

In the present disclosure, engineered proline hydroxylases that overcome the deficiencies of the wild-type cis-4-proline hydroxylase of *Sinorhizobium meliloti* are described. The engineered proline hydroxylase polypeptides derived from the wild-type enzyme of *Sinorhizobium meliloti* are capable of efficiently converting in vitro free proline to cis-4-hydroxyproline, but also capable of efficiently converting a range of substrates, including the conversion of L-pipecolic acid (i.e., (2S)-piperidine-2-carboxylic acid) to cis-5-hydroxypipecolic acid (i.e., 2S,5S)-5-hydroxypiperidine-2-carboxylic acid). Significantly, the present disclosure identifies amino acid residue positions and corresponding mutations in the proline hydroxylase polypeptide sequence that improve enzyme properties as compared to the naturally occurring enzyme, including among others, activity, stability, expression, regioselectivity, stereoselectivity, substrate tolerance, and substrate specificity. In particular, the present disclosure provides engineered polypeptides capable of efficiently converting substrate compound (2), (2S)-piperidine-2-carboxylic acid, to product compound (1), (2S,5S)-5-hydroxypiperidine-2-carboxylic acid (as illustrated in Scheme 1 above) in presence of a co-substrate under suitable reaction conditions.

In some embodiments, the engineered proline hydroxylase polypeptides show increased activity in the conversion proline and (2S)-piperidine-2-carboxylic acid to product cis-4-hydroxy proline and (2S,5S)-5-hydroxypiperidine-2-carboxylic acid, respectively, in a defined time with the same amount of enzyme as compared to the wild-type enzyme. In some embodiments, the engineered proline hydroxylase polypeptide has at least about 1.2 fold, 1.5 fold, 2 fold, 3 fold, 4 fold, 5 fold, or 10 fold or more activity under suitable reaction conditions as compared to the polypeptide represented by SEQ ID NO:2.

In some embodiments, the engineered proline hydroxylase polypeptides have increased regioselectivity as compared to the wild-type proline hydroxylase. Specifically, the naturally occurring enzyme converts proline to, primarily if not exclusively, cis-4-hydroxyproline, and converts (2S)-piperidine-2-carboxylic acid to mixture of diastereomeric products comprising compound (1), (2S,5S)-5-hydroxypiperidine-2-carboxylic acid and compound (1a), (2S,3R)-3-hydroxypiperidine-2-carboxylic acid. In some embodiments, the engineered proline hydroxylase polypeptides herein are capable of selectively forming compound (1) in excess of product compound (1a). In some embodiments, the engineered polypeptides are capable of selectively forming compound (1) in excess of product compound (1a), where the ratio of compound (1) formed over compound (1a) under suitable reaction conditions is at least 1.5, 2, 3, 4, 5, or 6 or more.

In some embodiments, the engineered proline hydroxylase polypeptides are capable of converting the substrate compound (2) to product compound (1) without forming significant amounts of trans-5-hydroxypipecolic acid (i.e., (2S,5R)-5-hydroxypiperidine-2-carboxylic acid). In some embodiments, the engineered proline hydroxylase polypeptides are capable of converting the substrate compound (2) to product compound (1) under suitable reaction conditions in greater than 90%, 91%, 92%, 93%, 94%, 95%, 96%, 97%, 98%, 99%, 99.5 or greater diastereomeric excess of (2S, 5R)-5-hydroxypiperidine-2-carboxylic acid.

In some embodiments, the engineered proline hydroxylase polypeptides are capable of converting substrate compound (2) to product compound (1) under suitable reaction conditions with increased tolerance for the presence of substrate relative to the reference polypeptide of SEQ ID NO: 2. Thus, in some embodiments the engineered proline hydroxylase polypeptides are capable of converting substrate compound (2) to product compound (1) at a substrate loading concentration of at least about 10 g/L, about 20 g/L, about 30 g/L, about 40 g/L, about 50 g/L, about 70 g/L, about 100 g/L, about 125 g/L, about 150 g/L. about 175 g/L or about 200 g/L or more with a percent conversion of at least about 40%, at least about 50%, at least about 60%, at least about 70%, at least about 80%, at least about 90%, at least about 95%, at least about 98%, or at least about 99%, in a reaction time of about 120 h or less, 72 h or less, about 48 h or less, about 36 h or less, or about 24 h less, under suitable reaction conditions.

The suitable reaction conditions under which the above-described improved properties of the engineered polypeptides carry out the hydroxylation reaction can be determined with respect to concentrations or amounts of polypeptide, substrate, co-substrate, transition metal cofactor, reductant, buffer, co-solvent, pH, conditions including temperature and reaction time, and/or conditions with the polypeptide immobilized on a solid support, as further described below and in the Examples.

The exemplary engineered polypeptides having proline hydroxylase activity with improved properties, particularly in the conversion of compound (2) to compound (1), comprises an amino acid sequence that has one or more residue differences as compared to SEQ ID NO:2 at the following residue positions: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271. The specific amino acid differences at each of these positions that are associated with the improved properties of the exemplary polypeptides of Tables 2A, 2B, 2C, 2D, 2E, 2F, 2G, and 2H include: X2K; X2T; X3S; X4Q; X4L; X4E; X4S; X5I; X5L; X5M; X9I; X13T; X17V; X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

The structure and function information for exemplary non-naturally occurring (or engineered) proline hydroxylase polypeptides of the present disclosure are based on the conversion of compound (2) to compound (1), the results of which are shown below in Tables 2A, 2B, 2C, 2D, 2E, 2F, 2G, and 2H. The odd numbered sequence identifiers (i.e., SEQ ID NOs) refer to the nucleotide sequence encoding the amino acid sequence provided by the even numbered SEQ ID NOs. The exemplary sequences are provided in the electronic sequence listing file accompanying this disclosure, which is hereby incorporated by reference herein. The amino acid residue differences are based on comparison to the reference sequence of SEQ ID NO: 2 (or SEQ ID NO: 4, or 6), which represent the naturally occurring amino acid sequence of the cis-4-proline hydroxylase of *Sinorhizobium meliloti*. The activity of each engineered polypeptide relative to the reference polypeptide of SEQ ID NO: 2 was determined as conversion of the substrate, (2S)-piperidine-2-carboxylic acid, to product, (2S,5S)-5-hydroxypiperidine-2-carboxylic acid over a set time period and temperature in a high-throughput (HTP) assay, which was used as the primary screen. The HTP assay values in Tables 2A, 2B, and 2F were determined using *E. coli*. clear cell lysates in 96 well-plate format of ~200 L volume per well following assay reaction conditions as noted in the table and the Examples. In some instances, a shake flask powder (SFP) or downstream processed (DSP) powder assay was used as a secondary screen to assess the properties of the engineered proline hydroxylases, the results of which are provided in Tables 2C, 2D, 2E, 2G, and 2H. The SFP forms provide a more purified powder preparation of the engineered polypeptides and can contain the engineered polypeptides that are up to about 30% of total protein. The DSP preparations can provide an even further purified form of the engineered polypeptide since the preparations can contain the engineered proline hydroxylases that are up to about 80% of total protein. The engineered proline hydroxylases were also examined for their regioselectivities by measuring the ratio (expressed as the selectivity ratio) of product compound (1), (2S,5S)-5-hydroxypiperidine-2-carboxylic acid, to product compound (1a), (2S,3R)-3-hydroxypiperidine-2-carboxylic acid, formed in the reactions.

TABLE 2A

Engineered Polypeptides and Relative Enzyme Improvements Using HTP Preparations

| SEQ ID NO: (nt/aa) | Amino Acid Differences (relative to SEQ ID NO: 2) | Activity[1,2] (Condition A) (Relative to SEQ ID NO: 2) |
|---|---|---|
| 1/2 | N/A | 1 |
| 3/4 | N/A | 1[3] |
| 5/6 | N/A | 1[3] |
| 7/8 | A42E | 1.53 |
| 9/10 | I103L | 2.37 |
| 11/12 | I103Q | 2.26 |
| 13/14 | F116L | 1.15 |
| 15/16 | N131Y | 1.7 |
| 17/18 | A150S | 2.07 |
| 19/20 | S29A; H166T | 1.47 |
| 21/22 | H166T | 1.90 |
| 23/24 | H166Q | 4.96 |
| 25/26 | S30V | 1.33 |
| 27/28 | S30P | 2.75 |
| 29/30 | A36T | 1.8 |
| 31/32 | S59G | 1.54 |
| 33/34 | V57T | 1.54 |
| 35/36 | Q52P; S225Y | 1.3 |
| 37/38 | V57A | 1.43 |
| 39/40 | T115H | 1.68 |
| 41/42 | L112T | 1.87 |
| 43/44 | A66Q | 1.21 |
| 45/46 | H271K | 1.24 |
| 47/48 | T115D | 1.25 |
| 49/50 | T115G; L121F | 1.4 |
| 51/52 | H271R | 1.31 |
| 53/54 | L112V | 1.32 |
| 55/56 | T115S | 1.31 |
| 57/58 | V25R; V58A | 1.49 |
| 59/60 | S2K | 1.55 |
| 61/62 | S2T | 1.52 |
| 63/64 | E13T | 1.6 |
| 65/66 | H4Q | 6.27 |
| 67/68 | H4L | 2.44 |
| 69/70 | F5I | 2.32 |
| 71/72 | F5L | 3.9 |
| 73/74 | F5M | 1.94 |
| 75/76 | V9I | 2.81 |
| 77/78 | H4E | 1.28 |
| 79/80 | H4L; T115A | 1.22 |
| 81/82 | H45 | 1.75 |
| 83/84 | S225W | 1.47 |
| 85/86 | S225L | 1.6 |
| 87/88 | L230V | 1.28 |
| 89/90 | N131F | 1.26 |
| 91/92 | T92V | 1.37 |
| 93/94 | V95M | 1.73 |
| 95/96 | T115G | 1.37 |
| 97/98 | T3S | 6.43 |

[1]HTP Assay Condition A (see also Example 4): Cells grown in 96 well plates were lysed with 100 μL Lysis Buffer (1 mg/mL lysozyme, 0.5 mg/mL polymyxin B sulfate (PMBS), and 50 mM phosphate buffer, pH 6.3). The reaction conditions for a 200 μL reaction comprised: 10 g/L substrate compound (2); 19 g/L α-ketoglutaric acid; 21 g/L L-ascorbic acid; 1.5 mM Mohr's salt; 50 mM potassium phosphate buffer, pH 6.3 (pH adjusted with KOH); 100 μL crude lysate; and reaction temperature at about 25° C. (room temperature) for about 24 h. Plates were covered with an O₂ permeable seal and shaken on a titre-plate shaker at speed #2.5.
[2]Activity relative to SEQ ID NO: 2 is calculated as the % conversion of the product formed per % conversion of the corresponding SEQ ID NO: 2 under the reaction conditions specified. % Conversion was quantified by firstly dividing the areas of the product peak by the sum of the areas of the substrate, product and impurities/side product peak as determined by HPLC analysis and then subtracting it with the % conversion of the negative control (overlapping peak).
[3]The amino acid sequences of polypeptides represented by SEQ ID NO: 4 and 6 are identical to the naturally occurring proline hydroxylase amino acid sequence of SEQ ID NO: 2, but which were prepared in E. coli using the differently codon-optimized genes of SEQ ID NO: 3 and 5, respectively. The codon optimized genes of SEQ ID NO: 3 and 5 exhibited at 1.2-fold increased expression of the proline hydroxylase polypeptide in E. coli as compared to the expression of SEQ ID NO: 1.

TABLE 2B

Engineered Polypeptides and Relative Enzyme Improvements Using HTP Preparations

| SEQ ID NO: (nt/aa) | Amino Acid Differences (relative to SEQ ID NO: 2) | Activity (Condition B)[1] (relative to SEQ ID NO: 112)[2] |
|---|---|---|
| 113/114 | C86S; T92V; I103L; M151S; H166Q; G270E | 2.3 |
| 115/116 | I103Q; F116L; H166L; S225L | 1.53 |
| 117/118 | A66Q; I103L; H166Q | 1.48 |
| 119/120 | A66Q; I103L; H166Q | 1.81 |
| 121/122 | A66Q; T92V; I103L; H166Q | 1.67 |
| 123/124 | T92V; I103L; H166Q | 1.51 |
| 125/126 | A66Q; T92V; I103L; D113E; T115S; H166Q | 1.86 |
| 127/128 | V25R; A66Q; T92V; I103L; T115E; H166Q | 1.54 |

[1]HTP Assay Condition B (see also Example 4): Cells grown in 96 well plates were lysed with 100 μL Lysis Buffer (1 mg/mL lysozyme, 0.5 mg/mL polymyxin B sulfate (PMBS), and 50 mM phosphate buffer, pH 6.3). The reaction conditions for a 200 μL reaction comprised: 10 g/L substrate compound (2); 19 g/L α-ketoglutaric acid; 21 g/L ascorbic acid; 1.5 mM Mohr's salt; 50 mM phosphate buffer, pH 6.3 (pH adjusted with KOH); 100 μL crude lysate; and a reaction temperature of c.a. 25° C. (room temperature) for about c.a. 24 h. The plates were covered by an O₂ permeable seal, and the plates shaken on a titre-plate shaker at speed #2.5.
[2]Activity relative to SEQ ID NO: 112 is calculated as the % conversion of the product formed as compared to the % conversion of the corresponding SEQ ID NO: 112 under the reaction conditions specified. % Conversion was quantified by firstly dividing the areas of the product peak by the sum of the areas of the substrate, product and impurities/side product peak as determined by HPLC analysis and then subtracting it with the % conversion of the negative control (overlapping peak).

TABLE 2C

Engineered Polypeptides and Relative Enzyme Improvements Using "Mini-DSP" Enzyme Preparations

| SEQ ID NO: (nt/aa) | Amino Acid Differences (relative to SEQ ID NO: 2) | % Conv[1] | Selectivity Ratio: (1)/(1a)[2] |
|---|---|---|---|
| 1/2 | N/A | 16.6[3] | 1.6 |
| 3/4 | N/A | 49.6[3] | 2.1 |
| 9/10 | I103L | 21.2[3] | 5 |
| 23/24 | H166Q | 53.7[3] | 2.5 |
| 99/100 | H166Q | 51.8[3] | 2.4 |
| 101/102 | I103L | 24.5[3] | 3.1 |
| 103/104 | I103L; H166Q | 67.3[3] | 5.5 |
| 105/106 | I103L; N131Y; H166Q | 40[3] | 5.7 |
| 107/108 | T3S; I103L; H166Q | 66.9[4] | 5.2 |
| 129/130 | T3S; A66Q; T92V; I103L; H166Q | 67.8[4] | 5.1 |
| 131/132 | T3S; V25R; A66Q; T92V; I103L; T115E; H166Q | 79.7[4] | 5.6 |
| 133/134 | T3S; V25R; A66Q; T92V; I103L; H166Q | 69.9[4] | 5.1 |

[1]% Conversion was quantified by dividing the area of the product peak by the sum of the areas of the substrate compound (2), product compound (1) and product compound (1a) peak as determined by HPLC analysis.
[2]Selectivity ratio refers to the ratio of HPLC areas for product compound (1) over product compound (1a).
[3]Reaction Condition D was used: Reaction was carried out in a 2 mL reaction vessel. Reaction mixture comprised: 10 g/L compound (2); 19 g/L α-ketoglutaric acid; 21 g/L L-ascorbic acid; 1.5 mM Mohr's salt; 50 mM potassium phosphate buffer, pH 6.3; 20 g/L protein of Mini-DSP powder preparation; and a reaction temperature of about c.a. 25° C. (room temperature) for about c.a. 24 h. Reactions were stirred at 1200 rpm and reaction vial kept open to the atmosphere.
[4]Reaction Condition E was used: Reaction was carried out in a 250 mL two neck round bottom flask. Initial mixture of 60 mL of 50 mM potassium phosphate buffer was charged with 0.146 g (1.5 g/L) of Mohr's salt (ammonium iron[II] sulfate hexahydrate), 3.46 g (35 g/L) of α-ketoglutaric acid and 1.36 g (14 g/L) of ascorbic acid with pH adjusted to 6.3 with 50% KOH. Enzyme was added to mixture as 0.2 g (2 g/L) mini DSP preparation pre-dissolved in 16 mL 50 mM potassium phosphate buffer, pH 6.3, with 1 mL antifoam, with stirring for 15 minutes. Substrate was added to the mixture as 2 g (20 g/L) of compound (2) (pre-dissolved in 24 mL 50 mM potassium phosphate buffer, pH 6.3) with stirring at 25° C. under oxygen sparging (flow rate = 2 L/h).

TABLE 2D

Engineered Polypeptides and Relative Enzyme Improvements Using Full DSP Preparations

| SEQ ID NO: (nt/aa) | Amino Acid Differences (relative to SEQ ID NO: 2) | Condition D[1] % Conv[5] | Condition D[1] Selectivity Ratio (1)/(1a)[6] | Condition F[2] % Conv[5] | Condition F[2] Selectivity Ratio (1)/(1a)[6] | Condition E[4] % Conv[5] | Condition E[4] Selectivity Ratio (1)/(1a)[6] |
|---|---|---|---|---|---|---|---|
| 1/2 | N/A | 83.5 | 5.7 | 46.4 | 1.9 | — | — |
| 103/104 | I103L; H166Q | 86.7 | 8.1 | 71.3 | 4.7 | — | — |
| 107/108 | T3S; I103L; H166Q | — | — | 74.7 | 6 | — | — |
| 109/110 | A26T; I103L; H166Q | — | — | 73.5 | 4.6 | — | — |
| 131/132 | T3S; V25R; A66Q; T92V; I103L; T115E; H166Q | — | — | — | — | 66.9 | 6.5:1 |

[1] Reaction Condition D was used: Reaction was carried out in a 2 mL reaction vessel. Reaction mixture comprised: 10 g/L substrate compound (2); 19 g/L α-ketoglutaric acid; 21 g/L L-ascorbic acid; 1.5 mM Mohr's salt; 50 mM potassium phosphate buffer, pH 6.3; 20 g/L Full DSP enzyme powder; and a reaction temperature of about 25° C. for about 24 h. Reactions were stirred at 1200 rpm, and the vial kept open to the atmosphere.
[2] Reaction Condition F was used: Reaction was carried out in a 1 mL reaction vessel. Reaction mixture comprised: 20 g/L substrate compound (2); 38 g/L α-ketoglutaric acid; 21 g/L L-ascorbic acid; 1.5 mM Mohr's salt; 50 mM potassium phosphate buffer, pH 6.3; 10 g/L Full DSP enzyme powder; and a reaction temperature of about 25° C. for c.a. 24 h. Reactions were stirred at 1200 rpm, and the vial kept open to the atmosphere.
[4] DSP Reaction Condition E was used: Reaction was carried out in a 250 mL two neck round bottom flask. Initial mixture of 60 mL of 50 mM potassium phosphate buffer was charged with 0.146 g (1.5 g/L) of Mohr's salt (ammonium iron[II] sulfate hexahydrate), 3.46 g (35 g/L) of α-ketoglutaric acid and 1.36 g (14 g/L) of L-ascorbic acid with pH adjusted to 6.3 with 50% KOH. Enzyme was added to the mixture as 0.2 g (2 g/L) Full DSP powder pre-dissolved in 16 mL 50 mM potassium phosphate buffer, pH 6.3, with 1 mL antifoam, with stirring for 15 minutes. Substrate was added to the mixture as 2 g (20 g/L) of compound (2) (pre-dissolved in 24 mL 50 mM phosphate buffer, pH 6.3) with stirring at 25° C. under oxygen sparging (flow rate = 2 L/h).
[5] % Conversion was quantified by dividing the area of the product peak by the sum of the areas of the substrate, product compound (1) and product compound (1a) peak as determined by HPLC analysis.
[6] Selectivity ratio refers to the ratio of HPLC areas for product compound (1) over the product compound (1a).

TABLE 2E

Engineered Polypeptides and Relative Enzyme Improvements Using SFP Preparations

| SEQ ID NO: (nt/aa) | Amino Acid Differences (relative to SEQ ID NO: 2) | Activity[1] | % Conv[4] | Selectivity Ratio (1)/(1a)[4] |
|---|---|---|---|---|
| 111/112 | I103L; H166Q | 0.19 [2] | 3.9 | 3.1 |
| 125/126 | A66Q; T92V; I103L; D113E; T115S; H166Q | 1.8 [3] | 11.1 | 3.1 |
| 127/128 | V25R; A66Q; T92V; I103L; T115E; H166Q | 1.8 [3] | 5.9 | 3.5 |

[1] SFP Reaction Condition C was used: Reaction was carried out in a 200 μL reaction vessel. Reaction mixture comprised: 30 g/L substrate compound (2); 52.5 g/L α-ketoglutaric acid; 21 g/L L-ascorbic acid; 2.25 mM Mohr's salt; 50 mM potassium phosphate buffer, pH 6.3 (pH adjusted with KOH); 5 g/L protein of SFP enzyme powder preparation; and a reaction temperature of c.a. 25° C. for 24 h. Plates were covered with an O₂ permeable seal and shaken on a titre-plate shaker at speed #2.5.
[2] Activity relative to SEQ ID NO: 108 is calculated as the % conversion of the product formed as compared to the % conversion of the corresponding SEQ ID NO: 108 under the reaction conditions specified. % Conversion was quantified by firstly dividing the areas of the product peak by the sum of the areas of the substrate, product and impurities/side product peak as determined by HPLC analysis and then subtracting it with the % conversion of the negative control (overlapping peak).
[3] Activity relative to SEQ ID NO: 124 is calculated as the % conversion of the product formed per % conversion of the corresponding SEQ ID NO: 124 under the reaction conditions specified. % Conversion was quantified by firstly dividing the areas of the product peak by the sum of the areas of the substrate, product and impurities/side product peak as determined by HPLC
[4] Reaction conditions used for % Conv and Selectivity Ratio differed from SFP Reaction Conditions above as follows. Reaction in a 100 mL vessel. Reaction mixture comprised: 20 g/L of substrate compound (2); 2 g/L of SFP enzyme powder preparation; 14 g/L of ascorbic acid; 35 g/L ketoglutaric acid; 1.5 g/L Mohr's salt; 1% (v/v) antifoam; and oxygen sparging at 2 L/h.

TABLE 2F

Engineered Polypeptides and Relative Enzyme Improvements Using HTP Preparations

| SEQ ID NO: (nt/aa) | Amino Acid Differences (relative to SEQ ID NO: 2) | Fold-improved activity[1] | Fold-improved activity[2] (+ascorbic acid preinc.) | Fold-improved selectivity[3] |
|---|---|---|---|---|
| 137/138 | V25R; A66Q; T92V; I103L; E114N; T115E; H166Q; | 1.5 | n.d. | 1 |
| 139/140 | V25R; A66Q; T92V; I103L; T115E; M140L; H166Q; | 1.7 | n.d. | 1.1 |

TABLE 2F-continued

Engineered Polypeptides and Relative Enzyme Improvements Using HTP Preparations

| SEQ ID NO: (nt/aa) | Amino Acid Differences (relative to SEQ ID NO: 2) | Fold-improved activity[1] | Fold-improved activity[2] (+ascorbic acid preinc.)[2] | Fold-improved selectivity[3] |
|---|---|---|---|---|
| 141/142 | V25R; A66Q; T92V; S98T; I103L; T115E; H166Q; | 4.1 | n.d. | 1.1 |
| 143/144 | V25R; A42L; A66Q; T92V; I103L; T115E; H166Q; | 0.8 | n.d. | 1.3 |
| 145/146 | A17V; V25R; A26W; A66Q; T92V; I103L; T115E; H166Q; | 3.8 | n.d. | 0.8 |
| 147/148 | V25R; A62Q; A66Q; T92V; I103L; T115E; H166Q; | 1.5 | n.d. | 0.9 |
| 149/150 | V25R; A26R; A66Q; T92V; I103L; T115E; H166Q; | 1.7 | n.d. | 0.9 |
| 151/152 | V25R; A66Q; T92V; I103L; T115E; M151A; H166Q; | 1.4 | n.d. | 1 |
| 153/154 | V25R; A66Q; A88R; T92V; I103L; T115E; H166Q; | 1.4 | n.d. | 0.9 |
| 155/156 | V25R; A66Q; T92V; I103L; T115E; H166Q; V188G; | 4.4 | n.d. | 0.9 |
| 157/158 | E24R; V25R; A66Q; T92V; I103L; T115E; H166Q; | 1.5 | n.d. | 0.9 |
| 159/160 | E24S; V25R; A66Q; T92V; I103L; T115E; H166Q; | 1.6 | n.d. | 0.9 |
| 161/162 | V25R; A66Q; T92V; S98F; I103L; T115E; H166Q; | 0.9 | n.d. | 1.3 |
| 163/164 | T3S; V25R; A42L; A66Q; T92V; I103L; T115E; H166Q; | + | n.d. | + |
| 165/166 | T3S; V25R; A42L; A66Q; T92V; S98T; I103L; T115E; H166Q; | + | n.d. | + |
| 167/168 | T3S; V25R; A42L; A66Q; T92V; S98T; I103L; T115E; H166Q; V188G; | + | n.d. | + |
| 169/170 | E24S; V25R; A42L; A66Q; T92V; I103L; T115E; H166Q; V188G; | 1.43 | 1.66 | 4.46 |
| 171/172 | E24S; V25R; A42L; A62Q; A66Q; T92V; S98T; I103L; E114N; T115E; M140L; H166Q; | 1.60 | 1.54 | 4.30 |
| 173/174 | E24S; V25R; A42L; A66Q; T92V; S98T; I103L; E114N; T115E; H166Q; | 1.77 | 2.41 | 5.92 |
| 175/176 | E24S; V25R; A26R; A42L; A66Q; T92V; I103L; T115E; H166Q; | 1.73 | 1.70 | 4.50 |
| 177/178 | V25R; A42L; A62Q; A66Q; T92V; I103L; T115E; M140L; H166Q; V188G; | 1.41 | 1.62 | 4.98 |
| 179/180 | E24S; V25R; A26R; A42L; A66Q; A88R; T92V; I103L; T115E; M140L; H166Q; | 2.59 | 1.81 | 3.94 |
| 181/182 | E24S; V25R; A26R; A42L; A66Q; A88R; T92V; S98T; I103L; E114N; T115E; M140L; H166Q; V188G; | 1.68 | 1.41 | 4.31 |
| 183/184 | E24S; V25R; A42L; A62Q; A66Q; T92V; I103L; E114N; T115E; M140L; H166Q; | 1.46 | 3.13 | 4.84 |
| 185/186 | E24S; V25R; A26R; A42L; A66Q; A88R; T92V; I103L; E114N; T115E; H166Q; | 1.71 | 2.08 | 4.17 |
| 187/188 | E24S; V25R; A42L; A66Q; T92V; I103L; T115E; M140L; H166Q; | 1.68 | 2.11 | 4.47 |
| 189/190 | E24S; V25R; A42L; A66Q; T92V; S98T; I103L; E114N; T115E; H166Q; | + | 1.58 | 4.21 |
| 191/192 | V25R; A26R; A42L; A66Q; T92V; I103L; E114N; T115E; M151H; H166Q; | 1.87 | 1.53 | 3.77 |
| 193/194 | E24S; V25R; A42L; A62Q; A66Q; T92V; S98T; I103L; T115E; M140L; M151H; H166Q; | 2.19 | 1.53 | 4.08 |
| 195/196 | V25R; A42L; A66Q; T92V; I103L; E114N; T115E; H166Q; | 1.62 | 1.87 | 5.45 |
| 197/198 | V25R; A42L; A62Q; A66Q; T92V; I103L; T115E; M140L; M151H; H166Q; I205V; | + | 1.73 | 3.74 |
| 199/200 | E24S; V25R; A42L; A66Q; A88R; T92V; I103L; E114N; T115E; H166Q; | 1.51 | 2.29 | 4.32 |
| 201/202 | E24S; V25R; A26R; A42L; A62Q; A66Q; T92V; I103L; T115E; M151H; H166Q; | 1.16 | 1.85 | 5.34 |
| 203/204 | E24S; V25R; A26R; A42L; A66Q; A88R; T92V; I103L; E114N; T115E; H166Q; | 2.02 | 2.01 | 4.11 |
| 205/206 | E24S; V25R; A26R; A42L; A62Q; A66Q; T92V; I103L; T115E; M140L; M151H; H166Q; | + | 1.58 | 3.76 |
| 207/208 | E24S; V25R; A26R; A42L; A66Q; A88R; T92V; I103L; E114N; T115E; H166Q; Q186G; | + | 1.50 | 3.59 |
| 209/210 | E24S; V25R; A26W; A42L; A66Q; A88R; T92V; I103L; T115E; M140L; H166Q; | 1.23 | 1.50 | 3.64 |

TABLE 2F-continued

Engineered Polypeptides and Relative Enzyme Improvements Using HTP Preparations

| SEQ ID NO: (nt/aa) | Amino Acid Differences (relative to SEQ ID NO: 2) | Fold-improved activity[1] | Fold-improved activity[2] (+ascorbic acid preinc.)[2] | Fold-improved selectivity[3] |
|---|---|---|---|---|
| 211/212 | E24S; V25R; A26R; A42L; A62Q; A66Q; A88R; T92V; I103L; E114N; T115E; M140L; M151H; H166Q; Q186G; | + | 2.28 | 3.95 |
| 213/214 | E24S; V25R; A42L; A66Q; T92V; S98F; I103L; T115E; M140L; H166Q; V188G; | + | 1.51 | 6.2 |
| 215/216 | E24S; V25R; A26R; A42L; A62Q; A66Q; A88R; T92V; S98F; I103L; E114S; T115E; M140L; M151H; H166Q; | + | 1.32 | 6.3 |
| 217/218 | E24S; V25R; A26R; A42L; A66Q; T92V; S98F; I103L; T115E; M140L; M151H; H166Q; | + | 1.33 | 6.5 |
| 219/220 | E24S; V25R; A42L; A66Q; T92V; S98F; I103L; T115E; H166Q; | + | 1.53 | 8.8 |
| 221/222 | T3S; E24S; V25R; A42L; A66Q; T92V; S98T; I103L; E114N; T115E; H166Q; | + | n.d. | + |
| 223/224 | T3S; E24S; V25R; A26R; A42L; A66Q; A88R; T92V; I103L; T115E; M140L; H166Q; | + | n.d. | + |
| 225/226 | T3S; E24S; V25R; A42L; A62Q; A66Q; T92V; I103L; E114N; T115E; M140L; H166Q; | + | n.d. | + |
| 227/228 | T3S; E24S; V25R; A26R; A42L; A66Q; A88R; T92V; I103L; T115E; M140L; H166Q; | + | n.d. | + |

[1]HTP Assay - Conditions F
For polypeptides of SEQ ID NO: 138-168: Cells grown in 96 well plates were lysed with 100 μL Lysis Buffer (1 mg/mL lysozyme, 0.5 mg/mL polymyxin B sulfate (PMBS), and 50 mM phosphate buffer, pH 6.3). The reaction conditions for a 200 μL reaction comprised: 30 g/L substrate compound (2); 52.5 g/L α-ketoglutaric acid; 21 g/L L-ascorbic acid; 2.25 g/L Mohr's salt; 50 mM potassium phosphate buffer, pH 6.3 (pH adjusted with KOH); 100 μL crude lysate; and reaction temperature at about 25° C. (room temperature) for about 24 h. Plates were covered with an $O_2$ permeable seal and shaken on a titre-plate shaker at speed #2.5. Activity was calculated as the % conversion of the product formed as compared to the % conversion of the corresponding reference polypeptide of SEQ ID NO: 128 under the reaction conditions specified. % Conversion was quantified by firstly dividing the areas of the product peak by the sum of the areas of the substrate, product and impurities/side product peak as determined by HPLC analysis and then subtracting it with the % conversion of the negative control (overlapping peak).
For polypeptides of SEQ ID NO: 170-228: Same as for SEQ ID NO: 138-168 except reaction temperature at 30° C. Activity was calculated as the % conversion of the product formed as compared to the % conversion of the corresponding reference polypeptide of SEQ ID NO: 144 under the reaction conditions specified. % Conversion was quantified by firstly dividing the areas of the product peak by the sum of the areas of the substrate, product and impurities/side product peak as determined by HPLC analysis and then subtracting it with the % conversion of the negative control (overlapping peak).
[2]HTP Assay Conditions G - Ascorbic Acid Preincubation
HTP assays of the polypeptides of SEQ ID NO: 170-228 also were carried out following 2 h hour preincubation of the lysate in ascorbic acid. Preincubation procedure: 100 μL of lysate was transferred into a new deep-well plate followed by the addition of 20 μL/well of ascorbic acid stock solution. The plate was shaken at room temperature, speed 2.5 for 2 h. HTP activity assay was carried out using the HTP Assay Conditions at 30° C. for SEQ ID NO: 170-228 as described above.
[3]Improved Selectivity:
Improved selectivity for the 2,5-regioisomer product of compound (1) versus the 2,3-regioisomer product of compound (1a) produced in the HTP Assays carried out under Condition F was determined using LC-MS. LC-MS Sample Preparation: 10 μL of HTP Assay reaction mixture was pipetted out and diluted twenty thousand fold (in three stages) with 1:1 mixture of MeCN:water. The sample was vortexed and spun down at 12,000 r.p.m. for 5 minutes. The supernatant was transferred into a 2 mL vial for LC-MS analysis using analysis parameters described in Example 7.
"+" indicates activity or selectivity improved from 1-fold to 5-fold relative to SEQ ID NO: 2.
"n.d." indicates "not determined"

TABLE 2G

Engineered Polypeptides and Relative Enzyme Improvements Using SFP Preparations

| SEQ ID NO: (nt/aa) | Amino Acid Differences (relative to SEQ ID NO: 2) | Fold-improved activity[1] | % conversion[2] | Selectivity Ratio (1)/(1a)[3] |
|---|---|---|---|---|
| 127/128 | V25R; A66Q; T92V; I103L; T115E; H166Q | 1 | 8.9 | 3.9:1 |
| 137/138 | V25R; A66Q; T92V; I103L; E114N; T115E; H166Q; | 0.9 | 8.2 | 3.2:1 |
| 139/140 | V25R; A66Q; T92V; I103L; T115E; M140L; H166Q; | 1.2 | 10.4 | 3.4:1 |
| 141/142 | V25R; A66Q; T92V; S98T; I103L; T115E; H166Q; | 1.9 | 16.7 | 3.5:1 |
| 143/144 | V25R; A42L; A66Q; T92V; I103L; T115E; H166Q; | 1.3 | 11.8 | 4.5:1 |
| 173/174 | E24S; V25R; A42L; A66Q; T92V; S98T; I103L; E114N; T115E; H166Q; | 1.8 | 8.9 | 3.9:1 |
| 179/180 | E24S; V25R; A26R; A42L; A66Q; A88R; T92V; I103L; T115E; M140L; H166Q; | 2.9 | 8.2 | 3.2:1 |

TABLE 2G-continued

Engineered Polypeptides and Relative Enzyme Improvements Using SFP Preparations

| SEQ ID NO: (nt/aa) | Amino Acid Differences (relative to SEQ ID NO: 2) | Fold-improved activity[1] | % conversion[2] | Selectivity Ratio (1)/(1a)[3] |
|---|---|---|---|---|
| 183/184 | E24S; V25R; A42L; A62Q; A66Q; T92V; I103L; E114N; T115E; M140L; H166Q; | 1.8 | 10.4 | 3.4:1 |
| 185/186 | E24S; V25R; A26R; A42L; A66Q; A88R; T92V; I103L; E114N; T115E; H166Q; | 1.9 | 16.7 | 3.5:1 |
| 187/188 | E24S; V25R; A42L; A66Q; T92V; I103L; T115E; M140L; H166Q; | 1.2 | 11.8 | 4.5:1 |
| 199/200 | E24S; V25R; A42L; A66Q; A88R; T92V; I103L; E114N; T115E; H166Q; | 1.7 | 8.9 | 3.9:1 |
| 203/204 | E24S; V25R; A26R; A42L; A66Q; A88R; T92V; I103L; E114N; T115E; H166Q; | 1.8 | 8.2 | 3.2:1 |

[1] SFP Activity Assay - Conditions G
This assay was carried out on a 5 mL scale with final reaction mixture conditions: 10 g/L SFP of polypeptide, 30 g/L substrate of compound (2), 52.5 g/L α-ketoglutaric acid, 21 g/L ascorbic acid, 2.25 g/L Mohr's salt in 50 mM phosphate buffer pH 6.3. A premix stock solution consisting of the following was prepared: 37.5 g/L (187.5 mg) substrate, 65.63 g/L (328 mg) α-ketoglutaric acid, and 26.25 g/L (131.3 mg) ascorbic acid. After pH was adjusted 2.81 g/L (14 mg) of Mohr's salt at were added and dissolved in 5 mL of 50 mM phosphate buffer, pH 6.3 (for each vial reaction) and pH was adjusted to pH 6.3 with 50% KOH. A 50 g/L SFP enzyme stock solution was prepared by dissolving 100 mg SFP preparation of the desired polypeptide variant in 2 mL of 50 mM phosphate buffer pH 6.3. The assay was initiated by adding 4 mL of the premix stock solution into a glass vial followed by 1 mL of enzyme stock solution. The vial was stirred at 250 rpm, room temperature using a magnetic hot plate stirrer for 24 h. 10 mL of 75% acetonitrile (MeCN) in water was added to quench the reaction with stirring. 1 mL of the quenched reaction was then taken to a Costar 96 deep well 2 mL assay block and spun down for 10 min at 4000 r.p.m. Dansylation and HPLC analysis was carried out as described for SFP assays in Example 3.
Activity was calculated as the % conversion of the product formed as compared to the % conversion of the corresponding reference polypeptide of SEQ ID NO: 128 under the reaction conditions specified. % Conversion was quantified by firstly dividing the areas of the product peak by the sum of the areas of the substrate, product and impurities/side product peak as determined by HPLC analysis and then subtracting it with the % conversion of the negative control (overlapping peak).
[2] % Conversion was quantified by dividing the area of the product peak by the sum of the areas of the substrate compound (2), product compound (1) and product compound (1a) peak as determined by HPLC analysis.
[3] Selectivity ratio refers to the ratio of HPLC areas for product compound (1) over product compound (1a).

TABLE 2H

Engineered Polypeptides and Relative Enzyme Improvements Using DSP Preparations

| SEQ ID NO: (nt/aa) | Amino Acid Differences (relative to SEQ ID NO: 2) | % conversion[3] | Selectivity Ratio (1)/(1a)[4] |
|---|---|---|---|
| | Condition H[1] | | |
| 131/132 | T3S; V25R; A66Q; T92V; I103L; T115E; H166Q | 30.0 | 5.1:1 |
| 163/164 | T3S; V25R; A42L; A66Q; T92V; I103L; T115E; H166Q; | 21.9 | 8.6:1 |
| 165/166 | T3S; V25R; A42L; A66Q; T92V; S98T; I103L; T115E; H166Q; | 21.0 | 9.4:1 |
| 167/168 | T3S; V25R; A42L; A66Q; T92V; S98T; I103L; T115E; H166Q; V188G; | 18.3 | 9.7:1 |
| 221/222 | T3S; E24S; V25R; A42L; A66Q; T92V; S98T; I103L; E114N; T115E; H166Q; | 21.0 | 9:1 |
| 223/224 | T3S; E24S; V25R; A26R; A42L; A66Q; A88R; T92V; I103L; T115E; M140L; H166Q; | 33.0 | 6.7:1 |
| 225/226 | T3S; E24S; V25R; A42L; A62Q; A66Q; T92V; I103L; E114N; T115E; M140L; H166Q; | 24.9 | 6.5:1 |
| | Condition I[2] | | |
| 223/224 | T3S; E24S; V25R; A26R; A42L; A66Q; A88R; T92V; I103L; T115E; M140L; H166Q; | 51.7 | 6.7:1 |
| 227/228 | T3S; E24S; V25R; A26R; A42L; A66Q; A88R; T92V; I103L; T115E; M140L; H166Q; | 77.02 | 6.7:1 |

[1] DSP Assay - Condition H:
This DSP assay was carried out on a 10 mL scale. A solution of substrate of compound (2) (0.30 g) in 2 ml of 50 mM potassium phosphate buffer (pH 6.3) was prepared and added to a pre-stirred mixture of DSP polypeptide enzyme (0.05 g), antifoam Y-30 emulsion (100 to 300 µL), Mohr's salt (0.021 g), α-ketoglutaric acid (0.51 g) and ascorbic acid (0.204 g) in 7 mL of 50 mM potassium phosphate buffer (pH 6.3). The resulting mixture was continuously sparged with oxygen (2 L/h) at stirred 25° C. for 24 h. Reaction progress was monitored by HPLC as described in Example 6.
[2] DSP Assay - Condition I:
This DSP assay was carried out on a 100 mL scale. A solution of substrate of compound (2) (3.0 g) in 20 ml of 50 mM potassium phosphate buffer (pH 6.3) was prepared and added to a pre-stirred mixture of DSP polypeptide enzyme (0.5 g), antifoam Y-30 emulsion (1 mL), Mohr's salt (0.21 g), α-ketoglutaric acid (5.1 g) and ascorbic acid (2.04 g) in 70 mL of 50 mM potassium phosphate buffer (pH 6.3). The resulting mixture was continuously sparged with oxygen (2 L/h) and stirred at 25° C. for 24 h. Reaction progress was monitored by HPLC as described in Example 6.
[3] % Conversion was quantified by dividing the area of the product peak by the sum of the areas of the substrate compound (2), product compound (1) and product compound (1a) peak as determined by HPLC analysis.
[4] Selectivity ratio refers to the ratio of HPLC areas for product compound (1) over product compound (1a).

From an analysis of the exemplary polypeptides, improvements in enzyme properties are associated with residue differences as compared to SEQ ID NO:2 at residue positions X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271. The specific residue differences at each of these positions that are associated with the improved properties include: X2K; X2T; X3S; X4Q; X4L; X4E; X4S; X5I; X5L; X5M; X9I; X13T; X17V, X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

The specific enzyme properties associated with the residues differences as compared to SEQ ID NO:2 at the residue positions above include, among others, enzyme activity, regioselectivity, polypeptide expression, and substrate tolerance. Improvements in enzyme activity and substrate tolerance are associated with residue differences at residue positions X3; X17; X24; X25; X26; X29; X30; X36; X42; X52; X57; X58; X59; X62; X66; X86; X88; X92; X95; X103; X112; X113; X114; X115; X116; X121; X131; X140; X150; X151; X166; X188; X225; X230; X270; and X271. Improvements in regioselectivity are associated with residue differences at residue positions: X3; X25; X42; X66; X92; X98; X103; X115; X131; and X166. Improvements in polypeptide expression are associated with residue differences at residue positions: X2; X4; X5; X9; and X13. Accordingly, the residue differences at the foregoing residue positions can be used individually or in various combinations to produce engineered proline hydroxylase polypeptides having the desired improved properties, including, among others, enzyme activity, regioselectivity, stereoselectivity, and substrate tolerance. Other residue differences affecting polypeptide expression can be used to increase expression of the engineered proline hydroxylase.

In light of the guidance provided herein, it is further contemplated that any of the exemplary engineered polypeptides of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228 can be used as the starting amino acid sequence for synthesizing other engineered proline hydroxylase polypeptides, for example by subsequent rounds of evolution that incorporate new combinations of various amino acid differences from other polypeptides in Tables 2A, 2B, 2C, 2D, 2E, 2F, 2G, and 2H, and other residue positions described herein. Further improvements may be generated by including amino acid differences at residue positions that had been maintained as unchanged throughout earlier rounds of evolution.

Accordingly, in some embodiments, the engineered polypeptide having proline hydroxylase activity comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO:2 at residue positions selected from: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271.

In some embodiments, the engineered polypeptide having proline hydroxylase activity with improved properties as compared to SEQ ID NO:2, comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, and one or more residue differences as compared to SEQ ID NO:2 at residue positions selected from: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271. In some embodiments, the reference amino acid sequence is selected from SEQ ID NO: 10, 24, 104, 106, 108, 110, 132, 164, 222, 224, 226, and 228. In some embodiments, the reference amino acid sequence is SEQ ID NO:10. In some embodiments, the reference amino acid sequence is SEQ ID NO:24. In some embodiments, the reference amino acid sequence is SEQ ID NO:104. In some embodiments, the reference amino acid sequence is SEQ ID NO:108. In some embodiments, the reference amino acid sequence is SEQ ID NO:110. In some embodiments, the reference amino acid sequence is SEQ ID NO:132. In some embodiments, the reference amino acid sequence is SEQ ID NO:164. In some embodiments, the reference amino acid sequence is SEQ ID NO:222. In some embodiments, the reference amino acid sequence is SEQ ID NO:224. In some embodiments, the reference amino acid sequence is SEQ ID NO:226. In some embodiments, the reference amino acid sequence is SEQ ID NO:228.

In some embodiments, the engineered polypeptide having proline hydroxylase activity with improved properties as compared to SEQ ID NO:2, comprises an amino acid sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, and having one or more residue differences as compared to SEQ ID NO:2 at residue positions selected from: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271. In some embodiments, the amino acid sequence is selected from SEQ ID NO: 10, 24, 104, 106, 108, 110, 132, 164, 222, 224, 226, and 228. In some embodiments, the amino acid sequence is SEQ ID NO:10. In some embodiments, the amino acid sequence is SEQ ID NO:24. In some embodiments, the amino acid sequence is SEQ ID NO:104. In some embodiments, the amino acid sequence is SEQ ID NO:108. In some embodiments, the amino acid sequence is SEQ ID NO:110. In some embodiments, the amino acid sequence is SEQ ID NO:132. In some embodiments, the reference amino acid sequence is SEQ ID NO:164. In some embodiments, the reference amino acid sequence is SEQ ID NO:222. In some embodiments, the reference amino acid sequence is SEQ ID NO:224. In some embodiments, the reference amino acid sequence is SEQ ID NO:226. In some embodiments, the reference amino acid sequence is SEQ ID NO:228.

In some embodiments, the residue differences at residue positions X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271 are selected from X2K; X2T; X3S; X4Q; X4L; X4E; X4S; X5I; X5L; X5M; X9I; X13T; X17V, X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

Accordingly, in some embodiments, the engineered proline hydroxylase polypeptides displaying one or more of the improved properties described herein can comprise an amino acid sequence having the amino acid sequence identity to a reference sequence as described above, and one or more residue differences as compared to SEQ ID NO:2 selected from: X2K; X2T; X3S; X4Q; X4L; X4E; X4S; X5I; X5L; X5M; X9I; X13T; X17V, X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

In some embodiments, the engineered proline hydroxylase has an amino acid sequence comprising at least one or more residue differences as compared to SEQ ID NO:2 selected from: X25R; X26T; X103L; X115E; X131Y/F; and X166Q.

In some embodiments, the engineered proline hydroxylase polypeptide comprises an amino acid sequence having at least a combination of residues differences as compared to SEQ ID NO:2 selected from: (a) X103L and X166Q; (b) X52P and X255Y; (c) X4E/L/S and X115A; (d) X25R and X58A; (e) X29A and X166T/Q/L; (f) X115H/D/G and X121F; (g) X3S, X103L, and X166Q; (h) X103L, X131Y/F, and X166T/Q/L; (i) X26T, X103L and X166T/Q/L; (j) X25R, X66Q, X92V and X115E; (k) X25R, X66Q, X92V, X103L, X115E, and X166Q; and (l) X3S, X25R, X66Q, X92V, X103L, X115E, and X166Q.

As will be appreciated by the skilled artisan, in some embodiments, one or a combination of residue differences above that is selected can be kept constant (i.e., maintained) in the engineered proline hydroxylases as a core feature, and additional residue differences at other residue positions incorporated into the sequence to generate additional engineered proline hydroxylase polypeptides with improved properties. Accordingly, it is to be understood for any engineered proline hydroxylase containing one or a subset of the residue differences above, the present disclosure contemplates other engineered proline hydroxylases that comprise the one or subset of the residue differences, and additionally one or more residue differences at the other residue positions disclosed herein. By way of example and not limitation, an engineered proline hydroxylase comprising a residue difference at residue position X103, can further incorporate one or more residue differences at the other residue positions, e.g., X2; X3; X4; X5; X9; X13; X17; X24; X25; X26; X29; X30; X36; X42; X52; X57; X58; X59; X62; X66; X86; X88; X92; X95; X98; X112; X113; X114; X115; X116; X121; X131; X140; X150; X151; X166; X186; X188; X205; X225; X230; X270; and X271. Another example is an engineered proline hydroxylase comprising a residue difference at residue position X166, which can further comprise one or more residue differences at the other residue positions, e.g., X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X186; X188; X205; X225; X230; X270; and X271.

As noted above, the engineered polypeptides having proline hydroxylase activity are also capable of converting substrate compound (2) to product compound (1). In some embodiments, the engineered proline hydroxylase polypeptide is capable of converting the substrate compound (2) to the product compound (1) with at least 1.2 fold, 1.5 fold, 2 fold, 3 fold, 4 fold, 5 fold, 10 fold or more activity relative to the activity of the reference polypeptide of SEQ ID NO: 2. In some embodiments, the engineered proline hydroxylase polypeptide capable of converting the substrate compound (2) to the product compound (1) with at least 1.2 fold, 1.5 fold, 2 fold, 3 fold, 4 fold, 5 fold, 10 fold or more activity relative to the activity of the reference polypeptide of SEQ ID NO:2 comprises an amino acid sequence having one or more features selected from: X2K; X2T; X3S; X4Q; X4L; X4E; X4S; X5I; X5L; X5M; X9I; X13T; X17V, X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

In some embodiments, the engineered proline hydroxylase polypeptide is capable of converting the substrate compound (2) to the product compound (1) with at least 1.2 fold the activity relative to SEQ ID NO:2 and comprises an amino acid sequence selected from: SEQ ID NO: 8, 10, 12, 14, 16, 18, 20, 22, 24, 26, 28, 30, 32, 34, 36, 38, 40, 42, 44, 46, 48, 50, 52, 54, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments, the engineered proline hydroxylase polypeptide is capable of converting the substrate compound (2) to the product compound (1) with at least 2 fold the activity relative to SEQ ID NO:2 and comprises an amino acid sequence having one or more residue differences selected from: X3S; X30P; X86S; X103L; X103Q; X113E; X115E; X150S; X166Q; X151S; X225L; and 270E.

In some embodiments, the engineered proline hydroxylase polypeptide capable of converting the substrate compound (2) to the product compound (1) with at least 2 fold the activity relative to SEQ ID NO:2 comprises an amino acid sequence selected from: SEQ ID NO: 10, 12, 18, 24, 28, 66, 68, 70, 72, 76, 98, 100, 102, 104, 106, 108, 110; 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments, the engineered proline hydroxylase polypeptide is capable of converting at least 50% or more, 60% or more, 70% or more, 89% or more, 90% or more, 91% or more, 92% or more, 93% or more, 94% or more, or 95% or more of compound (2) to compound (1) in 120 h or less, 72 h or less, 48 h or less, or 24 or less, at a substrate loading of about 100 g/L, about 50 g/L, or about 20 g/L under HTP Assay conditions, under SFP Assay conditions, or DSP Assay conditions. In some embodiments, the engineered proline hydroxylase polypeptide is capable of converting at least 50% or more of compound (2) to compound (1) in 24 h or less at a substrate loading of about 20 g/L under DSP Assay conditions at about 25° C.

In some embodiments, the engineered proline hydroxylase polypeptide is capable of converting substrate compound (2) to product compound (1) in excess of compound (1a). The residue differences identified in the exemplary engineered proline hydroxylases of Tables 2A, 2B, 2C, 2D, 2E, 2F, 2G, and 2H are shown to maintain or increase the regioselectivity for compound (1) over compound (1a) in the conversion reaction. In some embodiments, the engineered proline hydroxylase polypeptides are capable of converting substrate compound (2) to product compound (1) in excess of compound (1a), where the ratio of compound (1) formed over compound (1a) is at least a ratio of 1.5, 2, 3, 4, 5, or 6 or more, particularly under HTP Assay, SFP Assay, or DSP Assay conditions.

In some embodiments, the engineered proline hydroxylase polypeptide capable of converting substrate compound (2) to product compound (1) in excess of compound (1a) in at least a ratio of 2 or greater comprises an amino acid sequence have at least one or more of the following features: X103L; X115E; X166Q and X131Y. In some embodiments, the engineered proline hydroxylase capable of converting substrate compound (2) to product compound (1) in excess of compound (1a) in at least a ratio of 2 or greater comprises an amino acid sequence selected from SEQ ID NO: 10, 24, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments, the engineered proline hydroxylase polypeptide capable of converting substrate compound (2) to product compound (1) in excess of compound (1a) in at least a ratio of 4 or greater comprises an amino acid sequence have at least the features X103L and X166Q. In some embodiments, the engineered proline hydroxylase capable of converting substrate compound (2) to product compound (1) in excess of compound (1a) in at least a ratio of 4 or greater comprises an amino acid sequence selected from SEQ ID NO: 104, 106, 108, 110, 130, 132 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments, the engineered proline hydroxylase is capable of converting substrate compound (2) to product compound (1) in stereometric excess of compound (1R), (2S,5R)-5-hydroxypiperidine-2-carboxylic acid,

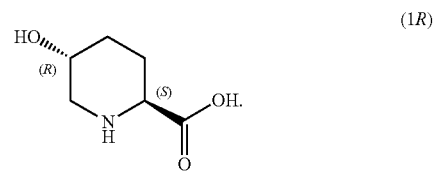

(1R)

The wild-type enzyme is characterized by its ability to convert (2S)-piperidine-2-carboxylic acid to (2S,5S)-5-hydroxypiperidine-2-carboxylic acid, with little if any of the trans hydroxy product (1R). As shown herein, the residue differences in the exemplary engineered proline hydroxylase polypeptides of Tables 2A, 2B, 2C, 2D, 2E, 2F, 2G, and 2H maintain the high diastereoselectivity, including those polypeptides with non-conservative changes to the amino acid sequence. In some embodiments, the engineered proline hydroxylase capable of converting substrate compound (2) to product compound (1) in diastereomeric excess of compound (1R) comprises an amino acid sequence having one or more features selected from: X2K; X2T; X3S; X4Q; X4L; X4E; X4S; X5I; X5L; X5M; X9I; X13T; X17V; X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R. In some embodiments, the product compound (1) is formed in at least 90%, 95%, 96%, 97%, 98%, 99%, or greater diastereomeric excess of the compound (1R). In some embodiments, no detectable amount of trans hydroxy product (1R) is formed by the engineered polypeptides under suitable reaction conditions.

In some embodiments, the engineered proline hydroxylase has an amino acid sequence comprising one or more residue differences as compared to SEQ ID NO:2 that increase expression of the engineered proline hydroxylase activity in a bacterial host cell, particularly in E. coli. In some embodiments, the amino acid sequence that show increased expression in a bacterial host cell comprises one or more residue differences selected from: X2K; X2T; X4Q; X4L; X4E; X4S; X5I; X5L; X5M; X9I; and X13T.

In some embodiments, the engineered proline hydroxylase polypeptide with improved properties in the conversion of compound (2) to compound (1) has an amino acid sequence comprising a sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments, the engineered polypeptide having proline hydroxylase activity, comprises an amino acid sequence having at least 80%, 85%, 86%, 87%, 88%, 89%, 90%, 91%, 92%, 93%, 94%, 95%, 96%, 97%, 98%, or 99% identity to one of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, and the amino acid residue differences as compared to SEQ ID NO:2 present in any one of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, as provided in Tables 2A, 2B, 2C, 2D, 2E, 2F, 2G, and 2H.

In addition to the residue positions specified above, any of the engineered proline hydroxylase polypeptides disclosed herein can further comprise other residue differences relative to SEQ ID NO:2 at other residue positions, i.e., residue positions other than X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271. Residue differences at these other residue positions can provide for additional variations in the amino acid sequence without adversely affecting the ability of the polypeptide to carry out the conversion of proline to cis-4-hydroxyproline as well as conversion of compound (2) to compound (1). Accordingly, in some embodiments, in addition to the amino acid residue differences present in any one of the engineered proline hydroxylase polypeptides selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, the sequence can further comprise 1-2, 1-3, 1-4, 1-5, 1-6, 1-7, 1-8, 1-9, 1-10, 1-11, 1-12, 1-14, 1-15, 1-16, 1-18, 1-20, 1-22, 1-24, 1-26, 1-30, 1-35, 1-40, 1-45, or 1-50 residue differences at other amino acid residue positions as compared to the SEQ ID NO:2. In some embodiments, the number of amino acid residue differences as compared to the reference sequence can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45 or 50 residue positions. In some embodiments, the number of amino acid residue differences as compared to the reference sequence can be 1, 2, 3, 4, 5, 6, 7, 8, 9, 10, 11, 12, 13, 14, 15, 16, 18, 20, 21, 22, 23, 24, or 25 residue positions. The residue difference at these other positions can be conservative changes or non-conservative changes. In some embodiments, the residue differences can comprise conservative substitutions and non-conservative substitutions as compared to the naturally occurring proline hydroxylase polypeptide of SEQ ID NO: 2.

In some embodiments, the present disclosure also provides engineered polypeptides that comprise a fragment of any of the engineered proline hydroxylase polypeptides described herein that retains the functional activity and/or improved property of that engineered proline hydroxylase. Accordingly, in some embodiments, the present disclosure provides a polypeptide fragment capable of converting compound (2) to compound (1) under suitable reaction conditions, wherein the fragment comprises at least about 80%, 90%, 95%, 96%, 97%, 98%, or 99% of a full-length amino acid sequence of an engineered proline hydroxylase polypeptide of the present disclosure, such as an exemplary engineered proline hydroxylase polypeptide selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments, the engineered proline hydroxylase polypeptide can have an amino acid sequence comprising a deletion of any one of the engineered proline hydroxylase polypeptides described herein, such as the exemplary engineered polypeptides of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228. Thus, for each and every embodiment of the engineered proline hydroxylase polypeptides of the disclosure, the amino acid sequence can comprise deletions of one or more amino acids, 2 or more amino acids, 3 or more amino acids, 4 or more amino acids, 5 or more amino acids, 6 or more amino acids, 8 or more amino acids, 10 or more amino acids, 15 or more amino acids, or 20 or more amino acids, up to 10% of the total number of amino acids, up to 10% of the total number of amino acids, up to 20% of the total number of amino acids, or up to 30% of the total number of amino acids of the proline hydroxylase polypeptides, where the associated functional activity and/or improved properties of the engineered proline hydroxylase described herein are maintained. In some embodiments, the deletions can comprise 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residues. In some embodiments, the number of deletions can be 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residues. In some embodiments, the deletions can comprise deletions of 1, 2, 3, 4, 5, 6, 7, 8, 9, 10, 11, 12, 13, 14, 15, 16, 18, 20, 21, 22, 23, 24, or 25 amino acid residues.

In some embodiments, the engineered proline hydroxylase polypeptide herein can have an amino acid sequence comprising an insertion as compared to any one of the engineered proline hydroxylase polypeptides described herein, such as the exemplary engineered polypeptides of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228. Thus, for each and every embodiment of the proline hydroxylase polypeptides of the disclosure, the insertions can comprise one or more amino acids, 2 or more amino acids, 3 or more amino acids, 4 or more amino acids, 5 or more amino acids, 6 or more amino acids, 8 or more amino acids, 10 or more amino acids, 15 or more amino acids, 20 or more amino acids, 30 or more amino acids, 40 or more amino acids, or 50 or more amino acids, where the associated functional activity and/or improved properties of the engineered proline hydroxylase described herein is maintained. The insertions can be to amino or carboxy terminus, or internal portions of the proline hydroxylase polypeptide.

In some embodiments, the engineered proline hydroxylase polypeptide herein can have an amino acid sequence comprising a sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, and optionally one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the number of amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

In the above embodiments, the suitable reaction conditions for the engineered polypeptides can be those described in Tables 2A, 2B, 2C, 2D, 2E, 2F, 2G, and 2H. Accordingly, in some embodiments, the suitable reaction conditions are HTP Assay conditions, which can comprise: 10 g/L or 20 g/L substrate compound loading; 19 g/L α-ketoglutaric acid; 21 g/L L-ascorbic acid; 1.5 mM Mohr's salt; 50 mM potassium phosphate buffer, pH 6.3 (pH adjusted with KOH); 100 μL crude lysate; and a reaction temperature at about 25° C. (room temperature) for a reaction time of about 24 h.

In some embodiments, the suitable reaction conditions are those described for shake flask powder (SFP) assays, which can comprise: 30 g/L substrate compound loading; 52.5 g/L α-ketoglutaric acid; 21 g/L L-ascorbic acid; 2.25 mM Mohr's salt; 50 mM potassium phosphate buffer, pH 6.3 (pH adjusted with KOH); 5 g/L protein of SFP enzyme powder preparation; and a reaction temperature of c.a. 25° C. (room temperature) for a reaction time of about 24 h.

In some embodiments, the suitable reaction conditions are those described for mini downstream process powder (DSP) assays, which comprise: 10 g/L or 20 g/L substrate loading; 19 g/L α-ketoglutaric acid; 21 g/L L-ascorbic acid; 1.5 mM Mohr's salt; 50 mM potassium phosphate buffer, pH 6.3; 20 g/L protein of DSP powder preparation; and a reaction temperature of about 25° C. (room temperature) for about reaction time of about 24 h.

Guidance for use of these foregoing reaction conditions and the proline hydroxylase polypeptides are given in, among others, Tables 2A, 2B, 2C, 2D, 2E, 2F, 2G, and 2H, and the Examples.

In some embodiments, the polypeptides of the disclosure can be in the form of fusion polypeptides in which the engineered polypeptides are fused to other polypeptides, such as, by way of example and not limitation, antibody tags (e.g., myc epitope), purification sequences (e.g., His tags for binding to metals), and cell localization signals (e.g., secretion signals). Thus, the engineered polypeptides described herein can be used with or without fusions to other polypeptides.

It is to be understood that the polypeptides described herein are not restricted to the genetically encoded amino acids. In addition to the genetically encoded amino acids, the polypeptides described herein may be comprised, either in whole or in part, of naturally occurring and/or synthetic non-encoded amino acids. Certain commonly encountered non-encoded amino acids of which the polypeptides described herein may be comprised include, but are not limited to: the D-stereomers of the genetically-encoded amino acids; 2,3-diaminopropionic acid (Dpr); α-aminoisobutyric acid (Aib); ε-aminohexanoic acid (Aha); δ-aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4-chlorophenylalanine (Pcf); 2-fluorophenylalanine (Off); 3-fluorophenylalanine (Mff); 4-fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opcf); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β-2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutanic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aGly); propargylglycine (pgGly); homoalanine (hAla); norvaline (nVal); homoleucine (hLeu), homovaline (hVal); homoisoleucine (hIle); homoarginine (hArg); N-acetyl lysine (AcLys); 2,4- diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, FL, at pp. 3-70 and the references cited therein, all of which are incorporated by reference). These amino acids may be in either the L- or D-configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N-methyl amino acids (L-configuration); 1-aminocyclopent-(2 or 3)-ene-4-carboxylic acid; pipecolic acid; azetidine-3-carboxylic acid; homoproline (hPro); and 1-aminocyclopentane-3-carboxylic acid.

In some embodiments, the engineered polypeptides can be in various forms, for example, such as an isolated preparation, as a substantially purified enzyme, whole cells transformed with gene(s) encoding the enzyme, and/or as cell extracts and/or lysates of such cells. The enzymes can be lyophilized, spray-dried, precipitated or be in the form of a crude paste, as further discussed below.

In some embodiments, the engineered polypeptides can be provided on a solid support, such as a membrane, resin, solid carrier, or other solid phase material. A solid support can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a solid support can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location.

In some embodiments, the engineered polypeptides having proline hydroxylase activity of the present disclosure can be immobilized on a solid support such that they retain their improved activity, stereoselectivity, and/or other improved properties relative to the reference polypeptide of SEQ ID NO: 2. In such embodiments, the immobilized polypeptides can facilitate the biocatalytic conversion of the substrate compounds of formula (II), (VI) or other suitable substrates, to the product compound of formula (I), (V), or corresponding products, respectively (e.g., as shown in Schemes 1, 2 and 3), and after the reaction is complete are easily retained (e.g., by retaining beads on which polypeptide is immobilized) and then reused or recycled in subsequent reactions. Such immobilized enzyme processes allow for further efficiency and cost reduction. Accordingly, it is further contemplated that any of the methods of using the proline hydroxylase polypeptides of the present disclosure can be carried out using the same proline hydroxylase polypeptides bound or immobilized on a solid support.

Methods of enzyme immobilization are well-known in the art. The engineered polypeptides can be bound non-covalently or covalently. Various methods for conjugation and immobilization of enzymes to solid supports (e.g., resins, membranes, beads, glass, etc.) are well known in the art and described in e.g., Yi et al., "Covalent immobilization of o-transaminase from *Vibrio fluvialis* JS17 on chitosan beads," *Process Biochemistry* 42(5): 895-898 (May 2007); Martin et al., "Characterization of free and immobilized (S)-aminotransferase for acetophenone production," *Applied Microbiology and Biotechnology* 76(4): 843-851 (September 2007); Koszelewski et al., "Immobilization of ω-transaminases by encapsulation in a sol-gel/celite matrix," *Journal of Molecular Catalysis B: Enzymatic*, 63: 39-44 (April 2010); Truppo et al., "Development of an Improved Immobilized CAL-B for the Enzymatic Resolution of a Key Intermediate to Odanacatib," *Organic Process Research & Development*, published online: dx.doi.org/10.1021/op200157c; Hermanson, G. T., Bioconjugate Techniques, Second Edition, Academic Press (2008); Mateo et al., "Epoxy sepabeads: a novel epoxy support for stabilization of industrial enzymes via very intense multipoint covalent attachment," *Biotechnology Progress* 18(3):629-34 (2002); and Bioconjugation Protocols: Strategies and Methods, In Methods in Molecular Biology, C. M. Niemeyer ed., Humana Press (2004); the disclosures of each which are incorporated by reference herein. Solid supports useful for immobilizing the engineered proline hydroxylases of the present disclosure include but are not limited to beads or resins comprising polymethacrylate with epoxide functional groups, polymethacrylate with amino epoxide functional groups, styrene/DVB copolymer or polymethacrylate with octadecyl functional groups. Exemplary solid supports useful for immobilizing the engineered proline hydroxylase polypeptides of the present disclosure include, but are not limited to, chitosan beads, Eupergit C, and SEPABEADs (Mitsubishi), including the following different types of SEPABEAD: EC-EP, EC-HFA/S, EXA252, EXE119 and EXE120.

In some embodiments, the polypeptides described herein can be provided in the form of kits. The enzymes in the kits may be present individually or as a plurality of enzymes. The kits can further include reagents for carrying out the enzymatic reactions, substrates for assessing the activity of enzymes, as well as reagents for detecting the products. The kits can also include reagent dispensers and instructions for use of the kits.

In some embodiments, the kits of the present disclosure include arrays comprising a plurality of different proline hydroxylase polypeptides at different addressable position, wherein the different polypeptides are different variants of a reference sequence each having at least one different improved enzyme property. In some embodiments, a plurality of polypeptides immobilized on solid supports can be configured on an array at various locations, addressable for robotic delivery of reagents, or by detection methods and/or instruments. The array can be used to test a variety of substrate compounds for conversion by the polypeptides. Such arrays comprising a plurality of engineered polypeptides and methods of their use are described in, e.g., WO2009/008908A2.

5.4 Polynucleotides Encoding Engineered Proline Hydroxylases, Expression Vectors and Host Cells In another aspect, the present disclosure provides polynucleotides encoding the engineered proline hydroxylase polypeptides described herein. The polynucleotides may be operatively linked to one or more heterologous regulatory sequences that control gene expression to create a recombinant polynucleotide capable of expressing the polypeptide. Expression constructs containing a heterologous polynucleotide encoding the engineered proline hydroxylase can be introduced into appropriate host cells to express the corresponding proline hydroxylase polypeptide.

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode the improved proline hydroxylase enzymes. Thus, having knowledge of a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made encoding the polypeptides described herein by selecting combinations based on the possible codon choices, and all such variations are to be considered specifically disclosed for any polypeptide described herein, including the amino acid sequences presented in Tables 2A, 2B, 2C, 2D, 2E, 2F, 2G, and 2H and disclosed in the sequence listing incorporated by reference herein as SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In various embodiments, the codons are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. In some embodiments, all codons need not be replaced to optimize the codon usage of the proline hydroxylases since the natural sequence will comprise preferred codons and because use of preferred codons may not be required for all amino acid residues. Consequently, codon optimized polynucleotides encoding the proline hydroxylase enzymes may contain preferred codons at about 40%, 50%, 60%, 70%, 80%, or greater than 90% of codon positions of the full length coding region.

In some embodiments, the polynucleotide comprises a codon optimized nucleotide sequence encoding the naturally occurring proline hydroxylase polypeptide amino acid sequence, as represented by SEQ ID NO:2. In some embodiments, the polynucleotide has a nucleic acid sequence comprising at least 80%, 85%, 90%, 91%, 92%, 93%, 94%, 95%, 96%, 97%, 98%, 99% or more identity to the codon optimized nucleic acid sequences of SEQ ID NO: 1, 3, or 5, each of which encodes the identical polypeptide sequences of SEQ ID NO:2, 4, or 6, respectively. The codon optimized sequences of SEQ ID NO:1, 3, or 5 enhance expression of the encoded, wild-type proline hydroxylase, providing preparations of enzyme capable of converting in vitro over 80% of compound (2) to compound (1) under mini-DSP Assay conditions, and converting over 45% of compound (2) to compound (1) under DSP Assay conditions. In some embodiments, the codon optimized polynucleotide sequence can enhance expression of the proline hydroxylase by at least 1.2 fold, 1.5 fold or 2 fold or greater as compared to the naturally occurring polynucleotide sequence from *Sinorhizobium meliloti*, which is disclosed herein as SEQ ID NO: 135.

In some embodiments, the polynucleotides are capable of hybridizing under highly stringent conditions to a reference sequence of SEQ ID NO: 1, 3, or 5, or a complement thereof, and encodes a polypeptide having proline hydroxylase activity.

In some embodiments, as described above, the polynucleotide encodes an engineered polypeptide having proline hydroxylase activity with improved properties as compared to SEQ ID NO: 2, where the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, and one or more residue differences as compared to SEQ ID NO:2 selected from: X2K; X2T; X3S; X4Q; X4L; X4E; X4S; X5I; X5L; X5M; X9I; X13T; X17V; X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R. In some embodiments, the reference amino acid sequence is selected from SEQ ID NO: 10, 24, 104, 106, 108, 110, 132, 164, 222, 224, 226, and 228. In some embodiments, the reference amino acid sequence is SEQ ID NO:10. In some embodiments, the reference amino acid sequence is SEQ ID NO:24. In some embodiments, the reference amino acid sequence is SEQ ID NO:104. In some embodiments, the reference amino acid sequence is SEQ ID NO:108. In some embodiments, the reference amino acid sequence is SEQ ID NO:110. In some embodiments, the reference amino acid sequence is SEQ ID NO:132. In some embodiments, the reference amino acid sequence is SEQ ID NO:164. In some embodiments, the reference amino acid sequence is SEQ ID NO:222. In some embodiments, the reference amino acid sequence is SEQ ID NO:224. In some embodiments, the reference amino acid sequence is SEQ ID NO:226. In some embodiments, the reference amino acid sequence is SEQ ID NO:228.

In some embodiments, the polynucleotide encodes a proline hydroxylase polypeptide capable of converting substrate compound (2) to product compound (1) with improved properties as compared to SEQ ID NO:2, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2 and one or more residue differences as compared to SEQ ID NO: 2 at residue positions selected from: X2; X3; X4; X5; X9; X13;

X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271.

In some embodiments, the polynucleotide encodes a proline hydroxylase polypeptide capable of converting substrate compound (2) to product compound (1) with improved properties as compared to SEQ ID NO:2, wherein the polypeptide comprises an amino acid sequence having at least 80%, 85%, 86%, 87%, 88%, 89%, 90%, 91%, 92%, 93%, 94%, 95%, 96%, 97%, 98%, 99% or more sequence identity to reference sequence SEQ ID NO:2, and at least a combination of residue differences as compared to SEQ ID NO: 2 selected from: (a) X103L and X166Q; (b) X52P and X255Y; (c) X4E/L/S and X115A; (d) X25R and X58A; (e) X29A and X166T/Q/L; (f) X115H/D/G and X121F; (g) X3S, X103L, and X166Q; (h) X103L, X131Y/F, and X166T/Q/L; (i) X26T, X103L and X166T/Q/L; (j) X25R, X66Q, X92V and X115E; (k) X25R, X66Q, X92V, X103L, X115E, and X166Q; and (l) X3S, X25R, X66Q, X92V, X103L, X115E, and X166Q.

In some embodiments, the polynucleotide encodes an engineered proline hydroxylase polypeptide capable of converting substrate compound (2) to product compound (1) with improved enzyme properties as compared to the reference polypeptide of SEQ ID NO: 2, wherein the polypeptide comprises an amino acid sequence having at least 80%, 85%, 86%, 87%, 88%, 89%, 90%, 91%, 92%, 93%, 94%, 95%, 96%, 97%, 98%, or 99% identity to a reference polypeptide selected from any one of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, with the proviso that the amino acid sequence comprises any one of the set of residue differences as compared to SEQ ID NO: 2 contained in any one of the polypeptide sequences of SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, as listed in Tables 2A, 2B, 2C, 2D, 2E, 2F, 2G, and 2H.

In some embodiments, the polynucleotide encoding the engineered proline hydroxylase comprises an polynucleotide sequence selected from SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, and 227.

In some embodiments, the polynucleotides are capable of hybridizing under highly stringent conditions to a reference polynucleotide sequence selected from SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, and 227, or a complement thereof, and encodes a polypeptide having proline hydroxylase activity with one or more of the improved properties described herein. In some embodiments, the polynucleotide capable of hybridizing under highly stringent conditions encodes a proline hydroxylase polypeptide that has an amino acid sequence comprising one or more residue differences as compared to SEQ ID NO: 2 at residue positions selected from: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271. In some embodiments, the residue differences at residue positions X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271 are selected from X2K; X2T; X3S; X4Q; X4L; X4E; X4S; X5I; X5L; X5M; X9I; X13T; X17V; X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

In some embodiments, the polynucleotides encode the polypeptides described herein but have at least about 80%, 85%, 86%, 87%, 88%, 89%, 90%, 91%, 92%, 93%, 94%, 95%, 96%, 97%, 98%, or 99% or more sequence identity at the nucleotide level to a reference polynucleotide encoding the engineered proline hydroxylase. In some embodiments, the reference polynucleotide sequence is selected from SEQ ID NO: 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, and 227.

An isolated polynucleotide encoding an improved proline hydroxylase polypeptide may be manipulated in a variety of ways to provide for expression of the polypeptide. In some embodiments, the polynucleotides encoding the polypeptides can be provided as expression vectors where one or more control sequences is present to regulate the expression of the polynucleotides and/or polypeptides. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3$^{rd}$ Ed., Cold Spring Harbor Laboratory Press; and Current Protocols in Molecular Biology, Ausubel. F. ed., Greene Pub. Associates, 1998, updates to 2006.

In some embodiments, the control sequence includes among others, a promoter, leader sequence, polyadenylation sequence, propeptide sequence, signal peptide sequence, and transcription terminator. Suitable promoters can be selected based on the host cells used. For bacterial host cells, suitable promoters for directing transcription of the nucleic acid constructs of the present disclosure, include the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proc. Natl Acad. Sci. USA 75: 3727-3731), as well as the tac promoter (DeBoer et al., 1983, Proc. Natl Acad. Sci. USA 80: 21-25). Exemplary promoters for filamentous fungal host cells, include promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8:423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention. For example, exemplary transcription terminators for bacterial cells are described in Ermolaeva et al., 2001, J. Mol. Biol. 301:27-33. Exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence that contains a translation initiation sequence. The leader sequence is operably linked to the 5' terminus of the nucleic acid sequence encoding the polypeptide. Any leader sequence that is functional in initiating translation in the host cell of choice may be used. Exemplary bacterial translation initiation sequence can be obtained from any expressed bacterial gene, such as from *E. coli.*, *Bacillus subtilis*, *Lactococcus lactic*, and Sinorhizobium melitoti (see, e.g., Sakai, et al., 2001, J. Mol. Evol. 52:164-170; Ma et al., 2002, J Bacteriol. 184 (20): 5733-5745). In some embodiments, artificial translation initiation sequences (e.g., Shine-Delgarno sequence) can be used (see, e.g., Vimberg et al., 2007, BMC Molecular Biology 8:100). Exemplary leaders for filamentous fungal host cells are obtained from the genes for *Aspergillus oryzae* TAKA amylase and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention. Exemplary polyadenylation sequences for filamentous fungal host cells can be from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are described by Guo and Sherman, 1995, Mol Cell Bio 15:5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. Any signal peptide coding region which directs the expressed polypeptide into the secretory pathway of a host cell of choice may be used in the present invention. Effective signal peptide coding regions for bacterial host cells are the signal peptide coding regions obtained from the genes for *Bacillus* NC1B 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiol Rev 57: 109-137. Effective signal peptide coding regions for filamentous fungal host cells can be the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells can be from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences, which allow the regulation of the expression of the polypeptide relative to the growth of the host cell. Examples of regulatory systems are those which cause the expression of the gene to be turned on or off in response to a chemical or physical stimulus, including the presence of a regulatory compound. In prokaryotic host cells, suitable regulatory sequences include the lac, tac, and trp operator systems. In yeast host cells, suitable regulatory systems include, as examples, the ADH2 system or GAL1 system. In filamentous fungi, suitable regulatory sequences include the TAKA alpha-amylase promoter, *Aspergillus niger* glucoamylase promoter, and *Aspergillus oryzae* glucoamylase promoter.

In another aspect, the present disclosure is also directed to a recombinant expression vector comprising a polynucleotide encoding an engineered proline hydroxylase polypeptide, and one or more expression regulating regions such as a promoter and a terminator, a replication origin, etc., depending on the type of hosts into which they are to be introduced. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present disclosure may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The expression vector preferably contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Embodiments for use in an *Aspergillus* cell include the amdS and pyrG genes of *Aspergillus nidulans* or *Aspergillus oryzae* and the bar gene of *Streptomyces hygroscopicus*.

In another aspect, the present disclosure provides a host cell comprising a polynucleotide encoding an improved proline hydroxylase polypeptide of the present disclosure, the polynucleotide being operatively linked to one or more control sequences for expression of the proline hydroxylase enzyme in the host cell. Host cells for use in expressing the polypeptides encoded by the expression vectors are well known in the art and include but are not limited to, bacterial cells, such as *E. coli, Bacillus subtilis, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Exemplary host cells are *Escherichia coli* W3110 (ΔfhuA) and BL21.

Accordingly, in another aspect, the present disclosure provides methods of manufacturing the engineered proline hydroxylase polypeptides, where the method can comprise culturing a host cell capable of expressing a polynucleotide encoding the proline hydroxylase polypeptide under conditions suitable for expression of the polypeptide. The method can further comprise isolating or purifying the expressed proline hydroxylase polypeptide, as described herein Appropriate culture mediums and growth conditions for the above-described host cells are well known in the art. Polynucleotides for expression of the proline hydroxylase may be introduced into cells by various methods known in the art. Techniques include among others, electroporation, biolistic particle bombardment, liposome mediated transfection, calcium chloride transfection, and protoplast fusion.

In the embodiments herein, the improved polypeptides and corresponding polynucleotides can be obtained using methods used by those skilled in the art. The parental, naturally occurring polynucleotide sequence encoding the naturally occurring cis-4-proline hydroxylase of *Sinorhizobium meliloti* is described in US patent publication no. US20110091942 and International patent publication no. WO2009139365, incorporated herein by reference. The engineered proline hydroxylases described herein can be obtained by subjecting the polynucleotide encoding the naturally occurring or another engineered proline hydroxylase to mutagenesis and/or directed evolution methods, as discussed herein. An exemplary directed evolution technique is mutagenesis and/or DNA shuffling as described in Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. Other directed evolution procedures that can be used include, among others, staggered extension process (StEP), in vitro recombination (Zhao et al., 1998, Nat. Biotechnol. 16:258-261), mutagenic PCR (Caldwell et al., 1994, PCR Methods Appl. 3:S136-S140), and cassette mutagenesis (Black et al., 1996, Proc Natl Acad Sci USA 93:3525-3529). Mutagenesis and directed evolution techniques useful for the purposes herein are also described in the following references: Ling, et al., 1997, Anal. Biochem. 254(2):157-78; Dale et al., 1996, "Oligonucleotide-directed random mutagenesis using the phosphorothioate method," In Methods Mol. Biol. 57:369-74; Smith, 1985, Ann. Rev. Genet. 19:423-462; Botstein et al., 1985, Science 229:1193-1201; Carter, 1986, Biochem. J. 237:1-7; Kramer et al., 1984, Cell, 38:879-887; Wells et al., 1985, Gene 34:315-323; Minshull et al., 1999, Curr Opin Chem Biol 3:284-290; Christians et al., 1999, Nature Biotech 17:259-264; Crameri et al., 1998, Nature 391:288-291; Crameri et al., 1997, Nature Biotech 15:436-438; Zhang et al., 1997, Proc Natl Acad Sci USA 94:45-4-4509; Crameri et al., 1996, Nature Biotech 14:315-319; Stemmer, 1994, Nature 370:389-391; Stemmer, 1994, Proc Natl Acad Sci USA 91:10747-10751; WO 95/22625; WO 97/0078; WO 97/35966; WO 98/27230; WO 00/42651; WO 01/75767 and U.S. Pat. No. 6,537,746. All publications are incorporated herein by reference.

The clones obtained following mutagenesis treatment can be screened for engineered proline hydroxylases having one or more desired improved enzyme properties. For example, where the improved enzyme property desired is regioselectivity, enzyme activity may be measured for production of compound (1) and compound (1a). Clones containing a polynucleotide encoding a proline hydroxylase with the desired characteristics, e.g., increased ratio of compound (1) over compound (1a), are then isolated, sequenced to identify the nucleotide sequence changes (if any), and used to express the enzyme in a host cell. Measuring enzyme activity from the expression libraries can be performed using the standard biochemistry techniques, such as HPLC analysis and/or derivatization of products (pre or post separation), e.g., with dansyl chloride or OPA (see, e.g., Yaegaki et al., 1986, J Chromatogr. 356(1):163-70).

Where the sequence of the engineered polypeptide is known, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides encoding portions of the proline hydroxylase can be prepared by chemical synthesis using, e.g., the classical phosphoramidite method described by Beaucage et al., 1981, Tet Lett 22:1859-69, or the method described by Matthes et al., 1984, EMBO J. 3:801-05, e.g., as it is typically practiced in automated synthetic methods. According to the phosphoramidite method, oligonucleotides are synthesized, e.g., in an automatic DNA synthesizer, purified, annealed, ligated and cloned in appropriate vectors. In addition, essentially any nucleic acid can be obtained from any of a variety of commercial sources. In some embodiments, additional variations can be created by synthesizing oligonucleotides containing deletions, insertions, and/or substitutions, and combining the oligonucleotides in various permutations to create engineered proline hydroxylases with improved properties.

Accordingly, in some embodiments, a method for preparing the engineered proline hydroxylases polypeptide can comprise: (a) synthesizing a polynucleotide encoding a polypeptide comprising an amino acid sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228, and having one or more residue differences as compared to SEQ ID NO:2 at residue positions selected from: X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271; and (b) expressing the proline hydroxylase polypeptide encoded by the polynucleotide.

In some embodiments of the method, the residue differences at residue positions X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271 are selected from X2K; X2T; X3S; X4Q; X4L; X4E; X4S; X5I; X5L; X5M; X9I; X13T; X17V, X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

In some embodiments of the method, the polynucleotide can encode an engineered proline hydroxylase that has optionally one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions can be conservative or non-conservative substitutions.

In some embodiments, any of the engineered proline hydroxylase enzymes expressed in a host cell can be recovered from the cells and/or the culture medium using any one or more of the well known techniques for protein purification, including, among others, lysozyme treatment, sonication, filtration, salting-out, ultra-centrifugation, and chromatography. Suitable solutions for lysing and the high efficiency extraction of proteins from bacteria, such as *E. coli*, are commercially available, such as CelLytic B™ from Sigma-Aldrich of St. Louis MO Chromatographic techniques for isolation of the proline hydroxylase polypeptide include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

In some embodiments, affinity techniques may be used to isolate the improved proline hydroxylase enzymes. For affinity chromatography purification, any antibody which specifically binds the proline hydroxylase polypeptide may be used. For the production of antibodies, various host animals, including but not limited to rabbits, mice, rats, etc., may be immunized by injection with a proline hydroxylase polypeptide, or a fragment thereof. The proline hydroxylase polypeptide or fragment may be attached to a suitable carrier, such as BSA, by means of a side chain functional group or linkers attached to a side chain functional group. In some embodiments, the affinity purification can use a specific ligand bound by the proline hydroxylase, such as poly(L-proline) or dye affinity column (see, e.g., EP0641862; Stellwagen, E., 2001, "Dye Affinity Chromatography," In Current Protocols in Protein Science Unit 9.2-9.2.16).

5.7 Methods of Using the Engineered Proline Hydroxylase Enzymes

In another aspect, the proline hydroxylases described herein can be used in a process for converting a suitable substrate to its hydroxylated product. Generally, the process for performing the hydroxylation reaction comprises contacting or incubating the substrate compound in presence of a co-substrate, such as α-ketoglutarate, with a proline hydroxylase polypeptide of the disclosure under reaction conditions suitable for formation of the hydroxylated product.

In some embodiments, the proline hydroxylases can be used in the conversion of substrate compound (II) to product compound (I), as illustrated in Scheme 2:

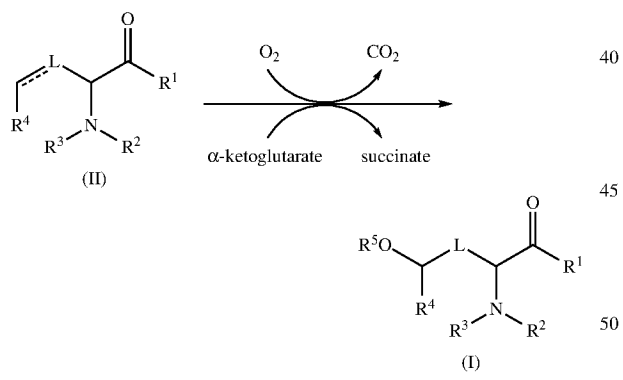

wherein
L is selected from the group consisting of a bond, $(C_1$-$C_4)$alkylene and $(C_2$-$C_4)$alkenylene;
$R^1$ is selected from the group consisting of hydroxy, amino, $(C_1$-$C_6)$alkyloxy, aryloxy, $(C_1$-$C_6)$alkylthio and arylthio;
$R^2$ and $R^3$ are each independently selected from the group consisting of hydrogen and optionally substituted $(C_1$-$C_6)$alkyl, $(C_2$-$C_6)$alkenyl, and $(C_2$-$C_6)$alkynyl;
$R^4$ is selected from the group consisting of optionally substituted $(C_1$-$C_6)$alkyl, $(C_2$-$C_6)$alkenyl, $(C_2$-$C_6)$alkynyl, aryl, heteroaryl, cycloalkyl, heterocycloalkyl; or $R^4$ together with one of $R^1$ or $R^2$ is a $(C_1$-$C_5)$alkylene or $(C_2$-$C_5)$alkenylene and forms a 5- to 8-membered heterocyclic ring containing the nitrogen atom, wherein the ring is optionally substituted with 1 to 4 independently selected $R^6$ groups;
$R^5$ is hydrogen or a bond that forms an epoxide with a carbon atom of L;
each occurrence of $R^6$ is independently selected from the group consisting of halo, $(C_1$-$C_6)$alkyl, and $(C_1$-$C_6)$alkyloxy; and
--- represents an optional bond to a carbon atom of L to form a double bond,
with the provisos that
(i) when $R^4$ does not form a ring with one $R^2$ or $R^3$, or when $R^4$ forms a 5-membered heterocyclic ring containing the nitrogen atom with one of $R^2$ or $R^3$, then L is a methylene;
(ii) when $R^4$ forms a 6-membered heterocyclic ring containing the nitrogen atom with one of $R^2$ or $R^3$, then L is a bond or ethylene; and
(iii) when $R^5$ is a bond to a carbon atom of L to form an epoxide, then $R^4$ forms the heterocyclic ring containing the nitrogen atom with one of $R^2$ or $R^3$ and L is a $(C_1$-$C_4)$alkylene or $(C_2$-$C_4)$alkenylene.

Accordingly, in some embodiments, a process for preparing product compound (I) can comprise contacting the substrate compound of formula (II)

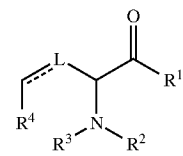

(II)

wherein
L, $R^1$, $R^2$, $R^3$, $R^4$, and $R^6$ are as defined above,
--- represents an optional bond to a carbon atom of L to form a double bond
with an engineered polypeptide disclosed herein in presence of a co-substrate under suitable reaction conditions.

In some embodiments of the process, the compound of formula (I) comprises the compound of formula (Ia),

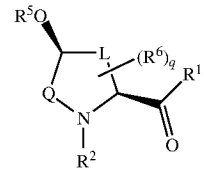

(Ia)

wherein
Q is selected from the group consisting of a $(C_1$-$C_5)$alkylene and $(C_2$-$C_5)$alkenylene;
L is selected from the group consisting of a bond, $(C_1$-$C_4)$alkylene and $(C_2$-$C_4)$alkenylene;
$R^1$ is selected from the group consisting of hydroxy, amino, $(C_1$-$C_6)$alkyloxy, aryloxy, $(C_1$-$C_6)$alkylthio and arylthio;
$R^2$ is selected from the group consisting of hydrogen and optionally substituted $(C_1$-$C_6)$alkyl, $(C_2$-$C_6)$alkenyl, and $(C_2$-$C_6)$alkynyl;
$R^5$ is hydrogen, or a bond to a carbon atom of L to form an epoxide;

each occurrence of $R^6$ is selected from the group consisting of halo, $(C_1-C_6)$alkyl, and $(C_1-C_6)$alkyloxy; and q is an integer from 0 to 4;

wherein the sum of ring carbon atoms for Q+L is an integer from 2 to 5;

with the provisos that (i) when the sum of ring carbon atoms for Q+L is 2, then L is a methylene; and (ii) when the sum of ring carbon atoms for Q+L is 3, then L is either a bond or ethylene.

Accordingly, a process for preparing the compound of formula (Ia) comprises contacting the compound of formula (IIa),

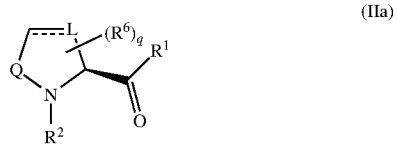

(IIa)

wherein

L, Q, $R^1$, $R^2$, $R^6$, and q are as defined above for the compound of formula (Ta); and --- represents an optional bond to a carbon atom of L to form a double bond;

with an engineered polypeptide of the disclosure in presence of a co-substrate under suitable reaction conditions.

In some embodiments of the process, the compound of formula (Ia) comprises the compound of formula (Tb),

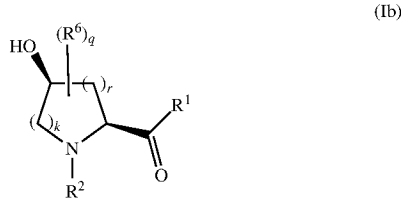

(Ib)

wherein $R^1$ is selected from the group consisting of hydroxy, amino, $(C_1-C_6)$alkyloxy, aryloxy, $(C_1-C_6)$alkylthio and arylthio;

$R^2$ is selected from the group consisting of hydrogen and optionally substituted $(C_1-C_6)$alkyl, $(C_2-C_6)$alkenyl, and $(C_2-C_6)$alkynyl;

each occurrence of $R^6$ is independently selected from the group consisting of halo, $(C_1-C_6)$alkyl, and $(C_1-C_6)$alkyloxy; and k is an integer from 1 to 5;

r is an integer from 0 to 4;

wherein k+r is 3, 4 or 5; and q is an integer from 0 to 4;

with the proviso that when k+r is 3, then k is 1 or 3.

Accordingly, a process for preparing the compound of formula (Ib) comprises contacting the compound of formula (IIb),

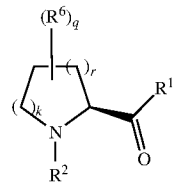

(IIb)

wherein $R^1$, $R^2$, $R^6$, k, r and q are as defined above for the compound of formula (Ib);

with an engineered polypeptide of the disclosure in presence of a co-substrate under suitable reaction conditions. In some embodiments, k is 1 and r is 2, 3, or 4.

In some embodiments of the process, the compound of formula (Ia) comprises the compound of formula (Ic),

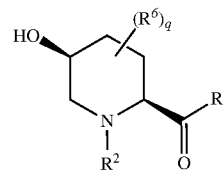

(Ic)

wherein $R^1$ is selected from the group consisting of hydroxy, amino, $(C_1-C_6)$alkyloxy, aryloxy, $(C_1-C_6)$alkylthio and arylthio;

$R^2$ is selected from the group consisting of hydrogen and optionally substituted $(C_1-C_6)$alkyl, $(C_2-C_6)$alkenyl, and $(C_2-C_6)$alkynyl;

each occurrence of $R^6$ is independently selected from the group consisting of hydrogen, halo, $(C_1-C_6)$alkyl, and $(C_1-C_6)$alkyloxy; and q is an integer from 0 to 4.

Accordingly, a process for preparing the compound of formula (Ic) comprises contacting the compound of formula (IIc),

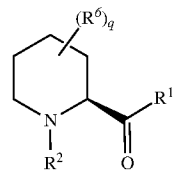

(IIc)

wherein $R^1$, $R^2$, $R^6$ and q are as defined above for the compound of formula (Ic);

with an engineered polypeptide of the disclosure in presence of a co-substrate under suitable reaction conditions.

In some embodiments of the process, the compound of formula (Ic) is formed in excess of product compound of formula (Ic3),

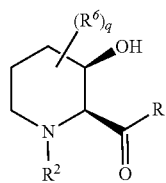

Accordingly, a process for preparing the compound of formula (Ic) in excess of the compound of formula (Ic3) comprises contacting the compound of formula (IIc) with an engineered polypeptide described herein having regioselectivity for product compound (1) over product compound (1a) in presence of a co-substrate under suitable reaction conditions. In some embodiments of the process, the product compound of formula (Ic) is formed in excess of the product compound of formula (Ic3), where the ratio of compound (Ic) formed over compound (Ic3) is at least 1.5, 2, 3, 4, 5, or 6 or greater.

In some embodiments of the process, product compound (Ic) is formed in diastereomeric excess of compound (IcR),

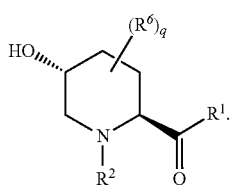

In some embodiments of the process, the product compound (Ic) is formed in at least 90%, 95%, 96%, 97%, 98%, 99%, or greater diastereomeric excess of compound (IcR). In some embodiments, no detectable amount of compound (IcR) is formed in the process.

In some embodiments of the process for preparation of the product compounds of formula (Ic), $R^1$ is hydroxy, $R^2$ is hydrogen, and q is 0. As such, in some embodiments of the process, the compound of formula (I) comprises the compound of formula (1),

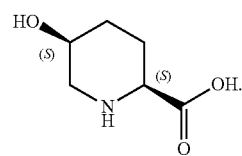

Accordingly, a process for preparing the compound of formula (1) comprises contacting the compound of formula (2),

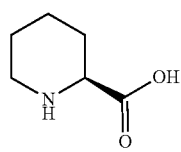

with an engineered polypeptide of the disclosure in presence of a co-substrate under suitable reaction conditions.

In some embodiments of the process, the product compound (1) is formed in excess of product compound (1a). In some embodiments, the product compound (1) is formed in excess over compound (1a) in a ratio of at least 1.5, 2, 3, 4, 5 or 6 or greater. In some embodiments of the process, the engineered polypeptide useful for preparing compound (1) in excess of the compound of formula (1a) comprises contacting the compound of formula (2) with an engineered polypeptide described herein having regioselectivity for product compound (1) over compound (1a) under suitable reaction conditions.

In some embodiments of the process, product compound (1) is formed in diastereomeric excess of compound (1R),

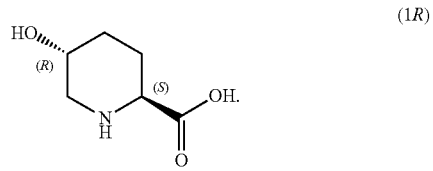

In some embodiments of the process, the product compound (1) is formed in at least 90%, 95%, 96%, 97%, 98%, 99%, or greater diastereomeric excess of compound (1R). In some embodiments, no detectable amount of compound (1R) is formed in the process.

In some embodiments, the compound of formula (Ia) comprises the compound of formula (Ie),

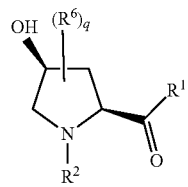

wherein
$R^1$ is selected from the group consisting of hydroxy, amino, $(C_1-C_6)$alkyloxy, aryloxy, $(C_1-C_6)$alkylthio and arylthio;
$R^2$ is selected from the group consisting of hydrogen and optionally substituted $(C_1-C_6)$alkyl, $(C_2-C_6)$alkenyl, and $(C_2-C_6)$alkynyl;
each occurrence of $R^6$ is independently selected from the group consisting of hydrogen, halo, $(C_1-C_6)$alkyl, and $(C_1-C_6)$alkyloxy; and
q is an integer from 0 to 3.

Accordingly, in some embodiments, a process for preparing the product compound of formula (Ie) comprises contacting the compound of formula (IIe),

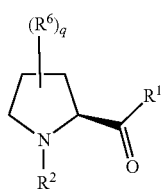

wherein R$^1$, R$^2$, R$^6$ and q are as defined for the compound of formula (Ie),
with an engineered polypeptide of the disclosure in presence of a co-substrate under suitable reaction conditions.

In some embodiments of the process, the compound of formula (Ie) is formed in diastereomeric excess of compound of formula (IeR),

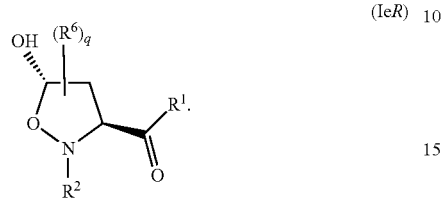

(IeR)

In some embodiments of the process, the product compound of formula (Ie) is formed in at least 90%, 95%, 96%, 97%, 98%, 99%, or greater diastereomeric excess of the compound of formula (IeR). In some embodiments, no detectable amount of the compound of formula (IeR) is formed.

In some embodiments of the process for preparing the product compound of formula (Ie), R$^1$ is hydroxy, R$^2$ is hydrogen, and q is 0. As such, in some embodiments, the compound of formula (Ie) comprises compound (3),

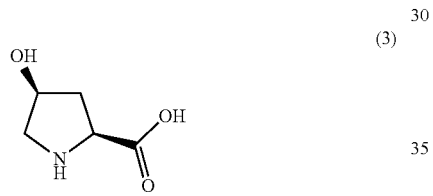

(3)

wherein the process for preparing compound (3) comprises contacting compound (4),

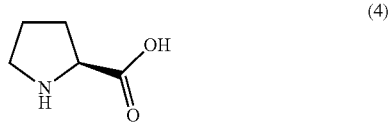

(4)

with an engineered polypeptide of the disclosure in presence of a co-substrate under suitable reaction conditions.

In some embodiments of the process, compound (3) is formed in diastereomeric excess of compound (3R),

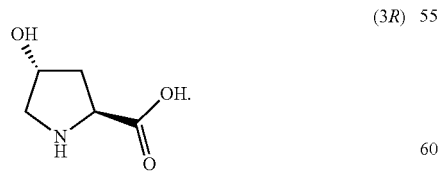

(3R)

In some embodiments of the process, the product compound (3) is formed in at least 90%, 95%, 96%, 97%, 98%, 99%, or greater diastereomeric excess of the compound (3R). In some embodiments, no detectable amount of the compound (3R) is formed.

In some embodiments, the compound of formula (Ia) comprises compound (5),

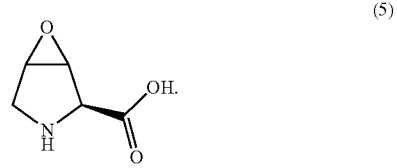

(5)

Accordingly, a process for preparing compound (5) comprises contacting compound (6);

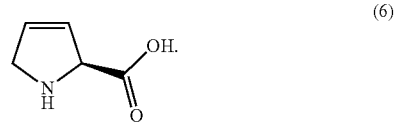

(6)

with an engineered polypeptide of the disclosure in presence of a co-substrate under suitable reaction conditions.

In some embodiments, the compound of formula (I) comprises the compound of formula (III),

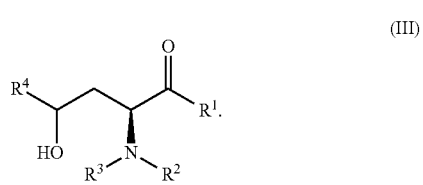

(III)

wherein,

R$^1$ is selected from the group consisting of hydroxy, amino, (C$_1$-C$_6$)alkyloxy, aryloxy, (C$_1$-C$_6$)alkylthio and arylthio;

R$^2$ and R$^3$ are each independently selected from the group consisting of hydrogen and optionally substituted (C$_1$-C$_6$) alkyl, (C$_2$-C$_6$)alkenyl, and (C$_2$-C$_6$)alkynyl; and R$^4$ is selected from the group consisting of optionally substituted alkyl, alkenyl, alkynyl, aryl, heteroaryl, cycloalkyl, and heterocycloalkyl;

In some embodiments, the optionally substituted alkyl is selected from the group consisting of carboxy(C$_1$-C$_6$)alkyl, aminocarbonyl(C$_1$-C$_6$)alkyl, amino(C$_1$-C$_6$)alkyl, thiol(C$_1$-C$_6$)alkyl, and alkylthio(C$_1$-C$_6$)alkyl, alkylsulfonyl(C$_1$-C$_6$)alkyl, aryl(C$_1$-C$_6$)alkyl, heteroaryl(C$_1$-C$_6$)alkyl, cycloalkyl(C$_1$-C$_6$)alkyl, and heterocycloalkyl(C$_1$-C$_6$)alkyl.

Accordingly, in some embodiments, a process for preparing the compound of formula (III) comprises contacting the compound of formula (IV),

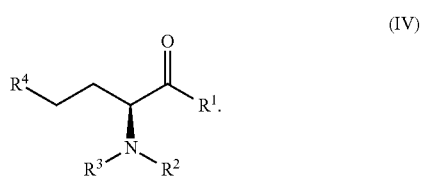

(IV)

wherein, $R^1$, $R^2$, $R^3$ and $R^4$ are as defined above for the compound of formula (III), with an engineered polypeptide of the disclosure in presence of a co-substrate under suitable reaction conditions.

In some embodiments, the engineered polypeptides can be used in a process for carrying out the conversion shown in Scheme 3, Scheme 3

(VI) → (V)

O₂ → CO₂
α-ketoglutarate → succinate wherein, $R^1$ is selected from the group consisting of hydroxy, amino, $(C_1\text{-}C_6)$alkyloxy, aryloxy, $(C_1\text{-}C_6)$alkylthio and arylthio;

$R^2$ and $R^3$ are independently selected from the group consisting of hydrogen and optionally substituted $(C_1\text{-}C_6)$ alkyl, $(C_2\text{-}C_6)$alkenyl, and $(C_2\text{-}C_6)$alkynyl;

each occurrence of $R^6$ is independently selected from the group consisting of halo, $(C_1\text{-}C_6)$alkyl, and $(C_1\text{-}C_6)$alkyloxy;

$R^7$ is selected from the group consisting of hydrogen, halo, and optionally substituted $(C_1\text{-}C_6)$alkyl and $(C_1\text{-}C_6)$ alkyloxy; or $R^7$ together with one of $R^2$ or $R^3$ forms a 5- to 7-membered heterocyclic ring containing the nitrogen atom;

q is an integer from 0 to 4; and

---- represent optional double bonds that form an aryl ring.

Accordingly, in some embodiments, a process for preparing the compound of formula (V) comprises contacting the compound of formula (VI), (VI)

wherein $R^1$, $R^2$, $R^3$, $R^6$, $R^7$, and q are as defined for the compound of formula (V), with an engineered polypeptide of the disclosure in presence of a co-substrate under suitable reaction conditions.

In some embodiments, the compound of formula (V) comprises the compound of formula (Va), (Va)

wherein, $R^1$ is selected from the group consisting of hydroxy, amino, $(C_1\text{-}C_6)$alkyloxy, aryloxy, $(C_1\text{-}C_6)$alkylthio and arylthio;

$R^2$ and $R^3$ are independently selected from the group consisting of hydrogen and optionally substituted $(C_1\text{-}C_6)$ alkyl, $(C_2\text{-}C_6)$alkenyl, and $(C_2\text{-}C_6)$alkynyl;

each occurrence of $R^6$ is independently selected from the group consisting of halo, $(C_1\text{-}C_6)$alkyl, and $(C_1\text{-}C_6)$alkyloxy; and q is an integer from 0 to 4.

Accordingly, in some embodiments, a process for preparing the compound of formula (Va) comprises contacting the compound of formula (VIa), (VIa)

wherein $R^1$, $R^2$, $R^3$, $R^6$, and q are as defined above for the compound of formula (Va), with an engineered polypeptide of the disclosure in presence of a co-substrate under suitable reaction conditions.

For the foregoing processes, any of the engineered proline hydroxylases described herein can be used. By way of example and without limitation, in some embodiments, the processes can use an engineered proline hydroxylase polypeptide comprising an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments of the processes, the engineered proline hydroxylase polypeptide comprises an amino acid sequence having one or more residue differences as compared to SEQ ID NO:2 at residue positions X2; X3; X4; X5; X9; X13; X17; X24; X25; X26; X29; X30; X36; X42; X52; X57; X58; X59; X62; X66; X86; X88; X92; X95; X98; X103; X112; X113; X114; X115; X116; X121; X131; X140; X150; X151; X166; X186; X188; X205; X225; X230; X270; and X271.

In some embodiments of the processes, the residue differences at residue positions X2; X3; X4; X5; X9; X13; X17; X24; X25; X26; X29; X30; X36; X42; X52; X57; X58;

X59; X62; X66; X86; X88; X92; X95; X98; X103; X112; X113; X114; X115; X116; X121; X131; X140; X150; X151; X166; X186; X188; X205; X225; X230; X270; and X271 are selected from X2K; X2T; X3S; X4Q; X4L; X4E; X4S; X5I; X5L; X5M; X9I; X13T; X17V; X24R; X24S; X25R; X26R; X26T; X26W; X29A; X30V; X30P; X36T; X42E; X52P; X57T; X57A; X58A; X59G; X62Q; X66Q; X86S; X88R; X92V; X95M; X98F; X98T; X103L; X103Q; X112T; X112V; X113E; X114N; X115E; X115H; X115D; X115G; X115S; X115A; X116L; X121F; X131Y; X131F; X140L; X150S; X151A; X151H; X151S; X166T; X166L; X166Q; X186G; X188G; X205V; X225L; X225Y; X225W; X230V; X270E; X271K; and X271R.

As noted above, in some embodiments for preparing product compound of formula (Ic) in excess over the compound of formula (Ic3), or for preparing compound (1) in excess over compound (1a), the engineered polypeptide can comprise an amino acid sequence having one or more features selected from: X103L; X115E; X131Y and X166Q. Exemplary engineered polypeptides with the relevant regioselectivity can comprise an amino acid sequence selected from the group consisting of SEQ ID NO: 10, 24, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

In some embodiments, exemplary proline hydroxylases polypeptides capable of carrying out the processes herein can have an amino acid sequence comprising a sequence selected from SEQ ID NO: 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228. Guidance on the choice and use of the engineered proline hydroxylases is provided in the descriptions herein, for example Tables 2A, 2B, 2C, 2D, 2E, 2F, 2G, and 2H and the Examples.

In the embodiments herein and illustrated in the Examples, various ranges of suitable reaction conditions that can be used in the processes, include but are not limited to, substrate loading, co-substrate loading, reductant, divalent transition metal, pH, temperature, buffer, solvent system, polypeptide loading, and reaction time. Further suitable reaction conditions for carrying out the process for biocatalytic conversion of substrate compounds to product compounds using an engineered proline hydroxylase polypeptide described herein can be readily optimized in view of the guidance provided herein by routine experimentation that includes, but is not limited to, contacting the engineered proline hydroxylase polypeptide and substrate compound under experimental reaction conditions of concentration, pH, temperature, and solvent conditions, and detecting the product compound.

Suitable reaction conditions using the engineered proline hydroxylase polypeptides typically comprise a co-substrate, which is used stoichiometrically in the hydroxylation reaction. Generally, the co-substrate for proline hydroxylases is α-ketoglutarate, also referred to as α-ketoglutaric acid and 2-oxoglutaric acid. Other analogs of α-ketoglutarate that are capable of serving as co-substrates for proline hydroxylases can be used. An exemplary analog that may serve as a co-substrate is 2-oxoadipate. Because the co-substrate is used stoichiometrically, the co-substrate is present at an equimolar or higher amount than that of the substrate compound, i.e., the molar concentration of co-substrate is equivalent to or higher than the molar concentration of substrate compound. In some embodiments, the suitable reaction conditions can comprise a co-substrate molar concentration of at least 1 fold, 1.5 fold, 2 fold, 3 fold 4 fold or 5 fold or more than the molar concentration of the substrate compound. In some embodiments, the suitable reaction conditions can comprise a co-substrate concentration, particularly α-ketoglutarate, of about 0.001 M to about 2 M, 0.01 M to about 2 M, 0.1 M to about 2 M, 0.2 M to about 2 M, about 0.5 M to about 2 M, or about 1 M to about 2 M. In some embodiments, the reaction conditions comprise a co-substrate concentration of about 0.001, 0.01, 0.1, 0.2, 0.3, 0.4, 0.5, 0.6, 0.7, 0.8, 1, 1.5, or 2 M. In some embodiments, additional co-substrate can be added during the reaction.

Substrate compound in the reaction mixtures can be varied, taking into consideration, for example, the desired amount of product compound, the effect of substrate concentration on enzyme activity, stability of enzyme under reaction conditions, and the percent conversion of substrate to product. In some embodiments, the suitable reaction conditions comprise a substrate compound loading of at least about 0.5 to about 200 g/L, 1 to about 200 g/L, 5 to about 150 g/L, about 10 to about 100 g/L, 20 to about 100 g/L or about 50 to about 100 g/L. In some embodiments, the suitable reaction conditions comprise a substrate compound loading of at least about 0.5 g/L, at least about 1 g/L, at least about 5 g/L, at least about 10 g/L, at least about 15 g/L, at least about 20 g/L, at least about 30 g/L, at least about 50 g/L, at least about 75 g/L, at least about 100 g/L, at least about 150 g/L or at least about 200 g/L, or even greater. The values for substrate loadings provided herein are based on the molecular weight of compound (2), however it also contemplated that the equivalent molar amounts of various hydrates and salts of compound (2) also can be used in the process. In addition, substrate compounds covered by formulas (II) and (VI), including compounds of formula (IIa), (IVa) and (VIa) can also be used in appropriate amounts, in light of the amounts used for compound (2).

In carrying out the proline hydroxylase mediated processes described herein, the engineered polypeptide may be added to the reaction mixture in the form of a purified enzyme, partially purified enzyme, whole cells transformed with gene(s) encoding the enzyme, as cell extracts and/or lysates of such cells, and/or as an enzyme immobilized on a solid support. Whole cells transformed with gene(s) encoding the engineered proline hydroxylase enzyme or cell extracts, lysates thereof, and isolated enzymes may be employed in a variety of different forms, including solid (e.g., lyophilized, spray-dried, and the like) or semisolid (e.g., a crude paste). The cell extracts or cell lysates may be partially purified by precipitation (ammonium sulfate, polyethyleneimine, heat treatment or the like, followed by a desalting procedure prior to lyophilization (e.g., ultrafiltration, dialysis, and the like). Any of the enzyme preparations (including whole cell preparations) may be stabilized by crosslinking using known crosslinking agents, such as, for example, glutaraldehyde or immobilization to a solid phase (e.g., Eupergit C, and the like).

The gene(s) encoding the engineered proline hydroxylase polypeptides can be transformed into host cell separately or together into the same host cell. For example, in some embodiments one set of host cells can be transformed with gene(s) encoding one engineered proline hydroxylase polypeptide and another set can be transformed with gene(s) encoding another engineered proline hydroxylase polypeptide. Both sets of transformed cells can be utilized together in the reaction mixture in the form of whole cells, or in the form of lysates or extracts derived therefrom. In other embodiments, a host cell can be transformed with gene(s) encoding multiple engineered proline hydroxylase polypeptide. In some embodiments the engineered polypeptides can be expressed in the form of secreted polypeptides and the culture medium containing the secreted polypeptides can be used for the proline hydroxylase reaction.

The improved activity and/or stereoselectivity of the engineered proline hydroxylase polypeptides disclosed herein provides for processes wherein higher percentage conversion can be achieved with lower concentrations of the engineered polypeptide. In some embodiments of the process, the suitable reaction conditions comprise an engineered polypeptide amount of about 1% (w/w), 2% (w/w), 5% (w/w), 10% (w/w), 20% (w/w), 30% (w/w), 40% (w/w), 50% (w/w), 75% (w/w), 100% (w/w) or more of substrate compound loading.

In some embodiments, the engineered polypeptide is present at about 0.01 g/L to about 50 g/L; about 0.05 g/L to about 50 g/L; about 0.1 g/L to about 40 g/L; about 1 g/L to about 40 g/L; about 2 g/L to about 40 g/L; about 5 g/L to about 40 g/L; about 5 g/L to about 30 g/L; about 0.1 g/L to about 10 g/L; about 0.5 g/L to about 10 g/L; about 1 g/L to about 10 g/L; about 0.1 g/L to about 5 g/L; about 0.5 g/L to about 5 g/L; or about 0.1 g/L to about 2 g/L. In some embodiments, the proline hydroxylase polypeptide is present at about 0.01 g/L, 0.05 g/L, 0.1 g/L, 0.2 g/L, 0.5 g/L, 1, 2 g/L, 5 g/L, 10 g/L, 15 g/L, 20 g/L, 25 g/L, 30 g/L, 35 g/L, 40 g/L, or 50 g/L.

In some embodiments, the reactions conditions also comprise a divalent transition metal capable of serving as a cofactor in the oxidation reaction. Generally, the divalent transition metal co-factor is ferrous ion, i.e., $Fe^{+2}$. The ferrous ion may be provided in various forms, such as ferrous sulfate ($FeSO_4$), ferrous chloride ($FeCl_2$), ferrous carbonate ($FeCO_3$), and the salts of organic acids such as citrates, lactates and fumarates. An exemplary source of ferrous sulfate is Mohr's salt, which is ferrous ammonium sulfate $(NH_4)_2Fe(SO_4)_2$ and is available in anhydrous and hydrated (i.e., hexahydrate) forms. While ferrous ion is the transition metal co-factor found in the naturally occurring proline hydroxylase and functions efficiently in the engineered enzymes, it is to be understood that other divalent transition metals capable of acting as a co-factor can be used in the processes. In some embodiments, the divalent transition metal co-factor can comprise $Mn^{+2}$ and $Cr^{+2}$. In some embodiments, the reaction conditions can comprises a divalent transition metal cofactor, particularly $Fe^{+2}$, at a concentration of about 0.1 mM to 10 mM, 0.1 mM to about 5 mM, 0.5 mM to about 5 mM, about 0.5 mM to about 3 mM or about 1 mM to about 2 mM. In some embodiments, the reaction conditions comprise a divalent transition metal co-factor concentration of about 0.1 mM, 0.2 mM, 0.5 mM, 1 mM, 1.5 mM, 2 mM, 3 mM, 5 mM, 7.5 mM or 10 mM. In some embodiments, higher concentrations of divalent transition metal cofactor can be used, for example up to 50 mM or up to 100 mM.

In some embodiments, the reaction conditions can further comprise a reductant capable of reducing ferric ion, $Fe^{+3}$ to ferrous ion, $Fe^{+2}$. In some embodiments, the reductant comprises ascorbic acid, typically L-ascorbic acid. While ascorbic acid is not required for the hydroxylation reaction, enzymatic activity is enhanced in its presence. Without being bound by theory, the ascorbate is believed to maintain or regenerate the enzyme-$Fe^{+2}$ form, which is the active form mediating the hydroxylation reaction. Generally, the reaction conditions can comprise an ascorbic acid concentration that corresponds proportionately to the substrate loading. In some embodiments, the ascorbic acid is present in at least about 0.1 fold, 0.2 fold 0.3 fold, 0.5 fold, 0.75 fold, 1 fold, 1.5 fold, or at least 2 fold the molar amount of substrate. In some embodiments, the reductant, particularly L-ascorbic acid, is at a concentration of about 0.001 M to about 0.5 M, about 0.01M to about 0.5 M, about 0.01 M to about 0.4 M, about 0.1 to about 0.4 M, or about 0.1 to about 0.3 M. In some embodiments, the reductant, particularly ascorbic acid, is at a concentration of about 0.001 M, 0.005 M, 0.01 M, 0.02M, 0.03 M, 0.05 M, 0.1 M, 0.15 M, 0.2 M, 0.3 M, 0.4 M, or 0.5 M.

In some embodiments, the reaction conditions comprise molecular oxygen, i.e., $O_2$. Without being bound by theory, one atom of oxygen from molecular oxygen is incorporated into the substrate compound to form the hydroxylated product compound. The $O_2$ may be present naturally in the reaction solution, or introduced and/or supplemented into the reaction artificially. In some embodiments, the reaction conditions can comprise forced aeration (e.g., sparging) with air, $O_2$ gas, or other $O_2$-containing gases. In some embodiments, the $O_2$ in the reaction can be increased by increasing the pressure of the reaction with $O_2$ or an $O_2$-containing gas. This can be done by carrying out the reaction in a vessel that can be pressurized with $O_2$ gas. In some embodiments, the $O_2$ gas can be sparged through the reaction solution at a rate of at least 1 liter per hour (L/h), at least 2 L/h, at least 3 L/h, at least 4 L/h, at least 5 L/h, or greater. In some embodiments, the $O_2$ gas can be sparged through the reaction solution at a rate of between about 1 L/h and 10 L/h, between about 2 L/h and 7 L/h, or between about 3 L/h and 5 L/h.

During the course of the reaction, the pH of the reaction mixture may change. The pH of the reaction mixture may be maintained at a desired pH or within a desired pH range. This may be done by the addition of an acid or a base, before and/or during the course of the reaction. Alternatively, the pH may be controlled by using a buffer. Accordingly, in some embodiments, the reaction condition comprises a buffer. Suitable buffers to maintain desired pH ranges are known in the art and include, by way of example and not limitation, borate, phosphate, 2-(N-morpholino)ethanesulfonic acid (MES), 3-(N-morpholino)propanesulfonic acid (MOPS), acetate, triethanolamine, and 2-amino-2-hydroxymethyl-propane-1,3-diol (Tris), and the like. In some embodiments, the buffer is phosphate. In some embodiments of the process, the suitable reaction conditions comprise a buffer (e.g., phosphate) concentration of from about 0.01 to about 0.4 M, 0.05 to about 0.4 M, 0.1 to about 0.3 M, or about 0.1 to about 0.2 M. In some embodiments, the reaction condition comprises a buffer (e.g., phosphate) concentration of about 0.01, 0.02, 0.03, 0.04, 0.05, 0.07, 0.1, 0.12, 0.14, 0.16, 0.18, 0.2, 0.3, or 0.4 M. In some embodiments, the reaction conditions comprise water as a suitable solvent with no buffer present.

In the embodiments of the process, the reaction conditions can comprise a suitable pH. The desired pH or desired pH range can be maintained by use of an acid or base, an appropriate buffer, or a combination of buffering and acid or base addition. The pH of the reaction mixture can be controlled before and/or during the course of the reaction. In some embodiments, the suitable reaction conditions comprise a solution pH from about 4 to about 10, pH from about 5 to about 10, pH from about 5 to about 9, pH from about 6 to about 9, pH from about 6 to about 8. In some embodiments, the reaction conditions comprise a solution pH of about 4, 4.5, 5, 5.5, 6, 6.5, 7, 7.5, 8, 8.5, 9, 9.5, or 10.

In the embodiments of the processes herein, a suitable temperature can be used for the reaction conditions, for example, taking into consideration the increase in reaction rate at higher temperatures, and the activity of the enzyme during the reaction time period. Accordingly, in some embodiments, the suitable reaction conditions comprise a temperature of about 10° C. to about 60° C., about 10° C. to about 55° C., about 15° C. to about 60° C., about 20° C. to about 60° C., about 20° C. to about 55° C., about 25° C. to about 55° C., or about 30° C. to about 50° C. In some embodiments, the suitable reaction conditions comprise a temperature of about 10° C., 15° C., 20° C., 25° C., 30° C., 35° C., 40° C., 45° C., 50° C., 55° C., or 60° C. In some embodiments, the temperature during the enzymatic reaction can be maintained at a specific temperature throughout the course of the reaction. In some embodiments, the temperature during the enzymatic reaction can be adjusted over a temperature profile during the course of the reaction.

The processes of the disclosure are generally carried out in a solvent. Suitable solvents include water, aqueous buffer solutions, organic solvents, polymeric solvents, and/or co-solvent systems, which generally comprise aqueous solvents, organic solvents and/or polymeric solvents. The aqueous solvent (water or aqueous co-solvent system) may be pH-buffered or unbuffered. In some embodiments, the processes using the engineered proline hydroxylase polypeptides can be carried out in an aqueous co-solvent system comprising an organic solvent (e.g., ethanol, isopropanol (IPA), dimethyl sulfoxide (DMSO), dimethylformamide (DMF) ethyl acetate, butyl acetate, 1-octanol, heptane, octane, methyl t butyl ether (MTBE), toluene, and the like), ionic or polar solvents (e.g., 1-ethyl 4 methylimidazolium tetrafluoroborate, 1-butyl-3-methylimidazolium tetrafluoroborate, 1-butyl 3 methylimidazolium hexafluorophosphate, glycerol, polyethylene glycol, and the like). In some embodiments, the co-solvent can be a polar solvent, such as a polyol, dimethylsulfoxide (DMSO), or lower alcohol. The non-aqueous co-solvent component of an aqueous co-solvent system may be miscible with the aqueous component, providing a single liquid phase, or may be partly miscible or immiscible with the aqueous component, providing two liquid phases. Exemplary aqueous co-solvent systems can comprise water and one or more co-solvents selected from an organic solvent, polar solvent, and polyol solvent. In general, the co-solvent component of an aqueous co-solvent system is chosen such that it does not adversely inactivate the proline hydroxylase enzyme under the reaction conditions. Appropriate co-solvent systems can be readily identified by measuring the enzymatic activity of the specified engineered proline hydroxylase enzyme with a defined substrate of interest in the candidate solvent system, utilizing an enzyme activity assay, such as those described herein.

In some embodiments of the process, the suitable reaction conditions comprise an aqueous co-solvent, where the co-solvent comprises DMSO at about 1% to about 50% (v/v), about 1 to about 40% (v/v), about 2% to about 40% (v/v), about 5% to about 30% (v/v), about 10% to about 30% (v/v), or about 10% to about 20% (v/v). In some embodiments of the process, the suitable reaction conditions can comprise an aqueous co-solvent comprising DMSO at about 1% (v/v), about 5% (v/v), about 10% (v/v), about 15% (v/v), about 20% (v/v), about 25% (v/v), about 30% (v/v), about 35% (v/v), about 40% (v/v), about 45% (v/v), or about 50% (v/v).

In some embodiments, the reaction conditions can comprise a surfactant for stabilizing or enhancing the reaction. Surfactants can comprise non-ionic, cationic, anionic and/or amphiphilic surfactants. Exemplary surfactants, include by way of example and not limitation, nonyl phenoxypolyethoxylethanol (NP40), TRITON-X-100, polyoxyethylenestearylamine, cetyltrimethylammonium bromide, sodium oleylamidosulfate, polyoxyethylene-sorbitanmonostearate, hexadecyldimethylamine, etc. Any surfactant that may stabilize or enhance the reaction may be employed. The concentration of the surfactant to be employed in the reaction may be generally from 0.1 to 50 mg/ml, particularly from 1 to 20 mg/ml.

In some embodiments, the reaction conditions can include an antifoam agent, which aids in reducing or preventing formation of foam in the reaction solution, such as when the reaction solutions are mixed or sparged. Anti-foam agents include non-polar oils (e.g., minerals, silicones, etc.), polar oils (e.g., fatty acids, alkyl amines, alkyl amides, alkyl sulfates, etc.), and hydrophobic (e.g., treated silica, polypropylene, etc.), some of which also function as surfactants. Exemplary anti-foam agents include, Y-30® (Dow Corning), poly-glycol copolymers, oxy/ethoxylated alcohols, and polydimethylsiloxanes. In some embodiments, the anti-foam can be present at about 0.001% (v/v) to about 5% (v/v), about 0.01% (v/v) to about 5% (v/v), about 0.1% (v/v) to about 5% (v/v), or about 0.1% (v/v) to about 2% (v/v). In some embodiments, the anti-foam agent can be present at about 0.001% (v/v), about 0.01% (v/v), about 0.1% (v/v), about 0.5% (v/v), about 1% (v/v), about 2% (v/v), about 3% (v/v), about 4% (v/v), or about 5% (v/v) or more as desirable to promote the reaction.

The quantities of reactants used in the hydroxylase reaction will generally vary depending on the quantities of product desired, and concomitantly the amount of proline hydroxylase substrate employed. Those having ordinary skill in the art will readily understand how to vary these quantities to tailor them to the desired level of productivity and scale of production.

In some embodiments, the order of addition of reactants is not critical. The reactants may be added together at the same time to a solvent (e.g., monophasic solvent, biphasic aqueous co-solvent system, and the like), or alternatively, some of the reactants may be added separately, and some together at different time points. For example, the cofactor, co-substrate, proline hydroxylase, and substrate may be added first to the solvent.

The solid reactants (e.g., enzyme, salts, etc.) may be provided to the reaction in a variety of different forms, including powder (e.g., lyophilized, spray dried, and the like), solution, emulsion, suspension, and the like. The reactants can be readily lyophilized or spray dried using methods and equipment that are known to those having ordinary skill in the art. For example, the protein solution can be frozen at −80° C. in small aliquots, then added to a pre-chilled lyophilization chamber, followed by the application of a vacuum.

For improved mixing efficiency when an aqueous co-solvent system is used, the proline hydroxylase, and cofactor may be added and mixed into the aqueous phase first. The organic phase may then be added and mixed in, followed by addition of the proline hydroxylase substrate and co-substrate. Alternatively, the proline hydroxylase substrate may be premixed in the organic phase, prior to addition to the aqueous phase.

The hydroxylation process is generally allowed to proceed until further conversion of substrate to hydroxylated product does not change significantly with reaction time, e.g., less than 10% of substrate being converted, or less than 5% of substrate being converted). In some embodiments, the reaction is allowed to proceed until there is complete or near complete conversion of substrate to product. Transformation of substrate to product can be monitored using known methods by detecting substrate and/or product, with or without derivatization. Suitable analytical methods include gas chromatography, HPLC, MS, and the like.

In some embodiments of the process, the suitable reaction conditions comprise a substrate loading of at least about 5 g/L, 10 g/L, 20 g/L, 30 g/L, 40 g/L, 50 g/L, 60 g/L, 70 g/L, 100 g/L, or more, and wherein the method results in at least about 50%, 60%, 70%, 80%, 90%, 95% or greater conversion of substrate compound to product compound in about 48h or less, in about 36 h or less, or in about 24 h or less.

The engineered proline hydroxylase polypeptides of the present disclosure when used in the process under suitable reaction conditions result in an excess of the cis-hydroxylated product in at least 90%, 95%, 96%, 97%, 98%, 99%, or greater diastereomeric excess over the trans-hydroxylated product. In some embodiments, no detectable amount of compound trans-hydroxylated product is formed.

In further embodiments of the processes for converting substrate compound to hydroxylated product compound using the engineered proline hydroxylase polypeptides, the suitable reaction conditions can comprise an initial substrate loading to the reaction solution which is then contacted by the polypeptide. This reaction solution is then further supplemented with additional substrate compound as a continuous or batchwise addition over time at a rate of at least about 1 g/L/h, at least about 2 g/L/h, at least about 4 g/L/h, at least about 6 g/L/h, or higher. Thus, according to these suitable reaction conditions, polypeptide is added to a solution having an initial substrate loading of at least about 20 g/L, 30 g/L, or 40 g/L. This addition of polypeptide is then followed by continuous addition of further substrate to the solution at a rate of about 2 g/L/h, 4 g/L/h, or 6 g/L/h until a much higher final substrate loading of at least about 30 g/L, 40 g/L, 50 g/L, 60 g/L, 70 g/L, 100 g/L, 150 g/L, 200 g/L or more, is reached. Accordingly, in some embodiments of the process, the suitable reaction conditions comprise addition of the polypeptide to a solution having an initial substrate loading of at least about 20 g/L, 30 g/L, or 40 g/L followed by addition of further substrate to the solution at a rate of about 2 g/L/h, 4 g/L/h, or 6 g/L/h until a final substrate loading of at least about 30 g/L, 40 g/L, 50 g/L, 60 g/L, 70 g/L, 100 g/L or more, is reached. This substrate supplementation reaction condition allows for higher substrate loadings to be achieved while maintaining high rates of conversion of substrate to hydroxylated product of at least about 50%, 60%, 70%, 80%, 90% or greater conversion of substrate. In some embodiments of this process, the substrate added is in a solution comprising α-ketoglutarate at an equimolar or higher amount of the further added substrate.

In some embodiments of the processes, the reaction using an engineered proline hydroxylase polypeptide can comprise the following suitable reaction conditions: (a) substrate loading at about 5 g/L to 30 g/L; (b) about 0.1 g/L to 10 g/L of the engineered polypeptide; (c) about 19 g/L (0.13 M) to 57 g/L (0.39 M) of α-ketoglutarate; (d) about 14 g/L (0.08 M) to 63 g/L (0.36 M) ascorbic acid; (e) about 1.5 g/L (3.8 mM) to 4.5 g/L (11.5 mM) of $FeSO_4$; (f) a pH of about 6 to 7; (g) temperature of about 20° to 40° C.; and (h) reaction time of 2-24 h.

In some embodiments of the processes, the reaction using an engineered proline hydroxylase polypeptide can comprise the following suitable reaction conditions: (a) substrate loading at about 10 g/L to 100 g/L; (b) about 1 g/L to about 50 g/L of engineered polypeptide; (c) α-ketoglutarate at about 1 to 2 molar equivalents of substrate compound; (d) ascorbic acid at about 0.25 to 0.75 molar equivalents of substrate compound; (e) about 0.5 mM to about 12 mM of $FeSO_4$; (f) pH of about 6 to 8; (g) temperature of about 20° to 40° C.; and (h) reaction time of 6 to 120 h.

In some embodiments, additional reaction components or additional techniques carried out to supplement the reaction conditions. These can include taking measures to stabilize or prevent inactivation of the enzyme, reduce product inhibition, shift reaction equilibrium to hydroxylated product formation.

In further embodiments, any of the above described process for the conversion of substrate compound to product compound can further comprise one or more steps selected from: extraction; isolation; purification; and crystallization of product compound. Methods, techniques, and protocols for extracting, isolating, purifying, and/or crystallizing the hydroxylated product from biocatalytic reaction mixtures produced by the above disclosed processes are known to the ordinary artisan and/or accessed through routine experimentation. Additionally, illustrative methods are provided in the Examples below.

Various features and embodiments of the disclosure are illustrated in the following representative examples, which are intended to be illustrative, and not limiting.

6. EXAMPLES

Example 1: Synthesis, Optimization, and Screening Engineered Proline hydroxylase Polypeptides Gene synthesis and optimization: The polynucleotide sequence encoding the reported wild-type cis-4-proline hydroxylase polypeptide from *Sinorhizobium meliloti*, as represented by SEQ ID NO: 2, was synthesized as the gene of SEQ ID NO: 1. The synthetic gene of SEQ ID NO: 1 was cloned into a pCK110900 vector system (see e.g., US Patent Application Publication 20060195947, which is hereby incorporated by reference herein) and subsequently expressed in *E. coli* W311fhuA. The *E. coli* W3110 expresses the proline hydroxylase polypeptides under the control of the lac promoter. Based on sequence comparisons with other proline hydroxylases and computer modeling of the enzyme structure docked to the substrate proline, residue positions associated with the active site, peptide loops, solution/substrate interface, and potential stability positions were identified and subjected to mutagenesis. These first round variants were screened under HTP Assay conditions with (2S)-piperidine-2-carboxylic acid as substrate. Variants with increased enzymatic activity and/or expression were identified. Two additional codon optimized polynucleotides encoding the amino acid sequence of the naturally occurring enzyme was also generated (i.e., SEQ ID NO:3 and 5) for comparison purposes. The codon optimized polynucleotides 3 and 5 expressing the naturally occurring cis-4-proline hydroxylase showed increased expression relative to the polynucleotide of SEQ ID NO:1. The residue differences from the first round screening were combined in various permutations and screened for improved properties under HTP Assay, SFP Assay, and DSP Assay conditions. The engineered proline hydroxylase polypeptide sequences and specific mutations and relative activities obtained from the screens are listed in Table 2A, 2B, 2C, 2D, 2E, 2F, 2G, and 2H.

Example 2: Production of Engineered Proline Hydroxylases

The engineered proline hydroxylase polypeptides were produced in *E. coli* W3110 under the control of the lac promoter. Enzyme preparations for HTP, DSP, and SFP assays were made as follows.

High-throughput (HTP) growth, expression, and lysate preparation. Cells were picked and grown overnight in LB media containing 1% glucose and 30 µg/mL chloramphenicol (CAM), 30° C., 200 rpm, 85% humidity. A 20 µL aliquot of overnight growth was transferred to a deep well plate containing 380 µL 2×TB growth media containing 30 µg/mL CAM, 1 mM IPTG, and incubated for ~18 h at 30° C., 200 rpm, 85% humidity. Cell cultures were centrifuged at 4000 rpm, 4° C. for 10 min., and the media discarded. Cell pellets were resuspended in 100 µL Lysis Buffer (50 mM phosphate buffer, pH 6.3, containing 100 µM Mohr's salt (i.e., $(NH_4)_2Fe(SO_4)_2$), 0.5 mg/mL PMBS (polymyxin B sulfate) and 1 mg/mL Lysozyme). Lysis Buffer was prepared fresh by adding to 60 mL of 50 mM phosphate buffer, pH 6.3, 60 mg Lysozyme and 30 mg of PMBS. After mixing the Lysozyme solution, 0.6 mL of 10 mM Mohr's salt solution (in $H_2O$) was added.

Production of shake flask powders (SFP): A shake-flask procedure was used to generate engineered proline hydroxylase polypeptide powders used in secondary screening assays or in the biocatalytic processes disclosed herein. Shake flask powder (SFP) provides a more purified preparation (e.g., up to 30% of total protein) of the engineered enzyme as compared to the cell lysate used in HTP assays. A single colony of *E. coli* containing a plasmid encoding an engineered polypeptide of interest is inoculated into 50 mL Luria Bertani broth containing 30 µg/ml chloramphenicol and 1% glucose. Cells are grown overnight (at least 16 hours) in an incubator at 30° C. with shaking at 250 rpm. The culture is diluted into 250 mL Terrific Broth (12 g/L bactotryptone, 24 g/L yeast extract, 4 mL/L glycerol, 65 mM potassium phosphate, pH 7, 1 mM $MgSO_4$) containing 30 µg/ml chloramphenicol, in a 1 liter flask to an optical density of 600 nm (OD600) of 0.2 and allowed to grow at 30° C. Expression of the proline hydroxylase gene is induced by addition of isopropyl-β-D-thiogalactoside ("IPTG") to a final concentration of 1 mM when the OD600 of the culture is 0.6 to 0.8. Incubation is then continued overnight (at least 16 hours). Cells are harvested by centrifugation (5000 rpm, 15 min, 4° C.) and the supernatant discarded. The cell pellet is resuspended with an equal volume of cold (4° C.) 50 mM potassium phosphate buffer, pH 6.3, and harvested by centrifugation as above. The washed cells are resuspended in two volumes of the cold 50 mM potassium phosphate buffer, pH 6.3 and passed through a French Press twice at 12,000 psi while maintained at 4° C. Cell debris is removed by centrifugation (9000 rpm, 45 minutes, 4° C.). The clear lysate supernatant is collected and stored at −20° C. Lyophilization of frozen clear lysate provides a dry shake-flask powder of crude engineered polypeptide. Alternatively, the cell pellet (before or after washing) can be stored at 4° C. or −80° C.

Production of downstream process powders (DSP): DSP powders provide a more purified preparation of the engineered proline hydroxylase enzyme as compared to the cell lysate used in the HTP or SFP assays. Larger-scale fermentation of the engineered proline hydroxylase for production of DSP powders (~100-120 g from 10 L) can be carried out as a short batch followed by a fed batch process according to standard bioprocess methods. Briefly, proline hydroxylase expression is induced by addition of IPTG to a final concentration of 1 mM. Following fermentation, the cells are harvested and resuspended in 50 mM phosphate buffer, then mechanically disrupted by homogenization. The cell debris and nucleic acid are flocculated with polyethylenimine (PEI) and the suspension clarified by centrifugation. The resulting clear supernatant is concentrated using a tangential cross-flow ultrafiltration membrane to remove salts and water. The concentrated and partially purified enzyme concentrate can then be dried in a lyophilizer and packaged (e.g., in polyethylene containers).

Example 3: Analytical Procedures

Method 1—HPLC Analysis of HTP Assay Reactions: In a 96 deep well format assay block, 10 µL of reaction solution was diluted with 230 µL of 5% sodium bicarbonate solution followed by 160 µL of dansyl chloride solution (6 mg/mL dansyl chloride in MeCN). The plate was heat sealed, centrifuged, and placed in an incubator at 55° C. for 45 minutes. The reaction solution turns from yellow to light yellow when derivatization with dansyl chloride is complete. In cases where the solution remained yellow, the plate was heated for another 15 min. After incubation, the plate was centrifuged for 5 min at 4000 rpm. A 200 µL aliquot of supernatant was transferred into a 96 Corning plate for HPLC analysis. The final concentration of the substrate was below 0.25 g/L.

The quenched reaction was subject to HPLC analysis under the following conditions.

| Column | Agilent Poroshell120 SB-CI8 50 × 4.6 mm (2.7 11 m) with guard column |
|---|---|
| Temperature | 30° C. |
| Mobile Phase | Solution A: 2 mM Ammonium Acetate pH 3.3 |
| | Solution B: Acetonitrile |
| | Mobile Phase Profile |

| Time: min | A% | B% | Flow rate: mL/min |
|---|---|---|---|
| 0.00 | 80 | 20 | 2.0 |
| 2.00 | 30 | 70 | 2.0 |
| 3.00 | 30 | 70 | 2.0 |

| | |
|---|---|
| Postime | 1 min |
| Detection Wavelength | 250 nm |
| Column Temperature | 25° C. |
| Injection Volume | 10 µL |
| Total Runtime | 4 min |
| Response Factor (Substrate area/Product area) | N.A. |

Conversion of compound (2) to compound (1) was determined from the resulting chromatograms as follows:

% Conversion={(RF×Product Area)/[(RF×Product Area)+Substrate Area]}×100 where

Response Factor (RF)=Substrate Area/Product Area.

This method was used for rapid identification for conversion of (2S)-piperidine-2-carboxylic acid to hydroxypiperidine-2-carboxylic acid.

The chromatographic elution profiles, denoted as "Response time", are as follows:

| | | |
|---|---|---|
| (2S,5S)-1-(5-(dimethylamino)naphthalene-1-ylsulfonyl)-5-hydroxypiperidine-2-carboxylic acid | 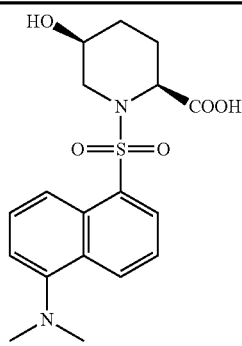 | Response time: 1.59 min |
| (2S,3R)-1-(5-(dimethylamino)naphthalene-l-ylsulfonyl)-3-hydroxypiperidine-2-carboxylic acid | 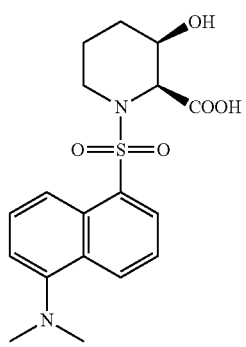 [SMILES: CN(C)c1cccc2c(S(=O)(=O)N3CCC[C@@H](O)[C@H]3C(=O)O)cccc12] | Response time: 1.76 min |
| (S)-1-(5-(dimethylamino)naphthalene-1-ylsulfonyl)piperidine-2-carboxylic acid | 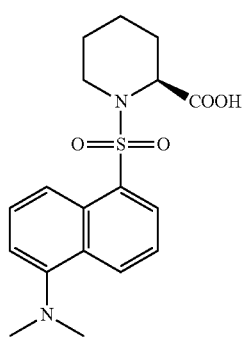 [SMILES: CN(C)c1cccc2c(S(=O)(=O)N3CCCC[C@H]3C(=O)O)cccc12] | Response time: 2.23 min |

Method 2—HPLC Analysis of DSP and SFP Reactions: A 10 µL of reaction solution from a DSP or SFP reaction was pipetted into a 1.5 ml Eppendorf tube and diluted with 230 µL of 5% sodium bicarbonate. A 160 µL aliquot of dansyl chloride solution (6 mg/ml dansyl chloride in MeCN) was then added. The tube was heated with open cover at 55° C. for at least 30 minutes in a heating block to ensure full derivatization, as indicated by change in color of the derivatization mixture from a yellow to a light yellow color. The tube was vortexed and then centrifuged at 12,000 rpm for 5 minutes. A 200 µL aliquot of supernatant was transferred into a 2 ml HPLC vial with insert. The vial was submitted to reverse phase HPLC-UV for analysis, as described below. The final concentration of the substrate was below 0.25 gat.

The quenched reaction was subject to HPLC analysis under the following conditions.

| | |
|---|---|
| Column | Supelco Ascentis Express C18 100 × 4.6 mm (2.7 11 m), attached |

-continued

| Mobile Phase | Solution A: 2 mM Ammonium Acetate, pH 3.3 Solution B: Acetonitrile Mobile Phase Profile | | | |
|---|---|---|---|---|
| | Time: min | A % | B % | Flow rate: mL/min |
| | 0 | 80 | 20 | 1.0 |
| | 9.0 | 27.5 | 72.5 | 1.0 |
| | 9.1 | 0 | 100 | 1.0 |
| | 12.0 | 0 | 100 | 1.0 |
| | 12.1 | 80 | 20 | 1.0 |
| Postime | 2.90 min | | | |
| Detection Wavelength | 250 nm | | | |
| Column Temperature | 25° C. | | | |
| Injection Volume | 10 µL | | | |
| Total Runtime | 15.0 min | | | |
| Response Factor (RF) (Substrate area/Product area) | N.A. | | | |

The chromatographic elution profiles are as follows:

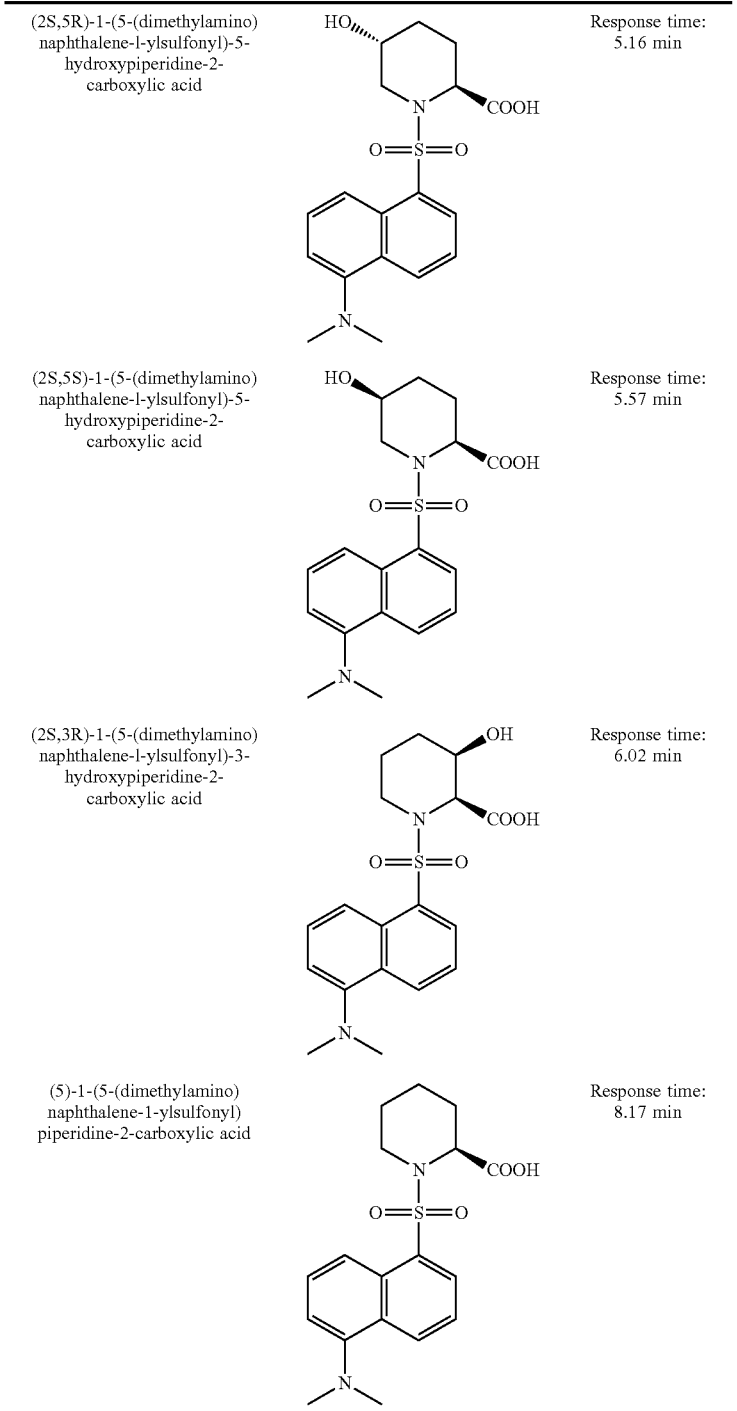

| Compound | Response time |
|---|---|
| (2S,5R)-1-(5-(dimethylamino)naphthalene-l-ylsulfonyl)-5-hydroxypiperidine-2-carboxylic acid | 5.16 min |
| (2S,5S)-1-(5-(dimethylamino)naphthalene-l-ylsulfonyl)-5-hydroxypiperidine-2-carboxylic acid | 5.57 min |
| (2S,3R)-1-(5-(dimethylamino)naphthalene-l-ylsulfonyl)-3-hydroxypiperidine-2-carboxylic acid | 6.02 min |
| (S)-1-(5-(dimethylamino)naphthalene-1-ylsulfonyl)piperidine-2-carboxylic acid | 8.17 min |

Example 4: High Throughput (HTP) Screening of Proline Hydroxylases for Conversion of Compound (2) to Compound (1)

HTP Screening Assays: High-throughput screening used to guide primary selection of variants was carried out in 96-well plates using cell lysates. Two conditions, Condition A and Condition B, were used.

Condition A reactions were carried out as follows. Cells were grown in 96-well plates as described above and lysates prepared by dispensing 100 μL Lysis Buffer into each well. Lysis buffer was prepared by dissolving 30 mg of lysozyme and 15 mg of PMBS in 30 mL of 50 mM phosphate buffer, pH 6.3. A 600 μL volume of 10 mM Mohr's salt, freshly prepared in sterile water, was added to the lysozyme solution. The plate was heat sealed and then shaken on a titre-plate shaker at Speed #8 for 2 h at room temperature. Subsequently, the plate was quick-spun to settle the lysate at the bottom of the plate. This crude lysate was to be used for the reaction.

The Condition A reactions in 200 μL scale were carried out in 98 well plates. A premix stock solution was prepared by dissolving 1.33 g of α-ketoglutaric acid and 1.47 g of L-ascorbic acid in 31.5 mL of 50 mM phosphate buffer, pH 6.3 (pH adjusted by using KOH). After mixing, the pH was adjusted to 6.3 with KOH. To the pH adjusted premix, 41.16 mg of Mohr's salt was added. The solution turns cloudy due to the low solubility of Mohr's salt in aqueous solvents.

To each 100 μL of crude lysates prepared above, 90 μL of the premix stock solution was added into each well, followed immediately by 10 uL/well of a 200 g/L substrate stock solution, i.e., compound (2) prepared in 50 mM phosphate buffer, pH 6.3. The plate was sealed with an AirPore seal (Qiagen) and the reaction left to proceed overnight on a titre-shaker, with shaking speed of #2.5 at room temperature.

Condition A has the following final reaction parameters: (a) 10 g/L substrate loading; (b) 19 g/L α-ketoglutaric acid; (c) 21 g/L ascorbic acid; (d) 1.5 mM Mohr's salt; (e) 50 mM phosphate buffer, pH 6.3 (pH adjusted with KOH); (f) ambient temperature (20° C. to 25° C.); and (g) reaction time of about c.a. 24 h.

Following the overnight incubation, the plates were centrifuged at 4000 rpm for 5 min at room temperature. The reaction samples were derivatized and quenched by aliquoting 10 μL of the clear reaction mix into a 96 deep well plate containing 230 μL/well of 5% sodium bicarbonate (aq). A 160 μL volume of 6 mg/mL of dansyl chloride in MeCN was added to each well, the plate heat sealed, and then quick spun to settle the reaction solution to the bottom of the well. The plate was then heated at 55° C. for at least 45 min without shaking, and centrifuged at 4000 rpm for 10 min at room temperature. A 200 μL volume of the derivatized solution was transferred into a 96 round bottom plate and submitted for HPLC analysis.

Condition B reactions were carried out as follows. Cells were grown in 96-well plates as described above and lysates prepared by dispensing 100 μL of Lysis Buffer into each well. Lysis buffer was freshly prepared by dissolving 30 mg of lysozyme and 15 mg of PMBS in 30 mL of 50 mM phosphate buffer, pH 6.3, followed by 600 μL volume of 10 mM Mohr's salt, freshly prepared in sterile water. The lysis plate was heat sealed and then shaken on a titre-plate shaker at Speed #8 for 2 h at room temperature. Subsequently, the plate was quick-spun to settle the lysate at the bottom of the plate. This 100 μL crude lysate was to be used for the reaction.

The Condition B reactions in 200 μL scale were carried out in 98 well plates. A premix stock solution was prepared by dissolving 1.33 g of α-ketoglutaric acid and 1.47 g of L-ascorbic acid in 31.5 mL of 50 mM phosphate buffer, pH 6.3 (pH adjusted by using KOH). After mixing, the pH was adjusted to 6.3 with KOH. To the pH adjusted premix, 41.16 mg of Mohr's salt was added.

To each 100 μL of crude lysates prepared above, 90 μL of the premix stock solution was added into each well, followed immediately by 10 uL/well of a 200 g/L substrate stock solution, i.e., compound (2) prepared in 50 mM phosphate buffer, pH 6.3. The plate was sealed with an AirPore® seal (Qiagen) and the reaction left to proceed overnight on a titre-shaker, with shaking speed of #2.5 at room temperature.

Condition B has the following final reaction parameters: (a) 10 g/L substrate loading; (b) 19 g/L α-ketoglutaric acid; (c) 21 g/L ascorbic acid; (d) 1.5 mM Mohr's salt; (e) 50 mM phosphate buffer pH 6.3 (pH adjusted with KOH); (f) ambient temperature (20° C. to 25° C.); and (g) reaction time of c.a. 24 h.

Following the overnight incubation, the plates were centrifuged at 4000 rpm for 5 min at room temperature. The reaction samples were derivatized and quenched by aliquoting 10 μL of the clear reaction mix into a 96 deep well plate containing 230 μL/well of 5% sodium bicarbonate (aq). A 160 μL volume of 6 mg/mL of dansyl chloride in MeCN was added to each well, the plate heat sealed, and then quick spun to settle the reaction solution to the bottom of the well. The plate was then heated at 55° C. for at least 45 min with shaking on an Infors HT Microtron with a shaking speed of 500 rpm. The plates were centrifuged at 4000 rpm for 10 min at room temperature. A 200 μL volume of the derivatized solution was transferred into a 96 round bottom plate and submitted for HPLC for analysis.

Example 5: Process for Conversion of Compound (2) to Compound (1) Using Shake Flask Powder (SFP) Preparations A 200 μL scale reaction using SFP enzyme powder was carried out as follows. A premix stock solution was freshly prepared by dissolving 1.05 g of α-ketoglutaric acid, 420 mg of L-ascorbic acid, and 600 mg of substrate (2S)-piperidine-2-carboxylic acid in 10 mL of 50 mM phosphate buffer, pH 6.3 (pH adjusted by using KOH). After thoroughly mixing the solution, the pH was adjusted to 6.3 using KOH. To the pH adjusted premix solution, 45 mg of Mohr's salt was added.

A stock solution of enzyme was prepared by dissolving 20 mg of SFP enzyme powder into 2 mL of 50 mM phosphate buffer, pH 6.3. To initiate the reaction, 100 μL of enzyme solution was added into a plate followed by 100 μL of premix stock solution for a final reaction volume of 200 μL. The plate was sealed with an AirPore® seal (Qiagen) and the reaction allowed to proceed overnight (c.a., 24 h) with shaking on a titre-plate shaker (speed #2.5) at room temperature.

The SFP Assay condition (i.e., Condition C) has the following final parameters: (a) 5 g/L enzyme powder loading; (b) 30 g/L substrate loading; (c) 52.5 g/L α-ketoglutaric acid; (d) 21 g/L L-ascorbic acid; (e) 2.25 mM Mohr's salt; (f) 50 mM potassium phosphate buffer, pH 6.3 (pH adjusted with KOH), (g) reaction temperature at ambient room temperature; and (h) reaction time of about c.a. 24 h. In some reactions, the reaction conditions further contained 1% (v/v) Y-30® antifoam (Dow Corning), and the reaction solution was sparged with $O_2$ gas at 2 L/h.

The reactions were quenched with 400 μL of 75% MeCN and 25% $H_2O$. The plates were shaken for 10 min at room temperature and centrifuged at 4000 rpm. Derivatization was carried out by transferring 20 μL of quenched reaction to a 96 deep well plate containing 230 μL/well of 5% sodium bicarbonate (aq). A 150 μL aliquot of 21 mg/mL dansyl chloride in MeCN was added to each well. The plate was heat sealed and quick spun, and the plates incubated at 65° C. for at least 1 h with shaking on an Infors HT Microtron at a shaking speed of 500 rpm. The plates were then centrifuged at 4000 rpm for 10 min at room temperature. A 200 μL volume of the derivatized solution was transferred into a 96 round bottom plate and submitted for analysis by HPLC.

Example 6: Process for Conversion of Compound (2) to Compound (1) Using Downstream Process Powder (DSP) Preparations Two reaction conditions were used for downstream process powder (DSP) preparations. The first reaction conditions, referred to as "mini-DSP" conditions (i.e., Condition D) were carried out on a 1 mL scale as follows. A premix stock solution was freshly prepared by dissolving 120 mg of (2S)-piperidine-2-carboxylic acid (i.e., L-pipecolic acid), 228 mg of α-ketoglutaric acid and 252 mg of L-ascorbic acid in 11.88 mL of 50 mM phosphate buffer, pH 6.3. The pH of the premix solution was then adjusted to 6.3 using KOH. A 120 µL volume of 150 mM Mohr's salt (in sterile water) was added to form the premix stock solution.

Reactions were run by weighing 20 mg of the DSP enzyme powder into a vial followed by 1 mL of premix stock solution. The solution was thoroughly mixed, and the vial left open overnight (~24 h) at room temperature. The reaction solution was stirred at 1200 rpm during the course of the reaction.

The "mini DSP" reaction conditions have the following parameters: (a) 20 g/L substrate loading; (b) 34 g/L α-ketoglutaric acid (1.5 equivalents of substrate); (c) 13.6 g/L ascorbic acid (0.5 equivalents of substrate); (d) 1.5 mM Mohr's salt; (e) 20 g/L protein of DSP enzyme preparation; (f) 50 mM phosphate buffer, pH 6.3 (pH adjusted with KOH); (f) ambient temperature; and (g) reaction time of ~24 h. In some reactions, the reaction solution further contained 1% (v/v) of Y-30® antifoam (Dow Corning) and the reaction solution was sparged with $O_2$ gas at 2 L/h during the course of the reaction.

To follow the course of the reaction, 10 µL samples were taken and dissolved in 230 µL of 5% sodium bicarbonate (aqueous). A 160 µL volume of 6 mg/mL of dansyl chloride in MeCN was then added to the mixture, the tubes thoroughly mixed, and then heated, uncapped at 50° C. for 30 minutes. The samples were then centrifuged, and the clear supernatant analyzed by HPLC as described in Example 2.

The second reaction conditions, referred to as "full DSP" conditions, were carried out as follows. A premix stock solution was freshly prepared for 1 mL scale reactions by dissolving 240 mg of (2S)-piperidine-2-carboxylic acid (L-pipecolic acid), 228 mg of α-ketoglutaric acid, and 252 mg of L-ascorbic acid in 11.88 mL of 50 mM phosphate buffer, pH 6.3. The pH of the premix solution was adjusted to 6.3 with KOH. A 120 µL volume of 150 mM Mohr's salt (in sterile water) was added to form the premix stock solution.

Reactions were run by weighing 10 mg of the DSP enzyme powder and adding 1 mL of premix stock solution. After mixing, the vial was left open overnight (~24 h) at room temperature. The reaction solution was stirred at 1200 rpm during the course of the reaction.

The "full DSP" reaction conditions has the following parameters; (a) 10 g/L substrate loading; (b) 38 g/L α-ketoglutaric acid; (c) 21 g/L ascorbic acid; (d) 1.5 mM Mohr's salt; (e) 10 g/L DSP enzyme preparation; (f) 50 mM phosphate buffer, pH 6.3 (pH adjusted with KOH); (f) reaction temperature of 25° C.; and (g) reaction time of c.a. 24 h. In some reactions, the reaction solution contained t % (v/v) Y-30® antifoam (Dow Corning), and the reaction solution was sparged with $O_2$ gas at 2 L/h.

To follow the course of the reaction, 10 µL samples were removed and mixed with 230 µL of 5% sodium bicarbonate (aq). A 160 µL volume of 6 mg/mL of dansyl chloride in MeCN was then added to the mixture. The tubes were thoroughly mixed and then heated, uncapped at 50° C. for 30 minutes. The samples were then centrifuged and the clear supernatant analyzed by HPLC as described in Example 2.

Example 7: Process for Conversion of Compounds of Formula (II) to Compounds of Formula (I) Using DSP Powders of Engineered Proline Hydroxylase Polypeptides The ability of the engineered proline hydroxylases to recognize substrates other than proline or pipecolic acid were examined. The reaction conditions comprised (a) 20 g/L substrate loading; (b) 35 g/L α-ketoglutaric acid; (c) 14 g/L ascorbic acid; (d) 1.5 mM Mohr's salt; (e) 10 g/L protein of DSP enzyme preparation of SEQ ID NO: 108; (f) 50 mM phosphate buffer, pH 6.3 (pH adjusted with KOH); (f) reaction temperature of 25° C.; and (g) reaction time of ~24 h. The negative controls used enzyme preparations obtained from cells transformed with expression vector that did not have a gene encoding a proline hydroxylase.

| Substrate | Substrate Structure | Neg Control | Rxn | Product(s) | Product Structure(s) |
|---|---|---|---|---|---|
| L-pipecolic acid | [structure] | − | +++++ | 2 regioisomers | [structure] [structure] |
| L-proline | [structure] | − | ++++ | 1 isomer | [structure] |

| Substrate | Substrate Structure | Neg Control | Rxn | Product(s) | Product Structure(s) |
|---|---|---|---|---|---|
| L-norvaline | | + | ++ | 2 isomers | |
| S-(1,2,3,4)-tetrahydro-3-isoquinoline carboxylic acid | | + | ++ | 3 major products | |

The reactions were quenched by diluting 2000-fold in 50:50 acetonitrile:$H_2O$, and the reaction products analyzed by LC/MS/MS.

LC/MS/MS analysis for pipecolic acid, proline and norvaline was carried out under the following conditions:

| Column | ChiroBiotic TAG 250 × 4.6 mm, 5 μm |
|---|---|
| Mobile Phase | Solution A: 0.1% formic acid |
| | Solution B: 0.1% formic acid in Acetonitrile |
| | A:B = 50:50 |
| Postime | 5.0 min |
| MS conditions | Source dependent parameters: CUR 30, IS 5500, TEM 590° C., GS1 60, GS2 60, DP30, EP10, CE 20 |
| | MRM: 130/84 (pipecolic acid RT 4.2 min), 146/100 and 146/82 (hydroxylated pipecolic acid 3.2 min and 3.7 min) |
| | MRM: 116/70 (proline RT 3.4 min), 132/86 and 132/68 (hydroxylproline RT 2.7 min) |
| | MRM: 118/72 (norvaline RT 2.7 min), 134/88, 134/74 and 134/70 (hydroxylated norvaline RT 2.6 & 2.7 min) |
| Column Temperature | Not controlled |
| Injection Volume | 2 μL |

The quenched reaction for tetrahydroisoquinoline carboxylic acid was subject to LC/MS/MS analysis under the following conditions:

| Column | Poroshell EC C18 100 × 4.6 mm, 2.7 μm |
|---|---|
| Mobile Phase | Solution A: 0.5 mM perfluoroheptanoic acid |
| | Solution B: Acetonitrile |

| Time (min) | Flow (ml/min) | A | B |
|---|---|---|---|
| 0-1.5 | 0.8 | 97 | 3 |
| 9 | 0.8 | 70 | 30 |
| 12 | 0.8 | 70 | 30 |
| 13 | 0.8 | 97 | 3 |
| 20 | 0.8 | 97 | 3 |

| Postime | 20 min |
|---|---|
| MS conditions | Source dependent parameters: CUR 30, IS 5500, TEM 600° C., GS1 60, G52 60, DP30, EP10, CE 30 |
| | MRM: 194/148 and 194/146 (hydroxylated tetrahydroisoquinoline carboxylic acid RT 5.7 min, 7.26 min and 9.73 min) |
| Column Temperature | Not controlled |
| Injection Volume | 2 μL |

Example 8: Process for Conversion of L-Pipecolic Acid (Compound (2)) to (2S,5S)-5-Hydroxypiperidine-2-Carboxylic Acid (Compound (1)) Followed by Boc-Protection Step Enzymatic reaction: A solution of L-pipecolic acid (15 g) dissolved in 138 ml of 50 mM potassium phosphate buffer, pH 6.3 was charged to a pre-mixed solution containing: (i) DSP preparation of the polypeptide of SEQ ID NO: 132 (5 g); (ii) Antifoam Y-30 emulsion (5 mL); (iii) Mohr's salt (1.08 g); (iv) α-ketoglutaric acid (25.5 g); and (iv) ascorbic acid (10.2 g); all dissolved in 250 mL of 50 mM potassium phosphate buffer, pH 6.3. The resulting mixture was stirred and sparged with oxygen at a rate of 3 L/h and 25° C. The progress of the enzymatic reaction was monitored by HPLC using Method 2 of Example 3. The conversion of L-pipecolic acid to (2S,5S)-5-hydroxypiperidine-2-carboxylic acid followed a reaction course of ~78% conversion at 25 h, ~92% conversion at 45 h, and ~94% conversion by 52 h, but did not reach higher conversion at 75h. The region purity of the (2S,5S)-5-hydroxypiperidine-2-carboxylic acid product after 52 h reaction was 6:1.

Boc-protection: Crude mixture from the enzymatic reaction was adjusted to pH 9.5 with KOH (50% w/w), heated to 60° C. for 1 h, and then cooled to room temperature. Thereafter, Celite filter-aid (15 g) was added with stirring (10 minutes) and the mixture was filtered through a 1 cm thick pad of Celite 545. The filter cake was washed with water (60 mL) and the filtrate charged with NaOH (38.5 mL at 10 M) and di-tert-butyl dicarbonate ($Boc_2$-O) (42.2 g in 75 mL THF). Upon reaction completion (~96% conversion in two days) the aqueous phase was washed twice with heptanes (2×125 mL). The heptane washings were discarded and the aqueous phase was adjusted to pH 3.5 with 5 M HCl, and treated with NaCl (40 g). The aqueous phase was extracted with t-butyl methyl ether (TBME) (3×125 mL), and the resulting organic phase extracts were combined, dried over $MgSO_4$, filtered and concentrated to give crude (2S,5S)-1-(tert-butoxycarbonyl)-5-hydroxypiperidine-2-carboxylic acid.

Isolation: A solution of the crude (2S,5S)-1-(tert-butyloxycarbonyl)-5-hydroxypyridine-2-carboxylic acid product (25 g) in TBME (250 mL) was agitated with a magnetic stirrer bar, insolubles were filtered, and rinsed with TBME (150 mL). The concentrated filtrate was dried under vacuum overnight and dissolved in isopropyl acetate (100 mL) and heptane (100 mL). The resulting mixture was heated at 80° C. for 20-25 minutes, insolubles were removed by hot filtration, filtrate was cooled and stirred for 24 h at room temperature. The solid was filtered and the cake washed with chilled (0 to 5° C.) heptanes-isopropyl acetate mixture (1:1 of 50 mL). Solid product was collected and dried under vacuum overnight to afford purified (2S,5S)-1-(tert-butyloxycarbonyl)-5-hydroxypyridine-2-carboxylic acid (8.6 g, 30% yield).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An engineered polypeptide having proline hydroxylase activity, comprising an amino acid sequence having at least 95% sequence identity to SEQ ID NO:2 and having a residue difference at residue position X25.

2. The engineered polypeptide of claim 1, wherein the polypeptide further comprises one or more residue differences at residue positions selected from X2; X4; X5; X9; X13; X26; X29; X30; X36; X42; X52, X57; X58; X59; X66; X92; X95; X112; X115; X116; X121; X131; X150; X151; X225; X230; and X271.

3. The engineered polypeptide of claim 1, wherein the amino acid sequence further comprises at least a combination of amino acid differences selected from:

(a) X103L and X166Q;
(b) X52P and X255Y;
(c) X4E/L/S and X115A;
(d) X25R and X58A;
(e) X29A and X166T/Q/L;
(f) X115H/D/G and X121F;
(g) X3S, X103L, and X166Q;
(h) X103L, X131Y/F, and X166T/Q/L;
(i) X26T, X103L and X166T/Q/L;
(j) X25R, X66Q, X92V and X115E;
(k) X25R, X66Q, X92V, X103L, X115E, and X166Q; and
(l) X3S, X25R, X66Q, X92V, X103L, X115E, and X166Q.

4. The engineered polypeptide of claim 1, wherein the polypeptide further comprises one or more residue differences as compared to the sequence of SEQ ID NO: 2 at residue positions selected from: X17, X24, X26, X62, X88, X98, X114, X140, X151, X186, X188, and X205.

5. The engineered polypeptide of claim 4, wherein the residue differences at residue positions X17, X24, X26, X62, X88, X98, X114, X140, X151, X186, X188, and X205 are selected from X17V, X24R, X24S, X26R, X26W, X62Q, X88R, X98F, X98T, X114N, X140L, XI51A, X151H, X186G, X188G, and X205V.

6. The engineered polypeptide of claim 1, wherein the proline hydroxylase activity of the polypeptide converts substrate compound (2), (2S)-piperidine-2-carboxylic acid,

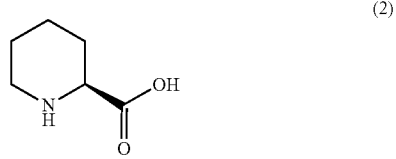

(2)

to product compound (1), (2S,5S)-5-hydroxypiperidine-2-carboxylic acid,

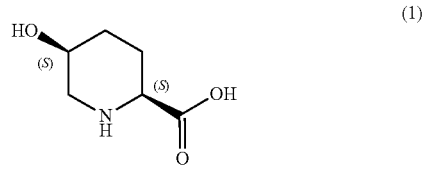

(1)

under suitable reaction conditions.

7. The engineered polypeptide of claim 6, wherein the proline hydroxylase activity of the polypeptide converts substrate compound (2) to product compound (1) with at least 2 fold the activity of SEQ ID NO:2, and wherein the amino acid sequence further comprises one or more residue differences selected from the group consisting of: X4Q; X4L; X51; X5L; X24S; X30P; X66Q; X86S; X92V; X113E; X115E; X150S; X166Q; X151S; X225L; and X270E.

8. The engineered polypeptide of claim 1, wherein the proline hydroxylase activity polypeptide converts substrate compound (2) to product compound (1) in excess of product compound (1a), (2S,3R)-3-hydroxypiperidine-2-carboxylic acid,

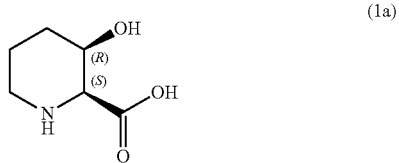

(1a)

and wherein the amino acid sequence further comprises one or more residue differences selected from the group consisting of: X115E; X131Y and X166Q.

9. The engineered polypeptide of claim 1, wherein the polypeptide forms product compound (1),

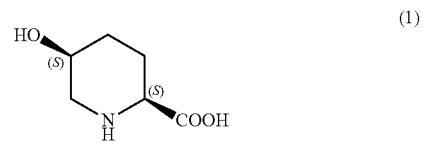

(1)

in diastereomeric excess of product compound (1R), (2S,5R)-5-hydroxypiperidine-2-carboxylic acid,

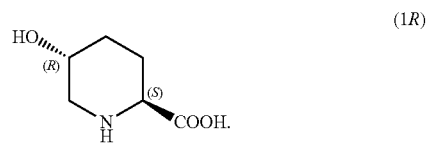

(1R)

10. The engineered polypeptide of claim 1 having proline hydroxylase activity, wherein the amino acid sequence comprises a sequence selected from the group consisting of SEQ ID NO: 58 128, 132, 134, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, and 228.

11. The engineered polypeptide of claim 1 the residue difference at position X25 is X25R.

12. The engineered polypeptide of claim 2, wherein the one or more residue differences at positions X2; X4; X5; X9; X13; X26; X29; X30; X36; X42; X52; X57; X58; X59; X66; X92; X95; X112; X115; X116; X121; X131; X150; X151; X225; X230; and X271 are selected from X2K; X2T; X4Q; X4L; X4E; X4S; X51; X5L; X5M; X91; X13T; X26T; X29A; X30V; X30P; X36T; X42E; X52P; X57T; X57A; X58A; X59G; X66Q; X86S; X92V; X95M; X112T; X112V; X113E, X115E; X115H; X115D; X115G; X115S; X115A; X116L; X121F; X131Y; X131F; X150S; X151S; X225L; X225Y; X225W; X230V; X270E; X271K; and X271R.

* * * * *

```
                         SEQUENCE LISTING

Sequence total quantity: 228
SEQ ID NO: 1            moltype = DNA  length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 1
atgtctacgc atttccttgg caaggtcaaa ttcgacgagg ccagattagc cgaagatctg  60
tctactttag aagtcgctga gttttctagt gcatattcgg acttcgcttg tggaaagtgg 120
gaagcatgtg ttttacgcaa cagaacaggc atgcaagaag aagacattgt ggtttctcac 180
aatgcgcccg cattagcgac ccctttatct aaatcactgc cgtacttgaa tgagcttgtt 240
gaaacacact tcgactgcag tgcggttaga tatacgcgta tcgtgcgtgt ctccgagaac 300
gcctgcatta tccctcatag tgattatttg gagctcgatg aaacgttcac ccggctgcac 360
ctcgtgttgg atactaacag tggttgtgcc aacactgagg aagataagat attccacatg 420
ggtctgggcg agatctggtt tctggacgca atgttacctc attctgctgc ctgcttttct 480
aaaactccta gactgcatct catgatagat tttgaagcta ccgccttccc ggaatccttc 540
ttacgcaatg tggaacagcc tgtaactact cgcgacatgg tagaccctcg taagaattg  600
acggacgaag ttatagaagg cattttaggg ttctccataa tcatcagtga agcgaattac 660
cgcgagatcg tctctatcct ggccaaatta cacttctttt ataaagcgga ctgtcggtcc 720
atgtatgatt ggcttaaaga aatatgtaaa cgccggggag atcccgcgtt gattgagaag 780
acagcgagtc tcgaacgttt cttttgggg catcgtgaac gggagaagt aatgacgtat 840
taa                                                                843

SEQ ID NO: 2            moltype = AA  length = 280
FEATURE                 Location/Qualifiers
source                  1..280
                        mol_type = protein
                        organism = Sinorhizobium meliloti
SEQUENCE: 2
MSTHFLGKVK FDEARLAEDL STLEVAEFSS AYSDFACGKW EACVLRNRTG MQEEDIVVSH  60
NAPALATPLS KSLPYLNELV ETHFDCSAVR YTRIVRVSEN ACIIPHSDYL ELDETFTRLH 120
LVLDTNSGCA NTEEDKIFHM GLGEIWFLDA MLPHSAACFS KTPRLHLMID FEATAFPESF 180
LRNVEQPVTT RDMVDPRKEL TDEVIEGILG FSIIISEANY REIVSILAKL HFFYKADCRS 240
MYDWLKEICK RRGDPALIEK TASLERFFLG HRERGEVMTY                       280

SEQ ID NO: 3            moltype = DNA  length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 3
atgagtaccc actttctcgg caaagtgaaa ttcgatgaag cacggcttgc agaagacttg  60
tctacgctgg aagtggcgga attttcctcc gcgtatagtg attttgcctg cggaaaatgg 120
gaagcatgtg ttcttagaaa ccgtacaggt atgcaagaag aggatattgt ggtttcccat 180
aacgcaccgg ctcttgcaac cccgctgagt aaatcattgc cttaccttaa tgaattagtt 240
gagacacatt tcgactgttc ggctgtccgt tacacgcgta ttgtaagagt gagcgagaac 300
gcgtgcatta taccacattc agattacctc gagcttacg agacatttac cagattgcat 360
ctggtcttgg ataccaactc aggttgtgcc aataccgaag aggacaagat attccatatg 420
ggtctcggtg aaatatggtt cttggatgcg atgctgcctc atagtgcagc atgttttct  480
aagacgccta gactgcatct gatgattgac ttcgaagcta cagcgtttcc cgaatcattt 540
ttacgaaacg tcgaacagcc ggttaccacc cgtgatatgg tcgaccctag aaaagaatta 600
acggacgaag tgatcgaagg tatactcggc ttttctatta tcatatcgga ggcgaactac 660
cgtgaaatcg tgtctatttt agcgaagctg cacttctttt ataaagccga ttgccggtcg 720
atgtatgatt ggctgaaaga aatttgcaag agacggggag acccgcgct tattgaaag  780
acggcttcat tggaacgctt cttttaggc cacagagaac gcggggaagt aatgacctac 840
taa                                                                843
```

```
SEQ ID NO: 4              moltype = AA   length = 280
FEATURE                   Location/Qualifiers
source                    1..280
                          mol_type = protein
                          organism = Sinorhizobium meliloti
SEQUENCE: 4
MSTHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 5              moltype = DNA  length = 843
FEATURE                   Location/Qualifiers
misc_feature              1..843
                          note = Codon-optimized proline 4-hydroxylase gene from
                          Sinorhizobium meliloti
source                    1..843
                          mol_type = other DNA
                          organism = synthetic construct
SEQUENCE: 5
atgagcaccc atttcttggg caaggtcaag ttcgatgaag cgcgattggc agaagatcta   60
tctaccttgg aagttgccga gttctcgagt gcatactcgg acttcgcgtg cggtaaatgg  120
gaggcatgcg tgctacgcaa tcggaccgga atgcaggagg aagatatcgt cgtaagtcac  180
aacgctcctg cactcgccac gccgctgagc aagtcgctgc cgtatctgaa cgaacttgtt  240
gaaacccact tcgattgcag cgctgttcgg tatacaagaa ttgtccgtgt atcgaaaaac  300
gcatgtataa tcccccatag tgattaccta gaactagatg agaccttcac aaggttacac  360
ctggtgttag acactaattc aggatgcgct aatactgagg aagataaaat atttcatatg  420
ggactgggag agatttggtt ccttgacgct atgttaccgc atagcgctgc ttgttttttcc  480
aaaactccgc gcctgcatct gatgatcgac tttgaggcta ccgcttttcc cgaatctttt  540
ctgcgaaatg tcgaacaacc agtgacaaca cgagacatgg ttgatcctcg aaggaaacta  600
accgatgagg ttatcgaagg tattctgggg ttttcaataa ttattagcga agccaattac  660
cgggaaattg tttctattct ggcgaagcta cacttcttct acaaggcaga ctgtcgatca  720
atgtacgact ggctgaagga aatctgcaaa cgtcgagggg atcctgcact tattgaaaag  780
accgcctcgc tcgagcgatt ttttctaggg caccgtgaac gtggcgaggt gatgacatac  840
taa                                                                843

SEQ ID NO: 6              moltype = AA   length = 280
FEATURE                   Location/Qualifiers
source                    1..280
                          mol_type = protein
                          organism = Sinorhizobium meliloti
SEQUENCE: 6
MSTHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 7              moltype = DNA  length = 843
FEATURE                   Location/Qualifiers
misc_feature              1..843
                          note = Engineered variant of proline 4-hydroxylase from
                          Sinorhizobium meliloti
source                    1..843
                          mol_type = other DNA
                          organism = synthetic construct
SEQUENCE: 7
atgtctacgc atttccttgg caaggtcaaa ttcgacgagg ccagattagc cgaagatctg   60
tctactttag aagtcgctga gttttctagt gcatattcgg acttcgcttg tggaaagtgg  120
gaagagtgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta ttgtcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttttct  480
aaaactccta gactgcatct catgatagat tttgaagcta ccgccttccc ggaatctttt  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttcttct ataaagcgga ctgtcggtcc  720
atgtatgatt ggcttaaaga aatatgtaaa cgccggggag atcccgcgtt gattgagaag  780
acagcgagtc tcgaacgttt cttttgggg catcgtgaac gcgagaagt aatgacgtat  840
taa                                                                843

SEQ ID NO: 8              moltype = AA   length = 280
FEATURE                   Location/Qualifiers
REGION                    1..280
                          note = Engineered variant of proline 4-hydroxylase from
```

```
                        Sinorhizobium meliloti
source                  1..280
                        mol_type = protein
                        organism = synthetic construct
SEQUENCE: 8
MSTHFLGKVK FDEARLAEDL STLEVAEFSS AYSDFACGKW EECVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 9            moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 9
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg tttacgcaa cagaacaggc atgcaagaag aagacattgt ggtttctcac   180
aatgcgcccg cattagcgac ccctttatct aaatcactgc cgtacttgaa tgagcttgtt   240
gaaacacact tcgactgcag tgcggttaga tatacgcgta tcgtgcgtgt ctccgagaac   300
gcctgcttga tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcgagaagt aatgacgtat    840
taa                                                                 843

SEQ ID NO: 10           moltype = AA   length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 10
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACLIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 11           moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 11
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg tttacgcaa cagaacaggc atgcaagaag aagacattgt ggtttctcac   180
aatgcgcccg cattagcgac ccctttatct aaatcactgc cgtacttgaa tgagcttgtt   240
gaaacacact tcgactgcag tgcggttaga tatacgcgta tcgtgcgtgt ctccgagaac   300
gcctgccaga tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcgagaagt aatgacgtat    840
taa                                                                 843

SEQ ID NO: 12           moltype = AA   length = 280
FEATURE                 Location/Qualifiers
REGION                  1..280
```

```
                        note = Engineered variant of proline 4-hydroxylase from
                            Sinorhizobium meliloti
source                  1..280
                        mol_type = protein
                        organism = synthetic construct
SEQUENCE: 12
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACQIPHSDYL ELDETFTRLH   120
LVLDTNSGCA NTEEDKIFHM GLGEIWFLDA MLPHSAACFS KTPRLHLMID FEATAPPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 13           moltype = DNA  length = 843
FEATURE                 Location/Qualifiers
misc_feature            1..843
                        note = Engineered variant of proline 4-hydroxylase from
                            Sinorhizobium meliloti
source                  1..843
                        mol_type = other DNA
                        organism = synthetic construct
SEQUENCE: 13
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact cgactgcagt gcggttaga tatacgcgta tcgtgcgtgt ctccgagaac    300
gcctgcatta tccctcatag tgattatttg gagctcgatg aaacgctgac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcgagaagt aatgacgtat    840
taa                                                                 843

SEQ ID NO: 14           moltype = AA  length = 280
FEATURE                 Location/Qualifiers
REGION                  1..280
                        note = Engineered variant of proline 4-hydroxylase from
                            Sinorhizobium meliloti
source                  1..280
                        mol_type = protein
                        organism = synthetic construct
SEQUENCE: 14
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETLTRLH   120
LVLDTNSGCA NTEEDKIFHM GLGEIWFLDA MLPHSAACFS KTPRLHLMID FEATAPPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 15           moltype = DNA  length = 843
FEATURE                 Location/Qualifiers
misc_feature            1..843
                        note = Engineered variant of proline 4-hydroxylase from
                            Sinorhizobium meliloti
source                  1..843
                        mol_type = other DNA
                        organism = synthetic construct
SEQUENCE: 15
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact cgactgcagt gcggttaga tatacgcgta tcgtgcgtgt ctccgagaac    300
gcctgcatta tccctcatag tgattatttg gagctcgatg aaacgttcac ccggctgcac   360
ctcgtgttgg atactaacag tggttgtgcc tatactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcgagaagt aatgacgtat    840
taa                                                                 843

SEQ ID NO: 16           moltype = AA  length = 280
FEATURE                 Location/Qualifiers
```

-continued

```
REGION                    1..280
                          note = Engineered variant of proline 4-hydroxylase from
                            Sinorhizobium meliloti
source                    1..280
                          mol_type = protein
                          organism = synthetic construct
SEQUENCE: 16
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA YTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 17             moltype = DNA   length = 843
FEATURE                   Location/Qualifiers
misc_feature              1..843
                          note = Engineered variant of proline 4-hydroxylase from
                            Sinorhizobium meliloti
source                    1..843
                          mol_type = other DNA
                          organism = synthetic construct
SEQUENCE: 17
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac cccttttatct aaatcactgc cgtacttgaa tgagcttgtt   240
gaaacacact tcgactgcag tgcggttaga tatacgcgta tcgtgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacagt atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taagaattg    600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                 843

SEQ ID NO: 18             moltype = AA   length = 280
FEATURE                   Location/Qualifiers
REGION                    1..280
                          note = Engineered variant of proline 4-hydroxylase from
                            Sinorhizobium meliloti
source                    1..280
                          mol_type = protein
                          organism = synthetic construct
SEQUENCE: 18
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDS MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 19             moltype = DNA   length = 843
FEATURE                   Location/Qualifiers
misc_feature              1..843
                          note = Engineered variant of proline 4-hydroxylase from
                            Sinorhizobium meliloti
source                    1..843
                          mol_type = other DNA
                          organism = synthetic construct
SEQUENCE: 19
atgtctacgc atttccttgg caaggtcaaa ttcgacgagg ccagattagc cgaagatctg    60
tctactttag aagtcgctga gtttgctagt gcatattcgg acttcgcttg tggaaagtgg   120
gaagcatgcg ttttacgcaa cagaacaggc atgcaagaag aagacattgt ggtttctcac   180
aatgcgcccg cattagcgac cccttttatct aaatcactgc cgtacttgaa tgagcttgtt   240
gaaacacact tcgactgcag tgcggttaga tatacgcgta tcgtgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgactct catgatagat tttgaagcta ccgccttccc ggaatccttc   540
ttacgcaatg tggaacagcc tgtaactact cgcgacatgg tagaccctcg taagaattg    600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                 843

SEQ ID NO: 20             moltype = AA   length = 280
```

```
FEATURE                 Location/Qualifiers
REGION                  1..280
                        note = Engineered variant of proline 4-hydroxylase from
                          Sinorhizobium meliloti
source                  1..280
                        mol_type = protein
                        organism = synthetic construct
SEQUENCE: 20
MSTHFLGKVK FDEARLAEDL STLEVAEFAS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLTLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 21           moltype = DNA  length = 843
FEATURE                 Location/Qualifiers
misc_feature            1..843
                        note = Engineered variant of proline 4-hydroxylase from
                          Sinorhizobium meliloti
source                  1..843
                        mol_type = other DNA
                        organism = synthetic construct
SEQUENCE: 21
atgtctacgc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg tttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgca aagataagat attccacatg  420
ggtctgggcg agatctggtt tctggacgca atgttacctc attctgctgc ctgcttttct  480
aaaactccta gactgacgct catgatagat tttgaagcta ccgccttccc ggaatccttc  540
ttacgcaatg tggaacagcc tgtaactact cgcgacatgg tagaccctcg taagaattg   600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgcggggag atcccgcgtt gattgagaag  780
acagcgagtc tcgaacgttt cttttttggg catcgtgaac gcggagaagt aatgacgtat  840
taa                                                                843

SEQ ID NO: 22           moltype = AA  length = 280
FEATURE                 Location/Qualifiers
REGION                  1..280
                        note = Engineered variant of proline 4-hydroxylase from
                          Sinorhizobium meliloti
source                  1..280
                        mol_type = protein
                        organism = synthetic construct
SEQUENCE: 22
MSTHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLTLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 23           moltype = DNA  length = 843
FEATURE                 Location/Qualifiers
misc_feature            1..843
                        note = Engineered variant of proline 4-hydroxylase from
                          Sinorhizobium meliloti
source                  1..843
                        mol_type = other DNA
                        organism = synthetic construct
SEQUENCE: 23
atgtctacgc acttccttgg caaggtcaaa ttcgacgagg ccagattagc cgaagatctg   60
tctactttag aagtcgctga gttttctagt gcatattcgg acttcgcttg tggaaagtgg  120
gaagcatgtg tttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcagct catgatagat tttgaagcta ccgccttccc ggaatccttc  540
ttacgcaatg tggaacagcc tgtaactact cgcgacatgg tagaccctcg taagaattg   600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgcggggag atcccgcgtt gattgagaag  780
acagcgagtc tcgaacgttt cttttttggg catcgtgaac gcggagaagt aatgacgtat  840
taa                                                                843
```

```
SEQ ID NO: 24            moltype = AA   length = 280
FEATURE                  Location/Qualifiers
REGION                   1..280
                         note = Engineered variant of proline 4-hydroxylase from
                         Sinorhizobium meliloti
source                   1..280
                         mol_type = protein
                         organism = synthetic construct
SEQUENCE: 24
MSTHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 25            moltype = DNA   length = 843
FEATURE                  Location/Qualifiers
misc_feature             1..843
                         note = Engineered variant of proline 4-hydroxylase from
                         Sinorhizobium meliloti
source                   1..843
                         mol_type = other DNA
                         organism = synthetic construct
SEQUENCE: 25
atgtctacgc atttccttgg caaggtcaaa ttcgacgagg ccagattagc cgaagatctg   60
tctactttag aagtcgctga gttttctgtt gcatattcag acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 26            moltype = AA   length = 280
FEATURE                  Location/Qualifiers
REGION                   1..280
                         note = Engineered variant of proline 4-hydroxylase from
                         Sinorhizobium meliloti
source                   1..280
                         mol_type = protein
                         organism = synthetic construct
SEQUENCE: 26
MSTHFLGKVK FDEARLAEDL STLEVAEFSV AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 27            moltype = DNA   length = 843
FEATURE                  Location/Qualifiers
misc_feature             1..843
                         note = Engineered variant of proline 4-hydroxylase from
                         Sinorhizobium meliloti
source                   1..843
                         mol_type = other DNA
                         organism = synthetic construct
SEQUENCE: 27
atgtctacgc atttccttgg caaggtcaaa ttcgacgagg ccagattagc cgaagatctg   60
tctactttag aagtcgctga gttttctccg gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843
```

```
SEQ ID NO: 28          moltype = AA  length = 280
FEATURE                Location/Qualifiers
REGION                 1..280
                       note = Engineered variant of proline 4-hydroxylase from
                         Sinorhizobium meliloti
source                 1..280
                       mol_type = protein
                       organism = synthetic construct
SEQUENCE: 28
MSTHFLGKVK FDEARLAEDL STLEVAEFSP AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 29          moltype = DNA  length = 843
FEATURE                Location/Qualifiers
misc_feature           1..843
                       note = Engineered variant of proline 4-hydroxylase from
                         Sinorhizobium meliloti
source                 1..843
                       mol_type = other DNA
                       organism = synthetic construct
SEQUENCE: 29
atgtctacgc atttccttgg caaggtcaaa ttcgacgagg ccagattagc cgaagatctg   60
tctactttag aagtcgctga gttttctagt gcatattcgg acttcacttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact cgactgcagt gcggttagat atacgcgtgt cgtgcgtgt ctccgagaac   300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg atctggtt tctggacgca atgttacctc attctgctgc ctgcttttct    480
aaaactccta gactgcatct catgatagat tttgaagcta ccgccttccc ggaatcctt   540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatct ctctatcct ggccaaatta cacttctttt ataaagcgga ctgtcggtcc   720
atgtatgatt ggcttaaaga aatatgtaaa cgccggggag atcccgcgtt gattgagaag  780
acagcgagtc tcgaacgttt cttttttggg catcgtgaac gcgagaagt aatgacgtat   840
taa                                                                843

SEQ ID NO: 30          moltype = AA  length = 280
FEATURE                Location/Qualifiers
REGION                 1..280
                       note = Engineered variant of proline 4-hydroxylase from
                         Sinorhizobium meliloti
source                 1..280
                       mol_type = protein
                       organism = synthetic construct
SEQUENCE: 30
MSTHFLGKVK FDEARLAEDL STLEVAEFSS AYSDFTCGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 31          moltype = DNA  length = 843
FEATURE                Location/Qualifiers
misc_feature           1..843
                       note = Engineered variant of proline 4-hydroxylase from
                         Sinorhizobium meliloti
source                 1..843
                       mol_type = other DNA
                       organism = synthetic construct
SEQUENCE: 31
atgtctacgc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggttggtcac  180
aatgcgcccg cattagcgac ccctttatct aaatcactgc cgtacttgaa tgagcttgtt  240
gaaacacact cgactgcagt gcggttagat atacgcgta cgtgcgtgt ctccgagaac    300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg atctggtt tctggacgca atgttacctc attctgctgc ctgcttttct    480
aaaactccta gactgcatct catgatagat tttgaagcta ccgccttccc ggaatcctt   540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatct ctctatcct ggccaaatta cacttctttt ataaagcgga ctgtcggtcc   720
atgtatgatt ggcttaaaga aatatgtaaa cgccggggag atcccgcgtt gattgagaag  780
acagcgagtc tcgaacgttt cttttttggg catcgtgaac gcgagaagt aatgacgtat   840
```

```
                                                                           843
taa SEQ ID NO: 32            moltype = AA  length = 280
FEATURE                  Location/Qualifiers
REGION                   1..280
                         note = Engineered variant of proline 4-hydroxylase from
                           Sinorhizobium meliloti
source                   1..280
                         mol_type = protein
                         organism = synthetic construct
SEQUENCE: 32
MSTHFLGKVK FDEARLAEDL STLEVAEFSS AYSDFACGKW EACVLRNRTG MQEEDIVVGH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 33            moltype = DNA  length = 843
FEATURE                  Location/Qualifiers
misc_feature             1..843
                         note = Engineered variant of proline 4-hydroxylase from
                           Sinorhizobium meliloti
source                   1..843
                         mol_type = other DNA
                         organism = synthetic construct
SEQUENCE: 33
atgtctacgc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattac ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctggggc agatctggtt tctggacgca atgttacctc actctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 34            moltype = AA  length = 280
FEATURE                  Location/Qualifiers
REGION                   1..280
                         note = Engineered variant of proline 4-hydroxylase from
                           Sinorhizobium meliloti
source                   1..280
                         mol_type = protein
                         organism = synthetic construct
SEQUENCE: 34
MSTHFLGKVK FDEARLAEDL STLEVAEFSS AYSDFACGKW EACVLRNRTG MQEEDITVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 35            moltype = DNA  length = 843
FEATURE                  Location/Qualifiers
misc_feature             1..843
                         note = Engineered variant of proline 4-hydroxylase from
                           Sinorhizobium meliloti
source                   1..843
                         mol_type = other DNA
                         organism = synthetic construct
SEQUENCE: 35
atgtctacgc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcctgaag aagacattac ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctggggc agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taagaattg  600
acggacgaag ttatagaagg cattttaggg ttctccataa tcatcagtga agcgaattac  660
cgcgagatcg tctatatcct ggccaaatta cacttctttt ataaagcgga ctgtcggtcc  720
atgtatgatt ggcttaaaga aatatgtaaa cgccggggag atcccgcgtt gattgagaag  780
```

```
acagcgagtc tcgaacgttt cttttttggg catcgtgaac gcggagaagt aatgacgtat    840
taa                                                                 843

SEQ ID NO: 36           moltype = AA   length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 36
MSTHFLGKVK FDEARLAEDL STLEVAEFSS AYSDFACGKW EACVLRNRTG MPEEDIVVSH     60
NAPALATPLS KSLPYLNELV ETHFDCSAVR YTRIVRVSEN ACIIPHSDYL ELDETFTRLH    120
LVLDTNSGCA NTEEDKIFHM GLGEIWFLDA MLPHSAACFS KTPRLHLMID FEATAFPESF    180
LRNVEQPVTT RDMVDPRKEL TDEVIEGILG FSIIISEANY REIVYILAKL HFFYKADCRS    240
MYDWLKEICK RRGDPALIEK TASLERFFLG HRERGEVMTY                          280

SEQ ID NO: 37           moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 37
atgtctacgc atttccttgg caaggtcaaa ttcgacgagg ccagattagc cgaagatctg     60
tctacttag aagtcgctga gttttctagt gcatattcgg acttcgcttg tggaaagtgg    120
gaagcatgtg ttttacgcaa cagaacaggc atgcaagaag aagacattgc tgtttctcac    180
aatgcgcccg cattagcgac ccctttatct aaatcactgc cgtacttgaa tgagcttgtt    240
gaaacacact tcgactgcag tgcggttaga tatacgcgta tcgtgcgtgt ctccgagaac    300
gcctgcatta tccctcatag tgattatttg gagctcgatg aaacgttcac ccggctgcac    360
ctcgtgttgg atactaacag tggttgtgcc aacactgagg aagataagat attccacatg    420
ggtctgggcg agatctggtt tctggacgca atgttacctc attctgctgc ctgctttttct   480
aaaactccta gactgcatct catgatagat tttgaagcta ccgccttccc ggaatccttc    540
ttacgcaatg tggaacagcc tgtaactact cgcgacatgg tagaccctcg taagaattg    600
acggacgaag ttatagaagg catttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttttggg catcgtgaac gcggagaagt aatgacgtat    840
taa                                                                 843

SEQ ID NO: 38           moltype = AA   length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 38
MSTHFLGKVK FDEARLAEDL STLEVAEFSS AYSDFACGKW EACVLRNRTG MQEEDIAVSH     60
NAPALATPLS KSLPYLNELV ETHFDCSAVR YTRIVRVSEN ACIIPHSDYL ELDETFTRLH    120
LVLDTNSGCA NTEEDKIFHM GLGEIWFLDA MLPHSAACFS KTPRLHLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 39           moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 39
atgtctacgc atttccttgg caaggtcaaa ttcgacgagg ccagattagc cgaagatctg     60
tctacttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattagcgac ccctttatct aaatcactgc cgtacttgaa tgagcttgtt    240
gagacacact tcgactgcag tgcggttaga tatacgcgta tcgtgcgtgt ctccgagaac    300
gcctgcatta tccctcatag tgattatttg gagctcgatg aacatttcac ccggctgcac    360
ctcgtgttgg atactaacag tggttgtgcc aacactgagg aagataagat attccacatg    420
ggtctgggcg agatctggtt tctggacgca atgttacctc attctgctgc ctgctttttct   480
aaaactccta gactgcatct catgatagat tttgaagcta ccgccttccc ggaatccttc    540
ttacgcaatg tggaacagcc tgtaactact cgcgacatgg tagaccctcg taagaattg    600
acggacgaag ttatagaagg catttaggg ttctccataa tcatcagtga agcgaattac    660
cgcgagatcg tctctatcct ggccaaatta cacttctttt ataaagcgga ctgtcggtcc    720
```

```
atgtatgatt ggcttaaaga aatatgtaaa cgccggggag atcccgcgtt gattgagaag    780
acagcgagtc tcgaacgttt cttttggggg catcgtgaac gcggagaagt aatgacgtat    840
taa                                                                  843

SEQ ID NO: 40            moltype = AA   length = 280
FEATURE                  Location/Qualifiers
REGION                   1..280
                         note = Engineered variant of proline 4-hydroxylase from
                         Sinorhizobium meliloti
source                   1..280
                         mol_type = protein
                         organism = synthetic construct
SEQUENCE: 40
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDEHFTRLH    120
LVLDTNSGCA NTEEDKIFHM GLGEIWFLDA MLPHSAACFS KTPRLHLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 41            moltype = DNA   length = 843
FEATURE                  Location/Qualifiers
misc_feature             1..843
                         note = Engineered variant of proline 4-hydroxylase from
                         Sinorhizobium meliloti
source                   1..843
                         mol_type = other DNA
                         organism = synthetic construct
SEQUENCE: 41
atgtctacgc atttccttgg caaggtcaaa ttcgacgagg ccagattagc cgaagatctg    60
tctactttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattagcgac cccctttatct aaatcactgc cgtacttgaa tgagcttgtt   240
gaaacacact tcgactgcag tgcggttaga tatacgcgta tcgtgcgtgt ctccgagaac    300
gcctgcatta tccctcatag tgattatttg gagacgttca cccggctgac                360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcatct catgatagat tttgaagcta ccgccttccc ggaatccttc    540
ttacgcaatg tggaacagcc tgtaactact cgcgacatgg tagaccctcg taagaattg    600
acggacgaag ttatagaagg catttagggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttggggg catcgtgaac gcggagaagt aatgacgtat    840
taa                                                                  843

SEQ ID NO: 42            moltype = AA   length = 280
FEATURE                  Location/Qualifiers
REGION                   1..280
                         note = Engineered variant of proline 4-hydroxylase from
                         Sinorhizobium meliloti
source                   1..280
                         mol_type = protein
                         organism = synthetic construct
SEQUENCE: 42
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ETDETFTRLH    120
LVLDTNSGCA NTEEDKIFHM GLGEIWFLDA MLPHSAACFS KTPRLHLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 43            moltype = DNA   length = 843
FEATURE                  Location/Qualifiers
misc_feature             1..843
                         note = Engineered variant of proline 4-hydroxylase from
                         Sinorhizobium meliloti
source                   1..843
                         mol_type = other DNA
                         organism = synthetic construct
SEQUENCE: 43
atgtctacgc atttccttgg caaggtcaaa ttcgacgagg ccagattagc cgaagatctg    60
tctactttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattacagac cccctttatct aaatcactgc cgtacttgaa tgagcttgtt    240
gaaacacact tcgactgcag tgcggttaga tatacgcgta tcgtgcgtgt ctccgagaac    300
gcctgcatta tccctcatag tgattatttg gagctgttca cccggctgac                360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcatct catgatagat tttgaagcta ccgccttccc ggaatccttc    540
ttacgcaatg tggaacagcc tgtaactact cgcgacatgg tagaccctcg taagaattg    600
acggacgaag ttatagaagg catttagggg ttctccataa tcatcagtga agcgaattac    660
```

```
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                843
```

SEQ ID NO: 44            moltype = AA   length = 280
FEATURE                  Location/Qualifiers
REGION                   1..280
                         note = Engineered variant of proline 4-hydroxylase from
                           Sinorhizobium meliloti
source                   1..280
                         mol_type = protein
                         organism = synthetic construct
SEQUENCE: 44
MSTHFLGKVK FDEARLAEDL STLEVAEFSS AYSDFACGKW EACVLRNRTG MQEEDIVVSH    60
NAPALQTPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 45            moltype = DNA   length = 843
FEATURE                  Location/Qualifiers
misc_feature             1..843
                         note = Engineered variant of proline 4-hydroxylase from
                           Sinorhizobium meliloti
source                   1..843
                         mol_type = other DNA
                         organism = synthetic construct
SEQUENCE: 45
```
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact tcgactgcag tgcggttaga tatacgcgta tcgtgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg aagcgtgaac gcggagaagt aatgacgtat   840
taa                                                                843
```

SEQ ID NO: 46            moltype = AA   length = 280
FEATURE                  Location/Qualifiers
REGION                   1..280
                         note = Engineered variant of proline 4-hydroxylase from
                           Sinorhizobium meliloti
source                   1..280
                         mol_type = protein
                         organism = synthetic construct
SEQUENCE: 46
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG KRERGEVMTY                         280

SEQ ID NO: 47            moltype = DNA   length = 843
FEATURE                  Location/Qualifiers
misc_feature             1..843
                         note = Engineered variant of proline 4-hydroxylase from
                           Sinorhizobium meliloti
source                   1..843
                         mol_type = other DNA
                         organism = synthetic construct
SEQUENCE: 47
```
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact tcgactgcag tgcggttaga tatacgcgta tcgtgcgtgt ctccgagaac   300
gcctgcatta tccctcatag tgattatttg gagctcgatg aagatttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
```

```
acggacgaag ttatagaagg catttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttgggg catcgtgaac gcggagaagt aatgacgtat    840
taa                                                                  843
```

```
SEQ ID NO: 48          moltype = AA  length = 280
FEATURE                Location/Qualifiers
REGION                 1..280
                       note = Engineered variant of proline 4-hydroxylase from
                       Sinorhizobium meliloti
source                 1..280
                       mol_type = protein
                       organism = synthetic construct
SEQUENCE: 48
MSTHFLGKVK FDEARLAEDL STLEVAEFSS AYSDFACGKW EACVLRNRTG MQEEDIVVSH     60
NAPALATPLS KSLPYLNELV ETHFDCSAVR YTRIVRVSEN ACIIPHSDYL ELDEDFTRLH    120
LVLDTNSGCA NTEEDKIFHM GLGEIWFLDA MLPHSAACFS KTPRLHLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 49          moltype = DNA  length = 843
FEATURE                Location/Qualifiers
misc_feature           1..843
                       note = Engineered variant of proline 4-hydroxylase from
                       Sinorhizobium meliloti
source                 1..843
                       mol_type = other DNA
                       organism = synthetic construct
SEQUENCE: 49
atgtctacgc atttccttgg caaggtcaaa ttcgacgagg ccagattagc cgaagatctg     60
tctactttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattagcgac cccttatct aaatcactgc cgtacttgaa tgagcttgtt    240
gaaacacact tcgactgcag tgcggttaga tatacgcgta tcgtgcgtgt ctccgagaac    300
gcctgcatta tccctcatag tgattatttg gagctcgatg aaggttttcac ccggctgcac    360
ttcgtgttgg atactaacag tggttgtgcc aacactgagg aagataagat attccacatg    420
ggtctggggcg agatctggtt tctggacgca atgttacctc attctgctgc ctgcttttct    480
aaaactccta gactgcatct catgatagat tttgaagcta ccgccttccc ggaatccttc    540
ttacgcaatg tggaacagcc tgtaactact cgccgacatgg tagaccctcg taaagaattg    600
acggacgaag ttatagaagg catttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttgggg catcgtgaac gcggagaagt aatgacgtat    840
taa                                                                  843
```

```
SEQ ID NO: 50          moltype = AA  length = 280
FEATURE                Location/Qualifiers
REGION                 1..280
                       note = Engineered variant of proline 4-hydroxylase from
                       Sinorhizobium meliloti
source                 1..280
                       mol_type = protein
                       organism = synthetic construct
SEQUENCE: 50
MSTHFLGKVK FDEARLAEDL STLEVAEFSS AYSDFACGKW EACVLRNRTG MQEEDIVVSH     60
NAPALATPLS KSLPYLNELV ETHFDCSAVR YTRIVRVSEN ACIIPHSDYL ELDEGFTRLH    120
FVLDTNSGCA NTEEDKIFHM GLGEIWFLDA MLPHSAACFS KTPRLHLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 51          moltype = DNA  length = 843
FEATURE                Location/Qualifiers
misc_feature           1..843
                       note = Engineered variant of proline 4-hydroxylase from
                       Sinorhizobium meliloti
source                 1..843
                       mol_type = other DNA
                       organism = synthetic construct
SEQUENCE: 51
atgtctacgc atttccttgg caaggtcaaa ttcgacgagg ccagattagc cgaagatctg     60
tctactttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattagcgac cccttatct aaatcactgc cgtacttgaa tgagcttgtt    240
gaaacacact tcgactgcag tgcggttaga tatacgcgta tcgtgcgtgt ctccgagaac    300
gcctgcatta tccctcatag tgattatttg gagctcgatg aacgttcac ccggctgcac    360
ctcgtgttgg atactaacag tggttgtgcc aacactgagg aagataagat attccacatg    420
ggtctggggcg agatctggtt tctggacgca atgttacctc attctgctgc ctgcttttct    480
aaaactccta gactgcatct catgatagat tttgaagcta ccgccttccc ggaatccttc    540
```

```
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttgggg cggcgtgaac gcggagaagt aatgacgtat  840
taa                                                                843
```

| SEQ ID NO: 52 | moltype = AA length = 280 |
|---|---|
| FEATURE | Location/Qualifiers |
| REGION | 1..280 |
| | note = Engineered variant of proline 4-hydroxylase from Sinorhizobium meliloti |
| source | 1..280 |
| | mol_type = protein |
| | organism = synthetic construct |

```
SEQUENCE: 52
MSTHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG RRERGEVMTY                        280
```

| SEQ ID NO: 53 | moltype = DNA length = 843 |
|---|---|
| FEATURE | Location/Qualifiers |
| misc_feature | 1..843 |
| | note = Engineered variant of proline 4-hydroxylase from Sinorhizobium meliloti |
| source | 1..843 |
| | mol_type = other DNA |
| | organism = synthetic construct |

```
SEQUENCE: 53
atgtctacgc atttccttgg caaggtcaaa ttcgacgagg ccagattagc cgaagatctg   60
tctacttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac cccctttatct aaatcactgc cgtacttgaa tgagcttgtt  240
gaaacacact cgactgcag tgcggttaga tatacgcgta tcgtgcgtgt ctccgagaac  300
gcctgcatta tccctcatag tgattatttg gaggttgatg aaacgttcac ccggctgcac  360
ctcgtgttgg atactaacag tggttgtgcc aacactgagg aagataagat attccacatg  420
ggtctggggcg agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttgggg catcgtgaac gcggagaagt aatgacgtat  840
taa                                                                843
```

| SEQ ID NO: 54 | moltype = AA length = 280 |
|---|---|
| FEATURE | Location/Qualifiers |
| REGION | 1..280 |
| | note = Engineered variant of proline 4-hydroxylase from Sinorhizobium meliloti |
| source | 1..280 |
| | mol_type = protein |
| | organism = synthetic construct |

```
SEQUENCE: 54
MSTHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL EVDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280
```

| SEQ ID NO: 55 | moltype = DNA length = 843 |
|---|---|
| FEATURE | Location/Qualifiers |
| misc_feature | 1..843 |
| | note = Engineered variant of proline 4-hydroxylase from Sinorhizobium meliloti |
| source | 1..843 |
| | mol_type = other DNA |
| | organism = synthetic construct |

```
SEQUENCE: 55
atgtctacgc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac cccctttatct aaatcactgc cgtacttgaa tgagcttgtt  240
gaaacacact cgactgcag tgcggttaga tatacgcgta tcgtgcgtgt ctccgagaac  300
gcctgcatta tccctcatag tgattatttg gagctcgatg aaagtttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
```

```
aaaactccta gactgcatct catgatagat tttgaagcta ccgccttccc ggaatccttc    540
ttacgcaatg tggaacagcc tgtaactact cgcgacatgg tagaccctcg taaagaattg    600
acggacgaag ttatagaagg catttttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttttggg catcgtgaac gcggagaagt aatgacgtat    840
taa                                                                  843
```

| | |
|---|---|
| SEQ ID NO: 56 | moltype = AA length = 280 |
| FEATURE | Location/Qualifiers |
| REGION | 1..280 |
| | note = Engineered variant of proline 4-hydroxylase from Sinorhizobium meliloti |
| source | 1..280 |
| | mol_type = protein |
| | organism = synthetic construct |

```
SEQUENCE: 56
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDESFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREGEVMTY                          280
```

| | |
|---|---|
| SEQ ID NO: 57 | moltype = DNA length = 843 |
| FEATURE | Location/Qualifiers |
| misc_feature | 1..843 |
| | note = Engineered variant of proline 4-hydroxylase from Sinorhizobium meliloti |
| source | 1..843 |
| | mol_type = other DNA |
| | organism = synthetic construct |

```
SEQUENCE: 57
atgtctacgc atttccttgg caaggtcaaa ttcgacgagg ccagattagc cgaagatctg     60
tctactttag aacgtgctga gttttctagt gcatattcgg acttcgcttg tggaaagtgg    120
gaagcatgtg ttttacgcaa cagaacaggc atgcaagaag aagacattgt ggcttctcac    180
aatgcgcccg cattagcgac cccttttatct aaatcactgc cgtacttgaa tgagcttgtt   240
gaaacacact cgactgcagt gcgttagat atacgcgta tcgtgcgtgt ctccgagaac      300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctgacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttttaggg ttctccataa tcatcagtga agcgaattac  660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttttggg catcgtgaac gcggagaagt aatgacgtat   840
taa                                                                 843
```

| | |
|---|---|
| SEQ ID NO: 58 | moltype = AA length = 280 |
| FEATURE | Location/Qualifiers |
| REGION | 1..280 |
| | note = Engineered variant of proline 4-hydroxylase from Sinorhizobium meliloti |
| source | 1..280 |
| | mol_type = protein |
| | organism = synthetic construct |

```
SEQUENCE: 58
MSTHFLGKVK FDEARLAEDL STLERAEFSS AYSDFACGKW EACVLRNRTG MQEEDIVASH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREGEVMTY                          280
```

| | |
|---|---|
| SEQ ID NO: 59 | moltype = DNA length = 843 |
| FEATURE | Location/Qualifiers |
| misc_feature | 1..843 |
| | note = Engineered variant of proline 4-hydroxylase from Sinorhizobium meliloti |
| source | 1..843 |
| | mol_type = other DNA |
| | organism = synthetic construct |

```
SEQUENCE: 59
atgaagacgc atttccttgg caaggtcaaa ttcgacgagg ccagattagc cgaagatctg     60
tctactttag aagtgctga gttttctagt gcatattcgg acttcgcttg tggaaagtgg    120
gaagcatgtg ttttacgcaa cagaacaggc atgcaagaag aagacattgt ggcttctcac    180
aatgcgcccg cattagcgac cccttttatct aaatcactgc cgtacttgaa tgagcttgtt   240
gaaacacact cgactgcagt gcgttagat atacgcgta tcgtgcgtgt ctccgagaac     300
gcctgcatta tccctcatag tgattatttg gagctcgatg aaacgttcac ccggctgcac  360
ctcgtgttgg atactaacag tggttgtgcc aacactgagg aagataagat attccacatg  420
```

```
ggtctgggcg agatctggtt tctggacgca atgttacctc attctgctgc ctgcttttct  480
aaaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg catttttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttgggg catcgtgaac gcggagaagt aatgacgtat  840
taa                                                                  843

SEQ ID NO: 60           moltype = AA  length = 280
FEATURE                 Location/Qualifiers
REGION                  1..280
                        note = Engineered variant of proline 4-hydroxylase from
                          Sinorhizobium meliloti
source                  1..280
                        mol_type = protein
                        organism = synthetic construct
SEQUENCE: 60
MKTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HREREGVMTY                         280

SEQ ID NO: 61           moltype = DNA  length = 843
FEATURE                 Location/Qualifiers
misc_feature            1..843
                        note = Engineered variant of proline 4-hydroxylase from
                          Sinorhizobium meliloti
source                  1..843
                        mol_type = other DNA
                        organism = synthetic construct
SEQUENCE: 61
atgactacgc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg catttttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttgggg catcgtgaac gcggagaagt aatgacgtat  840
taa                                                                  843

SEQ ID NO: 62           moltype = AA  length = 280
FEATURE                 Location/Qualifiers
REGION                  1..280
                        note = Engineered variant of proline 4-hydroxylase from
                          Sinorhizobium meliloti
source                  1..280
                        mol_type = protein
                        organism = synthetic construct
SEQUENCE: 62
MTTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HREREGVMTY                         280

SEQ ID NO: 63           moltype = DNA  length = 843
FEATURE                 Location/Qualifiers
misc_feature            1..843
                        note = Engineered variant of proline 4-hydroxylase from
                          Sinorhizobium meliloti
source                  1..843
                        mol_type = other DNA
                        organism = synthetic construct
SEQUENCE: 63
atgtctacgc atttccttgg caaggtcaaa ttcgacactg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
```

```
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcatct catgatagat tttgaagcta ccgccttccc ggaatccttc    540
ttacgcaatg tggaacagcc tgtaactact cgcgacatgg tagaccctcg taagaattg     600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttggggg catcgtgaac gcggagaagt aatgacgtat    840
taa                                                                  843

SEQ ID NO: 64           moltype = AA  length = 280
FEATURE                 Location/Qualifiers
REGION                  1..280
                        note = Engineered variant of proline 4-hydroxylase from
                         Sinorhizobium meliloti
source                  1..280
                        mol_type = protein
                        organism = synthetic construct
SEQUENCE: 64
MSTHFLGKVK FDTARLAEDL STLEVAEFSS AYSDFACGKW EACVLRNRTG MQEEDIVVSH     60
NAPALATPLS KSLPYLNELV ETHFDCSAVR YTRIVRVSEN ACIIPHSDYL ELDETFTRLH    120
LVLDTNSGCA NTEEDKIFHM GLGEIWFLDA MLPHSAACFS KTPRLHLMID FEATAPFPESF   180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 65           moltype = DNA  length = 843
FEATURE                 Location/Qualifiers
misc_feature            1..843
                        note = Engineered variant of proline 4-hydroxylase from
                         Sinorhizobium meliloti
source                  1..843
                        mol_type = other DNA
                        organism = synthetic construct
SEQUENCE: 65
atgtctacgc agttccttgg caaggtcaaa ttcgacgagg ccagattagc cgaagatctg     60
tctactttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattagcgac ccctttatct aaatcactgc cgtacttgaa tgagcttgtt    240
gaaacacact tcgactgcag tgcggttaga tatacgcgta tcgtgcgtgt ctccgagaac    300
gcctgcatta tccctcatag tgattatttg gagctcgatg aaacgttcac ccggctgcac    360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcatct catgatagat tttgaagcta ccgccttccc ggaatccttc    540
ttacgcaatg tggaacagcc tgtaactact cgcgacatgg tagaccctcg taagaattg     600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttggggg catcgtgaac gcggagaagt aatgacgtat    840
taa                                                                  843

SEQ ID NO: 66           moltype = AA  length = 280
FEATURE                 Location/Qualifiers
REGION                  1..280
                        note = Engineered variant of proline 4-hydroxylase from
                         Sinorhizobium meliloti
source                  1..280
                        mol_type = protein
                        organism = synthetic construct
SEQUENCE: 66
MSTQFLGKVK FDEARLAEDL STLEVAEFSS AYSDFACGKW EACVLRNRTG MQEEDIVVSH     60
NAPALATPLS KSLPYLNELV ETHFDCSAVR YTRIVRVSEN ACIIPHSDYL ELDETFTRLH    120
LVLDTNSGCA NTEEDKIFHM GLGEIWFLDA MLPHSAACFS KTPRLHLMID FEATAPFPESF   180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 67           moltype = DNA  length = 843
FEATURE                 Location/Qualifiers
misc_feature            1..843
                        note = Engineered variant of proline 4-hydroxylase from
                         Sinorhizobium meliloti
source                  1..843
                        mol_type = other DNA
                        organism = synthetic construct
SEQUENCE: 67
atgtctacgt tgttccttgg caaggtcaaa ttcgacgagg ccagattagc cgaagatctg     60
tctactttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattagcgac ccctttatct aaatcactgc cgtacttgaa tgagcttgtt    240
gaaacacact tcgactgcag tgcggttaga tatacgcgta tcgtgcgtgt ctccgagaac    300
```

```
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                 843
```

| | | |
|---|---|---|
| SEQ ID NO: 68 | moltype = AA length = 280 | |
| FEATURE | Location/Qualifiers | |
| REGION | 1..280 | |
| | note = Engineered variant of proline 4-hydroxylase from Sinorhizobium meliloti | |
| source | 1..280 | |
| | mol_type = protein | |
| | organism = synthetic construct | |

```
SEQUENCE: 68
MSTLFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280
```

| | | |
|---|---|---|
| SEQ ID NO: 69 | moltype = DNA length = 843 | |
| FEATURE | Location/Qualifiers | |
| misc_feature | 1..843 | |
| | note = Engineered variant of proline 4-hydroxylase from Sinorhizobium meliloti | |
| source | 1..843 | |
| | mol_type = other DNA | |
| | organism = synthetic construct | |

```
SEQUENCE: 69
atgtctacgc atattcttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact cgactgcagt gcggttaga tatacgcgta tcgtgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                 843
```

| | | |
|---|---|---|
| SEQ ID NO: 70 | moltype = AA length = 280 | |
| FEATURE | Location/Qualifiers | |
| REGION | 1..280 | |
| | note = Engineered variant of proline 4-hydroxylase from Sinorhizobium meliloti | |
| source | 1..280 | |
| | mol_type = protein | |
| | organism = synthetic construct | |

```
SEQUENCE: 70
MSTHILGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280
```

| | | |
|---|---|---|
| SEQ ID NO: 71 | moltype = DNA length = 843 | |
| FEATURE | Location/Qualifiers | |
| misc_feature | 1..843 | |
| | note = Engineered variant of proline 4-hydroxylase from Sinorhizobium meliloti | |
| source | 1..843 | |
| | mol_type = other DNA | |
| | organism = synthetic construct | |

```
SEQUENCE: 71
atgtctacgc atttgcttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
```

```
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatct ctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 72              moltype = AA  length = 280
FEATURE                    Location/Qualifiers
REGION                     1..280
                           note = Engineered variant of proline 4-hydroxylase from
                            Sinorhizobium meliloti
source                     1..280
                           mol_type = protein
                           organism = synthetic construct
SEQUENCE: 72
MSTHLLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HREREVMTY                         280

SEQ ID NO: 73              moltype = DNA  length = 843
FEATURE                    Location/Qualifiers
misc_feature               1..843
                           note = Engineered variant of proline 4-hydroxylase from
                            Sinorhizobium meliloti
source                     1..843
                           mol_type = other DNA
                           organism = synthetic construct
SEQUENCE: 73
atgtctacgc atatgcttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 74              moltype = AA  length = 280
FEATURE                    Location/Qualifiers
REGION                     1..280
                           note = Engineered variant of proline 4-hydroxylase from
                            Sinorhizobium meliloti
source                     1..280
                           mol_type = protein
                           organism = synthetic construct
SEQUENCE: 74
MSTHMLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HREREVMTY                         280

SEQ ID NO: 75              moltype = DNA  length = 843
FEATURE                    Location/Qualifiers
misc_feature               1..843
                           note = Engineered variant of proline 4-hydroxylase from
                            Sinorhizobium meliloti
source                     1..843
                           mol_type = other DNA
                           organism = synthetic construct
SEQUENCE: 75
atgtctacgc atttccttgg caagattaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
```

```
aatgcgcccg cattagcgac ccctttatct aaatcactgc cgtacttgaa tgagcttgtt    240
gaaacacact tcgactgcag tgcggttaga tatacgcgta tcgtgcgtgt ctccgagaac    300
gcctgcatta tccctcatag tgattatttg gagctcgatg aaacgttcac ccggctgcac    360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcatct catgatagat tttgaagcta ccgccttccc ggaatccttc    540
ttacgcaatg tggaacagcc tgtaactact cgcgacatgg tagaccctcg taaagaattg    600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttttgggg catcgtgaac gcggagaagt aatgacgtat    840
taa                                                                  843

SEQ ID NO: 76           moltype = AA   length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 76
MSTHFLGKIK FDEARLAEDL STLEVAEFSS AYSDFACGKW EACVLRNRTG MQEEDIVVSH     60
NAPALATPLS KSLPYLNELV ETHFDCSAVR YTRIVRVSEN ACIIPHSDYL ELDETFTRLH    120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREREGEVMTY                         280

SEQ ID NO: 77           moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 77
atgtctacgg aattccttgg caaggtcaaa ttcgacgagg ccagattagc cgaagatctg     60
tctactttag aagtcgctga gttttctagt gcatattcgg acttcgcttg tggaaagtgg    120
gaagcatgtg ttttacgcaa cagaacaggc atgcaagaag aagacattgt ggtttctcac    180
aatgcgcccg cattagcgac ccctttatct aaatcactgc cgtacttgaa tgagcttgtt    240
gaaacacact tcgactgcag tgcggttaga tatacgcgta tcgtgcgtgt ctccgagaac    300
gcctgcatta tccctcatag tgattatttg gagctcgatg aaacgttcac ccggctgcac    360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcatct catgatagat tttgaagcta ccgccttccc ggaatccttc    540
ttacgcaatg tggaacagcc tgtaactact cgcgacatgg tagaccctcg taaagaattg    600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttttgggg catcgtgaac gcggagaagt aatgacgtat    840
taa                                                                  843

SEQ ID NO: 78           moltype = AA   length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 78
MSTEFLGKVK FDEARLAEDL STLEVAEFSS AYSDFACGKW EACVLRNRTG MQEEDIVVSH     60
NAPALATPLS KSLPYLNELV ETHFDCSAVR YTRIVRVSEN ACIIPHSDYL ELDETFTRLH    120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREREGEVMTY                         280

SEQ ID NO: 79           moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 79
atgtctacgc tcttccttgg caaggtcaaa ttcgacgagg ccagattagc cgaagatctg     60
tctactttag aagtcgctga gttttctagt gcatattcgg acttcgcttg tggaaagtgg    120
```

```
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact tcgactgcag tgcggttaga tatacgcgta tcgtgcgtgt ctccgagaac   300
gcctgcatta tccctcatag tgattatttg gagctcgatg aagcgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttttgggg catcgtgaac gcggagaagt aatgacgtat   840
taa                                                                  843

SEQ ID NO: 80            moltype = AA   length = 280
FEATURE                  Location/Qualifiers
REGION                   1..280
                         note = Engineered variant of proline 4-hydroxylase from
                           Sinorhizobium meliloti
source                   1..280
                         mol_type = protein
                         organism = synthetic construct
SEQUENCE: 80
MSTLFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDEAFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                        280

SEQ ID NO: 81            moltype = DNA   length = 843
FEATURE                  Location/Qualifiers
misc_feature             1..843
                         note = Engineered variant of proline 4-hydroxylase from
                           Sinorhizobium meliloti
source                   1..843
                         mol_type = other DNA
                         organism = synthetic construct
SEQUENCE: 81
atgtctacgt cattccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact tcgactgcag tgcggttaga tatacgcgta tcgtgcgtgt ctccgagaac   300
gcctgcatta tccccatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttttgggg catcgtgaac gcggagaagt aatgacgtat   840
taa                                                                  843

SEQ ID NO: 82            moltype = AA   length = 280
FEATURE                  Location/Qualifiers
REGION                   1..280
                         note = Engineered variant of proline 4-hydroxylase from
                           Sinorhizobium meliloti
source                   1..280
                         mol_type = protein
                         organism = synthetic construct
SEQUENCE: 82
MSTSFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                        280

SEQ ID NO: 83            moltype = DNA   length = 843
FEATURE                  Location/Qualifiers
misc_feature             1..843
                         note = Engineered variant of proline 4-hydroxylase from
                           Sinorhizobium meliloti
source                   1..843
                         mol_type = other DNA
                         organism = synthetic construct
SEQUENCE: 83
atgtctacgc atttccttgg caaggtcaaa ttcgacgagg ccagattagc cgaagatctg    60
```

```
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac cccctttatct aaatcactgc cgtacttgaa tgagcttgtt   240
gaaacacact tcgactgcag tgcggttaga tatacgcgta tcgtgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctggatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                 843

SEQ ID NO: 84          moltype = AA  length = 280
FEATURE                Location/Qualifiers
REGION                 1..280
                       note = Engineered variant of proline 4-hydroxylase from
                       Sinorhizobium meliloti
source                 1..280
                       mol_type = protein
                       organism = synthetic construct
SEQUENCE: 84
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVWILAKL HFFYKADCRS   240
MYDWLKEICK RRGDPALIEK TASLERFFLG HRERGEVMTY                         280

SEQ ID NO: 85          moltype = DNA  length = 843
FEATURE                Location/Qualifiers
misc_feature           1..843
                       note = Engineered variant of proline 4-hydroxylase from
                       Sinorhizobium meliloti
source                 1..843
                       mol_type = other DNA
                       organism = synthetic construct
SEQUENCE: 85
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac cccctttatct aaatcactgc cgtacttgaa tgagcttgtt   240
gaaacacact tcgactgcag tgcggttaga tatacgcgta tcgtgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tccttatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                 843

SEQ ID NO: 86          moltype = AA  length = 280
FEATURE                Location/Qualifiers
REGION                 1..280
                       note = Engineered variant of proline 4-hydroxylase from
                       Sinorhizobium meliloti
source                 1..280
                       mol_type = protein
                       organism = synthetic construct
SEQUENCE: 86
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVLILAKL HFFYKADCRS   240
MYDWLKEICK RRGDPALIEK TASLERFFLG HRERGEVMTY                         280

SEQ ID NO: 87          moltype = DNA  length = 843
FEATURE                Location/Qualifiers
misc_feature           1..843
                       note = Engineered variant of proline 4-hydroxylase from
                       Sinorhizobium meliloti
source                 1..843
                       mol_type = other DNA
                       organism = synthetic construct
SEQUENCE: 87
```

```
atgtctacgc atttccttgg caaggtcaaa ttcgacgagg ccagattagc cgaagatctg  60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttttct 480
aaaactccta gactgcatct catgatagat tttgaagctc ccgcctttcc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatct ctctatcct ggccaaagtg cacttctttt ataaagcgga ctgtcggtcc  720
atgtatgatt ggcttaaaga aatatgtaaa cgccggggag atcccgcgtt gattgagaag  780
acagcgagtc tcgaacgttt cttttggggg catcgtgaac gcgagaagt aatgacgtat  840
taa                                                                  843

SEQ ID NO: 88          moltype = AA   length = 280
FEATURE                Location/Qualifiers
REGION                 1..280
                       note = Engineered variant of proline 4-hydroxylase from
                       Sinorhizobium meliloti
source                 1..280
                       mol_type = protein
                       organism = synthetic construct
SEQUENCE: 88
MSTHFLGKVK FDEARLAEDL STLEVAEFSS AYSDFACGKW EACVLRNRTG MQEEDIVVSH  60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAPPESF  180
LRNVEQPVTT RDMVDPRKEL TDEVIEGILG FSIIISEANY REIVSILAKV HFFYKADCRS  240
MYDWLKEICK RRGDPALIEK TASLERFFLG HREREVMTY                         280

SEQ ID NO: 89          moltype = DNA   length = 843
FEATURE                Location/Qualifiers
misc_feature           1..843
                       note = Engineered variant of proline 4-hydroxylase from
                       Sinorhizobium meliloti
source                 1..843
                       mol_type = other DNA
                       organism = synthetic construct
SEQUENCE: 89
atgtctacgc atttccttgg caaggtcaaa ttcgacgagg ccagattagc cgaagatctg  60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc tttactgagg aagataagat attccacatg  420
ggtctgggcg agatctggtt tctggacgca atgttacctc attctgctgc ctgctttttct 480
aaaactccta gactgcatct catgatagat tttgaagcta ccgcctttcc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttggggg catcgtgaac gcgagaagt aatgacgtat  840
taa                                                                  843

SEQ ID NO: 90          moltype = AA   length = 280
FEATURE                Location/Qualifiers
REGION                 1..280
                       note = Engineered variant of proline 4-hydroxylase from
                       Sinorhizobium meliloti
source                 1..280
                       mol_type = protein
                       organism = synthetic construct
SEQUENCE: 90
MSTHFLGKVK FDEARLAEDL STLEVAEFSS AYSDFACGKW EACVLRNRTG MQEEDIVVSH  60
NAPALATPLS KSLPYLNELV ETHFDCSAVR YTRIVRVSEN ACIIPHSDYL ELDETFTRLH  120
LVLDTNSGCA FTEEDKIFHM GLGEIWFLDA MLPHSAACFS KTPRLHLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HREREVMTY                         280

SEQ ID NO: 91          moltype = DNA   length = 843
FEATURE                Location/Qualifiers
misc_feature           1..843
                       note = Engineered variant of proline 4-hydroxylase from
                       Sinorhizobium meliloti
source                 1..843
                       mol_type = other DNA
                       organism = synthetic construct
```

-continued

```
SEQUENCE: 91
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac cccctttatct aaatcactgc cgtacttgaa tgagcttgtt   240
gaaacacact tcgactgcag tgcggttaga tatgtgcgta tcgtgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggga atcccgcgtt gattgagaag   780
acagcgagtc tcgaacgttt cttttggggg catcgtgaac gcggagaagt aatgacgtat   840
taa                                                                 843

SEQ ID NO: 92            moltype = AA  length = 280
FEATURE                  Location/Qualifiers
REGION                   1..280
                         note = Engineered variant of proline 4-hydroxylase from
                         Sinorhizobium meliloti
source                   1..280
                         mol_type = protein
                         organism = synthetic construct
SEQUENCE: 92
MSTHFLGKVK FDEARLAEDL STLEVAEFSS AYSDFACGKW EACVLRNRTG MQEEDIVVSH    60
NAPALATPLS KSLPYLNELV ETHFDCSAVR YVRIVRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREREGVMTY                         280

SEQ ID NO: 93            moltype = DNA  length = 843
FEATURE                  Location/Qualifiers
misc_feature             1..843
                         note = Engineered variant of proline 4-hydroxylase from
                         Sinorhizobium meliloti
source                   1..843
                         mol_type = other DNA
                         organism = synthetic construct
SEQUENCE: 93
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac cccctttatct aaatcactgc cgtacttgaa tgagcttgtt   240
gaaacacact tcgactgcag tgcggttaga tatacgcgta tcatgcgtgt ctccgagaac   300
gcctgcatta tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcatct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggga gatcccgcgtt gattgagaag   780
acagcgagtc tcgaacgttt cttttggggg catcgtgaac gcggagaagt aatgacgtat   840
taa                                                                 843

SEQ ID NO: 94            moltype = AA  length = 280
FEATURE                  Location/Qualifiers
REGION                   1..280
                         note = Engineered variant of proline 4-hydroxylase from
                         Sinorhizobium meliloti
source                   1..280
                         mol_type = protein
                         organism = synthetic construct
SEQUENCE: 94
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIMRVSEN ACIIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREREGVMTY                         280

SEQ ID NO: 95            moltype = DNA  length = 843
FEATURE                  Location/Qualifiers
misc_feature             1..843
                         note = Engineered variant of proline 4-hydroxylase from
                         Sinorhizobium meliloti
source                   1..843
                         mol_type = other DNA
```

-continued

```
                       organism = synthetic construct
SEQUENCE: 95
atgtctacgc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaggcttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg catttttaggg ttctccataa tcatcagtga agcgaattac  660
cgcgagatcg tctctatcct ggccaaatta cacttcttct ataaagcgga ctgtcggtcc  720
atgtatgatt ggcttaaaga aatatgtaaa cgccggggag atcccgcgtt gattgagaag  780
acagcgagtc tcgaacgttt cttttttgggg catcgtgaac gcggagaagt aatgacgtat  840
taa                                                                843

SEQ ID NO: 96          moltype = AA   length = 280
FEATURE                Location/Qualifiers
REGION                 1..280
                       note = Engineered variant of proline 4-hydroxylase from
                        Sinorhizobium meliloti
source                 1..280
                       mol_type = protein
                       organism = synthetic construct
SEQUENCE: 96
MSTHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDEGFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 97          moltype = DNA   length = 843
FEATURE                Location/Qualifiers
misc_feature           1..843
                       note = Engineered variant of proline 4-hydroxylase from
                        Sinorhizobium meliloti
source                 1..843
                       mol_type = other DNA
                       organism = synthetic construct
SEQUENCE: 97
atgtctagcc atttccttgg caaggtcaaa ttcgacgagg ccagattagc cgaagatctg   60
tctactttag aagtcgctga gttttctagt gcatattcgg acttcgcttg tggaaagtgg  120
gaagcatgtg ttttacgcaa cagaacaggc atgcaagaag aagacattgt ggtttctcac  180
aatgcgcccg cattagcgac ccctttatct aaatcactgc cgtacttgaa tgagcttgtt  240
gaaacacact tcgactgcag tgcggttaga tatacgcgta tcgtgcgtgt ctccgagaac  300
gcctgcatta tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcatct catgatagat tttgaagcta ccgccttccc ggaatccttc  540
ttacgcaatg tggaacagcc tgtaactact cgcgacatgg tagaccctcg taaagaattg  600
acggacgaag ttatagaagg catttttaggg ttctccataa tcatcagtga agcgaattac  660
cgcgagatcg tctctatcct ggccaaatta cacttcttct ataaagcgga ctgtcggtcc  720
atgtatgatt ggcttaaaga aatatgtaaa cgccggggag atcccgcgtt gattgagaag  780
acagcgagtc tcgaacgttt cttttttgggg catcgtgaac gcggagaagt aatgacgtat  840
taa                                                                843

SEQ ID NO: 98          moltype = AA   length = 280
FEATURE                Location/Qualifiers
REGION                 1..280
                       note = Engineered variant of proline 4-hydroxylase from
                        Sinorhizobium meliloti
source                 1..280
                       mol_type = protein
                       organism = synthetic construct
SEQUENCE: 98
MSSHFLGKVK FDEARLAEDL STLEVAEFSS AYSDFACGKW EACVLRNRTG MQEEDIVVSH   60
NAPALATPLS KSLPYLNELV ETHFDCSAVR YTRIVRVSEN ACIIPHSDYL ELDETFTRLH  120
LVLDTNSGCA NTEEDKIFHM GLGEIWFLDA MLPHSAACFS KTPRLHLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 99          moltype = DNA   length = 843
FEATURE                Location/Qualifiers
misc_feature           1..843
                       note = Engineered variant of proline 4-hydroxylase from
                        Sinorhizobium meliloti
source                 1..843
```

```
                        mol_type = other DNA
                        organism = synthetic construct
SEQUENCE: 99
atgagtaccc actttctcgg caaagtgaaa ttcgatgaag cacggcttgc agaagacttg    60
tctacgctgg aagtggcgga attttcctcc gcgtatagtg attttgcctg cggaaaatgg   120
gaagcatgtg ttcttagaaa ccgtacaggt atgcaagaag aggatattgt ggtttcccat   180
aacgcaccgg ctcttgcaac cccgctgagt aaatcattgc cttaccttaa tgaattagtt   240
gagacacatt tcgactgttc ggctgtccgt tacacgcgta ttgtaagagt gagcgagaac   300
gcgtgcatta taccacattc agattaccte gagcttgacg agacatttac agattgcat    360
ctggtcttgg ataccaactc aggttgtgcc aataccgaag aggacaagat attccatatg   420
ggtctcggtg aaatatggtt cttggatgcg atgctgcctc atagtgcagc atgtttttct   480
aagacgccta gactgcagct gatgattgac ttcgaagcta cagcgtttcc cgaatcattt   540
ttacggaacg tcgaacagcc ggttaccacc cgtgatatgg tcgacccag  aaaagaatta   600
acggacgaag tgatcgaagg tatactcggc ttttctatta tcatatcgga ggcgaactac   660
cgtgaaatcg tgtctatttt agcgaagctg cacttctttt ataaagccga ttgccggtcg   720
atgtatgatt ggctgaaaga aattgcaag  agacggggag acccggcgct tattgaaaag   780
acggcttcat tggaacgctt ctttttaggc cacagagaac gcggggaagt aatgacctac   840
taa                                                                 843

SEQ ID NO: 100          moltype = AA  length = 280
FEATURE                 Location/Qualifiers
REGION                  1..280
                        note = Engineered variant of proline 4-hydroxylase from
                         Sinorhizobium meliloti
source                  1..280
                        mol_type = protein
                        organism = synthetic construct
SEQUENCE: 100
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 101          moltype = DNA  length = 843
FEATURE                 Location/Qualifiers
misc_feature            1..843
                        note = Engineered variant of proline 4-hydroxylase from
                         Sinorhizobium meliloti
source                  1..843
                        mol_type = other DNA
                        organism = synthetic construct
SEQUENCE: 101
atgagtaccc actttctcgg caaagtgaaa ttcgatgaag cacggcttgc agaagacttg    60
tctacgctgg aagtggcgga attttcctcc gcgtatagtg attttgcctg cggaaaatgg   120
gaagcatgtg ttcttagaaa ccgtacaggt atgcaagaag aggatattgt ggtttcccat   180
aacgcaccgg ctcttgcaac cccgctgagt aaatcattgc cttaccttaa tgaattagtt   240
gagacacatt tcgactgttc ggctgtccgt tacacgcgta ttgtaagagt gagcgagaac   300
gcgtgcctga taccacattc agattaccte gagcttgacg agacatttac agattgcat    360
ctggtcttgg ataccaactc aggttgtgcc aataccgaag aggacaagat attccatatg   420
ggtctcggtg aaatatggtt cttggatgcg atgctgcctc atagtgcagc atgtttttct   480
aagacgccta gactgcatct gatgattgac ttcgaagcta cagcgtttcc cgaatcattt   540
ttacggaacg tcgaacagcc ggttaccacc cgtgatatgg tcgacccag  aaaagaatta   600
acggacgaag tgatcgaagg tatactcggc ttttctatta tcatatcgga ggcgaactac   660
cgtgaaatcg tgtctatttt agcgaagctg cacttctttt ataaagccga ttgccggtcg   720
atgtatgatt ggctgaaaga aattgcaag  agacggggag acccggcgct tattgaaaag   780
acggcttcat tggaacgctt ctttttaggc cacagagaac gcggggaagt aatgacctac   840
taa                                                                 843

SEQ ID NO: 102          moltype = AA  length = 280
FEATURE                 Location/Qualifiers
REGION                  1..280
                        note = Engineered variant of proline 4-hydroxylase from
                         Sinorhizobium meliloti
source                  1..280
                        mol_type = protein
                        organism = synthetic construct
SEQUENCE: 102
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACLIPHSDYL ELDETFTRLH   120
LVLDTNSGCA NTEEDKIFHM GLGEIWFLDA MLPHSAACFS KTPRLHLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 103          moltype = DNA  length = 843
FEATURE                 Location/Qualifiers
misc_feature            1..843
                        note = Engineered variant of proline 4-hydroxylase from
                         Sinorhizobium meliloti
```

```
source                          1..843
                                mol_type = other DNA
                                organism = synthetic construct
SEQUENCE: 103
atgagtaccc actttctcgg caaagtgaaa ttcgatgaag cacggcttgc agaagacttg    60
tctacgctgg aagtggcgga attttcctcc gcgtatagtg attttgcctg cggaaaatgg   120
gaagcatgtg ttcttagaaa ccgtacaggt atgcaagaag aggatattgt ggtttcccat   180
aacgcaccgg ctcttgcaac cccgctgagt aaatcattgc cttaccttaa tgaattagtt   240
gagacacatt tcgactgttc ggctgtccgt tacacgcgta ttgtaagagt gagcgagaac   300
gcgtgcctga taccacattc agattacctc gagcttgacg agacatttac cagattgcat   360
ctggtcttgg ataccaactc aggttgtgcc aataccgaag aggacaagat attccatatg   420
ggtctcggtg aaatatggtt cttggatgcg atgctgcctc atagtgcagc atgttttttct   480
aagacgccta gactgcagct gatgattgac ttcgaagcta cagcgtttcc cgaatcattt   540
ttacggaacg tcgaacagcc ggttaccacc cgtgatatgg tcgacccctag aaaagaatta   600
acggacgaag tgatcgaagg tatactcggc ttttctatta tcatatcgga ggcgaactac   660
cgtgaaatcg tgtctatttt agcgaagctg cacttctttt ataaagccga ttgccggtcg   720
atgtatgatt ggctgaaaga aatttgcaag agacggggag acccggcgct tattgaaaag   780
acggcttcat tggaacgctt cttttttaggc cacagagaac gcggggaagt aatgacctac   840
taa                                                                 843

SEQ ID NO: 104                  moltype = AA  length = 280
FEATURE                         Location/Qualifiers
REGION                          1..280
                                note = Engineered variant of proline 4-hydroxylase from
                                Sinorhizobium meliloti
source                          1..280
                                mol_type = protein
                                organism = synthetic construct
SEQUENCE: 104
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIRVSEN ACLIPHSDYL ELDETFTRLH    120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 105                  moltype = DNA  length = 843
FEATURE                         Location/Qualifiers
misc_feature                    1..843
                                note = Engineered variant of proline 4-hydroxylase from
                                Sinorhizobium meliloti
source                          1..843
                                mol_type = other DNA
                                organism = synthetic construct
SEQUENCE: 105
atgagtaccc actttctcgg caaagtgaaa ttcgatgaag cacggcttgc agaagacttg    60
tctacgctgg aagtggcgga attttcctcc gcgtatagtg attttgcctg cggaaaatgg   120
gaagcatgtg ttcttagaaa ccgtacaggt atgcaagaag aggatattgt ggtttcccat   180
aacgcaccgg ctcttgcaac cccgctgagt aaatcattgc cttaccttaa tgaattagtt   240
gagacacatt tcgactgttc ggctgtccgt tacacgcgta ttgtaagagt gagcgagaac   300
gcgtgcctga taccacattc agattacctc gagcttgacg agacatttac cagattgcat   360
ctggtcttgg ataccaactc aggttgtgcc tataccgaag aggacaagat attccatatg   420
ggtctcggtg aaatatggtt cttggatgcg atgctgcctc atagtgcagc atgttttttct   480
aagacgccta gactgcagct gatgattgac ttcgaagcta cagcgtttcc cgaatcattt   540
ttacggaacg tcgaacagcc ggttaccacc cgtgatatgg tcgacccctag aaaagaatta   600
acggacgaag tgatcgaagg tatactcggc ttttctatta tcatatcgga ggcgaactac   660
cgtgaaatcg tgtctatttt agcgaagctg cacttctttt ataaagccga ttgccggtcg   720
atgtatgatt ggctgaaaga aatttgcaag agacggggag acccggcgct tattgaaaag   780
acggcttcat tggaacgctt cttttttaggc cacagagaac gcggggaagt aatgacctac   840
taa                                                                 843

SEQ ID NO: 106                  moltype = AA  length = 280
FEATURE                         Location/Qualifiers
REGION                          1..280
                                note = Engineered variant of proline 4-hydroxylase from
                                Sinorhizobium meliloti
source                          1..280
                                mol_type = protein
                                organism = synthetic construct
SEQUENCE: 106
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIRVSEN ACLIPHSDYL ELDETFTRLH    120
LVLDTNSGCA YTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 107                  moltype = DNA  length = 843
FEATURE                         Location/Qualifiers
misc_feature                    1..843
                                note = Engineered variant of proline 4-hydroxylase from
```

```
                        Sinorhizobium meliloti
source                  1..843
                        mol_type = other DNA
                        organism = synthetic construct
SEQUENCE: 107
atgagtagcc actttctcgg caaagtgaaa ttcgatgaag cacggcttgc agaagacttg    60
tctacgctgg aagtggcgga attttcctcc gcgtatagtg attttgcctg cggaaaatgg   120
gaagcatgtg ttcttagaaa ccgtacaggt atgcaagaag aggatattgt ggtttcccat   180
aacgcaccgg ctcttgcaac cccgctgagt aaatcattgc cttaccttaa tgaattagtt   240
gagacacatt tcgactgttc ggctgtccgt tacacgcgta ttgtaagagt gagcgagaac   300
gcgtgcctga taccattc agattacctc gagcttgacg agacatttac cagattgcat   360
ctggtcttgg ataccaactc aggttgtgcc aataccgaag aggacaagat attccatatg   420
ggtctcggtg aaatatggtt cttggatgcg atgctgcctc atagtgcagc atgtttttct   480
aagacgccta gactgcagct gatgattgac ttcgaagcta cagcgtttcc gaatcatttt   540
ttacggaacg tcgaacagcc ggttaccacc cgtgatatgg tcgacctag aaaagaatta   600
acggacgaag tgatcgaagg tatactcggc ttttctatta tcatatcgga ggcgaactac   660
cgtgaaatcg tgtctatttt agcgaagctg cacttctttt ataaagccga ttgccggtcg   720
atgtatgatt ggctgaaaga aatttgcaag agacggggag acccggcgct tattgaaaag   780
acggcttcat tggaacgctt cttttaggc cacagagaac gcggggaagt aatgacctac   840
taa                                                                 843

SEQ ID NO: 108          moltype = AA   length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 108
MSSHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACLIPHSDYL ELDETFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 109          moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 109
atgagtaccc actttctcgg caaagtgaaa ttcgatgaag cacggcttgc agaagacttg    60
tctacgctgg aagtgacgga attttcctcc gcgtatagtg attttgcctg cggaaaatgg   120
gaagcatgtg ttcttagaaa ccgtacaggt atgcaagaag aggatattgt ggtttcccat   180
aacgcaccgg ctcttgcaac cccgctgagt aaatcattgc cttaccttaa tgaattagtt   240
gagacacatt tcgactgttc ggctgtccgt tacacgcgta ttgtaagagt gagcgagaac   300
gcgtgcctga taccattc agattacctc gagcttgacg agacatttac cagattgcat   360
ctggtcttgg ataccaactc aggttgtgcc aataccgaag aggacaagat attccatatg   420
ggtctcggtg aaatatggtt cttggatgcg atgctgcctc atagtgcagc atgtttttct   480
aagacgccta gactgcagct gatgattgac ttcgaagcta cagcgtttcc gaatcatttt   540
ttacggaacg tcgaacagcc ggttaccacc cgtgatatgg tcgacctag aaaagaatta   600
acggacgaag tgatcgaagg tatactcggc ttttctatta tcatatcgga ggcgaactac   660
cgtgaaatcg tgtctatttt agcgaagctg cacttctttt ataaagccga ttgccggtcg   720
atgtatgatt ggctgaaaga aatttgcaag agacggggag acccggcgct tattgaaaag   780
acggcttcat tggaacgctt cttttaggc cacagagaac gcggggaagt aatgacctac   840
taa                                                                 843

SEQ ID NO: 110          moltype = AA   length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 110
MSTHFLGKVK FDEARLAEDL STLEVTEFSS AYSDFACGKW EACVLRNRTG MQEEDIVVSH    60
NAPALATPLS KSLPYLNELV ETHFDCSAVR YTRIVRVSEN ACLIPHSDYL ELDETFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 111          moltype = DNA   length = 843
FEATURE                 Location/Qualifiers
misc_feature            1..843
```

```
                        note = Engineered variant of proline 4-hydroxylase from
                           Sinorhizobium meliloti
source                  1..843
                        mol_type = other DNA
                        organism = synthetic construct
SEQUENCE: 111
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact cgactgcag tgcggttaga tatacgcgta tcgtgcgtgt ctccgagaac   300
gcctgcctga tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                 843

SEQ ID NO: 112         moltype = AA   length = 280
FEATURE                Location/Qualifiers
REGION                 1..280
                        note = Engineered variant of proline 4-hydroxylase from
                           Sinorhizobium meliloti
source                  1..280
                        mol_type = protein
                        organism = synthetic construct
SEQUENCE: 112
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACLIPHSDYL ELDETFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 113         moltype = DNA   length = 843
FEATURE                Location/Qualifiers
misc_feature            1..843
                        note = Engineered variant of proline 4-hydroxylase from
                           Sinorhizobium meliloti
source                  1..843
                        mol_type = other DNA
                        organism = synthetic construct
SEQUENCE: 113
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact cgacagcag tgcggttaga tatgtccgta tcgtgcgtgt ctccgagaac   300
gcctgcctga tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca tccttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggag catcgtgaac gcggagaagt aatgacgtat   840
taa                                                                 843

SEQ ID NO: 114         moltype = AA   length = 280
FEATURE                Location/Qualifiers
REGION                 1..280
                        note = Engineered variant of proline 4-hydroxylase from
                           Sinorhizobium meliloti
source                  1..280
                        mol_type = protein
                        organism = synthetic construct
SEQUENCE: 114
MSTHFLGKVK FDEARLAEDL STLEVAEFSS AYSDFACGKW EACVLRNRTG MQEEDIVVSH    60
NAPALATPLS KSLPYLNELV ETHFDSSAVR YVRIVRVSEN ACLIPHSDYL ELDETFTRLH   120
LVLDTNSGCA NTEEDKIFHM GLGEIWFLDA SLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLE HRERGEVMTY                         280

SEQ ID NO: 115         moltype = DNA   length = 843
FEATURE                Location/Qualifiers
```

```
misc_feature         1..843
                     note = Engineered variant of proline 4-hydroxylase from
                         Sinorhizobium meliloti
source               1..843
                     mol_type = other DNA
                     organism = synthetic construct
SEQUENCE: 115
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattagcgac ccctttatct aaatcactgc cgtacttgaa tgagcttgtt   240
gaaacacact tcgactgcag tgcggttaga tatacgcgta tcgtgcgtgt ctccgagaac   300
gcctgccaga tccctcatag tgattatttg gagctcgatg aaacgttaac ccggctgcat   360
ctcgtgttgg atactaacag tggttgtgcc aacactgagg aagataagat attccacatg   420
ggtctgggcg agatctggtt tctggacgca atgttacctc attctgctgc ctgctttttct  480
aaaactccta gactgcagct catgatagat tttgaagcta ccgccttccc ggaatccttc   540
ttacgcaatg tggaacagcc tgtaactact cgcgacatgg tagaccctcg taagaattg    600
acggacgaag ttatagaagg cattttaggg ttctccataa tcatcagtga agcgaattac   660
cgcgagatcg tcctgatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat    840
taa                                                                 843

SEQ ID NO: 116        moltype = AA  length = 280
FEATURE               Location/Qualifiers
REGION                1..280
                      note = Engineered variant of proline 4-hydroxylase from
                          Sinorhizobium meliloti
source                1..280
                      mol_type = protein
                      organism = synthetic construct
SEQUENCE: 116
MSTHFLGKVK FDEARLAEDL STLEVAEFSS AYSDFACGKW EACVLRNRTG MQEEDIVVSH     60
NAPALATPLS KSLPYLNELV ETHFDCSAVR YTRIVRVSEN ACQIPHSDYL ELDETLTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVLILAKL HFFYKADCRS   240
MYDWLKEICK RRGDPALIEK TASLERFFLG HRERGEVMTY                         280

SEQ ID NO: 117        moltype = DNA  length = 843
FEATURE               Location/Qualifiers
misc_feature          1..843
                      note = Engineered variant of proline 4-hydroxylase from
                          Sinorhizobium meliloti
source                1..843
                      mol_type = other DNA
                      organism = synthetic construct
SEQUENCE: 117
atgtctacgc atttccttgg caaggtcaaa ttcgacgagg ccagattagc cgaagatctg    60
tctactttag aagtcgctga gttttctagt gcatattcgg acttcgcttg tggaaagtgg   120
gaagcatgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tgcggttaga tatacgcgta tcgtgcgtgt ctccgagaac   300
gcctgcctga tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgctttttct  480
aaaactccta gactgcagct catgatagat tttgaagcta ccgccttccc ggaatccttc   540
ttacgcaatg tggaacagcc tgtaactact cgcgacatgg tagaccctcg taagaattg    600
acggacgaag ttatagaagg catttaggg ttctccataa tcatcagtga agcgaattac    660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat    840
taa                                                                 843

SEQ ID NO: 118        moltype = AA  length = 280
FEATURE               Location/Qualifiers
REGION                1..280
                      note = Engineered variant of proline 4-hydroxylase from
                          Sinorhizobium meliloti
source                1..280
                      mol_type = protein
                      organism = synthetic construct
SEQUENCE: 118
MSTHFLGKVK FDEARLAEDL STLEVAEFSS AYSDFACGKW EACVLRNRTG MQEEDIVVSH     60
NAPALQTPLS KSLPYLNELV ETHFDCSAVR YTRIVRVSEN ACLIPHSDYL ELDETFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 119        moltype = DNA  length = 843
```

```
FEATURE               Location/Qualifiers
misc_feature          1..843
                      note = Engineered variant of proline 4-hydroxylase from
                      Sinorhizobium meliloti
source                1..843
                      mol_type = other DNA
                      organism = synthetic construct
SEQUENCE: 119
atgtctacgc atttccttgg caaggtcaaa ttcgacgagg ccagattagc cgaagatctg    60
tctactttag aagttgctga gttttcttcc gcatattcgg acttcgcatg tggaaagtgg   120
gaagcatgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tgcggttaga tatacgcgta tcgtgcgtgt ctccgagaac   300
gcctgcctga tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttttaggg ttctccataa tcatcagtga agcgaattac   660
cgcgagatcg tctctatcct ggccaaatta cacttcttttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                  843

SEQ ID NO: 120        moltype = AA  length = 280
FEATURE               Location/Qualifiers
REGION                1..280
                      note = Engineered variant of proline 4-hydroxylase from
                      Sinorhizobium meliloti
source                1..280
                      mol_type = protein
                      organism = synthetic construct
SEQUENCE: 120
MSTHFLGKVK FDEARLAEDL STLEVAEFSS AYSDFACGKW EACVLRNRTG MQEEDIVVSH    60
NAPALQTPLS KSLPYLNELV ETHFDCSAVR YTRIVRVSEN ACLIPHSDYL ELDETFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREREGVMTY                         280

SEQ ID NO: 121        moltype = DNA  length = 843
FEATURE               Location/Qualifiers
misc_feature          1..843
                      note = Engineered variant of proline 4-hydroxylase from
                      Sinorhizobium meliloti
source                1..843
                      mol_type = other DNA
                      organism = synthetic construct
SEQUENCE: 121
atgtctacgc atttccttgg caaggtcaaa ttcgacgagg ccagattagc cgaagatctg    60
tctactttag aagtcgctga gttttcttcc gcatattcgg acttcgcttg tggaaagtgg   120
gaagcatgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tgcggttaga tatgtacgta tcgtgcgtgt ctccgagaac   300
gcctgcctga tccctcatag tgattatttg gagctcgatg aaacgttcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttttaggg ttctccataa tcatcagtga agcgaattac   660
cgcgagatcg tctctatcct ggccaaatta cacttcttttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                  843

SEQ ID NO: 122        moltype = AA  length = 280
FEATURE               Location/Qualifiers
REGION                1..280
                      note = Engineered variant of proline 4-hydroxylase from
                      Sinorhizobium meliloti
source                1..280
                      mol_type = protein
                      organism = synthetic construct
SEQUENCE: 122
MSTHFLGKVK FDEARLAEDL STLEVAEFSS AYSDFACGKW EACVLRNRTG MQEEDIVVSH    60
NAPALQTPLS KSLPYLNELV ETHFDCSAVR YVRIVRVSEN ACLIPHSDYL ELDETFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HREREGVMTY                         280
```

```
SEQ ID NO: 123          moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 123
atgtctacgc atttccttgg caaggtcaaa ttcgacgagg ccagattagc cgaagatctg   60
tctactttag aagttgctga gttttcttcc gcatattcgg acttcgcttg tggaaagtgg  120
gaagcatgtg ttttacgcaa cagaacaggc atgcaagaag aagacattgt ggtttctcac  180
aatgcgcccg cattagcgac cccctttatct aaatcactgc cgtacttgaa tgagcttgtt  240
gaaacacact tcgactgcag tgcggttaga tatgtacgta tcgtgcgtgt ctccgagaac  300
gcctgcctga tccctcatag tgattatttg gagctcgatg aaacgttcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttctct  480
aaaactccta gactgcagct catgatagat tttgaagctc ccgccttccc ggaatccttc  540
ttacgcaatg tggaacagcc tgtaactact cgcgacatgg tagaccctcg taaagaattg  600
acggacgaag ttatagaagg catttaggg ttctccataa tcatcagtga agcgaattac  660
cgcgagatcg tctctatcct ggccaaatta cacttcttt ataaagcgga ctgtcggtcc  720
atgtatgatt ggcttaaaga aaatatgtaaa cgccggggag atcccgcgtt gattgagaag  780
acagcgagtc tcgaacgttt ctttttgggg catcgtgaac gcggagaagt aatgacgtat  840
taa                                                                 843

SEQ ID NO: 124          moltype = AA    length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 124
MSTHFLGKVK FDEARLAEDL STLEVAEFSS AYSDFACGKW EACVLRNRTG MQEEDIVVSH   60
NAPALATPLS KSLPYLNELV ETHFDCSAVR YVRIVRVSEN ACLIPHSDYL ELDETFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 125          moltype = DNA   length = 843
FEATURE                 Location/Qualifiers
misc_feature            1..843
                        note = Engineered variant of proline 4-hydroxylase from
                        Sinorhizobium meliloti
source                  1..843
                        mol_type = other DNA
                        organism = synthetic construct
SEQUENCE: 125
atgtctacgc atttccttgg caaggtcaaa ttcgacgagg ccagattagc cgaagatctg   60
tctactttag aagttgctga gttttcttcc gcatattcgg acttcgcttg tggaaagtgg  120
gaagcatgtg ttttacgcaa cagaacaggc atgcaagaag aagacattgt ggtttctcac  180
aatgcgcccg cattacagac cccctttatct aaatcactgc cgtacttgaa tgagcttgtt  240
gaaacacact tcgactgcag tgcggttaga tatgtacgta tcgtgcgtgt ctccgagaac  300
gcctgcctga tccctcatag tgattatttg gagttggagg aatcattcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttctct  480
aaaactccta gactgcagct catgatagat tttgaagcta ccgccttccc ggaatccttc  540
ttacgcaatg tggaacagcc tgtaactact cgcgacatgg tagaccctcg taaagaattg  600
acggacgaag ttatagaagg catttaggg ttctccataa tcatcagtga agcgaattac  660
cgcgagatcg tctctatcct ggccaaatta cacttcttt ataaagcgga ctgtcggtcc  720
atgtatgatt ggcttaaaga aaatatgtaaa cgccggggag atcccgcgtt gattgagaag  780
acagcgagtc tcgaacgttt ctttttgggg catcgtgaac gcggagaagt aatgacgtat  840
taa                                                                 843

SEQ ID NO: 126          moltype = AA    length = 280
FEATURE                 Location/Qualifiers
REGION                  1..280
                        note = Engineered variant of proline 4-hydroxylase from
                        Sinorhizobium meliloti
source                  1..280
                        mol_type = protein
                        organism = synthetic construct
SEQUENCE: 126
MSTHFLGKVK FDEARLAEDL STLEVAEFSS AYSDFACGKW EACVLRNRTG MQEEDIVVSH   60
NAPALQTPLS KSLPYLNELV ETHFDCSAVR YVRIVRVSEN ACLIPHSDYL ELEESFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280
```

```
SEQ ID NO: 127          moltype = DNA  length = 843
FEATURE                 Location/Qualifiers
misc_feature            1..843
                        note = Engineered variant of proline 4-hydroxylase from
                          Sinorhizobium meliloti
source                  1..843
                        mol_type = other DNA
                        organism = synthetic construct
SEQUENCE: 127
atgtctacgc atttccttgg caaggtcaaa ttcgacgagg ccagattagc cgaagatctg   60
tctactttag aacgtgctga gttttcttcc gcatattcgg acttcgcttg tggaaagtgg  120
gaagcatgtg ttttacgcaa cagaacaggc atgcaagaag aagacattgt ggtttctcac  180
aatgcgcccg cattacagac cccttatct aaatcactgc cgtacttgaa tgagctttgtt  240
gaaacacact tcgactgcag tgcggttaga tatgtacgga tcgtgcgtgt ctccgagaac  300
gcctgcctga tccctcatag tgattatttg gagttggatg aagaattcac ccggctgcac  360
ctcgtgttga atactaacag tggttgtgcc aacactgagg aagataagat attccacatg  420
ggtctgttgg agatctggtt tctggacgca atgttacctc attctgctgc ctgcttttct  480
aaaactccta gactgcagct catgatagat tttgaagcta ccgccttccc ggaatccttc  540
ttacgcaatg tggaacagcc tgtaactact cgcgacatgg tagaccctcg taagaattg  600
acggacgaag ttatagaagg catttaggg ttctccataa tcatcagtga agcgaattac  660
cgcgagatcg tctctatcct ggccaaatta cacttctttt ataaagccga ttgtcggtac  720
atgtatgatt ggcttaaaga aatatgtaaa cgccggggag atcccgcgtt gattgagaag  780
acagcgagtc tcgaacgttt ctttttgggg catcgtgaac gcggagaagt aatgacgtat  840
taa                                                                843

SEQ ID NO: 128          moltype = AA  length = 280
FEATURE                 Location/Qualifiers
REGION                  1..280
                        note = Engineered variant of proline 4-hydroxylase from
                          Sinorhizobium meliloti
source                  1..280
                        mol_type = protein
                        organism = synthetic construct
SEQUENCE: 128
MSTHFLGKVK FDEARLAEDL STLERAEFSS AYSDFACGKW EACVLRNRTG MQEEDIVVSH   60
NAPALQTPLS KSLPYLNELV ETHFDCSAVR YVRIVRVSEN ACLIPHSDYL ELDEEFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 129          moltype = DNA  length = 843
FEATURE                 Location/Qualifiers
misc_feature            1..843
                        note = Engineered variant of proline 4-hydroxylase from
                          Sinorhizobium meliloti
source                  1..843
                        mol_type = other DNA
                        organism = synthetic construct
SEQUENCE: 129
atgagtagcc actttctcgg caaagtgaaa ttcgatgaag cacggcttgc agaagacttg   60
tctacgctgg aagtggcgga attttcctcc gcgtatagtg attttgcctg cggaaaatgg  120
gaagcatgtg ttcttagaaa ccgtacaggt atgcaagaag aggatattgt ggtttcccat  180
aacgcaccgg ctcttcagac cccgctgagt aaatcattgc cttacttaa tgaattagtt  240
gagacacatt tcgactgttc ggctgtccgt tacgttcgta ttgtaaggat gagcgagaac  300
gcgtgcctga taccacattc agattacctc gagcttgacg agacatttac cagattgcat  360
ctggtcttgg ataccaactc aggttgtgcc aataccgaag aggacaagat attccatatg  420
ggtctcggta aatatggtt cttggatgcg atgctgcctc atagtgcagc atgttttct  480
aagacgccta gactgcagct gatgattgac ttcgaagcta cagcgtttcc cgaatcattt  540
ttacggaacg tcgaacagcc ggttaccacc cgtgatatgg tcgaccctag aaaagaatta  600
acggacgaag tgatcgaagg tatactcggc ttttctatta tcatatcgga ggcgaactac  660
cgtgaaatcg tgtctatttt agcgaagctg cacttctttt ataaagccga ttgccggtcg  720
atgtatgatt ggctgaaaga aatttgcaag agacggggag acccggcgct tattgaaaag  780
acggcttcat tggaacgctt ctttttaggc cacagagaac gcggggaagt aatgacctac  840
taa                                                                843

SEQ ID NO: 130          moltype = AA  length = 280
FEATURE                 Location/Qualifiers
REGION                  1..280
                        note = Engineered variant of proline 4-hydroxylase from
                          Sinorhizobium meliloti
source                  1..280
                        mol_type = protein
                        organism = synthetic construct
SEQUENCE: 130
MSSHFLGKVK FDEARLAEDL STLEVAEFSS AYSDFACGKW EACVLRNRTG MQEEDIVVSH   60
NAPALQTPLS KSLPYLNELV ETHFDCSAVR YVRIVRVSEN ACLIPHSDYL ELDETFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
```

```
MYDWLKEICK RRGDPALIEK TASLERFFLG HRERGEVMTY                           280

SEQ ID NO: 131            moltype = DNA   length = 843
FEATURE                   Location/Qualifiers
misc_feature              1..843
                          note = Engineered variant of proline 4-hydroxylase from
                            Sinorhizobium meliloti
source                    1..843
                          mol_type = other DNA
                          organism = synthetic construct
SEQUENCE: 131
atgagtagcc actttctcgg caaagtgaaa ttcgatgaag cacggcttgc agaagacttg   60
tctacgctgg aacgtgcgga attttcctcc gcgtatagtg attttgcctg cggaaaatgg  120
gaagcatgtg ttcttagaaa ccgtacaggt atgcaagaag aggatattgt ggtttcccat  180
aacgcaccgg ctcttcagac cccgctgagt aaatcattgc cttaccttaa tgaattagtt  240
gagacacatt tcgactgttc ggctgtccgt tacgttcgta ttgtaagagt gagcgagaac  300
gcgtgcctga taccacattc agattacctc gagcttgacg aggagtttac cagattgcat  360
ctggtcttgg ataccaactc aggttgtgcc aataccgaag aggacaagat attccatatg  420
ggtctcggtg aaatatggtt cttggatgcg atgctgcctc atagtgcagc atgtttttct  480
aagacgccta gactgcagct gatgattgac ttcgaagcta cagcgtttcc cgaatcattt  540
ttacggaacg tcgaacagcc ggttaccacc cgtgatatgg tcgacctag aaaagaatta   600
acggacgaag tgatcgaagg tatactcggc ttttctatta tcatatcgga ggcgaactac  660
cgtgaaatcg tgtctatttt agcgaagctg cacttctttt ataaagccga ttgccggtcg  720
atgtatgatt ggctgaaaga aatttgcaag agacggggag accggcgct tattgaaaag   780
acggcttcat tggaacgctt ctttttaggc cacagagaac gcggggaagt aatgacctac  840
taa                                                                 843

SEQ ID NO: 132            moltype = AA   length = 280
FEATURE                   Location/Qualifiers
REGION                    1..280
                          note = Engineered variant of proline 4-hydroxylase from
                            Sinorhizobium meliloti
source                    1..280
                          mol_type = protein
                          organism = synthetic construct
SEQUENCE: 132
MSSHFLGKVK FDEARLAEDL STLERAEFSS AYSDFACGKW EACVLRNRTG MQEEDIVVSH   60
NAPALQTPLS KSLPYLNELV ETHFDCSAVR YVRIVRVSEN ACLIPHSDYL ELDEEFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 133            moltype = DNA   length = 843
FEATURE                   Location/Qualifiers
misc_feature              1..843
                          note = Engineered variant of proline 4-hydroxylase from
                            Sinorhizobium meliloti
source                    1..843
                          mol_type = other DNA
                          organism = synthetic construct
SEQUENCE: 133
atgagtagcc actttctcgg caaagtgaaa ttcgatgaag cacggcttgc agaagacttg   60
tctacgctgg aacgtgcgga attttcctcc gcgtatagtg attttgcctg cggaaaatgg  120
gaagcatgtg ttcttagaaa ccgtacaggt atgcaagaag aggatattgt ggtttcccat  180
aacgcaccgg ctcttcagac cccgctgagt aaatcattgc cttaccttaa tgaattagtt  240
gagacacatt tcgactgttc ggctgtccgt tacgttcgta ttgtaagagt gagcgagaac  300
gcgtgcctga taccacattc agattacctc gagcttgacg agacatttac cagattgcat  360
ctggtcttgg ataccaactc aggttgtgcc aataccgaag aggacaagat attccatatg  420
ggtctcggtg aaatatggtt cttggatgcg atgctgcctc atagtgcagc atgtttttct  480
aagacgccta gactgcagct gatgattgac ttcgaagcta cagcgtttcc cgaatcattt  540
ttacggaacg tcgaacagcc ggttaccacc cgtgatatgg tcgacctag aaaagaatta   600
acggacgaag tgatcgaagg tatactcggc ttttctatta tcatatcgga ggcgaactac  660
cgtgaaatcg tgtctatttt agcgaagctg cacttctttt ataaagccga ttgccggtcg  720
atgtatgatt ggctgaaaga aatttgcaag agacggggag accggcgct tattgaaaag   780
acggcttcat tggaacgctt ctttttaggc cacagagaac gcggggaagt aatgacctac  840
taa                                                                 843

SEQ ID NO: 134            moltype = AA   length = 280
FEATURE                   Location/Qualifiers
REGION                    1..280
                          note = Engineered variant of proline 4-hydroxylase from
                            Sinorhizobium meliloti
source                    1..280
                          mol_type = protein
                          organism = synthetic construct
SEQUENCE: 134
MSSHFLGKVK FDEARLAEDL STLERAEFSS AYSDFACGKW EACVLRNRTG MQEEDIVVSH   60
NAPALQTPLS KSLPYLNELV ETHFDCSAVR YVRIVRVSEN ACLIPHSDYL ELDETFTRLH  120
LVLDTNSGCA NTEEDKIFHM GLGEIWFLDA MLPHSAACFS KTPRLQLMID FEATAFPESF  180
```

```
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 135          moltype = DNA   length = 843
FEATURE                 Location/Qualifiers
source                  1..843
                        mol_type = other DNA
                        organism = Sinorhizobium meliloti
SEQUENCE: 135
atgagcaccc atttcttggg caaggtcaag ttcgatgaag cgcgattggc agaagatcta    60
tctaccttgg aagttgccga gttctcgagt gcatactcgg acttcgcgtg cggtaaatgg    120
gaggcatgcg tgctacgcaa tcggaccgga atgcaggagg aagatatcgt cgtaagtcac    180
aacgctcctg cactggccac gccgctgagc aagtcgctgc cgtatctgaa cgaacttgtt    240
gaaacccact tcgattgcag cgctgttcgg tatacaagaa ttgtccgtgt atcagaaaac    300
gcatgtataa tccccatag tgattaccta gaactagatg agaccttcac aaggttacac    360
ctggtgttag acactaattc aggatgcgct aatactgagg aagataaaat atttcatatg    420
ggactgggag agatttggtt ccttgacgct atgttaccgc atagcgctgc ttgttttttcc   480
aaaactccgc gcctgcatct gatgatcgac tttgaggcta ccgcttttcc cgaatctttt    540
ctgcgaaatg tcgaacaacc agtgacaaca cgagacatgg ttgatcctcg aaggaacta    600
accgatgagg ttatcgaagg tattctgggg ttttcaataa ttattagcga agccaattac    660
cgggaaattg tttctattct ggcgaagcta cacttcttct acaaggcaga ctgtcgatca    720
atgtacgact ggctgaagga aatctgcaaa cgtcgagggg atcctgcact tattgaaaag    780
accgcctcgc tcgagcgatt ttttctaggg caccgtgaac gtggcgaggt gatgacatac    840
taa                                                                 843

SEQ ID NO: 136          moltype = AA    length = 280
FEATURE                 Location/Qualifiers
source                  1..280
                        mol_type = protein
                        organism = Sinorhizobium meliloti
SEQUENCE: 136
MSTHFLGKVK FDEARLAEDL STLEVAEFSS AYSDFACGKW EACVLRNRTG MQEEDIVVSH    60
NAPALATPLS KSLPYLNELV ETHFDCSAVR YTRIVRVSEN ACIIPHSDYL ELDETFTRLH    120
LVLDTNSGCA NTEEDKIFHM GLGEIWFLDA MLPHSAACFS KTPRLHLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 137          moltype = DNA   length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 137
atgtctacgc atttccttgg caaggtcaaa ttcgacgagg ccagattagc cgaagatctg    60
tctactttag aacgtgctga gttttcttcc gcatattcgg acttcgcttg tggaaagtgg    120
gaagcatgtg ttttacgcaa cagaacaggc atgcaagaag aagacattgt ggtttctcac    180
aatgcgcccg cattacagac ccctttatct aaatcactgc cgtacttgaa tgagcttgtt    240
gaaacacact tcgactgcag tgcggttaga tatgtacgga tcgtgcgtgt ctccgagaac    300
gcctgcctga tccctcatag tgattatttg gagttggata tgaattcac ccggctgcac    360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcagct catgatagat tttgaagcta ccgcttttcc ggaatccttc    540
ttacgcaatg tggaacagcc tgtaactact cgcgacatgg tagaccctcg taaagaattg    600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttgggg catcgtgaac gcgagaagt aatgacgtat    840
taa                                                                 843

SEQ ID NO: 138          moltype = AA    length = 280
FEATURE                 Location/Qualifiers
REGION                  1..280
                        note = Codon-optimized proline 4-hydroxylase gene from
                          Sinorhizobium meliloti
source                  1..280
                        mol_type = protein
                        organism = synthetic construct
SEQUENCE: 138
MSTHFLGKVK FDEARLAEDL STLERAEFSS AYSDFACGKW EACVLRNRTG MQEEDIVVSH    60
NAPALQTPLS KSLPYLNELV ETHFDCSAVR YVRIVRVSEN ACLIPHSDYL ELDNEFTRLH    120
LVLDTNSGCA NTEEDKIFHM GLGEIWFLDA MLPHSAACFS KTPRLQLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 139          moltype = DNA   length = 843
FEATURE                 Location/Qualifiers
```

```
misc_feature        1..843
                    note = Codon-optimized proline 4-hydroxylase gene from
                        Sinorhizobium meliloti
source              1..843
                    mol_type = other DNA
                    organism = synthetic construct
SEQUENCE: 139
atgtctacgc atttccttgg caaggtcaaa ttcgacgagg ccagattagc cgaagatctg   60
tctactttag aacgtgctga gttttcttcc gcatattcgg acttcgcttg tggaaagtgg  120
gaagcatgtg ttttacgcaa cagaacaggc atgcaagaag aagacattgg ggtttctcac  180
aatgcgcccg cattacagac ccctttatct aaatcactgc cgtacttgaa tgagcttgtt  240
gaaacacact tcgactgcag tgcggttaga tatgtacgga tcgtgcgtgt ctccgagaac  300
gcctgcctga tccctcatag tgattatttg gagttggatg aagaattcac ccggctgcac  360
ctcgtgttgg atactaacag tggttgtgcc aacactgagg aagataagat attccactgg  420
ggtctgggcg agatctggtt tctggacgca atgttacctc attctgctgc ctgctttttct  480
aaaactccta gactgcagct catgatagat tttgaagcta ccgccttccc ggaatccttc  540
ttacgcaatg tggaacagcc tgtaactact cgcgacatgg tagaccctcg taaagaattg  600
acggacgaag ttatagaagg catttttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 140        moltype = AA  length = 280
FEATURE               Location/Qualifiers
REGION                1..280
                      note = Codon-optimized proline 4-hydroxylase gene from
                          Sinorhizobium meliloti
source                1..280
                      mol_type = protein
                      organism = synthetic construct
SEQUENCE: 140
MSTHFLGKVK FDEARLAEDL STLERAEFSS AYSDFACGKW EACVLRNRTG MQEEDIVVSH   60
NAPALQTPLS KSLPYLNELV ETHFDCSAVR YVRIVRVSEN ACLIPHSDYL ELDEEFTRLH  120
LVLDTNSGCA NTEEDKIFHL GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HREREGEVMTY                       280

SEQ ID NO: 141        moltype = DNA  length = 843
FEATURE               Location/Qualifiers
misc_feature          1..843
                      note = Codon-optimized proline 4-hydroxylase gene from
                          Sinorhizobium meliloti
source                1..843
                      mol_type = other DNA
                      organism = synthetic construct
SEQUENCE: 141
atgtctacgc atttcctcgg caaggtcaaa ttcgacgagg ccagattagc cgaagatctg   60
tctactttag aacgtgctga gttttcttcc gcatattcgg acttcgcttg tggaaagtgg  120
gaagcatgtg ttttacgcaa cagaacaggc atgcaagaag aagacattgt ggtttctcac  180
aatgcgcccg cattacagac ccctttatct aaatcactgc cgtacttgaa tgagcttgtt  240
gaaacacact tcgactgcag tgcggttaga tatgtacgga tcgtgcgtgt cactgagaac  300
gcctgcctga tccctcatag tgattatttg gagttggatg aagaattcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttttct  480
aaaactccta gactgcagct catgatagat tttgaagcta ccgccttccc ggaatccttc  540
ttacgcaatg tggaacagcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 142        moltype = AA  length = 280
FEATURE               Location/Qualifiers
REGION                1..280
                      note = Codon-optimized proline 4-hydroxylase gene from
                          Sinorhizobium meliloti
source                1..280
                      mol_type = protein
                      organism = synthetic construct
SEQUENCE: 142
MSTHFLGKVK FDEARLAEDL STLERAEFSS AYSDFACGKW EACVLRNRTG MQEEDIVVSH   60
NAPALQTPLS KSLPYLNELV ETHFDCSAVR YVRIVRVTEN ACLIPHSDYL ELDEEFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HREREGEVMTY                       280

SEQ ID NO: 143        moltype = DNA  length = 843
```

```
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 143
atgtctacgc atttccttgg caaggtcaaa ttcgacgagg ccagattagc cgaagatctg      60
tctactttag aacgtgctga gttttcttcc gcatattcgg acttcgcttg tggaaagtgg    120
gaactttgtg ttttacgcaa cagaacaggc atgcaagaag aagacattgt ggtttctcac    180
aatgcgcccg cattacagac ccctttatct aaatcactgc cgtacttgaa tgagcttgtt    240
gaaacacact tcgactgcag tgcggttaga tatgtacgga tcgtgcgtgt ctccgagaac    300
gcctgcctga tccctcatag tgattatttg gagttggatg aagaattcac ccggctgcac    360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcagct catgatagat tttgaagcta ccgccttccc ggaatccttc    540
ttacgcaatg tggaacagcc tgtaactact cgcgacatgg tagaccctcg taaagaattg    600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttgtggg catcgtgaac gcgagaagt aatgacgtat    840
taa                                                                    843

SEQ ID NO: 144          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 144
MSTHFLGKVK FDEARLAEDL STLERAEFSS AYSDFACGKW ELCVLRNRTG MQEEDIVVSH       60
NAPALQTPLS KSLPYLNELV ETHFDCSAVR YVRIVRVSEN ACLIPHSDYL ELDEEFTRLH     120
LVLDTNSGCA NTEEDKIFHM GLGEIWFLDA MLPHSAACFS KTPRLQLMID FEATAFPESF     180
LRNVEQPVTT RDMVDPRKEL TDEVIEGILG FSIIISEANY REIVSILAKL HFFYKADCRS     240
MYDWLKEICK RRGDPALIEK TASLERFFLG HREREVMTY                            280

SEQ ID NO: 145          moltype = DNA  length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 145
atgtctacgc atttccttgg caaggtcaaa ttcgacgagg ccagattagt cgaagatctg      60
tctactttag aacgttggga gttttcttcc gcatattcgg acttcgcttg tggaaagtgg    120
gaagcatgtg ttttacgcaa cagaacaggc atgcaagaag aagacattgt ggtttctcac    180
aatgcgcccg cattacagac ccctttatct aaatcactgc cgtacttgaa tgagcttgtt    240
gaaacacact tcgactgcag tgcggttaga tatgtacgga tcgtgcgtgt ctccgagaac    300
gcctgcctga tccctcatag tgattatttg gagttggatg aagaattcac ccggctgcac    360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcagct catgatagat tttgaagcta ccgccttccc ggaatccttc    540
ttacgcaatg tggaacagcc tgtaactact cgcgacatgg tagaccctcg taaagaattg    600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttgtggg catcgtgaac gcgagaagt aatgacgtat    840
taa                                                                    843

SEQ ID NO: 146          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 146
MSTHFLGKVK FDEARLVEDL STLERWEFSS AYSDFACGKW EACVLRNRTG MQEEDIVVSH       60
NAPALQTPLS KSLPYLNELV ETHFDCSAVR YVRIVRVSEN ACLIPHSDYL ELDEEFTRLH     120
LVLDTNSGCA NTEEDKIFHM GLGEIWFLDA MLPHSAACFS KTPRLQLMID FEATAFPESF     180
LRNVEQPVTT RDMVDPRKEL TDEVIEGILG FSIIISEANY REIVSILAKL HFFYKADCRS     240
MYDWLKEICK RRGDPALIEK TASLERFFLG HREREVMTY                            280
```

163

-continued

```
SEQ ID NO: 147          moltype = DNA   length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 147
atgtctacgc atttccttgg caaggtcaaa ttcgacgagg ccagattagc cgaagatctg    60
tctactttag aacgtgctga gttttcttcc gcatattcgg acttcgcttg tggaaagtgg   120
gaagcatgtg ttttacgcaa cagaacaggc atgcaagaag aagacattgt ggtttctcac   180
aatcagcccg cattacagac ccctttatct aaatcactgc cgtacttgaa tgagcttgtt   240
gaaacacact tcgactgcag tgcggttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagctc cgcctttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                 843

SEQ ID NO: 148          moltype = AA   length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 148
MSTHFLGKVK FDEARLAEDL STLERAEFSS AYSDFACGKW EACVLRNRTG MQEEDIVVSH    60
NQPALQTPLS KSLPYLNELV ETHFDCSAVR YVRIVRVSEN ACLIPHSDYL ELDEEFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 149          moltype = DNA   length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 149
atgtctacgc atttccttgg caaggtcaaa ttcgacgagg ccagattagc cgaagatctg    60
tctactttag aacgtaggga gttttcttcc gcatattcgg acttcgcttg tggaaagtgg   120
gaagcatgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tgcggttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgcctttcc cggaatcctt   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                 843

SEQ ID NO: 150          moltype = AA   length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 150
MSTHFLGKVK FDEARLAEDL STLERREFSS AYSDFACGKW EACVLRNRTG MQEEDIVVSH    60
NAPALQTPLS KSLPYLNELV ETHFDCSAVR YVRIVRVSEN ACLIPHSDYL ELDEEFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280
```

```
SEQ ID NO: 151          moltype = DNA  length = 843
FEATURE                 Location/Qualifiers
misc_feature            1..843
                        note = Codon-optimized proline 4-hydroxylase gene from
                         Sinorhizobium meliloti
source                  1..843
                        mol_type = other DNA
                        organism = synthetic construct
SEQUENCE: 151
atgtctacgc atttccttgg caaggtcaaa ttcgacgagg ccagattagc cgaagatctg    60
tctactttag aacgtgctga gttttcttcc gcatattcgg acttcgcttg tggaaagtgg   120
gaagcatgtg ttttacgcaa cagaacaggc atgcaagaag aagacattgt ggtttctcac   180
aatgcgcccg cattacagac cccttatcc aaatcactgc cgtacttgaa tgagcttgtt    240
gaaacacact cgactgcag tgcggttaga tatgtacgga tcgtgcgtgt ctccgagaac    300
gcctgcctga tccctcatag tgattatttg gagttggatg aagaattcac ccggctgcac   360
ctcgtgttga atactaacag tggttgtgcc aacactgagg aagataagat attccacatg   420
ggtctgggcg agatctggtt tctggacgca gcgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttagg ttctccataa tcatcagtga agcgaattac     660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttttgggg catcgtgaac gcggagaagt aatgacgtat  840
taa                                                                 843

SEQ ID NO: 152          moltype = AA  length = 280
FEATURE                 Location/Qualifiers
REGION                  1..280
                        note = Codon-optimized proline 4-hydroxylase gene from
                         Sinorhizobium meliloti
source                  1..280
                        mol_type = protein
                        organism = synthetic construct
SEQUENCE: 152
MSTHFLGKVK FDEARLAEDL STLERAEFSS AYSDFACGKW EACVLRNRTG MQEEDIVVSH    60
NAPALQTPLS KSLPYLNELV ETHFDCSAVR YVRIRVSEN ACLIPHSDYL ELDEEFTRLH   120
LVLDTNSGCA NTEEDKIFHM GLGEIWFLDA ALPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 153          moltype = DNA  length = 843
FEATURE                 Location/Qualifiers
misc_feature            1..843
                        note = Codon-optimized proline 4-hydroxylase gene from
                         Sinorhizobium meliloti
source                  1..843
                        mol_type = other DNA
                        organism = synthetic construct
SEQUENCE: 153
atgtctacgc atttccttgg caaggtcaaa ttcgacgagg ccagattagc cgaagatctg    60
tctactttag aacgtgctga gttttcttcc gcatattcgg acttcgcttg tggaaagtgg   120
gaagcatgtg ttttacgcaa cagaacaggc atgcaagaag aagacattgt ggtttctcac   180
aatgcgcccg cattacagac cccttatcc aaatcactgc cgtacttgaa tgagcttgtt    240
gaaacacact cgactgcag tcgtgttaga tatgtacgga tcgtgcgtgt ctccgagaac    300
gcctgcctga tccctcatag tgattatttg gagttggatg aagaattcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg catttagg ttctccataa tcatcagtga agcgaattac     660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttttgggg catcgtgaac gcggagaagt aatgacgtat  840
taa                                                                 843

SEQ ID NO: 154          moltype = AA  length = 280
FEATURE                 Location/Qualifiers
REGION                  1..280
                        note = Codon-optimized proline 4-hydroxylase gene from
                         Sinorhizobium meliloti
source                  1..280
                        mol_type = protein
                        organism = synthetic construct
SEQUENCE: 154
MSTHFLGKVK FDEARLAEDL STLERAEFSS AYSDFACGKW EACVLRNRTG MQEEDIVVSH    60
NAPALQTPLS KSLPYLNELV ETHFDCSRVR YVRIRVSEN ACLIPHSDYL ELDEEFTRLH   120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
```

MYDWLKEICK RRGDPALIEK TASLERFFLG HRERGEVMTY                              280

SEQ ID NO: 155          moltype = DNA   length = 843
FEATURE                 Location/Qualifiers
misc_feature            1..843
                        note = Codon-optimized proline 4-hydroxylase gene from
                            Sinorhizobium meliloti
source                  1..843
                        mol_type = other DNA
                        organism = synthetic construct
SEQUENCE: 155
atgtctacgc atttccttgg taaggtcaaa ttcgacgagg ccagattagc cgaagatctg   60
tctacttag aacgtgctga gttttcttcc gcatattcgg acttcgcttg tggaaagtgg   120
gaagcatgtg ttttacgcaa cagaacaggc atgcaagaag aagacattgt ggtttctcac   180
aatgcgcccg cattacagac cccctttatct aaatcactgc cgtacttgaa tgagcttgtt   240
gaaacacact cgactgcag tgcggttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacgat   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgggactact cgcgacatgg tagaccctcg taagaattg   600
acggacgaag ttatagaagg catttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                   843

SEQ ID NO: 156          moltype = AA   length = 280
FEATURE                 Location/Qualifiers
REGION                  1..280
                        note = Codon-optimized proline 4-hydroxylase gene from
                            Sinorhizobium meliloti
source                  1..280
                        mol_type = protein
                        organism = synthetic construct
SEQUENCE: 156
MSTHFLGKVK FDEARLAEDL STLERAEFSS AYSDFACGKW EACVLRNRTG MQEEDIVVSH   60
NAPALQTPLS KSLPYLNELV ETHFDCSAVR YVRIVRVSEN ACLIPHSDYL ELDEEFTRLH   120
LVLDTNSGCA NTEEDKIFHM GLGEIWFLDA MLPHSAACFS KTPRLQLMID FEATAFPESF   180
LRNVEQPGTT RDMVDPRKEL TDEVIEGILG FSIIISEANY REIVSILAKL HFFYKADCRS   240
MYDWLKEICK RRGDPALIEK TASLERFFLG HRERGEVMTY                          280

SEQ ID NO: 157          moltype = DNA   length = 843
FEATURE                 Location/Qualifiers
misc_feature            1..843
                        note = Codon-optimized proline 4-hydroxylase gene from
                            Sinorhizobium meliloti
source                  1..843
                        mol_type = other DNA
                        organism = synthetic construct
SEQUENCE: 157
atgtctacgc atttccttgg caaggtcaaa ttcgacgagg ccagattagc cgaagatctg   60
tctactttac gtcgtgctga gttttcttcc gcatattcgg acttcgcttg tggaaagtgg   120
gaagcatgtg ttttacgcaa cagaacaggc atgcaagaag aagacattgt ggtttctcac   180
aatgcgcccg cattacagac cccctttatct aaatcactgc cgtacttgaa tgagcttgtt   240
gaaacacact cgactgcag tgcggttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taagaattg   600
acggacgaag ttatagaagg catttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                   843

SEQ ID NO: 158          moltype = AA   length = 280
FEATURE                 Location/Qualifiers
REGION                  1..280
                        note = Codon-optimized proline 4-hydroxylase gene from
                            Sinorhizobium meliloti
source                  1..280
                        mol_type = protein
                        organism = synthetic construct
SEQUENCE: 158
MSTHFLGKVK FDEARLAEDL STLRRAEFSS AYSDFACGKW EACVLRNRTG MQEEDIVVSH   60
NAPALQTPLS KSLPYLNELV ETHFDCSAVR YVRIVRVSEN ACLIPHSDYL ELDEEFTRLH   120
LVLDTNSGCA NTEEDKIFHM GLGEIWFLDA MLPHSAACFS KTPRLQLMID FEATAFPESF   180

```
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                       280

SEQ ID NO: 159          moltype = DNA   length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 159
atgtctacgc atttccttgg caaggtcaaa ttcgacgagg ccagattagc cgaagatctg   60
tctactttaa gtcgtgctga gttttcttcc gcatattcgg acttcgcttg tggaaagtgg  120
gaagcatgtg ttttacgcaa cagaacaggc atgcaagaag aagacattgt ggtttctcac  180
aatgcgcccg cattacagac cccctttatct aaatcactgc cgtacttgaa tgagcttgtt  240
gaaacacact tcgactgcag tgcggttaga tatgtacgga tcgtgcgtgt ctccgagaac  300
gcctgcctga tccctcatag tgattatttg gagttggatg aagaattcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttttct  480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt ctttttgggg catcgtgaac gcggagaagt aatgacgtat   840
taa                                                                 843

SEQ ID NO: 160          moltype = AA   length = 280
FEATURE                 Location/Qualifiers
REGION                  1..280
                        note = Codon-optimized proline 4-hydroxylase gene from
                          Sinorhizobium meliloti
source                  1..280
                        mol_type = protein
                        organism = synthetic construct
SEQUENCE: 160
MSTHFLGKVK FDEARLAEDL STLSRAEFSS AYSDFACGKW EACVLRNRTG MQEEDIVVSH   60
NAPALQTPLS KSLPYLNELV ETHFDCSAVR YVRIVRVSEN ACLIPHSDYL ELDEEFTRLH  120
LVLDTNSGCA NTEEDKIFHM GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                       280

SEQ ID NO: 161          moltype = DNA   length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 161
atgtctacgc atttccttgg caaggtcaaa ttcgacgagg ccagattagc cgaagatctg   60
tctactttga acgtgctga gttttcttcc gcatattcgg acttcgcttg tggaaagtgg   120
gaagcatgtg ttttacgcaa cagaacaggc atgcaagaag aagacattgt ggtttctcac  180
aatgcgcccg cattacagac cccctttatct aaatcactgc cgtacttgaa tgagcttgtt  240
gaaacacact tcgactgcag tgcggttaga tatgtacgga tcgtgcgtgt ctttgagaac  300
gcctgcctga tccctcatag tgattatttg gagttggatg aagaattcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttttct  480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt ctttttgggg catcgtgaac gcggagaagt aatgacgtat   840
taa                                                                 843

SEQ ID NO: 162          moltype = AA   length = 280
FEATURE                 Location/Qualifiers
REGION                  1..280
                        note = Codon-optimized proline 4-hydroxylase gene from
                          Sinorhizobium meliloti
source                  1..280
                        mol_type = protein
                        organism = synthetic construct
SEQUENCE: 162
MSTHFLGKVK FDEARLAEDL STLERAEFSS AYSDFACGKW EACVLRNRTG MQEEDIVVSH   60
NAPALQTPLS KSLPYLNELV ETHFDCSAVR YVRIVRVFEN ACLIPHSDYL ELDEEFTRLH  120
```

```
LVLDTNSGCA NTEEDKIFHM GLGEIWFLDA MLPHSAACFS KTPRLQLMID FEATAFPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                       280

SEQ ID NO: 163          moltype = DNA   length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 163
atgagtagcc actttctcgg caaagtgaaa ttcgatgaag cacggcttgc agaagacttg   60
tctacgctgg aacgtgcgga attttcctcc gcgtatagtg attttgcctg cggaaaatgg  120
gaactgtgtg ttcttagaaa ccgtacaggt atgcaagaag aggatattgt ggtttcccat  180
aacgcaccgg ctcttcagac cccgctgagt aaatcattgc cttaccttaa tgaattagtt  240
gagacacatt tcgactgttc ggctgtccgt tacgttcgta ttgtaagagt gagcgagaac  300
gcgtgcctga taccacattc agattacctc gagcttgacg aggagtttac cagattgcat  360
ctggtcttgg ataccaactc aggttgtgcc aataccgaag aggacaagat attccatatg  420
ggtctcggtg aaatatggtt cttggatgcg atgctgcctc atagtgcagc atgtttttct  480
aagacgccta gactgcagct gatgattgac ttcgaagcta cagcgtttcc cgaatcattt  540
ttacggaacg tcgaacagcc ggttaccacc cgtgatatgg tcgacctag aaaagaatta  600
acggacgaag tgatcgaagg tatactcggc ttttctatta tcatatcgga ggcgaactac  660
cgtgaaatcg tgtctatttt agcgaagctg cacttctttt ataaagccga ttgccggtcg  720
atgtatgatt ggctgaaaga aatttgcaag agacggggag acccggcgct tattgaaaag  780
acggcttcat tggaacgctt cttttttagc cacagagaac gcggggaagt aatgacctac  840
taa                                                                843

SEQ ID NO: 164          moltype = AA   length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 164
MSSHFLGKVK FDEARLAEDL STLERAEFSS AYSDFACGKW ELCVLRNRTG MQEEDIVVSH   60
NAPALQTPLS KSLPYLNELV ETHFDCSAVR YVRIVRVSEN ACLIPHSDYL ELDEEFTRLH  120
LVLDTNSGCA NTEEDKIFHM GLGEIWFLDA MLPHSAACFS KTPRLQLMID FEATAFPPESF 180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 165          moltype = DNA   length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 165
atgagtagcc actttctcgg caaagtgaaa ttcgatgaag cacggcttgc agaagacttg   60
tctacgctgg aacgtgcgga attttcctcc gcgtatagtg attttgcctg cggaaaatgg  120
gaactgtgtg ttcttagaaa ccgtacaggt atgcaagaag aggatattgt ggtttcccat  180
aacgcaccgg ctcttcagac cccgctgagt aaatcattgc cttaccttaa tgaattagtt  240
gagacacatt tcgactgttc ggctgtccgt tacgttcgta ttgtaagagt gaccgagaac  300
gcgtgcctga taccacattc agattacctc gagcttgacg aggagtttac cagattgcat  360
ctggtcttgg ataccaactc aggttgtgcc aataccgaag aggacaagat attccatatg  420
ggtctcggtg aaatatggtt cttggatgcg atgctgcctc atagtgcagc atgtttttct  480
aagacgccta gactgcagct gatgattgac ttcgaagcta cagcgtttcc cgaatcattt  540
ttacggaacg tcgaacagcc ggttaccacc cgtgatatgg tcgacctag aaaagaatta  600
acggacgaag tgatcgaagg tatactcggc ttttctatta tcatatcgga ggcgaactac  660
cgtgaaatcg tgtctatttt agcgaagctg cacttctttt ataaagccga ttgccggtcg  720
atgtatgatt ggctgaaaga aatttgcaag agacggggag acccggcgct tattgaaaag  780
acggcttcat tggaacgctt cttttttagc cacagagaac gcggggaagt aatgacctac  840
taa                                                                843

SEQ ID NO: 166          moltype = AA   length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 166
MSSHFLGKVK FDEARLAEDL STLERAEFSS AYSDFACGKW ELCVLRNRTG MQEEDIVVSH   60
```

```
NAPALQTPLS KSLPYLNELV ETHFDCSAVR YVRIRVRVTEN ACLIPHSDYL ELDEEFTRLH    120
LVLDTNSGCA NTEEDKIFHM GLGEIWFLDA MLPHSAACFS KTPRLQLMID FEATAFPESF    180
LRNVEQPVTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 167          moltype = DNA  length = 843
FEATURE                 Location/Qualifiers
misc_feature            1..843
                        note = Codon-optimized proline 4-hydroxylase gene from
                         Sinorhizobium meliloti
source                  1..843
                        mol_type = other DNA
                        organism = synthetic construct
SEQUENCE: 167
atgagtagcc actttctcgg caaagtgaaa ttcgatgaag cacggcttgc agaagacttg    60
tctacgctgg aacgtgcgga attttcctcc gcgtatagtg attttgcctg cggaaaatgg    120
gaactgtgtg ttcttagaaa ccgtacaggt atgcaagaag aggatattgt ggtttcccat    180
aacgcaccgg ctcttcagac cccgctgagt aaatcattgc cttaccttaa tgaattagtt    240
gagacacatt tcgactgttc ggctgtccgt tacgttcgta ttgtaagagt gaccgagaac    300
gcgtgcctga taccacattc agattacctc gagcttgacg aggagtttac cagattgcat    360
ctggtcttga ataccaactc aggttgtgcc aataccgaag aggacaagat attccatatg    420
ggtctcggtg aaatatggtt cttggatgcg atgctgcctc atagtgcagc tgtttttcct    480
aagacgccta gactgcagct gatgattgac ttcgaagcta cagcgtttcc cgaatcattt    540
ttacggaacg tcgaacagcc gggcaccacc cgtgatatgg tcgacccgag aaaagaatta    600
acggacgaag tgatcgaagg tatactcggc ttttctatta tcatatcgga ggcgaactac    660
cgtgaaatcg tgtctatttt agcgaagctg cacttcttt ataaagccga tgccggtcg    720
atgtatgatt ggctgaaaga aatttgcaag agacggggag acccggcgct tattgaaaag    780
acggcttcat tggaacgctt cttttaggc cacagagaac gcggggaagt aatgacctac    840
taa                                                                 843

SEQ ID NO: 168          moltype = AA  length = 280
FEATURE                 Location/Qualifiers
REGION                  1..280
                        note = Codon-optimized proline 4-hydroxylase gene from
                         Sinorhizobium meliloti
source                  1..280
                        mol_type = protein
                        organism = synthetic construct
SEQUENCE: 168
MSSHFLGKVK FDEARLAEDL STLERAEFSS AYSDFACGKW ELCVLRNRTG MQEEDIVVSH    60
NAPALQTPLS KSLPYLNELV ETHFDCSAVR YVRIRVRVTEN ACLIPHSDYL ELDEEFTRLH    120
LVLDTNSGCA NTEEDKIFHM GLGEIWFLDA MLPHSAACFS KTPRLQLMID FEATAFPESF    180
LRNVEQPGTT RDMVDPRKEL TDEVIEGILG FSIIISEANY REIVSILAKL HFFYKADCRS    240
MYDWLKEICK RRGDPALIEK TASLERFFLG HRERGEVMTY                          280

SEQ ID NO: 169          moltype = DNA  length = 843
FEATURE                 Location/Qualifiers
misc_feature            1..843
                        note = Codon-optimized proline 4-hydroxylase gene from
                         Sinorhizobium meliloti
source                  1..843
                        mol_type = other DNA
                        organism = synthetic construct
SEQUENCE: 169
atgtctacgc atttccttgg caaggtcaaa ttcgacgagg ccagattagc cgaagatctg    60
tctacttta gtcgtgcaga gttttcttcc gcatattcgg acttcgcttg tggaaagtgg    120
gaactttgtg ttttacgcaa cagaacaggc atgcaagaag aagacattgt ggtttctcac    180
aatgcgcccg cattacagac ccctttatct aaatcactgc cgtacttgaa tgagcttgtt    240
gaaacacact tcgactgcag tgcggttaga tatgtacgga tcgtgcgtgt ctccgagaac    300
gcctgcctga tccctcatag tgattatttg gagttggatg aagaattcac ccggctgcac    360
ctcgtgttgg atactaacag tggttgtgcc aacactgagg aagataagat attccacatg    420
ggtctgggcg agatctggtt tctggacgca atgttacctc attctgctgc tgcttttct    480
aaaactccta gactgcagct catgatagat tttgaagcta ccgccttccc ggaatccttc    540
ttacgcaatg tggaacagcc tggtactact cgcgacatgg tagaccctcg taaagaattg    600
acggacgaag ttatagaagg catttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttgggg catcgtgaac gcggagaagt aatgacgtat    840
taa                                                                 843

SEQ ID NO: 170          moltype = AA  length = 280
FEATURE                 Location/Qualifiers
REGION                  1..280
                        note = Codon-optimized proline 4-hydroxylase gene from
                         Sinorhizobium meliloti
source                  1..280
                        mol_type = protein
                        organism = synthetic construct
SEQUENCE: 170
```

```
MSTHFLGKVK FDEARLAEDL STLSRAEFSS AYSDFACGKW ELCVLRNRTG MQEEDIVVSH   60
NAPALQTPLS KSLPYLNELV ETHFDCSAVR YVRIVRVSEN ACLIPHSDYL ELDEEFTRLH  120
LVLDTNSGCA NTEEDKIFHM GLGEIWFLDA MLPHSAACFS KTPRLQLMID FEATAFPPESF 180
LRNVEQPGTT RDMVDPRKEL TDEVIEGILG FSIIISEANY REIVSILAKL HFFYKADCRS  240
MYDWLKEICK RRGDPALIEK TASLERFFLG HRERGEVMTY                       280

SEQ ID NO: 171           moltype = DNA   length = 843
FEATURE                  Location/Qualifiers
misc_feature             1..843
                         note = Codon-optimized proline 4-hydroxylase gene from
                           Sinorhizobium meliloti
source                   1..843
                         mol_type = other DNA
                         organism = synthetic construct
SEQUENCE: 171
atgtctacgc atttccttgg caaggtcaaa ttcgacgagg ccagattagc cgaagatctg   60
tctactttaa gtcgtgcaga gttttcttcc gcatattcgg acttcgcttg tggaaagtgg  120
gaactttgtg ttttacgcaa cagaacaggc atgcaagaag aagacattgt ggtttctcac  180
aatcagcccg cattacagac ccctttatct aaatcactgc cgtacttgaa tgagcttgtt  240
gaaacacact tcgactgcag tgcggttaga tatgtacgga tcgtgcgtgt cacggagaac  300
gcctgcctga tccctcatag tgattatttg gagttggata acgaattcac ccggctgcac  360
ctcgtgttgg atactaacag tggttgtgcc aacactgagg aagataagat attccacctg  420
ggtctgggcg agatctggtt tctggacgca atgttacctc attctgctgc ctgcttttct  480
aaaactccta gactgcagct catgatagat tttgaagcta ccgccttccc ggaatccttc  540
ttacgcaatg tggaacagcc tgtaactact cgcgacatgg tagaccctcg taagaattg   600
acggacgaag ttatagaagg catttttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcgagaagt aatgacgtat   840
taa                                                                843

SEQ ID NO: 172           moltype = AA   length = 280
FEATURE                  Location/Qualifiers
REGION                   1..280
                         note = Codon-optimized proline 4-hydroxylase gene from
                           Sinorhizobium meliloti
source                   1..280
                         mol_type = protein
                         organism = synthetic construct
SEQUENCE: 172
MSTHFLGKVK FDEARLAEDL STLSRAEFSS AYSDFACGKW ELCVLRNRTG MQEEDIVVSH   60
NQPALQTPLS KSLPYLNELV ETHFDCSAVR YVRIVRVTEN ACLIPHSDYL ELDNEFTRLH  120
LVLDTNSGCA NTEEDKIFHL GLGEIWFLDA MLPHSAACFS KTPRLQLMID FEATAFPPESF 180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                       280

SEQ ID NO: 173           moltype = DNA   length = 843
FEATURE                  Location/Qualifiers
misc_feature             1..843
                         note = Codon-optimized proline 4-hydroxylase gene from
                           Sinorhizobium meliloti
source                   1..843
                         mol_type = other DNA
                         organism = synthetic construct
SEQUENCE: 173
atgtctacgc atttccttgg caaggtcaaa ttcgacgagg ccagattagc cgaagatctg   60
tctactttaa gtcgtgcaga gttttcttcc gcatattcgg acttcgcttg tggaaagtgg  120
gaactttgtg ttttacgcaa cagaacaggc atgcaagaag aagacattgt ggtttctcac  180
aatcgcgccg cattacagac ccctttatct aaatcactgc cgtacttgaa tgagcttgtt  240
gaaacacact tcgactgcag tgcggttaga tatgtacgga tcgtgcgtgt cacggagaac  300
gcctgcctga tccctcatag tgattatttg gagttggata acgaattcac ccggctgcac  360
ctcgtgttgg atactaacag tggttgtgcc aacactgagg aagataagat attccacatg  420
ggtctgggcg agatctggtt tctggacgca atgttacctc attctgctgc ctgcttttct  480
aaaactccta gactgcagct catgatagat tttgaagcta ccgccttccc ggaatccttc  540
ttacgcaatg tggaacagcc tgtaactact cgcgacatgg tagaccctcg taagaattg   600
acggacgaag ttatagaagg catttttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcgagaagt aatgacgtat   840
taa                                                                843

SEQ ID NO: 174           moltype = AA   length = 280
FEATURE                  Location/Qualifiers
REGION                   1..280
                         note = Codon-optimized proline 4-hydroxylase gene from
                           Sinorhizobium meliloti
source                   1..280
                         mol_type = protein
                         organism = synthetic construct
```

```
SEQUENCE: 174
MSTHFLGKVK FDEARLAEDL STLSRAEFSS AYSDFACGKW ELCVLRNRTG MQEEDIVVSH     60
NAPALQTPLS KSLPYLNELV ETHFDCSAVR YVRIVRVTEN ACLIPHSDYL ELDNEFTRLH    120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                          280

SEQ ID NO: 175          moltype = DNA   length = 843
FEATURE                 Location/Qualifiers
misc_feature            1..843
                        note = Codon-optimized proline 4-hydroxylase gene from
                           Sinorhizobium meliloti
source                  1..843
                        mol_type = other DNA
                        organism = synthetic construct
SEQUENCE: 175
atgtctacgc atttccttgg caaggtcaaa ttcgacgagg ccagattagc cgaagatctg     60
tctactttaa gtcgtcgtga gttttcttcc gcatattcgg acttcgcttg tggaaagtgg    120
gaactttgtg ttttacgcaa cagaacaggc atgcaagaag aagacattgt ggtttctcac    180
aatgcgcccg cattacagac ccctttatct aaatcactgc cgtacttgaa tgagcttgtt    240
gaaacacact tcgactgcag tgcggttaga tatgtacgga tcgtgcgtgt ctccgagaac    300
gcctgcctga tccctcatag tgattatttg gagttggatg aagaattcac ccggctgcac    360
ctcgtgttgg atactaacag tggttgtgcc aacactgagg aagataagat attccacatg    420
ggtctgggcg agatctggtt tctggacgca atgttacctc attctgctgc ctgcttttct    480
aaaactccta gactgcagct catgatagat tttgaagcta ccgccttccc ggaatccttc    540
ttacgcaatg tggaacagcc tgtaactact cgcgacatgg tagaccctcg taaagaattg    600
acggacgaag ttatagaagg catttttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttttggg catcgtgaac gcgagaagt aatgacgtat     840
taa                                                                  843

SEQ ID NO: 176          moltype = AA   length = 280
FEATURE                 Location/Qualifiers
REGION                  1..280
                        note = Codon-optimized proline 4-hydroxylase gene from
                           Sinorhizobium meliloti
source                  1..280
                        mol_type = protein
                        organism = synthetic construct
SEQUENCE: 176
MSTHFLGKVK FDEARLAEDL STLSRREFSS AYSDFACGKW ELCVLRNRTG MQEEDIVVSH     60
NAPALQTPLS KSLPYLNELV ETHFDCSAVR YVRIVRVSEN ACLIPHSDYL ELDEEFTRLH    120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                          280

SEQ ID NO: 177          moltype = DNA   length = 843
FEATURE                 Location/Qualifiers
misc_feature            1..843
                        note = Codon-optimized proline 4-hydroxylase gene from
                           Sinorhizobium meliloti
source                  1..843
                        mol_type = other DNA
                        organism = synthetic construct
SEQUENCE: 177
atgtctacgc atttccttgg caaggtcaaa ttcgacgagg ccagattagc cgaagatctg     60
tctactttag aacgtgcaga gttttcttcc gcatattcgg acttcgcttg tggaaagtgg    120
gaactttgtg ttttacgcaa cagaacaggc atgcaagaag aagacattgt ggtttctcac    180
aatcagcccg cattacagac ccctttatct aaatcactgc cgtacttgaa tgagcttgtt    240
gaaacacact tcgactgcag tgcggttaga tatgtacgga tcgtgcgtgt ctccgagaac    300
gcctgcctga tccctcatag tgattatttg gagttggatg aagaattcac ccggctgcac    360
ctcgtgttgg atactaacag tggttgtgcc aacactgagg aagataagat attccacctg    420
ggtctgggcg agatctggtt tctggacgca atgttacctc attctgctgc ctgcttttct    480
aaaactccta gactgcagct catgatagat tttgaagcta ccgccttccc ggaatccttc    540
ttacgcaatg tggaacagcc tgtactact cgcgacatgg tagaccctcg taaagaattg     600
acggacgaag ttatagaagg catttttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttttggg catcgtgaac gcgagaagt aatgacgtat     840
taa                                                                  843

SEQ ID NO: 178          moltype = AA   length = 280
FEATURE                 Location/Qualifiers
REGION                  1..280
                        note = Codon-optimized proline 4-hydroxylase gene from
                           Sinorhizobium meliloti
source                  1..280
                        mol_type = protein
```

```
                      organism = synthetic construct
SEQUENCE: 178
MSTHFLGKVK FDEARLAEDL STLERAEFSS AYSDFACGKW ELCVLRNRTG MQEEDIVVSH    60
NQPALQTPLS KSLPYLNELV ETHFDCSAVR YVRIVRVSEN ACLIPHSDYL ELDEEFTRLH   120
LVLDTNSGCA NTEEDKIFHL GLGEIWFLDA MLPHSAACFS KTPRLQLMID FEATAFPESF   180
LRNVEQPGTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 179         moltype = DNA   length = 843
FEATURE                Location/Qualifiers
misc_feature           1..843
                       note = Codon-optimized proline 4-hydroxylase gene from
                         Sinorhizobium meliloti
source                 1..843
                       mol_type = other DNA
                       organism = synthetic construct
SEQUENCE: 179
atgtctacgc atttccttgg caaggtcaaa ttcgacgagg ccagattagc cgaagatctg    60
tctacttaa gtcgtcgtga gttttcttcc gcatattcgg acttcgcttg tggaaagtgg   120
gaactttgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tcgtgttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacctg   420
ggtctgggcg agatctggtt tctggacgca atgttacctc attctgctgc ctgcttttct   480
aaaactccta gactgcagct catgatagat tttgaagctc ccgcctttcc ggaatccttc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt ctttttgggg catcgtgaac gcggagaagt aatgacgtat   840
taa                                                                843

SEQ ID NO: 180         moltype = AA   length = 280
FEATURE                Location/Qualifiers
REGION                 1..280
                       note = Codon-optimized proline 4-hydroxylase gene from
                         Sinorhizobium meliloti
source                 1..280
                       mol_type = protein
                       organism = synthetic construct
SEQUENCE: 180
MSTHFLGKVK FDEARLAEDL STLSRREFSS AYSDFACGKW ELCVLRNRTG MQEEDIVVSH    60
NAPALQTPLS KSLPYLNELV ETHFDCSRVR YVRIVRVSEN ACLIPHSDYL ELDEEFTRLH   120
LVLDTNSGCA NTEEDKIFHL GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 181         moltype = DNA   length = 843
FEATURE                Location/Qualifiers
misc_feature           1..843
                       note = Codon-optimized proline 4-hydroxylase gene from
                         Sinorhizobium meliloti
source                 1..843
                       mol_type = other DNA
                       organism = synthetic construct
SEQUENCE: 181
atgtctacgc atttccttgg caaggtcaaa ttcgacgagg ccagattagc cgaagatctg    60
tctacttaa gtcgtcgtga gttttcttcc gcatattcgg acttcgcttg tggaaagtgg   120
gaactttgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tcgtgttaga tatgtacgga tcgtgcgtgt cacggagaat   300
gcctgcctga tccctcatag tgattatttg gagttggata cgaattcac ccggctgcac   360
ctcgtgttgg atactaacag tggttgtgcc aacactgagg aagataagat attccacctg   420
ggtctgggcg agatctggtt tctggacgca atgttacctc attctgctgc ctgcttttct   480
aaaactccta gactgcagct catgatagat tttgaagcta ccgcctttcc ggaatccttc   540
ttacgcaatg tggaacagcc tgtactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt ctttttgggg catcgtgaac gcggagaagt aatgacgtat   840
taa                                                                843

SEQ ID NO: 182         moltype = AA   length = 280
FEATURE                Location/Qualifiers
REGION                 1..280
                       note = Codon-optimized proline 4-hydroxylase gene from
                         Sinorhizobium meliloti
source                 1..280
```

```
                        mol_type = protein
                        organism = synthetic construct
SEQUENCE: 182
MSTHFLGKVK FDEARLAEDL STLSRREFSS AYSDFACGKW ELCVLRNRTG MQEEDIVVSH  60
NAPALQTPLS KSLPYLNELV ETHFDCSRVR YVRIVRVTEN ACLIPHSDYL ELDNEFTRLH 120
LVLDTNSGCA NTEEDKIFHL GLGEIWFLDA MLPHSAACFS KTPRLQLMID FEATAFPESF 180
LRNVEQPGTT RDMVDPRKEL TDEVIEGILG FSIIISEANY REIVSILAKL HFFYKADCRS 240
MYDWLKEICK RRGDPALIEK TASLERFFLG HRERGEVMTY                      280

SEQ ID NO: 183          moltype = DNA   length = 843
FEATURE                 Location/Qualifiers
misc_feature            1..843
                        note = Codon-optimized proline 4-hydroxylase gene from
                         Sinorhizobium meliloti
source                  1..843
                        mol_type = other DNA
                        organism = synthetic construct
SEQUENCE: 183
atgtctacgc atttccttgg caaggtcaaa ttcgacgagg ccagattagc cgaagatctg  60
tctactttaa gtcgtgcaga gttttcttcc gcatattcgg acttcgcttg tggaaagtgg 120
gaactttgtg ttttacgcaa cagaacaggc atgcaagaag aagacattgt ggtttctcac 180
aatgcgcccg cattacagac ccctttatct aaatcactgc cgtacttgaa tgagcttgtt 240
gaaacacact tcgactgcag tcgcgttaga tatgtacgga tcgtgcgtgt ctccgagaac 300
gcctgcctga tccctcatag tgattatttg gagttggata acgaattcac ccggctgcac 360
ctcgtgttgg atactaacag tggttgtgcc aacactgagg aagataagat attccacctg 420
ggtctgggcg agatctggtt tctggacgca atgttacctc attctgctgc ctgcttttct 480
aaaactccta gactgcagct catgatagat tttgaagcta ccgccttccc ggaatccttc 540
ttacgcaatg tggaacagcc tgtaactact cgcgacatgg tagaccctcg taaagaattg 600
acggacgaag ttatagaagg catttttaggg ttctccataa tcatcagtga agcgaattac 660
cgcgagatcg tctctatcct ggccaaatta cacttctttt ataaagcgga ctgtcggtgc 720
atgtatgatt ggcttaaaga aatatgtaaa cgccggggag atcccgcgtt gattgagaag 780
acagcgagtc tcgaacgttt cttttttgggg catcgtgaac gcggagaagt aatgacgtat 840
taa                                                              843

SEQ ID NO: 184          moltype = AA   length = 280
FEATURE                 Location/Qualifiers
REGION                  1..280
                        note = Codon-optimized proline 4-hydroxylase gene from
                         Sinorhizobium meliloti
source                  1..280
                        mol_type = protein
                        organism = synthetic construct
SEQUENCE: 184
MSTHFLGKVK FDEARLAEDL STLSRAEFSS AYSDFACGKW ELCVLRNRTG MQEEDIVVSH  60
NQPALQTPLS KSLPYLNELV ETHFDCSAVR YVRIVRVSEN ACLIPHSDYL ELDNEFTRLH 120
LVLDTNSGCA NTEEDKIFHL GLGEIWFLDA MLPHSAACFS KTPRLQLMID FEATAFPESF 180
LRNVEQPVTT RDMVDPRKEL TDEVIEGILG FSIIISEANY REIVSILAKL HFFYKADCRS 240
MYDWLKEICK RRGDPALIEK TASLERFFLG HRERGEVMTY                      280

SEQ ID NO: 185          moltype = DNA   length = 843
FEATURE                 Location/Qualifiers
misc_feature            1..843
                        note = Codon-optimized proline 4-hydroxylase gene from
                         Sinorhizobium meliloti
source                  1..843
                        mol_type = other DNA
                        organism = synthetic construct
SEQUENCE: 185
atgtctacgc atttccttgg caaggtcaaa ttcgacgagg ccagattagc cgaagatctg  60
tctactttaa gtcgtcgtga gttttcttcc gcatattcgg acttcgcttg tggaaagtgg 120
gaactttgtg ttttacgcaa cagaacaggc atgcaagaag aagacattgt ggtttctcac 180
aatgcgcccg cattacagac ccctttatct aaatcactgc cgtacttgaa tgagcttgtt 240
gaaacacact tcgactgcag tcgtgttaga tatgtacgga tcgtgcgtgt ctccgagaac 300
gcctgcctga tccctcatag tgattatttg gagttggata acgaattcac ccggctgcac 360
ctcgtgttgg atactaacag tggttgtgcc aacactgagg aagataagat attccacatg 420
ggtctgggcg agatctggtt tctggacgca atgttacctc attctgctgc ctgcttttct 480
aaaactccta gactgcagct catgatagat tttgaagcta ccgccttccc ggaatccttc 540
ttacgcaatg tggaacagcc tgtaactact cgcgacatgg tagaccctcg taaagaattg 600
acggacgaag ttatagaagg catttttaggg ttctccataa tcatcagtga agcgaattac 660
cgcgagatcg tctctatcct ggccaaatta cacttctttt ataaagcgga ctgtcggtcc 720
atgtatgatt ggcttaaaga aatatgtaaa cgccggggag atcccgcgtt gattgagaag 780
acagcgagtc tcgaacgttt cttttttgggg catcgtgaac gcggagaagt aatgacgtat 840
taa                                                              843

SEQ ID NO: 186          moltype = AA   length = 280
FEATURE                 Location/Qualifiers
REGION                  1..280
                        note = Codon-optimized proline 4-hydroxylase gene from
                         Sinorhizobium meliloti
```

```
source                        1..280
                              mol_type = protein
                              organism = synthetic construct
SEQUENCE: 186
MSTHFLGKVK FDEARLAEDL STLSRREFSS AYSDFACGKW ELCVLRNRTG MQEEDIVVSH   60
NAPALQTPLS KSLPYLNELV ETHFDCSRVR YVRIRVRVSEN ACLIPHSDYL ELDNEFTRLH  120
LVLDTNSGCA NTEEDKIFHM GLGEIWFLDA MLPHSAACFS KTPRLQLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 187                moltype = DNA   length = 843
FEATURE                       Location/Qualifiers
misc_feature                  1..843
                              note = Codon-optimized proline 4-hydroxylase gene from
                                  Sinorhizobium meliloti
source                        1..843
                              mol_type = other DNA
                              organism = synthetic construct
SEQUENCE: 187
atgtctacgc atttccttgg caaggtcaaa ttcgacgagg ccagattagc cgaagatctg   60
tctactttaa gtcgtgcaga gttttcttcc gcatattcgg acttcgcttg tggaaagtgg  120
gaactttgtg ttttacgcaa cagaacaggc atgcaagaag aagacattgt ggtttctcac  180
aatgcgcccg cattacagac ccctttatct aaatcactgc cgtacttgaa tgagcttgtt  240
gaaacacact cgactgcag tgcggttaga tatgtacgga tcgtgcgtgt ctccgagaac  300
gcctgcctga tccctcatag tgattatttg gagttggatg aagaattcac ccggctgcac  360
ctcgtgttgg atactaacag tggttgtgcc aacactgagg aagataagat attccacctg  420
ggtctgggcg agatctggtt tctggacgca atgttacctc attctgctgc ctgctttttt  480
aaaactccta gactgcagct catgatagat tttgaagcta ccgcctttcc ggaatccttc  540
ttacgcaatg tggaacagcc tgtaactact cgcgacatgg tagaccctcg taagaattg   600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 188                moltype = AA   length = 280
FEATURE                       Location/Qualifiers
REGION                        1..280
                              note = Codon-optimized proline 4-hydroxylase gene from
                                  Sinorhizobium meliloti
source                        1..280
                              mol_type = protein
                              organism = synthetic construct
SEQUENCE: 188
MSTHFLGKVK FDEARLAEDL STLSRAEFSS AYSDFACGKW ELCVLRNRTG MQEEDIVVSH   60
NAPALQTPLS KSLPYLNELV ETHFDCSAVR YVRIRVRVSEN ACLIPHSDYL ELDEEFTRLH  120
LVLDTNSGCA NTEEDKIFHL GLGEIWFLDA MLPHSAACFS KTPRLQLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 189                moltype = DNA   length = 843
FEATURE                       Location/Qualifiers
misc_feature                  1..843
                              note = Codon-optimized proline 4-hydroxylase gene from
                                  Sinorhizobium meliloti
source                        1..843
                              mol_type = other DNA
                              organism = synthetic construct
SEQUENCE: 189
atgtctacgc atttccttgg caaggtcaaa ttcgacgagg ccagattagc cgaagatctg   60
tctactttat ctcgtgcaga gttttcttcc gcatattcgg acttcgcttg tggaaagtgg  120
gaactttgtg ttttacgcaa cagaacaggc atgcaagaag aagacattgt ggtttctcac  180
aatgcgcccg cattacagac ccctttatct aaatcactgc cgtacttgaa tgagcttgtt  240
gaaacacact cgactgcag tgcggttaga tatgtacgga tcgtgcgtgt cacggagaac  300
gcctgcctga tccctcatag tgattatttg gagttggata tgaattcac ccggctgcac   360
ctcgtgttgg atactaacag tggttgcgcc aacactgagg aagataagat attccacatg  420
ggtctgggcg agatctggtt tctggacgca atgttacctc attctgctgc ctgctttttt  480
aaaactccta gactgcagct catgatagat tttgaagcta ccgcctttcc ggaatccttc  540
ttacgcaatg tggaacaacc tgtgactact cgcgacatgg tagaccctcg taagaattg   600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 190                moltype = AA   length = 280
FEATURE                       Location/Qualifiers
REGION                        1..280
                              note = Codon-optimized proline 4-hydroxylase gene from
```

```
                           Sinorhizobium meliloti
source                     1..280
                           mol_type = protein
                           organism = synthetic construct
SEQUENCE: 190
MSTHFLGKVK FDEARLAEDL STLSRAEFSS AYSDFACGKW ELCVLRNRTG MQEEDIVVSH    60
NAPALQTPLS KSLPYLNELV ETHFDCSAVR YVRIVRVTEN ACLIPHSDYL ELDNEFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 191             moltype = DNA   length = 843
FEATURE                    Location/Qualifiers
misc_feature               1..843
                           note = Codon-optimized proline 4-hydroxylase gene from
                           Sinorhizobium meliloti
source                     1..843
                           mol_type = other DNA
                           organism = synthetic construct
SEQUENCE: 191
atgtctacgc atttccttgg caaggtcaaa ttcgacgagg ccagattagc cgaagatctg    60
tctactttag aacgtcgtga gttttcttcc gcatattcac acttcgcttg tggaaagtgg   120
gaactttgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tgcggttaga tatgtacgga tcgtgcgtgt ctccgagaac   300
gcctgcctga tccctcatag tgattatttg gagttggata atgaattcac ccggctgcac   360
ctcgtgttgg atactaacag tggttgtgcc aacactgagg aagataagat attccacatg   420
ggtctgggcg agatctggtt tctggacgca catttacctc attctgctgc ctgcttttct   480
aaaactccta gactgcagct catgatagat tttgaagcta ccgccttccc ggaatccttc   540
ttacgcaatg tggaacaacc tgtgactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcgagaagt aatgacgtat     840
taa                                                                 843

SEQ ID NO: 192             moltype = AA    length = 280
FEATURE                    Location/Qualifiers
REGION                     1..280
                           note = Codon-optimized proline 4-hydroxylase gene from
                           Sinorhizobium meliloti
source                     1..280
                           mol_type = protein
                           organism = synthetic construct
SEQUENCE: 192
MSTHFLGKVK FDEARLAEDL STLERREFSS AYSDFACGKW ELCVLRNRTG MQEEDIVVSH    60
NAPALQTPLS KSLPYLNELV ETHFDCSAVR YVRIVRVSEN ACLIPHSDYL ELDNEFTRLH   120
LVLDTNSGCA NTEEDKIFHM GLGEIWFLDA HLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 193             moltype = DNA   length = 843
FEATURE                    Location/Qualifiers
misc_feature               1..843
                           note = Codon-optimized proline 4-hydroxylase gene from
                           Sinorhizobium meliloti
source                     1..843
                           mol_type = other DNA
                           organism = synthetic construct
SEQUENCE: 193
atgtctacgc atttccttgg caaggtcaaa ttcgacgagg ccagattagc cgaagatctg    60
tctactttat ctcgtgcaga gttttcttcc gcatattcgg acttcgcttg tggaaagtgg   120
gaactttgtg ttttacgcaa cagaacaggc atgcaagaag aagacattgt ggtttctcac   180
aatcgcccg cattacagac ccctttatct aaatcactgc cgtacttgaa tgagcttgtt   240
gaaacacact tcgactgcag tgcggttaga tatgtacgga tcgtgcgtgt cacggagaac   300
gcctgcctga tccctcatag tgattatttg gagttggatg aagaattcac ccggctgcac   360
ctcgtgttgg atactaacag tggttgtgcc aacactgagg aagataagat attccacctg   420
ggtctgggcg agatctggtt tctggacgca catttacctc attctgctgc ctgcttttct   480
aaaactccta gactgcagct catgatagat tttgaagcta ccgccttccc ggaatccttc   540
ttacgcaatg tggaacagcc tgtgactact cgcgacatgg tagaccctcg taaagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcgagaagt aatgacgtat     840
taa                                                                 843

SEQ ID NO: 194             moltype = AA    length = 280
FEATURE                    Location/Qualifiers
REGION                     1..280
```

-continued

```
                        note = Codon-optimized proline 4-hydroxylase gene from
                            Sinorhizobium meliloti
source                  1..280
                        mol_type = protein
                        organism = synthetic construct
SEQUENCE: 194
MSTHFLGKVK FDEARLAEDL STLSRAEFSS AYSDFACGKW ELCVLRNRTG MQEEDIVVSH    60
NQPALQTPLS KSLPYLNELV ETHFDCSAVR YVRIRVRVTEN ACLIPHSDYL ELDEEFTRLH  120
LVLDTNSGCA NTEEDKIFHL GLGEIWFLDA HLPHSAACFS KTPRLQLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 195          moltype = DNA  length = 843
FEATURE                 Location/Qualifiers
misc_feature            1..843
                        note = Codon-optimized proline 4-hydroxylase gene from
                            Sinorhizobium meliloti
source                  1..843
                        mol_type = other DNA
                        organism = synthetic construct
SEQUENCE: 195
atgtctacgc atttccttgg caaggtcaaa ttcgacgagg ccagattagc cgaagatctg    60
tctactttag aacgtgcaga gttttcttcc gcatattcgg acttcgcttg tggaaagtgg   120
gaactttgtg tttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tgcggttaga tatgtacgaa tcgtgcgtgt ctccgagaac   300
gcctgcctga tccctcatag tgattatttg gagttggata tgaattcac ccggctgcac    360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagctc ccgccttccc ggaatcctc   540
ttacgcaatg tggaacagcc tgtaactact cgcgacatgg tagaccctcg taaagaattg   600
acggacgaag ttatagaagg cattttaggg ttctccataa tcatcagtga agcgaattac   660
cgcgagatct ctctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt ctttttgggg catcgtgaac gcggagaagt aatgacgtat    840
taa                                                                 843

SEQ ID NO: 196          moltype = AA  length = 280
FEATURE                 Location/Qualifiers
REGION                  1..280
                        note = Codon-optimized proline 4-hydroxylase gene from
                            Sinorhizobium meliloti
source                  1..280
                        mol_type = protein
                        organism = synthetic construct
SEQUENCE: 196
MSTHFLGKVK FDEARLAEDL STLERAEFSS AYSDFACGKW ELCVLRNRTG MQEEDIVVSH    60
NAPALQTPLS KSLPYLNELV ETHFDCSAVR YVRIRVRVSEN ACLIPHSDYL ELDNEFTRLH  120
LVLDTNSGCA NTEEDKIFHM GLGEIWFLDA MLPHSAACFS KTPRLQLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 197          moltype = DNA  length = 843
FEATURE                 Location/Qualifiers
misc_feature            1..843
                        note = Codon-optimized proline 4-hydroxylase gene from
                            Sinorhizobium meliloti
source                  1..843
                        mol_type = other DNA
                        organism = synthetic construct
SEQUENCE: 197
atgtctacgc atttccttgg caaggtcaaa ttcgacgagg ccagattagc cgaagatctg    60
tctactttag aacgtgctga gttttcttcc gcatattcgg acttcgcttg tggaaagtgg   120
gaactttgtg tttacgcaa cagaacaggc atgcaagaag aagacattgt ggtttctcac   180
aatcagcccg cattacagac ccctttatct aaatcactgc cgtacttgaa tgagcttgtt   240
gaaacacact tcgactgcag tgcggttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacctg   420
ggtctgggcg agatctggtt tctggacgca catttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taaagaattg   600
acggacgaag ttgtagaagg catttagggg ttctccataa tcatcagtga agcgaattac   660
cgcgagatct ctctatcct ggccaaatta cacttctttt ataaagcgga ctgtcggtcc    720
atgtatgatt ggcttaaaga aatatgtaaa cgccggggag atcccgcgtt gattgagaag   780
acagcgagtc tcgaacgttt ctttttgggg catcgtgaac gcggagaagt aatgacgtat    840
taa                                                                 843

SEQ ID NO: 198          moltype = AA  length = 280
FEATURE                 Location/Qualifiers
```

```
REGION                  1..280
                        note = Codon-optimized proline 4-hydroxylase gene from
                            Sinorhizobium meliloti
source                  1..280
                        mol_type = protein
                        organism = synthetic construct
SEQUENCE: 198
MSTHFLGKVK FDEARLAEDL STLERAEFSS AYSDFACGKW ELCVLRNRTG MQEEDIVVSH    60
NQPALQTPLS KSLPYLNELV ETHFDCSAVR YVRIVRVSEN ACLIPHSDYL ELDEEFTRLH   120
LVLDTNSGCA NTEEDKIFHL GLGEIWFLDA HLPHSAACFS KTPRLQLMID FEATAFPESF   180
LRNVEQPVTT RDMVDPRKEL TDEVVEGILG FSIIISEANY REIVSILAKL HFFYKADCRS   240
MYDWLKEICK RRGDPALIEK TASLERFFLG HRERGEVMTY                         280

SEQ ID NO: 199          moltype = DNA   length = 843
FEATURE                 Location/Qualifiers
misc_feature            1..843
                        note = Codon-optimized proline 4-hydroxylase gene from
                            Sinorhizobium meliloti
source                  1..843
                        mol_type = other DNA
                        organism = synthetic construct
SEQUENCE: 199
atgtctacgc atttccttgg caaggtcaaa ttcgacgagg ccagattagc cgaagatctg    60
tctactttat ctcgtgcaga gttttcttcc gcatattcgg acttcgcttg tggaaagtgg   120
gaactttgtg ttttacgcaa cagaacaggc atgcaagaag aagacattgt ggtttctcac   180
aatcagcccg cattacagac ccctttatct aaatcactgc cgtacttgaa tgagcttgtt   240
gaaacacact tcgactgcag tcgtgttaga tatgtacgga tcgtgcgtgt ctccgagaac   300
gcctgcctga tccctcatag tgattatttg gagttggata tgaattcac ccggctgcac    360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taagaattg    600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                 843

SEQ ID NO: 200          moltype = AA   length = 280
FEATURE                 Location/Qualifiers
REGION                  1..280
                        note = Codon-optimized proline 4-hydroxylase gene from
                            Sinorhizobium meliloti
source                  1..280
                        mol_type = protein
                        organism = synthetic construct
SEQUENCE: 200
MSTHFLGKVK FDEARLAEDL STLSRAEFSS AYSDFACGKW ELCVLRNRTG MQEEDIVVSH    60
NAPALQTPLS KSLPYLNELV ETHFDCSRVR YVRIVRVSEN ACLIPHSDYL ELDNEFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 201          moltype = DNA   length = 843
FEATURE                 Location/Qualifiers
misc_feature            1..843
                        note = Codon-optimized proline 4-hydroxylase gene from
                            Sinorhizobium meliloti
source                  1..843
                        mol_type = other DNA
                        organism = synthetic construct
SEQUENCE: 201
atgtctacgc atttccttgg caaggtcaaa ttcgacgagg ccagattagc cgaagatctg    60
tctactttat ctcgtcgtga gttttcttcc gcatattcgg acttcgcttg tggaaagtgg   120
gaactttgtg ttttacgcaa cagaacaggc atgcaagaag aagacattgt ggtttctcac   180
aatcagcccg cattacagac ccctttatct aaatcactgc cgtacttgaa tgagcttgtt   240
gaaacacact tcgactgcag tcgcgttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacatg   420
ggtctgggcg agatctggtt tctggacgca catttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taagaattg    600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttgggg catcgtgaac gcggagaagt aatgacgtat   840
taa                                                                 843

SEQ ID NO: 202          moltype = AA   length = 280
```

```
FEATURE                 Location/Qualifiers
REGION                  1..280
                        note = Codon-optimized proline 4-hydroxylase gene from
                          Sinorhizobium meliloti
source                  1..280
                        mol_type = protein
                        organism = synthetic construct
SEQUENCE: 202
MSTHFLGKVK FDEARLAEDL STLSRREFSS AYSDFACGKW ELCVLRNRTG MQEEDIVVSH    60
NQPALQTPLS KSLPYLNELV ETHFDCSAVR YVRIRVSEN ACLIPHSDYL ELDEEFTRLH   120
LVLDTNSGCA NTEEDKIFHM GLGEIWFLDA HLPHSAACFS KTPRLQLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 203          moltype = DNA  length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 203
atgtctacgc atttccttgg caaggtcaaa ttcgacgagg ccagattagc cgaagatctg    60
tctacttat ctcgtcgtga gttttcttcc gcatattcgg acttcgcttg tggaaagtgg   120
gaactttgtg tttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tcgtgttaga tatgtacgga tcgtgcgtgt ctccgagaac   300
gcctgcctga tccctcatag tgattatttg gagttggata atgaattcac ccggctgcac   360
ctcgtgttgg atactaacag tggttgtgcc aacactgagg aagataagat attccacatg   420
ggtctgggcg agatctggtt tctggacgca atgttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttttgggg catcgtgaac gcggagaagt aatgacgtat   840
taa                                                                  843

SEQ ID NO: 204          moltype = AA  length = 280
FEATURE                 Location/Qualifiers
REGION                  1..280
                        note = Codon-optimized proline 4-hydroxylase gene from
                          Sinorhizobium meliloti
source                  1..280
                        mol_type = protein
                        organism = synthetic construct
SEQUENCE: 204
MSTHFLGKVK FDEARLAEDL STLSRREFSS AYSDFACGKW ELCVLRNRTG MQEEDIVVSH    60
NAPALQTPLS KSLPYLNELV ETHFDCSRVR YVRIRVSEN ACLIPHSDYL ELDNEFTRLH   120
LVLDTNSGCA NTEEDKIFHM GLGEIWFLDA MLPHSAACFS KTPRLQLMID FEATAPPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 205          moltype = DNA  length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 205
atgtctacgc atttccttgg caaggtcaaa ttcgacgagg ccagattagc cgaagatctg    60
tctacttat ctcgtcgtga gttttcttcc gcatattcgg acttcgcttg tggaaagtgg   120
gaactttgtg tttacgcaa cagaacaggc atgcaagaag aagacattgt ggtttctcac   180
aatcagcccg cattacagac ccctttatct aaatcactgc cgtacttgaa tgagcttgtt   240
gaaacacact tcgactgcag tcgcgttaga tatgtacgga tcgtgcgtgt ctccgagaac   300
gcctgcctga tccctcatag tgattatttg gagttggatg aagaattcac ccggctgcac   360
ctcgtgttgg atactaacag tggttgtgcc aacactgagg aagataagat attccacctg   420
ggtctgggcg agatctggtt tctggacgca catttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taagaattg   600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttttgggg catcgtgaac gcggagaagt aatgacgtat   840
taa                                                                  843
```

```
SEQ ID NO: 206          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 206
MSTHFLGKVK FDEARLAEDL STLSRREFSS AYSDFACGKW ELCVLRNRTG MQEEDIVVSH   60
NQPALQTPLS KSLPYLNELV ETHFDCSAVR YVRIVRVSEN ACLIPHSDYL ELDEEFTRLH  120
LVLDTNSGCA NTEEDKIFHL GLGEIWFLDA HLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 207          moltype = DNA  length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 207
atgtctacgc atttccttgg caaggtcaaa ttcgacgagg ccagattagc cgaagatctg   60
tctactttat ctcgtcgtga gttttcttcc gcatattcag acttcgcttg tggaaagtgg  120
gaactttgtg ttttacgcaa cagaacaggc atgcaagaag aagacattgt ggtttctcac  180
aatgcgcccg cattacagac cccttttatct aaatcactgc cgtacttgaa tgagcttgtt  240
gaaacacact tcgactgcag tcgtgttaga tatgtacgga tcgtgcgtgt ctccgagaac  300
gcctgcctga tccctcatag tgattatttg gagttggata atgaattcac ccggctgcac  360
ctcgtgttgg atactaacag tggttgtgcc aacactgagg aagataagat attccacatg  420
ggtctgggcg agatctggtt tctggacgca atgttacctc attctgctgc ctgctttttct  480
aaaactccta gactgcagct catgatagat tttgaagcta ccgccttccc ggaatccttc  540
ttacgcaatg tggaaggtcc tgtgactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 208          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 208
MSTHFLGKVK FDEARLAEDL STLSRREFSS AYSDFACGKW ELCVLRNRTG MQEEDIVVSH   60
NAPALQTPLS KSLPYLNELV ETHFDCSRVR YVRIVRVSEN ACLIPHSDYL ELDNEFTRLH  120
LVLDTNSGCA NTEEDKIFHM GLGEIWFLDA MLPHSAACFS KTPRLQLMID FEATAFPESF  180
LRNVEGPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 209          moltype = DNA  length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 209
atgtctacgc atttccttgg caaggtcaaa ttcgacgagg ccagattagc cgaagatctg   60
tctactttat ctcgttggga gttttcttcc gcatattcgg acttcgcttg tggaaagtgg  120
gaactttgtg ttttacgcaa cagaacaggc atgcaagaag aagacattgt ggtttctcac  180
aatgcgcccg cattacagac cccttttatct aaatcactgc cgtacttgaa tgagcttgtt  240
gaaacacact tcgactgcag tcgtgttaga tatgtacgga tcgtgcgtgt ctccgagaac  300
gcctgcctga tccctcatag tgattatttg gagttggatg aagaattcac ccggctgcac  360
ctcgtgttgg atactaacag tggttgtgcc aacactgagg aagataagat attccacctg  420
ggtctgggcg agatctggtt tctggacgca atgttacctc attctgctgc ctgctttttct  480
aaaactccta gactgcagct catgatagat tttgaagcta ccgccttccc ggaatccttc  540
ttacgcaatg tggaacatgcc tgtaactact cgcgacatgg tagaccctcg taaagaattg  600
acggacgaag ttatagaagg cattttaggg ttctccataa tcatcagtga agcgaattac  660
cgcgagatcg tctctatcct ggccaaatta cacttctttt ataaagcgga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843
```

```
SEQ ID NO: 210           moltype = AA   length = 280
FEATURE                  Location/Qualifiers
REGION                   1..280
                         note = Codon-optimized proline 4-hydroxylase gene from
                           Sinorhizobium meliloti
source                   1..280
                         mol_type = protein
                         organism = synthetic construct
SEQUENCE: 210
MSTHFLGKVK FDEARLAEDL STLSRWEFSS AYSDFACGKW ELCVLRNRTG MQEEDIVVSH   60
NAPALQTPLS KSLPYLNELV ETHFDCSRVR YVRIVRVSEN ACLIPHSDYL ELDEEFTRLH  120
LVLDTNSGCA NTEEDKIFHL GLGEIWFLDA MLPHSAACFS KTPRLQLMID FEATAFPESF  180
LRNVEQPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 211           moltype = DNA   length = 843
FEATURE                  Location/Qualifiers
misc_feature             1..843
                         note = Codon-optimized proline 4-hydroxylase gene from
                           Sinorhizobium meliloti
source                   1..843
                         mol_type = other DNA
                         organism = synthetic construct
SEQUENCE: 211
atgtctacgc atttccttgg caaggtcaaa ttcgacgagg ccagattagc cgaagatctg   60
tctactttat ctcgtcgtga gttttcttcc gcatattcgg acttcgcttg tggaaagtgg  120
gaactttgtg ttttacgcaa cagaacaggc atgcaagaag aagacattgt ggtttctcac  180
aatcagcccg cattacagac cccttatct aaatcactgc cgtacttgaa tgagcttgtt   240
gaaacacact ttgactgcag tcgtgttaga tatgtacgga tcgtgcgtgt ctccgagaac  300
gcctgcctga tccctcatag tgattatttg gagttggata tgaattcac ccggctgcac   360
ctcgtgttgg atactaacag tggttgtgcc aacactgagg aagataagat attccacctg  420
ggtctgggcg agatctggtt tctggatgca catttacctc attctgctgc ctgcttttct  480
aaaactccta gactgcagct catgatagat tttgaagctc ccgccttccc ggaatccttc  540
ttacgcaatg tggaaggtcc tgtgactact cgcgacatgg tagaccctcg taaagaattg  600
acggacgaag ttatagaagg cattttaggg ttctccataa tcatcagtga agcgaattac  660
cgcgagatct ctctatcct ggccaaatta cacttctttt ataaagcgga ctgtcggtcc   720
atgtatgatt ggcttaaaga aatatgtaaa cgccggggag atcccgcgtt gattgagaag  780
acagcgagtc tcgaacgttt cttttttggg catcgtgaac gcgagaagt aatgacgtat    840
taa                                                                843

SEQ ID NO: 212           moltype = AA   length = 280
FEATURE                  Location/Qualifiers
REGION                   1..280
                         note = Codon-optimized proline 4-hydroxylase gene from
                           Sinorhizobium meliloti
source                   1..280
                         mol_type = protein
                         organism = synthetic construct
SEQUENCE: 212
MSTHFLGKVK FDEARLAEDL STLSRREFSS AYSDFACGKW ELCVLRNRTG MQEEDIVVSH   60
NQPALQTPLS KSLPYLNELV ETHFDCSRVR YVRIVRVSEN ACLIPHSDYL ELDNEFTRLH  120
LVLDTNSGCA NTEEDKIFHL GLGEIWFLDA HLPHSAACFS KTPRLQLMID FEATAFPESF  180
LRNVEGPVTT RDMVDPRKEL TDEVIEGILG FSIIISEANY REIVSILAKL HFFYKADCRS  240
MYDWLKEICK RRGDPALIEK TASLERFFLG HRERGEVMTY                        280

SEQ ID NO: 213           moltype = DNA   length = 843
FEATURE                  Location/Qualifiers
misc_feature             1..843
                         note = Codon-optimized proline 4-hydroxylase gene from
                           Sinorhizobium meliloti
source                   1..843
                         mol_type = other DNA
                         organism = synthetic construct
SEQUENCE: 213
atgtctacgc atttccttgg caaggtcaaa ttcgacgagg ccagattagc cgaagatctg   60
tctactttaa gtcgtgcaga gttttcttcc gcatattcgg acttcgcttg tggaaagtgg  120
gaactttgtg ttttacgcaa cagaacaggc atgcaagaag aagacattgt ggtttctcac  180
aatgcgcccg cattacagac cccttatct aaatcactgc cgtacttgaa tgagcttgtt   240
gaaacacact tcgactgcag tcgcgttaga tatgtacgga tcgtgcgtgt ctttgagaac  300
gcctgcctga tccctcatag tgattatttg gagttggatg aagaattcac ccggctgcac  360
ctcgtgttgg atactaacag tggttgtgcc aacactgagg aagataagat attccacctg  420
ggtctgggcg agatctggtt tctggacgca atgttacctc attctgctgc ctgcttttct  480
aaaactccta gactgcagct catgatagat tttgaagctc ccgccttccc ggaatccttc  540
ttacgcaatg tggaacagcc tggtactact cgcgacatgg tagaccctcg taaagaattg  600
acggacgaag ttatagaagg cattttaggg ttctccataa tcatcagtga agcgaattac  660
cgcgagatct ctctatcct ggccaaatta cacttctttt ataaagcgga ctgtcggtcc   720
atgtatgatt ggcttaaaga aatatgtaaa cgccggggag atcccgcgtt gattgagaag  780
acagcgagtc tcgaacgttt cttttttggg catcgtgaac gcgagaagt aatgacgtat    840
```

```
                                                                         843
taa SEQ ID NO: 214          moltype = AA  length = 280
FEATURE                 Location/Qualifiers
REGION                  1..280
                        note = Codon-optimized proline 4-hydroxylase gene from
                          Sinorhizobium meliloti
source                  1..280
                        mol_type = protein
                        organism = synthetic construct
SEQUENCE: 214
MSTHFLGKVK FDEARLAEDL STLSRAEFSS AYSDFACGKW ELCVLRNRTG MQEEDIVVSH    60
NAPALQTPLS KSLPYLNELV ETHFDCSAVR YVRIVRVFEN ACLIPHSDYL ELDEEFTRLH   120
LVLDTNSGCA NTEEDKIFHL GLGEIWFLDA MLPHSAACFS KTPRLQLMID FEATAFPESF   180
LRNVEQPGTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 215          moltype = DNA  length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 215
atgtctacgc atttccttgg caaggtcaaa ttcgacgagg ccagattagc cgaagatctg    60
tctactttat ctcgtcgtga gttttcttcc gcatattcgg acttcgcttg tggaaagtgg   120
gaactttgtg ttttacgcaa cagaacaggc atgcaagaag aagacattgt ggtttctcac   180
aatcagcccg cattacagac ccctttatct aaatcactgc cgtacttgaa tgagcttgtt   240
gaaacacact tcgactgcag tcgtgttaga tatgtacgga tcgtgcgtgt ctttgagaac   300
gcctgcctga tccctcatag tgattatttg gagttggata tgaattcac ccggctgcac    360
ctcgtgttgg atactaacag tggttgtgcc aacactgagg aagataagat attccacctg   420
ggtctgggcg agatctggtt tctggacgca catttacctc attctgctgc ctgcttttct   480
aaaactccta gactgcagct catgatagat tttgaagcta ccgccttccc ggaatccttc   540
ttacgcaatg tggaacaacc tgtaactact cgcgacatgg tagaccctcg taagaattg    600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
acagcgagtc tcgaacgttt cttttggggg catcgtgaac gcggagaagt aatgacgtat   840
taa                                                                 843

SEQ ID NO: 216          moltype = AA  length = 280
FEATURE                 Location/Qualifiers
REGION                  1..280
                        note = Codon-optimized proline 4-hydroxylase gene from
                          Sinorhizobium meliloti
source                  1..280
                        mol_type = protein
                        organism = synthetic construct
SEQUENCE: 216
MSTHFLGKVK FDEARLAEDL STLSRREFSS AYSDFACGKW ELCVLRNRTG MQEEDIVVSH    60
NQPALQTPLS KSLPYLNELV ETHFDCSRVR YVRIVRVFEN ACLIPHSDYL ELDSEFTRLH   120
LVLDTNSGCA NTEEDKIFHL GLGEIWFLDA HLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 217          moltype = DNA  length = 843
FEATURE                 Location/Qualifiers
misc_feature            1..843
                        note = Codon-optimized proline 4-hydroxylase gene from
                          Sinorhizobium meliloti
source                  1..843
                        mol_type = other DNA
                        organism = synthetic construct
SEQUENCE: 217
atgtctacgc atttccttgg caaggtcaaa ttcgacgagg ccagattagc cgaagatctg    60
tctactttat ctcgtcgtga gttttcttcc gcatattcgg acttcgcttg tggaaagtgg   120
gaactttgtg ttttacgcaa cagaacaggc atgcaagaag aagacattgt ggtttctcac   180
aatgcgcccg cattacagac ccctttatct aaatcactgc cgtacttgaa tgagcttgtt   240
gaaacacact tcgactgcag tcgcgttaga tatgtacgga tcgtgcgtgt ctttgagaac   300
gcctgtctga tccctcatag tgattatttg gagttggatg agaattcac ccggctgcac    360
ctcgtgttgg atactaacag tggttgtgcc aacactgagg aagataagat attccacctg   420
ggtctgggcg agatctggtt tctggatgca catttacctc attctgctgc ctgcttttct   480
aaaactccta gactgcagct catgatagat tttgaagcta ccgccttccc ggaatccttc   540
ttacgcaatg tggaacagcc tgtaactact cgcgacatgg tagaccctcg taagaattg    600
acggacgaag ttatagaagg cattttaggg ttctccataa tcatcagtga agcgaattac   660
cgcgagatcg tctctatcct ggccaaatta cacttctttt ataaagcgga ctgtcggtcc   720
atgtatgatt ggcttaaaga aatatgtaaa cgccggggag atcccgcgtt gattgagaag   780
```

```
acagcgagtc tcgaacgttt cttttttggg catcgtgaac gcggagaagt aatgacgtat    840
taa                                                                  843

SEQ ID NO: 218          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 218
MSTHFLGKVK FDEARLAEDL STLSRREFSS AYSDFACGKW ELCVLRNRTG MQEEDIVVSH  60
NAPALQTPLS KSLPYLNELV ETHFDCSAVR YVRIVRVFEN ACLIPHSDYL ELDEEFTRLH 120
LVLDTNSGCA NTEEDKIFHL GLGEIWFLDA HLPHSAACFS KTPRLQLMID FEATAFPESF 180
LRNVEQPVTT RDMVDPRKEL TDEVIEGILG FSIIISEANY REIVSILAKL HFFYKADCRS 240
MYDWLKEICK RRGDPALIEK TASLERFFLG HRERGEVMTY                        280

SEQ ID NO: 219          moltype = DNA  length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 219
atgtctacgc atttccttgg caaggtcaaa ttcgacgagg ccagattagc cgaagatctg   60
tctactttat ctcgtgcaga gttttcttcc gcatattcgg acttcgcttg tggaaagtgg  120
gaactttgtg tttacgcaa cagaacaggc atgcaagaag aagacattgt ggtttctcac  180
aatgcgcccg cattacagac cccttttatct aaatcactgc cgtacttgaa tgagcttgtt  240
gaaacacact cgactgcag tgcggttaga tatgtacgga tcgtgcgtgt ctttgagaac  300
gcctgcctga tccctcatag tgattatttg gagttggatg aagaattcac ccggctgcac  360
ctcgtgttgg atactaacag tggttgtgcc aacactgagg aagataagat attcccacatg  420
ggtctgggcg agatctggtt tctggacgca atgttacctc attctgctgc ctgctttctt  480
aaaactccta gactgcagct catgatagat tttgaagcta ccgccttccc ggaatccttc  540
ttacgcaatg tggaacaacc tgtgactact cgcgacatgg tagaccctcg taagaattg  600
acggacgaag ttatagaagg catttttaggg ttctccataa tcatcagtga agcgaattac  660
cgcgagatcg tctctatcct ggccaaatta cacttcttct ataaagccga ctgtcggtcc  720
atgtatgatt ggcttaaaga aatatgtaaa cgccggggag atcccgcgtt gattgagaag  780
acagcgagtc tcgaacgttt cttttttggg catcgtgaac gcggagaagt aatgacgtat  840
taa                                                                843

SEQ ID NO: 220          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 220
MSTHFLGKVK FDEARLAEDL STLSRAEFSS AYSDFACGKW ELCVLRNRTG MQEEDIVVSH  60
NAPALQTPLS KSLPYLNELV ETHFDCSAVR YVRIVRVFEN ACLIPHSDYL ELDEEFTRLH 120
LVLDTNSGCA NTEEDKIFHM GLGEIWFLDA MLPHSAACFS KTPRLQLMID FEATAFPESF 180
LRNVEQPVTT RDMVDPRKEL TDEVIEGILG FSIIISEANY REIVSILAKL HFFYKADCRS 240
MYDWLKEICK RRGDPALIEK TASLERFFLG HRERGEVMTY                        280

SEQ ID NO: 221          moltype = DNA  length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 221
atgagtagcc actttctcgg caaagtgaaa ttcgatgaag cacggcttgc agaagacttg   60
tctacgctga gtcgtgcaga attttcctcc gcgtatagtg attttgcctg cggaaaatgg  120
gaactgtgtg ttcttagaaa ccgtacaggt atgcaagaag aggatattgt ggttccccat  180
aacgcaccgg ctcttcagac cccgctgagt aaatcattgc cttaccttaa tgaattagtt  240
gagacacatt tcgactgttc ggctgtccgt tacgttcgta ttgtaagagt gaccgagaac  300
gcgtgcctga taccacattc agattacctc gagcttgaca cgagtttac cagattgcat  360
ctggtcttgg ataccaactc aggttgtgcc aataccgaag aggacaagat attccatatg  420
ggtctcggtg aaaatatggt tcttggatgcg atgctgcctc atagtgcagc atgtttttct  480
aagacgccta gactgcagct gatgattgac ttcgaagcta cagcgtttcc gaatcatttt  540
ttacggaacg tcgaacagcc ggttaccacc cgtgatatgg tcgacccag aaaagaatta  600
acggacgaag tgatcgaagg tatactcggc ttttctatta tcatatcgga ggcgaactac  660
cgtgaaatcg tgtctatttt agcgaagctg cacttctttt ataaagccga ttgccggtcg  720
```

```
atgtatgatt ggctgaaaga aatttgcaag agacggggag acccggcgct tattgaaaag    780
acggcttcat tggaacgctt cttttaggc cacagagaac gcggggaagt aatgacctac    840
taa                                                                  843
```

| SEQ ID NO: 222 | moltype = AA length = 280 |
|---|---|
| FEATURE | Location/Qualifiers |
| REGION | 1..280 |
| | note = Codon-optimized proline 4-hydroxylase gene from Sinorhizobium meliloti |
| source | 1..280 |
| | mol_type = protein |
| | organism = synthetic construct |

```
SEQUENCE: 222
MSSHFLGKVK FDEARLAEDL STLSRAEFSS AYSDFACGKW ELCVLRNRTG MQEEDIVVSH    60
NAPALQTPLS KSLPYLNELV ETHFDCSAVR YVRIVRVTEN ACLIPHSDYL ELDNEFTRLH   120
LVLDTNSGCA NTEEDKIFHM GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280
```

| SEQ ID NO: 223 | moltype = DNA length = 843 |
|---|---|
| FEATURE | Location/Qualifiers |
| misc_feature | 1..843 |
| | note = Codon-optimized proline 4-hydroxylase gene from Sinorhizobium meliloti |
| source | 1..843 |
| | mol_type = other DNA |
| | organism = synthetic construct |

```
SEQUENCE: 223
atgagtagcc actttctcgg caaagtgaaa ttcgatgaag cacggcttgc agaagacttg     60
tctacgctga gtcgtcgtga attttcctcc gcgtatagtg attttgcctg cggaaaatgg   120
gaactgtgtg ttcttagaaa ccgtacaggt atgcaagaag aggatattgt ggtttcccat   180
aacgcaccgg ctcttcagac cccgctgagt aaatcattgc cttaccttaa tgaattagtt   240
gagacacatt tcgactgttc gcgtgtccgt tacgttcgta ttgtaagagt gagcgagaac   300
gcgtgcctga taccacattc agattacctc gagcttgacg aggagtttac cagattgcat   360
ctggtcttgg ataccaactc aggttgtgcc aataccgaag aggacaagat attccatctg   420
ggtctcggtg aaatatggtt cttggatgcg atgctgcctc atagtgcagc atgtttttct   480
aagacgccta gactgcagct gatgattgac ttcgaagcta cagcgttccc gaatcatttt   540
ttacggaacg tcgaacagcc ggttaccacc cgtgatatgg tcgacctag aaaagaatta    600
acggacgaag tgatcgaagg tatactcggc ttttctatta tcatatcgga ggcgaactac   660
cgtgaaatcg tgtctatttt agcgaagctg cacttcttt ataaagccga ttgccggtcg   720
atgtatgatt ggctgaaaga aatttgcaag agacggggag acccggcgct tattgaaaag   780
acggcttcat tggaacgctt cttttaggc cacagagaac gcggggaagt aatgacctac   840
taa                                                                  843
```

| SEQ ID NO: 224 | moltype = AA length = 280 |
|---|---|
| FEATURE | Location/Qualifiers |
| REGION | 1..280 |
| | note = Codon-optimized proline 4-hydroxylase gene from Sinorhizobium meliloti |
| source | 1..280 |
| | mol_type = protein |
| | organism = synthetic construct |

```
SEQUENCE: 224
MSSHFLGKVK FDEARLAEDL STLSRREFSS AYSDFACGKW ELCVLRNRTG MQEEDIVVSH    60
NAPALQTPLS KSLPYLNELV ETHFDCSRVR YVRIVRVSEN ACLIPHSDYL ELDEEFTRLH   120
LVLDTNSGCA NTEEDKIFHL GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280
```

| SEQ ID NO: 225 | moltype = DNA length = 843 |
|---|---|
| FEATURE | Location/Qualifiers |
| misc_feature | 1..843 |
| | note = Codon-optimized proline 4-hydroxylase gene from Sinorhizobium meliloti |
| source | 1..843 |
| | mol_type = other DNA |
| | organism = synthetic construct |

```
SEQUENCE: 225
atgagtagcc actttctcgg caaagtgaaa ttcgatgaag cacggcttgc agaagacttg     60
tctacgctga gtcgtgcaga attttcctcc gcgtatagtg attttgcctg cggaaaatgg   120
gaactgtgtg ttcttagaaa ccgtacaggt atgcaagaag aggatattgt ggtttcccat   180
aaccagccgg ctcttcagac cccgctgagt aaatcattgc cttaccttaa tgaattagtt   240
gagacacatt tcgactgttc ggctgtccgt tacgttcgta ttgtaagagt gagcgagaac   300
gcgtgcctga taccacattc agattacctc gagcttgaca acgagtttac cagattgcat   360
ctggtcttgg ataccaactc aggttgtgcc aataccgaag aggacaagat attccatctg   420
ggtctcggtg aaatatggtt cttggatgcg atgctgcctc atagtgcagc atgtttttct   480
aagacgccta gactgcagct gatgattgac ttcgaagcta cagcgttccc gaatcatttt   540
ttacggaacg tcgaacagcc ggttaccacc cgtgatatgg tcgacctag aaaagaatta    600
acggacgaag tgatcgaagg tatactcggc ttttctatta tcatatcgga ggcgaactac   660
```

```
cgtgaaatcg tgtctatttt agcgaagctg cacttcttt ataaagccga ttgccggtcg    720
atgtatgatt ggctgaaaga aatttgcaag agacggggag acccggcgct tattgaaaag    780
acggcttcat tggaacgctt cttttaggc cacagagaac gcggggaagt aatgacctac    840
taa                                                                  843

SEQ ID NO: 226          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 226
MSSHFLGKVK FDEARLAEDL STLSRAEFSS AYSDFACGKW ELCVLRNRTG MQEEDIVVSH    60
NQPALQTPLS KSLPYLNELV ETHFDCSAVR YVRIVRVSEN ACLIPHSDYL ELDNEFTRLH   120
LVLDTNSGCA NTEEDKIFHL GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280

SEQ ID NO: 227          moltype = DNA  length = 843
FEATURE                 Location/Qualifiers
misc_feature            1..843
                        note = Codon-optimized proline 4-hydroxylase gene from
                        Sinorhizobium meliloti
source                  1..843
                        mol_type = other DNA
                        organism = synthetic construct
SEQUENCE: 227
atgtctagcc atttccttgg caaggtcaaa ttcgacgagg ccagattagc cgaagatctg     60
tctacttta gtcgtcgtga gttttcttcc gcatattcgg acttcgcttg tggaaagtgg    120
gaactttgtg ttttacgcaa cagaacaggc atgcaagaag aagacattgt ggtttctcac    180
aatgcgccg cattacagac cccttatct aaatcactgc cgtacttgaa tgagcttgtt    240
gaaacacact tcgactgcag tcgtgttaga tatgtacgga tcgtgcgtgt ctccgagaac    300
gcctgcctga tccctcatag tgattatttg gagttggatg aagaattcac ccggctgcac    360
ctcgtgttgg atactaacag tggttgtgcc aacactgagg aagataagat attccacctg    420
ggtctgggcg agatctggtt tctggacgca atgttacctc attctgctgc tgcttttct    480
aaaactccta gactgcagct catgatagat tttgaagcta ccgccttccc ggaatccttc    540
ttacgcaatg tggaacagcc tgtaactact cgcgacatgg tagaccctcg taaagaattg    600
acggacgaag ttatagaagg cattttaggg ttctccataa tcatcagtga agcgaattac    660
cgcgagatcg tctctatcct ggccaaatta cacttctttt ataaagcgga ctgtcggtcc    720
atgtatgatt ggcttaaaga aatatgtaaa cgccggggag atcccgcgtt gattgagaag    780
acagcgagtc tcgaacgttt cttttgggg catcgtgaac gcgagaagt aatgacgtat    840
taa                                                                 843

SEQ ID NO: 228          moltype = AA  length = 280
FEATURE                 Location/Qualifiers
REGION                  1..280
                        note = Codon-optimized proline 4-hydroxylase gene from
                        Sinorhizobium meliloti
source                  1..280
                        mol_type = protein
                        organism = synthetic construct
SEQUENCE: 228
MSSHFLGKVK FDEARLAEDL STLSRREFSS AYSDFACGKW ELCVLRNRTG MQEEDIVVSH    60
NAPALQTPLS KSLPYLNELV ETHFDCSRVR YVRIVRVSEN ACLIPHSDYL ELDEEFTRLH   120
LVLDTNSGCA NTEEDKIFHL GLGEIWFLDA MLPHSAACFS KTPRLQLMID FEATAFPESF   180
LRNVEQPVTT RDMVDPRKEL TDEVIEGILG FSIIISEANY REIVSILAKL HFFYKADCRS   240
MYDWLKEICK RRGDPALIEK TASLERFFLG HRERGEVMTY                         280
```